(12) United States Patent
Stavros et al.

(10) Patent No.: US 11,375,984 B2
(45) Date of Patent: Jul. 5, 2022

(54) METHOD AND SYSTEM FOR MANAGING FEATURE READING AND SCORING IN ULTRASOUND AND/OR OPTOACOUSTIC IMAGES

(71) Applicant: Seno Medical Instruments, Inc., San Antonio, TX (US)

(72) Inventors: Anthony Thomas Stavros, San Antonio, TX (US); Bryan Clingman, San Antonio, TX (US); Sandra G. Dykes, Boerne, TX (US)

(73) Assignee: Seno Medical Instruments, Inc., San Antonio, TX (US)

( * ) Notice: Subject to any disclaimer, the term of this patent is extended or adjusted under 35 U.S.C. 154(b) by 83 days.

(21) Appl. No.: 16/905,396

(22) Filed: Jun. 18, 2020

(65) Prior Publication Data

US 2020/0315589 A1    Oct. 8, 2020

Related U.S. Application Data

(63) Continuation-in-part of application No. 16/554,961, filed on Aug. 29, 2019, now Pat. No. 11,172,900, and
(Continued)

(51) Int. Cl.
*A61B 8/08* (2006.01)
*G16H 50/50* (2018.01)
(Continued)

(52) U.S. Cl.
CPC .......... *A61B 8/5261* (2013.01); *A61B 5/0035* (2013.01); *A61B 5/0095* (2013.01);
(Continued)

(58) Field of Classification Search
CPC ... A61B 8/5261; A61B 5/0035; A61B 5/0095; A61B 5/7267; A61B 5/7275;
(Continued)

(56) References Cited

U.S. PATENT DOCUMENTS

2010/0081963 A1* 4/2010 Gilhuly ................. G16H 50/50
                                                              600/554
2013/0030305 A1* 1/2013 Yu ........................ A61B 5/4244
                                                              600/476
(Continued)

FOREIGN PATENT DOCUMENTS

WO    2017049403 A1    3/2017
WO    2017070582 A1    4/2017

OTHER PUBLICATIONS

International Search Report and Written Opinion for corresponding PCT Application No. PCT/US2020/038473 dated Sep. 28, 2020 (14 pages).

*Primary Examiner* — Amara Abdi
(74) *Attorney, Agent, or Firm* — The Small Patent Law Group LLP; Dean D. Small

(57) ABSTRACT

Systems, methods and computer program products are provided for reading and scoring ultrasound and/or optoacoustic (US/OA) images that include at least one of OA images or US images acquired in connection with an examination for a region of interest (ROI). The system displays a first image that has an interior ROI outline separating an internal zone from a boundary zone. In some aspects, feature scores are obtained in connection with at least the boundary zone and peripheral zone of the first image and the feature scores are applied to a classification model to obtain at least one of a prognostic result or predictive result indicative of a trait of the lesion. In accordance with some aspects, an order in which feature scores are entered is automatically managed to obtain for the at least one of the peripheral zone or the boundary zone before the feature score is obtained for the internal zone.

56 Claims, 44 Drawing Sheets

Related U.S. Application Data a continuation-in-part of application No. 16/445,765, filed on Jun. 19, 2019.

(60) Provisional application No. 62/881,402, filed on Aug. 1, 2019, provisional application No. 62/863,910, filed on Jun. 20, 2019, provisional application No. 62/863,915, filed on Jun. 20, 2019, provisional application No. 62/863,917, filed on Jun. 20, 2019, provisional application No. 62/863,911, filed on Jun. 20, 2019, provisional application No. 62/863,926, filed on Jun. 20, 2019, provisional application No. 62/863,922, filed on Jun. 20, 2019, provisional application No. 62/863,928, filed on Jun. 20, 2019, provisional application No. 62/863,931, filed on Jun. 20, 2019, provisional application No. 62/744,606, filed on Oct. 11, 2018, provisional application No. 62/725,632, filed on Aug. 31, 2018.

(51) Int. Cl.
*A61B 5/00* (2006.01)
*A61B 8/00* (2006.01)
*G16H 50/20* (2018.01)
*G16H 30/40* (2018.01)

(52) U.S. Cl.
CPC .......... *A61B 5/7267* (2013.01); *A61B 5/7275* (2013.01); *A61B 5/7282* (2013.01); *A61B 5/7425* (2013.01); *A61B 5/7435* (2013.01); *A61B 5/7485* (2013.01); *A61B 8/085* (2013.01); *A61B 8/463* (2013.01); *A61B 8/465* (2013.01); *A61B 8/469* (2013.01); *A61B 8/5223* (2013.01); *G16H 30/40* (2018.01); *G16H 50/20* (2018.01); *G16H 50/50* (2018.01)

(58) Field of Classification Search
CPC ... A61B 5/7282; A61B 5/7425; A61B 5/7435; A61B 5/7485; A61B 8/085; A61B 8/463; A61B 8/465; A61B 8/469; A61B 8/5223; A61B 5/4312; G16H 30/40; G16H 50/20; G16H 50/50; G16H 50/30
See application file for complete search history.

(56) References Cited

U.S. PATENT DOCUMENTS

| | | | |
|---|---|---|---|
| 2015/0272462 A1* | 10/2015 | Nearing | A61B 5/316 600/512 |
| 2015/0342540 A1* | 12/2015 | An | A61N 1/3702 600/483 |
| 2016/0022238 A1* | 1/2016 | Park | A61B 6/5217 600/407 |
| 2016/0260211 A1* | 9/2016 | Gillies | A61B 6/50 |
| 2016/0343132 A1* | 11/2016 | Stavros | A61B 8/0825 |
| 2017/0128032 A1 | 5/2017 | Buchert et al. | |
| 2021/0259660 A1* | 8/2021 | Bharat | A61B 8/085 |

* cited by examiner

METHOD AND SYSTEM FOR MANAGING FEATURE READING AND SCORING IN ULTRASOUND AND/OR OPTOACOUSTIC IMAGES

RELATED APPLICATIONS

The present application represents a continuation-in-part application of, and claims priority to, U.S. application Ser. No. 16/554,961, Titled "METHODS AND SYSTEMS TO DETERMINE CANCER MOLECULAR SUBTYPES BASED ON ULTRASOUND AND/OR OPTOACOUSTIC (OA/US) FEATURES" which was filed on Aug. 29, 2019, and which claims priority to Provisional Application No. 62/725,632, filed on Aug. 31, 2018, titled "QUALITATIVE OPTOACOUSTIC IMAGING (OA/US) FEATURES OF BREAST CANCERS CORRELATE WITH MOLECULAR SUBTYPES", the complete subject matter of which is expressly incorporated herein by reference in its entirety.

The present application represents a continuation-in-part application of, and claims priority to, U.S. application Ser. No. 16/445,765, Titled "OPTOACOUSTIC IMAGE ANALYSYS METHOD AND SYSTEM FOR AUTOMATICALLY ESTIMATING LESION TRAITS" which was filed on Jun. 19, 2019, and which claims priority to Provisional Application No. 62/744,606, filed on Oct. 11, 2018, titled "OPTOACOUSTIC IMAGE ANALYSIS METHOD AND SYSTEM FOR AUTOMATICALLY ESTIMATING LESION TRAITS", the complete subject matter of which is expressly incorporated herein by reference in its entirety.

The present application claims priority to U.S. Provisional Application No. 62/863,910, Titled "METHOD AND SYSTEM FOR ULTRASOUND IMAGE FEATURE SCORING OF BREAST CANCERS" which was filed on 20 Jun. 2019; U.S. Provisional Application No. 62/863,911, Titled "METHOD AND SYSTEM FOR ULTRASOUND IMAGE FEATURE SCORING OF BREAST CANCERS" which was filed on 20 Jun. 2019; U.S. Provisional Application No. 62/863,915, Titled "REFERENCE KEY IMAGES FOR METHOD AND SYSTEM FOR ULTRASOUND IMAGE FEATURE SCORING OF BREAST CANCERS" which was filed on 20 Jun. 2019; U.S. Provisional Application No. 62/863,917, Titled "METHOD AND SYSTEM FOR PROVIDING SENOGRAMS BASED ON OPTOACOUSTIC AND ULTRASOUND IMAGE FEATURE SCORING OF BREAST CANCERS" which was filed on 20 Jun. 2019; U.S. Provisional Application No. 62/863,922, Titled "METHOD AND SYSTEM FOR PROVIDING REFERENCE IMAGE KEY FOR OPTOACOUSTIC AND ULTRASOUND IMAGE FEATURE SCORING OF BREAST CANCERS" which was filed on 20 Jun. 2019; U.S. Provisional Application No. 62/863,926, Titled "METHOD AND SYSTEM FOR PROVIDING ULTRASOUND FEATURES AS QUANTITATIVE PREDICTIVE BIOMARKER TO BETTER ESTIMATE RISK OF BREAST CANCERS" which was filed on 20 Jun. 2019; U.S. Provisional Application No. 62/863,928, Titled "METHOD AND SYSTEM FOR PROVIDING ULTRASOUND FEATURE SCORES AS PROGNOSTIC BIOMARKS TO BETTER ESTIMATE RISK OF BREAST CANCERS" which was filed on 20-Jun.-2019; U.S. Provisional Application No. 62/863,931, Titled "METHOD AND SYSTEM FOR PROVIDING OPTOACOUSTIC FEATURE SCORES TO ESTIMATE RISK OF BREAST CANCERS" which was filed on 20-Jun.-2019; U.S. Provisional Application No. 62/881,402, Titled "METHOD AND SYSTEM FOR UTILIZING ULTRASOUND FEATURE SCORES AS QUANTITATIVE AND PROGNOSTIC BIOMARKERS" which was filed on 1 Aug. 2019, the complete subject matter of which are expressly incorporated herein by reference in their entireties.

BACKGROUND

Worldwide, breast cancer is the most commonly diagnosed cancer, and the second leading cause of cancer death in women. Although the death rate from breast cancer has significantly decreased in the last 20 years, breast cancer is still one of the major causes of morbidity and mortality in western women. One of the major challenges for its treatment is its heterogeneous nature, which determines the therapeutic options. The somatic genomic landscape of mutations largely influences breast cancer prognosis and therapeutic approach. Breast cancers with differing receptor expression and gene amplification profiles have different risk factors for incidence, therapeutic response, disease progression, and preferential organ sites of metastases.

Ultrasound is used today in the evaluation of suspicious breast masses, and guiding biopsies. However, tissue architecture non-invasively assessed by breast ultrasound imaging does not provide enough prognostic information about cancers, and therefore has limited value to clinicians beyond the assessment of tumor size.

SUMMARY

In accordance with embodiments herein, a system for managing image reading of at least one of ultrasound (US) images or optoacoustic (OA) images (US/OA images) is provided. The system includes a display, a graphical user interface (GUI) and memory configured to store programmable instructions. The system includes one or more processors configured to execute the programmable instructions to obtain US/OA images that include at least one of OA images or US images acquired in connection with an examination for a region of interest (ROI). The system displays, on the display, at least a first image from the US/OA images. The first image has an interior ROI outline separating an internal zone from a boundary zone. The first image has an exterior ROI outline separating the boundary zone from a peripheral zone. The system obtains, at the GUI, a feature score at a first entry field associated with at least one of the peripheral zone or boundary zone for the first image. The system obtains, at the GUI, a feature score at a second entry field associated with the internal zone for the first image. The system automatically enables and disables the second entry field to manage an order in which the corresponding feature scores are entered, at the GUI, such that the feature score is obtained for the at least one of the peripheral zone or the boundary zone before the feature score is obtained for the internal zone.

Additionally or alternatively, the display may be further configured to display the first entry field and the GUI may be configured to receive the feature score at the first entry field. They may be configured to automatically disable the second entry field until the first entry field receives the feature score associated with the at least one of the peripheral zone or boundary zone. The display may be further configured to display an entry screen that includes and co-displays the first and second entry fields. The second entry field may be a disabled until the first entry field receives the corresponding feature score. The first entry field may be associated with the peripheral zone of a US image. The second entry field may be associated with the boundary zone of the US image. The entry screen may include and may co-display the first and second entry fields with a third entry field. The third entry field may be associated with at least one of an internal zone shape, internal zone texture or internal zone sound transmission of the US image.

Additionally or alternatively, the one or more processors may be further configured to automatically disable the second and third entry fields until the first entry field receives the corresponding feature score and disable the third entry field until the second entry field receives the corresponding feature score. The entry screen may include at least three out of five of the following features associated with US images: US peripheral zone, US boundary zone, US internal zone shape, US internal zone texture, and US internal zone sound transmission. The first entry field may be associated with the peripheral zone of an OA image and the second entry field may be associated with the boundary zone of the OA image. The entry screen may include and may co-display the first and second entry fields with a third entry field. The third entry field may be associated with at least one of an internal zone shape, internal zone texture or internal zone sound transmission of the OA image.

Additionally or alternatively, the one or more processors may be configured to automatically disable the second and third entry fields until the first entry field receives the corresponding feature score and disable the third entry field until the second entry field receives the corresponding feature score. The entry screen may include at least three out of five of the following features associated with OA images: OA peripheral radiating vessels, OA boundary zone vessels, OA internal zone vessels, OA internal zone hemoglobin, and OA internal zone blush. The display may be configured co-display a first US image and a first OA image. The display may be further configured to display a set of US entry fields associated with features of the US image. The set of US entry fields may include the first entry field. The display a set of OA entry fields may be associated with features of the OA image. The set of OA entry fields may include the second entry field and may display a set of non-US/OA entry fields associated with at least one of i) a mammogram Bi-RADS rating, ii) patient age, iii) mass diameter or iv) depth to posterior margin of a mass.

Additionally or alternatively, the display may be further configured to display an entry field for a depth of a posterior margin of a mass in the first image. The one or more processors may be further configured to manage an order in which the feature scores are assigned to a predetermined outside—to—inside order. The outside-to-inside order may require first assignment of one or more feature scores to the peripheral zone, second assignment of one or more feature scores to the boundary zone and third assignment of one or more feature scores to the internal zone. The one or more processors may be further configured to calculate and the display may be further configured to display at least one of false negative ratio, likelihood of malignancy, confidence interval, BI-RADS conversion bars, assignment of a BI-RADS category or assignment of a BI-RADS subcategories.

In accordance with embodiments herein, a computer implemented method for managing image reading of at least one of ultrasound (US) images or optoacoustic (OA) images (US/OA images). The method utilizes one or more processors configured to execute programmable instructions for obtaining US/OA images that include at least one of OA images or US images acquired in connection with an examination for a region of interest (ROI). The method displays at least a first image from the US/OA images. The first image has an interior ROI outline separating an internal zone from a boundary zone. The first image has an exterior ROI outline separating the boundary zone from a peripheral zone. The method obtains a feature score at a first entry field associated with at least one of the peripheral zone or boundary zone for the first image. The method obtains a feature score at a second entry field associated with the internal zone for the first image. The method automatically enables and disables the second entry field to manage an order in which the corresponding feature scores are entered such that the feature score is obtained for the at least one of the peripheral zone or the boundary zone before the feature score is obtained for the internal zone.

Additionally or alternatively, the method may display the first entry field and may receive the feature score at the first entry field. The automatically enabling and disabling may comprise disabling the second entry field until the first entry field receives the feature score associated with the at least one of the peripheral zone or boundary zone. The method may display an entry screen that may include and co-displays the first and second entry fields. The second entry field may be disabled until the first entry field receives the corresponding feature score. The first entry field may be associated with the peripheral zone of a US image. The second entry field may be associated with the boundary zone of the US image. The entry screen may include and may co-display the first and second entry fields with a third entry field. The third entry field may be associated with at least one of an internal zone shape, internal zone texture or internal zone sound transmission of the US image. The automatically enabling and disabling may further comprise automatically disabling the second and third entry fields until the first entry field receives the corresponding feature score and disabling the third entry field until the second entry field receives the corresponding feature score.

Additionally or alternatively, the entry screen may include at least three out of five of the following features associated with US images: US peripheral zone, US boundary zone, US internal zone shape, US internal zone texture, and US internal zone sound transmission. The first entry field may be associated with the peripheral zone of an OA image. The second entry field may be associated with the boundary zone of the OA image. The entry screen may include and may co-display the first and second entry fields with a third entry field. The third entry field may be associated with at least one of an internal zone shape, internal zone texture or internal zone sound transmission of the OA image. The automatically enabling and disabling may further comprise automatically disabling the second and third entry fields until the first entry field receives the corresponding feature score and disabling the third entry field until the second entry field receives the corresponding feature score.

Additionally or alternatively, the entry screen may include at least three out of five of the following features associated with OA images: OA peripheral radiating vessels, OA boundary zone vessels, OA internal zone vessels, OA internal zone hemoglobin, and OA internal zone blush. The displaying at least the first image from the US/OA images may further comprise co-displaying a first US image and a first OA image. The method may display a set of US entry fields associated with features of the US image. The set of US entry fields may include the first entry field. The method may display a set of OA entry fields associated with features of the OA image. The set of OA entry fields may include the second entry field. The method may display a set of non-US/OA entry fields associated with at least one of i) a mammogram Bi-RADS rating, ii) patient age, iii) mass diameter or iv) depth to posterior margin of a mass.

Additionally or alternatively, the method may display an entry field for a depth of a posterior margin of a mass in the first image. The automatically enabling and disabling may include managing an order in which the feature scores are assigned to a predetermined outside—to—inside order. The outside-to-inside order may require first assignment of one or more feature scores to a US/OA peripheral zone, second assignment of one or more feature scores to a US/OA boundary zone and third assignment of one or more feature scores to AUS/OA internal zone. The method may calculate and display at least one of a false negative ratio, likelihood of malignancy, confidence interval, BI-RADS conversion bars, assignment of a BI-RADS category or assignment of a BI-RADS subcategories.

In accordance with embodiments here, a system for analyzing at least one of ultrasound (US) images or optoacoustic (OA) images (US/OA images) is provided. The system includes a display configured to display at least a first image from at least one of OA images or US images acquired in connection with an examination for a region of interest (ROI). The first image includes a lesion. The first image is overlaid with an interior ROI outline separating an internal zone from a boundary zone of the ROI. The first image is overlaid with an exterior ROI outline separating the boundary zone from a peripheral zone. The system includes a graphical user interface (GUI), memory configured to store program instructions and one or more processors. The one or more processors are configured to execute the programmable instructions to obtain feature scores in connection with at least the boundary zone and peripheral zone of the first image, apply the feature scores to a classification model to obtain at least one of a prognostic result or a predictive result indicative of a trait of the lesion and output the at least one of the prognostic result or predictive result.

Additionally or alternatively, the feature scores may represent at least one of qualitative diagnostic biomarkers, semi-quantitative diagnostic biomarkers, prognostic biomarkers or monitoring biomarkers. The one or more processors may be further configured to apply the feature scores to the classification model to obtain, as the semi-quantitative diagnostic result, one or more of the following: i) percentage likelihood of malignancy of a mass, ii) a likelihood of a clinical event, disease progression or reoccurrence, iii) molecular subtype, iv) histologic grade, v) degree of angiogenesis, vi) likelihood of lymph node metastasis, vii) assess the status of a disease or condition to find evidence of exposure to, or effects of, a medical product or environmental agent, viii) change in a patient condition (e.g., tumor size and volume), ix) indicator of an effect of a response to an exposure intervention, x) detect or confirm a disease or condition, xi) identify specific disease subtype, xii) possibility that mutations in genes are predictive of response to certain inhibitors, xiv) likelihood that ER and PR possible breast cancers respond to endocrine therapy, xv) possibility that dense breast tissue is predictive of decreased sensitivity of mammography for detecting noncalcified breast cancer, xvi) one of one or more molecular subtypes or xvii) histologic grades.

Additionally or alternatively, the memory may be configured to store the classification model. The classification model may define a nonlinear relation between a combination of the feature scores and a positive predictive value of the at least one of the prognostic result or predictive result. The nonlinear relation may represent a sigmoidal curve. The sigmoidal curve may have initial, intermediate and final portions. The initial portion may correspond to low positive predictive values (PPVs) for a select combination of the feature scores and may exhibit a first slope increasing at a first rate over the initial portion. The intermediate portion may correspond to intermediate values for the select combination of the feature scores and may exhibit a second slope increasing at a second rate over the intermediate portion. The final portion may correspond to high values for the select combination of the feature scores and may exhibit a third slope decreasing at a third rate over the final portion. The second slope and second rate may be greater than the first slope and first rate, respectively.

Additionally or alternatively, the one or more processors may be further configured to obtain at least one of a maximum diameter of a mass or a depth to a posterior margin of the mass, and may apply the at least one of the maximum diameter or depth to the posterior margin of the mass, to the classification model, to obtain the at least one of the prognostic result or predictive result. The one or more processors may be further configured to apply the depth to the posterior margin of the mass to the classification model to account for reduced energy reaching the posterior margin of the mass. The feature scores may include a US boundary zone feature score and a US peripheral zone feature score, both of which may be utilized by the classification model to obtain the at least one of the prognostic result or predictive result. The feature scores may be obtained from at least one of 1) the GUI as user inputs, 2) an automatic segmentation and image analysis performed by the one or more processors or 3) from a remote computing device or server.

Additionally or alternatively, the predictive result may define a likelihood of malignancy (LOM) having a value between 2% and 100%. The semi-quantitative diagnostic result may not a binary indication regarding whether to perform a biopsy or not perform a biopsy. The feature scores may include a US internal zone sound transmission feature score. The memory may be configured to store the classification model. The classification model may be configured to overweight the US internal zone sound transmission feature score with respect to at least one other US feature score to obtain, as a prognostic result, an indication of lymph node metastasis. The classification model may be configured to recognize that shadowing in the US internal zone may be indicative of an increased risk of lymph node metastasis, while enhanced sound transmission may be indicative of a lowered risk of lymph node metastasis.

Additionally or alternatively, the feature score may include a US internal zone sound transmission feature score. The classification model may be configured to overweight the US internal zone sound transmission feature score with respect to at least one other feature scores to obtain, as the prognostic result, the prognostic result indicating a distinction between TNBC molecular subtype, luminal a molecular subtype and HER2 molecular subtype. The feature scores may include an indication of an extent to which ducts and/or lobules are disproportionately enlarged relative to a reference. The classification model may account for the extent of the enlargement of the ducts and/or lobules when outputting the predictive result. The predictive result may represent a semi-quantitative diagnostic result that includes a value for a likelihood of malignancy (LOM) along a range extending beyond 2% and 100%.

Additionally or alternatively, the one or more processors may be further configured to obtain an initial BI-RADS rating based on non-OA images. The semi-quantitative diagnostic result may include a determination of whether to at least one of i) downgrade the initial BI-RADS rating or ii) modify the initial BI-RADS rating to add a sub-categorization. The initial BI-RADS rating may be a BI-RADS 4 rating, without sub categorization. The semi-quantitative diagnostic result may include modifying the BI-RADS 4 rating to at least one of i) downgrading the BI-RADS 4 rating to a BI-RADS 3 rating or lower or ii) revising the BI-RADS 4 rating to add sub categorization for one of BI-RADS 4A or 4B. The one or more processors may be further configured to calculate and the display may be further configured to display, as the at least one of the prognostic result or predictive result, at least one of false negative ratio, likelihood of malignancy, confidence interval, BI-RADS conversion bars, assignment of a BI-RADS category or assignment of a BI-RADS subcategories.

In accordance with embodiments herein, a computer implemented method for analyzing at least one of ultrasound (US) images or optoacoustic (OA) images (US/OA images) is provided. The method utilizes one or more processors configured to execute programmable instructions for displaying at least a first image from at least one of OA images or US images acquired in connection with an examination for a region of interest (ROI). The first image is overlaid with an interior outline separating an internal zone from a boundary zone of the ROI. The first image is overlaid with an exterior outline separating the boundary zone from a peripheral zone of the ROI. The method receives feature scores in connection with the internal zone, boundary zone and peripheral zone of the first image. The method applies the feature scores to a classification model to obtain at least one of a prognostic result or predictive result indicative of a trait of the lesion and outputs the at least one of the prognostic result or predictive result.

Additionally or alternatively, the feature scores may represent at least one of qualitative diagnostic biomarkers, semi-quantitative diagnostic bio markers, prognostic biomarkers or monitoring biomarkers. The applying may further comprise applying the feature scores to the classification model to obtain, as the semi-quantitative diagnostic result, one or more of the following: i) percentage likelihood of malignancy of a mass, ii) a likelihood of a clinical event, disease progression or reoccurrence, iii) molecular subtype, iv) histologic grade, v) degree of angiogenesis, vi) likelihood of lymph node metastasis, vii) assess the status of a disease or condition to find evidence of exposure to, or effects of, a medical product or environmental agent, viii) change in a patient condition (e.g., tumor size and volume), ix) indicator of an effect of a response to an exposure intervention, x) detect or confirm a disease or condition, xi) identify specific disease subtype, xii) possibility that mutations in genes are predictive of response to certain inhibitors, xiv) likelihood that ER and PR possible breast cancers respond to endocrine therapy, xv) possibility that dense breast tissue is predictive of decreased sensitivity of mammography for detecting noncalcified breast cancer, xvi) one of one or more molecular subtypes or xvii) histologic grades.

Additionally or alternatively, the classification model may define a nonlinear relation between a combination of the feature scores and a positive predictive value of the at least one of the prognostic result or predictive result. The nonlinear relation may represent a sigmoidal curve. The sigmoidal curve may have initial, intermediate and final portions. The initial portion may correspond to low PPVs for the combination of the feature scores and may exhibit a first slope increasing at a first rate over the initial portion. The intermediate portion may correspond to intermediate values for the combination of the feature scores and may exhibit a second slope increasing at a second rate over the intermediate portion. The final portion may correspond to high values for the combination of the feature scores and exhibiting a third slope decreasing at a third rate over the final portion. The second slope and second rate may be greater than the first slope and first rate, respectively.

Additionally or alternatively, the method may obtain at least one of a maximum diameter of a mass or a depth to a posterior margin of the mass, and may apply the at least one of the maximum diameter or depth to the posterior margin of the mass, to the classification model, to obtain the at least one of the prognostic result or predictive result. The depth to the posterior margin of the mass to the classification model may account for reduced energy reaching the posterior margin of the mass. The feature scores may include a US boundary zone feature score and a US peripheral zone feature score, both of which are utilized by the classification model to obtain the at least one of the prognostic result or predictive result. The predictive result may define a likelihood of malignancy (LOM) having a value between 2% and 100%. The semi-quantitative diagnostic result may not be a binary indication regarding whether to perform a biopsy or not perform a biopsy.

Additionally or alternatively, the feature scores may include a US internal zone sound transmission feature score. The memory may be configured to store the classification model. The classification model may be configured to overweight the US internal zone sound transmission feature score with respect to at least one other US feature score to obtain, as a prognostic result, an indication of lymph node metastasis. The classification model may be configured to recognize that shadowing in the US internal zone may be indicative of an increased risk of lymph node metastasis, while enhanced sound transmission may be indicative of a lowered risk of lymph node metastasis.

Additionally or alternatively, the feature score may include a US internal zone sound transmission feature score. The classification model may be configured to overweight the US internal zone sound transmission feature score with respect to at least one other feature scores to obtain, as the prognostic result, a distinction between TNBC molecular subtype, luminal a molecular subtype and HER2 molecular subtype. The feature scores may include an indication of an extent to which ducts and/or lobules are disproportionately enlarged relative to a reference. The classification model may account for the extent of the enlargement of the ducts and/or lobules when outputting the prognostic result. The prognostic result may represent a semi-quantitative diagnostic result that may include a value for a likelihood of malignancy (LOM) along a range extending beyond 2% and 100%.

Additionally or alternatively, the method may include an initial BI-RADS rating based on non-OA images. The semi-quantitative diagnostic result may include a determination of whether to at least one of i) downgrade the initial BI-RADS rating or ii) modify the initial BI-RADS rating to add a sub categorization. The initial BI-RADS rating may be a BI-RADS 4 rating, without sub categorization. The semi-quantitative diagnostic result may include modifying the BI-RADS 4 rating to at least one of i) downgrading the BI-RADS 4 rating to a BI-RADS 3 rating or lower or ii) revising the BI-RADS 4 rating to add sub categorization for one of BI-RADS 4A or 4B. The one or more processors may be further configured to calculate and the display may be further configured to display, as the predictive result, at least one of false negative ratio, likelihood of malignancy, confidence interval, BI-RADS conversion bars, assignment of a BI-RADS category or assignment of a BI-RADS subcategories.

In accordance with embodiments herein, a system for analyzing at least one of ultrasound (US) images or optoacoustic (OA) images (US/OA images) is provided. The system includes a display configured to display at least a first image from at least one of OA images or US images acquired in connection with an examination for a region of interest (ROI). The first image includes a lesion. The first image is overlaid with an interior ROI outline separating an internal zone from a boundary zone of the ROI. The first image is overlaid with an exterior ROI outline separating the boundary zone from a peripheral zone. The system includes a graphical user interface (GUI), memory configured to store program instructions, and one or more processors. The one or more processors are configured to execute the programmable instructions to obtain feature scores in connection with at least the boundary zone and peripheral zone of the first image, apply the feature scores to a classification model to obtain at least one of a prognostic result or predictive result indicative of a trait of the lesion and output the at least one of the prognostic result or predictive result.

Additionally or alternatively, the feature scores may represent at least one of qualitative diagnostic biomarkers, semi-quantitative diagnostic biomarkers, prognostic biomarkers or monitoring biomarkers. The one or more processors may be further configured to apply the feature scores to the classification model to obtain, as the semi-quantitative diagnostic result, one or more of the following: i) percentage likelihood of malignancy of a mass, ii) a likelihood of a clinical event, disease progression or reoccurrence, iii) molecular subtype, iv) histologic grade, v) degree of angiogenesis, vi) likelihood of lymph node metastasis, vii) assess the status of a disease or condition to find evidence of exposure to, or effects of, a medical product or environmental agent, viii) change in a patient condition (e.g., tumor size and volume), ix) indicator of an effect of a response to an exposure intervention, x) detect or confirm a disease or condition, xi) identify specific disease subtype, xii) possibility that mutations in genes are predictive of response to certain inhibitors, xiv) likelihood that ER and PR possible breast cancers respond to endocrine therapy, xv) possibility that dense breast tissue is predictive of decreased sensitivity of mammography for detecting noncalcified breast cancer, xvi) one of one or more molecular subtypes or xvii) histologic grades.

In accordance with new and unique aspects herein, the system is provided for presenting indicia indicative of at least one of prognostic or predictive results in new and unique manners. The system comprises a graphical user interface (GUI) configured to receive user inputs; memory configured to store program instructions and to store at least a first image from at least one of OA images or US images acquired in connection with an examination for a region of interest (ROI); one or more processors configured to execute the programmable instructions to obtain at least one of a prognostic result or predictive result indicative of a trait of the lesion based on feature scores related to at least one of an internal zone, a boundary zone or a peripheral zone of the ROI in the first image; and a display configured to display indicia indicative of the at least one of the prognostic result or predictive result.

In accordance with new and unique aspects herein, the display is further configured to present indicia indicative of a prognostic result corresponding to a semi-quantitative diagnostic result, the indicia presenting at least one of graphical or alphanumeric text indicative of one or more of: i) percentage likelihood of malignancy of a mass, ii) a likelihood of a clinical event, disease progression or reoccurrence, iii) molecular subtype, iv) histologic grade, v) degree of angiogenesis, vi) likelihood of lymph node metastasis, vii) assess the status of a disease or condition to find evidence of exposure to, or effects of, a medical product or environmental agent, viii) change in a patient condition (e.g., tumor size and volume), ix) indicator of an effect of a response to an exposure intervention, x) detect or confirm a disease or condition, xi) identify specific disease subtype, xii) possibility that mutations in genes are predictive of response to certain inhibitors, xiv) likelihood that ER and PR possible breast cancers respond to endocrine therapy, xv) possibility that dense breast tissue is predictive of decreased sensitivity of mammography for detecting noncalcified breast cancer, xvi) one of one or more molecular subtypes or xvii) histologic grades.

Additionally or alternatively, the display is further configured to display at least a first image from at least one of OA images or US images acquired in connection with an examination for a region of interest (ROI). Additionally or alternatively, the display is further configured to present, in connection with molecular subtypes, at least one of graphical or alphanumeric text indicia indicative of at least one of a mean likelihood or upper and lower confidence indicator boundaries. Additionally or alternatively, the displays further configured to present at least one of graphical or alphanumeric indicia indicative of at least one of: 1) a predicted mean likelihood of malignancy (LOM) and a confidence interval, or 2) a mean false negative rate (FNR) with a select confidence interval. Additionally or alternatively, the indicia displayed includes a graphical indicia than extends from 0% faults negative ratio (FN are) to 100% likelihood of malignancy (LOM), the graphical indicia will include a vertical line at a select FNR level, with a segment of the graphical indicia to a left of the vertical line corresponding to predicted FNR and a segment of the graphical indicia to a right of the vertical line corresponding to predicted LOM. Additionally or alternatively, the graphical indicia include color coding in which a gradient of colors corresponds to higher or lower FNR or LOM, with colors changing gradually from one end to another end of the graphical indicia. Additionally or alternatively, the graphical indicia shows a mean predicted FNR or LOM with a circle, square, or other polygonal shape that is colored differently from the gradient of colors on an underlying FNR-LOM bar. Additionally or alternatively, the indicia displayed further includes a BI-RADS conversion bar that is co-displayed with a predicted FNR-LOM bar, the BI-RADS conversion bar subdivided into sections based upon positive predictive value (PPV) LOM ranges for each category of BI-RADS.

In accordance with new and unique aspects herein, the method is provided for presenting indicia indicative of at least one of prognostic or predictive results of traits of a lesion. The method comprises, under control of one or more processors configured with program instructions for, providing a graphical user interface (GUI) configured to receive user inputs related to at least a first image from at least one of OA images or US images acquired in connection with an examination for a region of interest (ROI); obtaining at least one of a prognostic result or predictive result indicative of a trait of the lesion based on feature scores related to at least one of an internal zone, a boundary zone or a peripheral zone of the ROI in the first image; and displaying indicia indicative of the at least one of the prognostic result or predictive result.

Additionally or alternatively, the indicia are indicative of a prognostic result corresponding to a semi-quantitative diagnostic result, the indicia presenting at least one of graphical or alphanumeric text indicative of one or more of: i) percentage likelihood of malignancy of a mass, ii) a likelihood of a clinical event, disease progression or reoccurrence, iii) molecular subtype, iv) histologic grade, v) degree of angiogenesis, vi) likelihood of lymph node metastasis, vii) assess the status of a disease or condition to find evidence of exposure to, or effects of, a medical product or environmental agent, viii) change in a patient condition (e.g., tumor size and volume), ix) indicator of an effect of a response to an exposure intervention, x) detect or confirm a disease or condition, xi) identify specific disease subtype, xii) possibility that mutations in genes are predictive of response to certain inhibitors, xiv) likelihood that ER and PR possible breast cancers respond to endocrine therapy, xv) possibility that dense breast tissue is predictive of decreased sensitivity of mammography for detecting noncalcified breast cancer, xvi) one of one or more molecular subtypes or xvii) histologic grades. Additionally or alternatively, the method further comprises displaying at least the first image from at least one of OA images or US images acquired in connection with an examination for a region of interest (ROI).

Additionally or alternatively, the indicia include, in connection with molecular subtypes, at least one of graphical or alphanumeric text indicia indicative of at least one of a mean likelihood or upper and lower confidence indicator boundaries. Additionally or alternatively, the indicia presents at least one of graphical or alphanumeric indicia indicative of at least one of: 1) a predicted mean likelihood of malignancy (LOM) and a confidence interval, or 2) a mean false negative rate (FNR) with a select confidence interval. Additionally or alternatively, the indicia displayed includes a graphical indicia than extends from 0% faults negative ratio (FN are) to 100% likelihood of malignancy (LOM), the graphical indicia will include a vertical line at a select FNR level, with a segment of the graphical indicia to a left of the vertical line corresponding to predicted FNR and a segment of the graphical indicia to a right of the vertical line corresponding to predicted LOM. Additionally or alternatively, the graphical indicia include color coding in which a gradient of colors corresponds to higher or lower FNR or LOM, with colors changing gradually from one and to another end of the graphical indicia. Additionally or alternatively, the graphical indicia illustrate a mean predicted FNR or LOM with a circle, square, or other polygonal shape that is colored differently from the gradient of colors on an underlying FNR-LOM bar. Additionally or alternatively, the method further comprises displaying a BI-RADS conversion bar that is co-displayed with a predicted FNR-LOM bar, the BI-RADS conversion bar subdivided into sections based upon positive predictive value (PPV) LOM ranges for each category of BI-RADS.

BRIEF DESCRIPTION OF THE DRAWINGS

FIG. 14D illustrates an example of a screenshot for a display presented in connection with OA feature scoring in accordance with embodiments herein.

FIG. 14E illustrates an example of a screenshot for the display once the score is selected for the peripheral radiating vessel.

DETAILED DESCRIPTION

Figure 1:
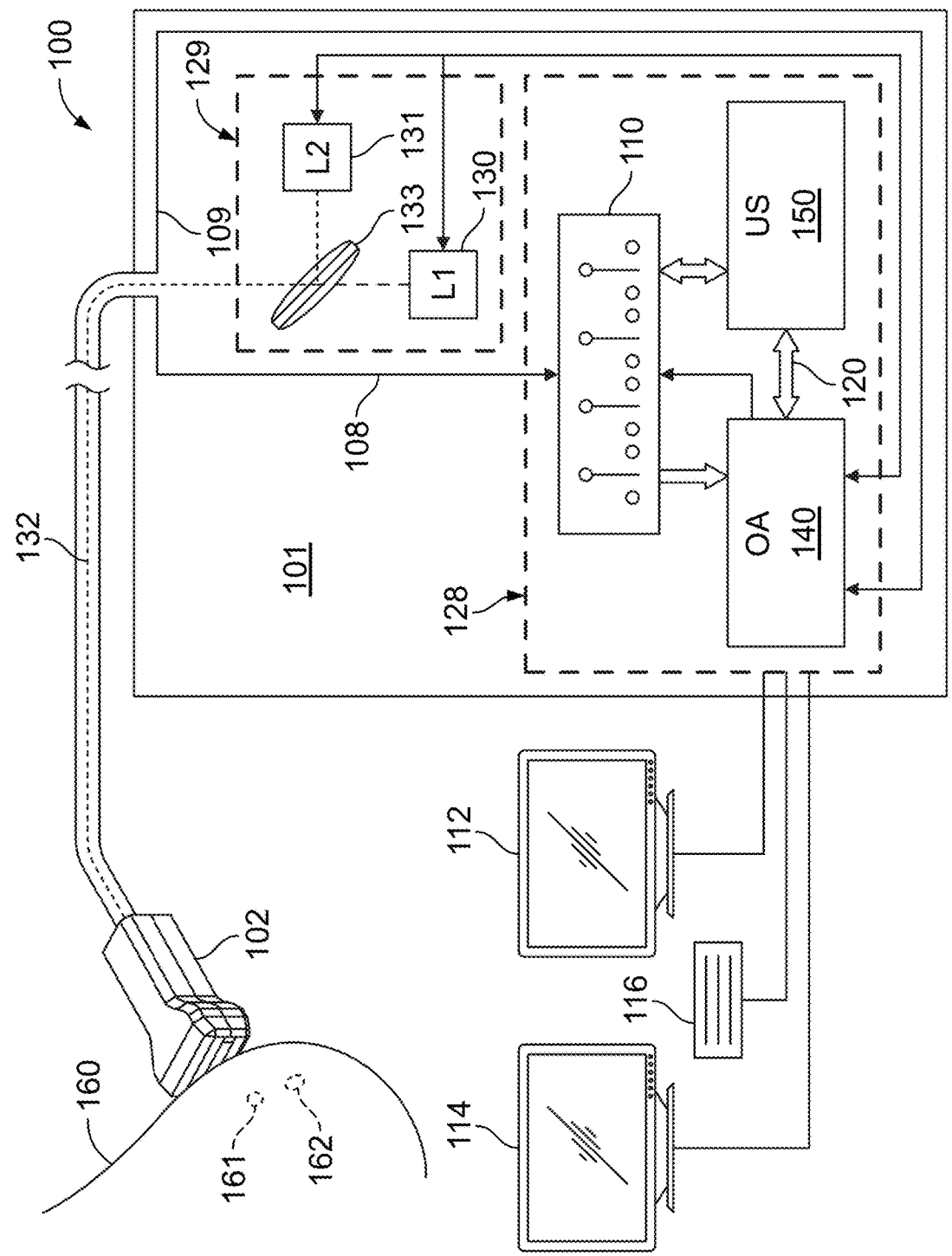
FIG. 1 shows a schematic block diagram illustrating an embodiment of a combined optoacoustic and ultrasound system that may be used as a platform for the methods and devices disclosed herein.

The following description and drawings are illustrative and are not to be construed as limiting. Numerous specific details are described to provide a thorough understanding. However, in certain instances, well-known or conventional details are not described in order to avoid obscuring the description. References to one or an embodiment in the present disclosure are not necessarily references to the same embodiment; and, such references mean at least one.

Reference in this specification to "one embodiment" or "an embodiment" means that a particular feature, structure, or characteristic described in connection with the embodiment is included in at least one embodiment of the disclosure. The appearances of the phrase "in one embodiment" in various places in the specification are not necessarily all referring to the same embodiment, nor are separate or alternative embodiments mutually exclusive of other embodiments. Moreover, various features are described which may be exhibited by some embodiments and not by others. Similarly, various requirements are described which may be requirements for some embodiments, but not other embodiments.

The systems and methods are described below with reference to, among other things, block diagrams, operational illustrations and algorithms of methods and devices to provide optoacoustic imaging with out-of-plane artifact suppression. It is understood that each block of the block diagrams, operational illustrations and algorithms and combinations of blocks in the block diagrams, operational illustrations and algorithms, can be implemented by means of analog or digital hardware and computer program instructions.

Reference will now be made in more detail to various embodiments of the present invention, examples of which are illustrated in the accompanying figures. As will be apparent to one of skill in the art, the data structures and processing steps described herein may be implemented in a variety of other ways without departing from the spirit of the disclosure and scope of the invention herein and should not be construed as being limited to the embodiments set forth herein. Rather, these embodiments are provided so that this disclosure will be thorough and complete, and will fully convey the concept of the disclosure to those skilled in the art.

In accordance with embodiments herein, methods and systems are described in one or more attachments to this specification where the related description is set forth in outline format, summary format, images and the like. All of the material submitted with and/or attached to the present specification is expressly incorporated herein by reference in its entirety.

Definitions

The term "AAB" shall mean acinar adenocarcinoma of the breast.

The term "ancillary feature score" shall mean a feature score assigned based on one or more features of interest within an ancillary image from an ancillary imaging modality, that does not include ultrasound imaging and does not include optoacoustic imaging.

The terms "BI-RADS" and "BR" shall mean Breast Imaging Reporting and Data System, and represents a method used by medical personnel to interpret and report in a standardized manner the results of mammography, ultrasound and MM used in breast cancer screening and diagnosis. By way of example, a BI-RADS 3 score may be indicative of a 2% or less probability of malignancy, a BI-RADS 4A score may be indicative of a probability of malignancy between 2% and less than or equal to 10%, a lower BI-RADS 4B score may be indicative of a probability of malignancy of greater than 10% and less than or equal to 25%, an upper BI-RADS 4B score may be indicative of a probability of malignancy of greater than 25%, a lower BI-RADS 4C score may be indicative of a probability of malignancy of less than or equal to 75%, and upper BI-RADS 4C score may be indicative of a probability of malignancy of greater than 75%, and a BI-RADS 5 score may be indicative of a probability of malignancy of greater than or equal to 95%.

The term "biomarker" shall mean an objective medical sign that is a measurable and quantifiable indicator of a physiologic or pathologic state of a mass, defined structure and/or living organism. The term biomarker shall include a defined characteristic that is measured as an indicator of normal biologic processes, genetic processes, or responses to an exposure or intervention, including therapeutic interventions. A biomarker may be derived from any substance, structure or process that can be measured in the body or its products and influence or predict the incidence or outcome of disease (e.g., positive predictive value of breast cancer). A biomarker is not a "symptom" which is a subjective perception of health or illness. Different types of biomarkers exist. For example, a diagnostic biomarker may be used for the detection or confirmation of a disease or condition and for identification of a specific disease subtype (e.g., BI-RADS descriptors, ER, PR, and HER2 (also known as ERBB2) status). The diagnostic biomarker may represent a measurable and quantifiable indicator of whether to perform a biopsy or forgo a biopsy of a mass or other definable structure within a patient region of interest. As another example, a predictive biomarker may be used to identify individuals who are more likely to experience a favorable or unfavorable response to an intervention, medical product, or environmental exposure compared with individuals without the predictive biomarker. For example, the predictive biomarker may represent a possibility that mutations in BRCA genes are predictive of response to PARP inhibitors in patients with advanced breast and ovarian cancer. As another example, the predictive biomarker may represent the likelihood that ER- and PR-positive breast cancers respond to endocrine therapy. As another example, the predictive biomarker may represent a possibility that dense breast tissue is predictive of decreased sensitivity of mammography for detecting noncalcified breast cancer. As another example, a prognostic biomarker may represent a degree of angiogenesis and/or a likelihood of lymph node metastasis. A prognostic biomarker may indicate a percentage chance/probability of malignancy for a mass or other definable structure. As another example, a prognostic biomarker may reflect a likelihood of a clinical event, disease progression, or recurrence irrespective of an intervention (e.g. TNM stage, tumor grade, tumor receptor status). The prognostic biomarker may be an indicator of a molecular subtype for a malignancy.

As another example, a monitoring biomarker may be serially measured to assess a status of a disease or condition or to find evidence of exposure to, or effects of, a medical product or environmental agent. Monitoring biomarkers may focus on changes in a patient's condition (e.g., tumor size and volume by imaging; prostate—specific antigen for monitoring of prostate cancer). The monitoring biomarker may provide an indicator of an effect a response to an exposure or intervention, including a therapeutic intervention or other treatment with respect to a malignancy.

The term "BZ" shall mean boundary zone.

The term "DAB" shall mean ductal adenocarcinoma of the breast.

The term "diagnostic imaging data set" shall mean a data set acquired by one or more of an ultrasound system, optoacoustic system, computed tomography (CT) system, magnetic resonance imaging (MM) system, positron emission tomography (PET) system, single-photon emission computed tomography (SPECT) system, x-ray system, angiography system, fluoroscopy system and the like. The data set may represent the raw data acquired by the corresponding system and/or one or more images generated from processing (e.g., rendering) the corresponding data set.

The terms "feature" and "feature of interest" refer to features of an OA image, US image and feature combinations thereof. The non-OA features may be US features, MM features, X-ray features, CT features, PET features, SPECT features or another medical diagnostic imaging modality. Nonlimiting examples of OA features include 1) internal vascularity and de-oxygenation, 2) peri-tumoral boundary zone vascularity and deoxygenation, 3) internal deoxygenated blush, 4) internal total blood, 5) external peri-tumoral radiating vessels, and 6) interfering artifact. Non-limiting examples of ultrasound features include 1) US Shape Score, 2) US Internal Texture, 3) US Sound Transmission, 4) US Capsular or Boundary Zone, 5) US Peripheral Zone, 6) Patient Age, 7) Mammogram-BIRADS, 8) Lesion Size (cm), and 9) Lesion Posterior Depth (cm). Additional and alternative features are described in U.S. Pat. No. 9,398,893, to Anthony Thomas Stavros et al., titled "system and method for diagnostic vector classification support", filed Mar. 11, 2014 as application Ser. No. 14/205,005, and issuing Jul. 26, 2016 (hereafter the Stavros '893 Patent), the complete and total subject matter of which is expressly incorporated herein by reference in its entirety.

The term "feature score" refers to a grade, rating, ranking or other evaluation information that is descriptive of one or more characteristics of a feature in an OA image and/or non-OA image. Non-limiting examples of feature scores include i) a numeric value along a range of numeric values, ii) a dimension measured from an OA or non-OA image, and/or iii) a word, phrase, or sentence describing a characteristic of the feature.

The term "horizontal", when used to refer to a direction within a US or OA image, shall mean a direction perpendicular to a scanning direction of an ultrasound transmission/reception and/or optoacoustic transmission/reception.

The term "IZ" shall mean internal zone.

The term "imaging biomarker" shall mean a biomarker that is present in, or derived from, an imaging data set and can be measured and quantified, from the imaging data set, to determine an indicator of a physiologic or pathologic state of the mass, defined structure and/or living organism within a region of interest, for which the imaging data set is obtained. An imaging biomarker represents a diagnostic, not a therapeutic, by providing useful information to guide therapy. An imaging biomarker may be semi-quantitative and may be an ordinal score in which the risk of a certain outcome increases with increasing ordinal score. Imaging procedures indirectly affect an outcome and utilize surrogate endpoints for accuracy (e.g., sensitivity, specificity, PPV, NPV, ROC, AUC). The endpoints are measurable and reproducible. Imaging biomarkers may not have a desired level of sensitivity or specificity to be utilized individually in isolation. However, select combinations of different imaging biomarkers will cumulatively provide a desired level of sensitivity and specificity. While embodiments herein describe certain combinations of different imaging biomarkers as applied utilizing ultrasound and/or Optoacoustic imaging of breast masses, it is recognized that the subject matter herein is not limited to the particular combinations of imaging biomarkers, nor the ultrasound and/or Optoacoustic imaging modalities, nor breast imaging. Instead, principals described herein may be applied to additional and alternative combinations of imaging biomarkers, additional and alternative imaging modalities, as well as other anatomical regions. Nonlimiting examples of descriptors for an imaging biomarker applicable to characterizing a mass as benign or malignant include margin, shape and orientation of the mass.

The term "LOM" shall mean likelihood or probability of malignancy.

The term "non-OA image" refers to any medical diagnostic image, other than an OA image, captured by one or more medical imaging modalities. A non-OA image constitutes an image that is captured based on an imaging principle that does not utilize transmission of optical light in two distinct frequency ranges to cause a volume of interest to generate acoustic signals. Non-limiting examples of non-OA images include ultrasound (US) images (transmissive and/or reflective), MRI images, X-ray images, CT images, PET images, and SPECT images. When the non-OA image is a US image, the US image may be captured by a US imaging system that is integrated with, coupled to or entirely separate from, an OA imaging system.

The term "NPV" shall mean negative predictive value.

The term "OA feature score" shall mean a feature score assigned based on one or more features of interest within an OA image.

The term "observation" refers to one or more OA images (alone or in combination with one or more non-OA images) that are collected from a patient during an OA examination. The observation may also include diagnostic information entered by a clinician, such as OA feature scores and/or non-OA feature scores.

The terms "optoacoustic image" and "OA image" refer to an image captured by an optoacoustic imaging system that utilizes transmit light at one or more frequencies into a volume of interest and receives an ultrasound data set that is processed and converted into an OA image.

The term "predictive result" shall include qualitative diagnostic results, quantitative predictive results, prognostic results, monitoring results and the like. For the avoidance of doubt, a predictive result does not include or refer to a binary indication between whether to obtain a biopsy or not obtain a biopsy. The following represent a nonlimiting list of predictive results that may be obtained: i) percentage chance/probability of malignancy of a mass, ii) a likelihood of a clinical event, disease progression or reoccurrence, iii) molecular subtype, iv) histologic grade, v) degree of angiogenesis, vi) likelihood of lymph node metastasis, vii) assess the status of a disease or condition to find evidence of exposure to, or effects of, a medical product or environmental agent, viii) change in a patient condition (e.g., tumor size and volume), ix) indicator of an effect of a response to an exposure intervention, x) detect or confirm a disease or condition, xi) identify specific disease subtype, xii) possibility that mutations in genes are predictive of response to certain inhibitors, xiv) likelihood that ER and PR possible breast cancers respond to endocrine therapy, xv) possibility that dense breast tissue is predictive of decreased sensitivity of mammography for detecting noncalcified breast cancer, xvi) one of one or more molecular subtypes or xvii) histologic grades.

The term "PPV" shall mean positive predictive value, and the term "PPV3" shall mean biopsy proven positive predictive value.

The term "PZ" shall mean peripheral zone.

The term "ROC AUC" shall mean receiver operator characteristics area under the curve.

The terms "obtain" or "obtaining", as used in connection with data, signals, information and the like, includes at least one of i) accessing memory of various systems or devices (e.g., a diagnostic imaging system, PACS workstation, medical network workstation, desktop computer, laptop computer, tablet device, smart phone or remote server) where the data, signals, information, etc. are stored, ii) receiving the data, signals, information, etc. over a wireless communications link between the various systems and devices, and/or iii) receiving the data, signals, information, etc. at a remote server over a network connection. The obtaining operation, when from the perspective of a diagnostic imaging system, may include collecting new imaging data in real time, and/or accessing memory to read stored data, signals, information, etc. from memory within the diagnostic imaging system. The obtaining operation, when from the perspective of a local non-imaging device (e.g., PACS workstation, medical network workstation, desktop computer, laptop computer, tablet device, smart phone), includes receiving the data, signals, information, etc. at a transceiver of the local non-imaging device where the data, signals, information, etc. are transmitted from the diagnostic imaging system and/or a remote server. The obtaining operation may be from the perspective of a remote server, such as when receiving the data, signals, information, etc. at a network interface from a local non-imaging device and/or directly from a diagnostic imaging system. The remote server may also obtain the data, signals, information, etc. from local memory and/or from other memory, such as within a cloud storage environment and/or from the memory of a workstation or clinician external programmer.

The terms "receive" and "receiving" when used in connection with OA/US feature scores and/or OA/US images, includes at least one of i) collecting OA/US data sets in real time from a diagnostic imaging system, while performing a patient scan; ii) receiving inputs, such as OA/US feature scores entered by medical personnel; iii) receiving an automatic output of a machine learning classifier that automatically assigns OA/US feature scores; iv) receiving the data, signals, information, etc. over a wired or wireless communications link between the various systems and devices, and/or iii) receiving the data, signals, information, etc. at a remote server over a network connection.

The term "TDLU" shall mean a terminal duct lobular unit.

The term "UL feature score" shall mean a feature score assigned based on one or more features of interest within an ultrasound only image.

The terms "US" and "UL" are used interchangeably to refer to ultrasound only, and not optoacoustics.

The terms "OA/US", "OA/UL", "OA/US" and "UL/OA" shall mean ultrasound and/or optoacoustic and shall include ultrasound only, optoacoustic only, or a combination of ultrasound and optoacoustic. For example, a OA/US data set (or US/OA data set) may include 1) only a US data set, with no OA data, 2) an OA data set, with no US data, or e) a US data set and an OA data set. As another example, a OA/US feature score (or US/OA feature score) may include 1) only a US feature score, with no OA feature score, 2) an OA feature score, with no US feature score, or 3) a US feature score and an OA feature score. As another example, an OA/US image (or US/OA image) may include 1) only a US image, with no OA image, 2) an OA image, with no US image, or 3) a US image and an OA image.

The term "vertical", when used to refer to a direction within a US or OA image, shall mean a direction parallel to a scanning direction of an ultrasound transmission/reception and/or opotoacoustic transmission/reception.

System Overview

FIG. 1 illustrates a block diagram of an optoacoustic system implemented in accordance with an embodiment herein. The optoacoustic system 100 includes a probe 102 connected via a light path 132 and an electrical path 108 to a system chassis 101. Within the system chassis 101 is housed a light subsystem 129 and a computing subsystem 128. The computing subsystem 128 includes one or more processors configured to implement specific program instructions for, among other things, optoacoustic control and analysis. In an embodiment, through the sampling of transducers in the probe 102, the optoacoustic system collects OA/US data in response to stimulation caused by pulsed light sources 130, 131 (i.e., the optoacoustic return signal) and to stimulation caused by acoustic output of the ultrasound transducer elements.

The optoacoustic system 100 comprises one or more light sources 130, 131 operating at different light wavelengths. In an embodiment, with light sources 130, 131 operating at different light wavelengths, the optoacoustic return signal from one light event from each of the light sources can be used in the method and system for presenting the optoacoustic data. In an embodiment, the device 100 comprises a single light source that may be operated at different wavelengths, such as a tunable laser that can change wavelengths quickly enough for use as described herein. In an embodiment, the device 100 comprises at least two light sources 130, 131, each being capable of tuning to a plurality of different wavelengths. In an embodiment, the device 100 comprises one light source 130 operating a one light wavelength, and at least one additional light source 131 capable of being tuned to a plurality of different wavelengths.

The one or more processors of the optoacoustic system 100 are configured to generate sinograms. The sinograms are processed to produce envelope images, including short envelope images and long envelope images. As used herein the term short envelope image refers to an envelope image corresponding to the short sinogram, and the term long envelope image refers to an envelope image corresponding to the long sinogram. In an embodiment, the short sinogram and long sinogram are each processed separately to produce a short envelope image and a long envelope image, respectively. The short and long envelope images are then used together to generate parametric images. From the parametric images, maps can be created of oxygenation, hemoglobin and masked oxygenation. These maps can be, in real time, co-registered data representing an ultrasound image of substantially the same volume, and can thereafter produce one or more of an oxygenation image, a hemoglobin image and a masked oxygenation image. In an embodiment, the oxygenation image, hemoglobin image and masked oxygenation image reflect information about the composition of the volume of tissue. The terms parametric map and parametric image are in some instances used interchangeably. The use of the term map generally relates to the correspondence between the image and a volume. Parametric maps may be represented in numerous ways, including, for example, as a single-channel (i.e., grayscale) representation, as a color (i.e., RGB) representation, or as a color with transparency (RGBA) representation. Parametric maps may be used to convey qualitative or quantitative information about one or more parameters. A parametric map or parametric image may be represented in computer memory or presented as a displayed representation, thus, as used herein, the term "image" or "map" do not necessarily imply a visual representation.

Sinograms may contain unwanted, inaccurate or insufficiently scaled data. These maladies of sinogram data may result from myriad reasons, including characteristics of the measuring instrument (e.g., the probe) or the light used, characteristics of the volume (i.e., the tissue), characteristics of the interaction between the volume and the probe or light, external stimuli, or other sources. Regardless of the source, a variety of processes can be used to remove unwanted aspects of the sinogram data.

Generally, in each of the following steps for processing the sinogram, the processing is performed on the time domain signal. In a preferred embodiment (and as discussed below) the probe 102 includes an acoustic lens that enables the sinogram data to be more focused on what is on the plane below that of the transducers—the image plane. In an illustrative embodiment, each channel of the sinogram data represents approximately 100 millimeters of distance in the volume. The acoustic lens generally rejects at least some portion of a signal propagating from points outside (e.g., orthogonal) to the image plane. Each transducer, however, receives signal from substantially all points of the image plane that lie within the approximately 100 millimeters distance. The received signal for a channel can be thought of as comprising the area of a semicircle of radius 100 millimeters on the image plane.

Figure 2:
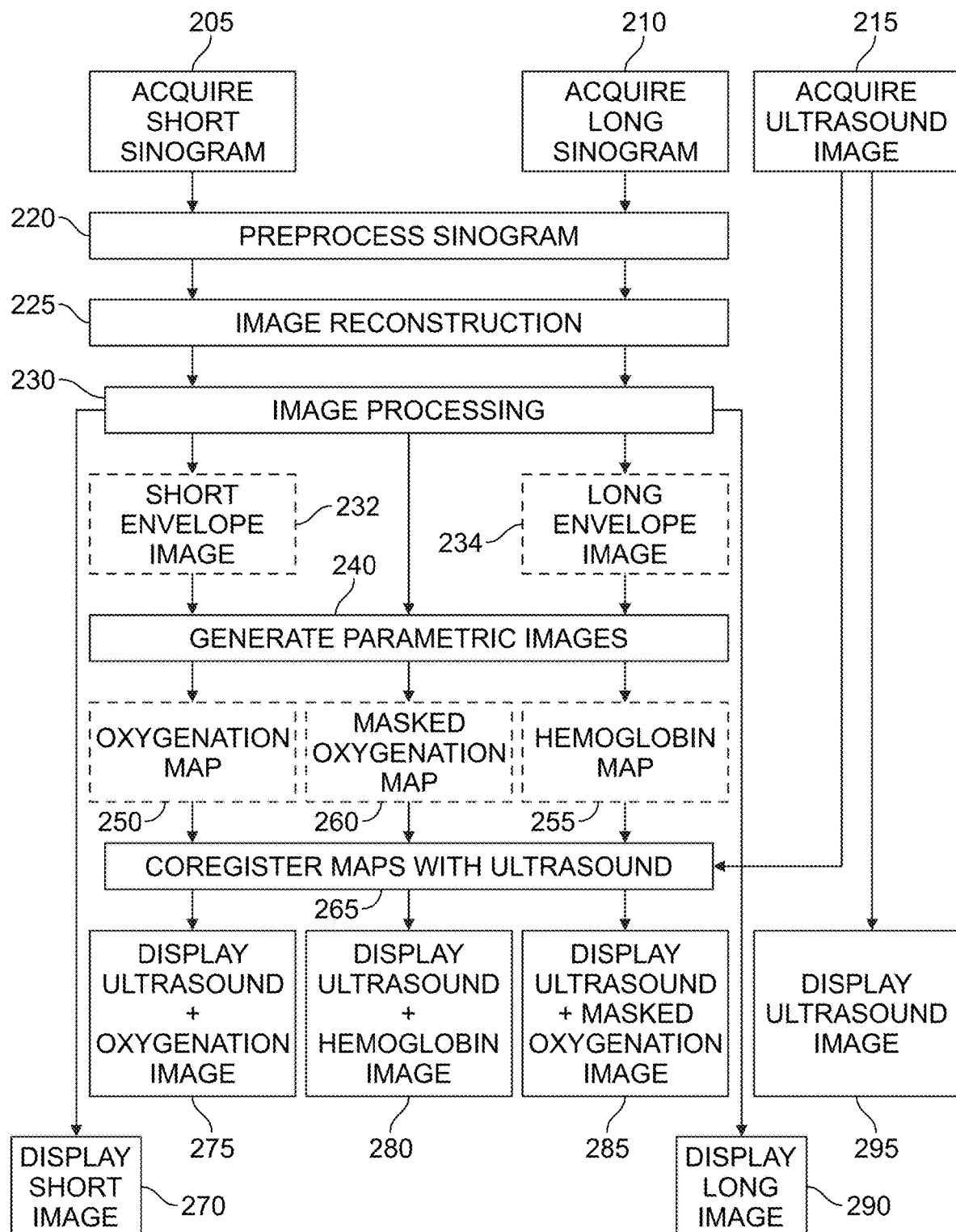
FIG. 2 shows a schematic block diagram illustrating hardware components of the system.

FIG. 2 illustrates an overview of a collection of operations for processing OA/US data. Beginning with the acquisition of three sets of data, namely, a short sinogram (step 205), a long sinogram (step 210) and an ultrasound image (step 215), the operations process the data to produce up to six separate images that may be useful in viewing various aspects of acquired OA/US data. For the purposes of illustration herein, it may be presumed that probe 102 movement is minimal, if any, between the acquisition of the three sets of data in steps 205, 210 and 215. In an example embodiment, a reasonable frame rate (e.g., 10 Hz), coupled with a reasonably steady hand used in handholding the probe may yield the three data sets having substantially minimal movement occurring there-between. It should be noted that the process described herein is not limited to being used with the three identified data sets. Use of additional data sets, such as, for example, data sets from additional wavelengths of light, may be used to further improve the resulting images. As will be discussed in more detail below, the short and long sinogram data are preprocessed (step 220) in one or more separate manners to reduce or compensate for undesired data in the sinogram, including characteristics of the measuring instrument (e.g., the probe) or the light used, characteristics of the volume (i.e., the tissue), characteristics of the interaction between the volume and the probe or light, external stimuli, or other sources. After the preprocessing, separate short and long images are reconstructed (step 225). In an embodiment, separate real and imaginary components of complex short and long images result from the reconstruction step. In an embodiment, the processing (step 230) of the reconstructed images is performed. The processing (step 230) may remove additional artifacts that can be identified in the reconstructed images, and in any event creates a short envelope image (232) and a long envelope image (234). In an embodiment, the short and long envelope images (232, 234) are used to generate parametric images (step 240) process. The generated parametric images (step 240) process outputs an oxygenation map (OA relative map) (250), a hemoglobin map (OA total hemoglobin map) (255) and a masked oxygenation map (OA combined map) (260). In an embodiment, any or all of the three maps are co-registered with, and overlaid upon, a gray scale B-mode ultrasound image (step 265). A display can be provided for display of one or more of the displayable images displayed in steps 270, 275, 280, 285, 290 and 295. In an embodiment, a group of two or more of the images may be displayed on the same screen, and the displayed grouped images may be commonly scaled and sized. In an embodiment, the group of all six images may be displayed on the same screen, and it may be commonly scaled and sized.

In an embodiment, the system performing processing on the optoacoustic data, and/or the system displaying the optoacoustic output—which may, but need not be the same as the system acquiring the sinogram—would provide the operator the ability to vary parameters used in processing, when processing or viewing optoacoustic images. In an embodiment, the system performing processing on the optoacoustic data, and/or the system displaying the optoacoustic output would provide the operator the ability to switch on and off, and potentially vary the order of, the processing steps used to process the optoacoustic images.

The optoacoustic system 100 may also be employed as multimodality, combined optoacoustic and ultrasound system. In an embodiment, the device 100 includes a probe 102 connected via a light path 132 and an electrical path 108 to a system chassis 101. Within the system chassis 101 is housed a light subsystem 129 and a computing subsystem 128. The computing subsystem 128 includes one or more computing components for ultrasound control and analysis and optoacoustic control and analysis; these components may be separate, or integrated. In an embodiment, the computing subsystem comprises a relay system 110, an optoacoustic processing and overlay system 140 and an ultrasound instrument 150. The system 100 may implement various types of network and data security measures, such as passwords, two-factor authentication, data encryption and the like.

In an illustrative embodiment, the light subsystem 129 may use Nd:YAG and Alexandrite lasers as its two light sources 130, 131, although other types or wavelengths, and additional lights, may also be used. Light sources 130, 131 should be capable of producing a short pulse of light, e.g., a pulse lasting less than about 100 ns, and more preferably around 5 ns. In an embodiment, the two light sources 130, 131 can be separately triggered. In an embodiment, the light output by the light sources 130, 131 may be projected onto the same light path 132 through the use of an optical element 133 that generally permits one light 130 to pass through from a first side to a second side, while reflecting one light source 131 that strikes the second side. The use of optical element 133 or a similar element permits the alignment of the output of two light sources 130, 131 such as lasers onto proximal end of the light path 132.

Figure 3A:
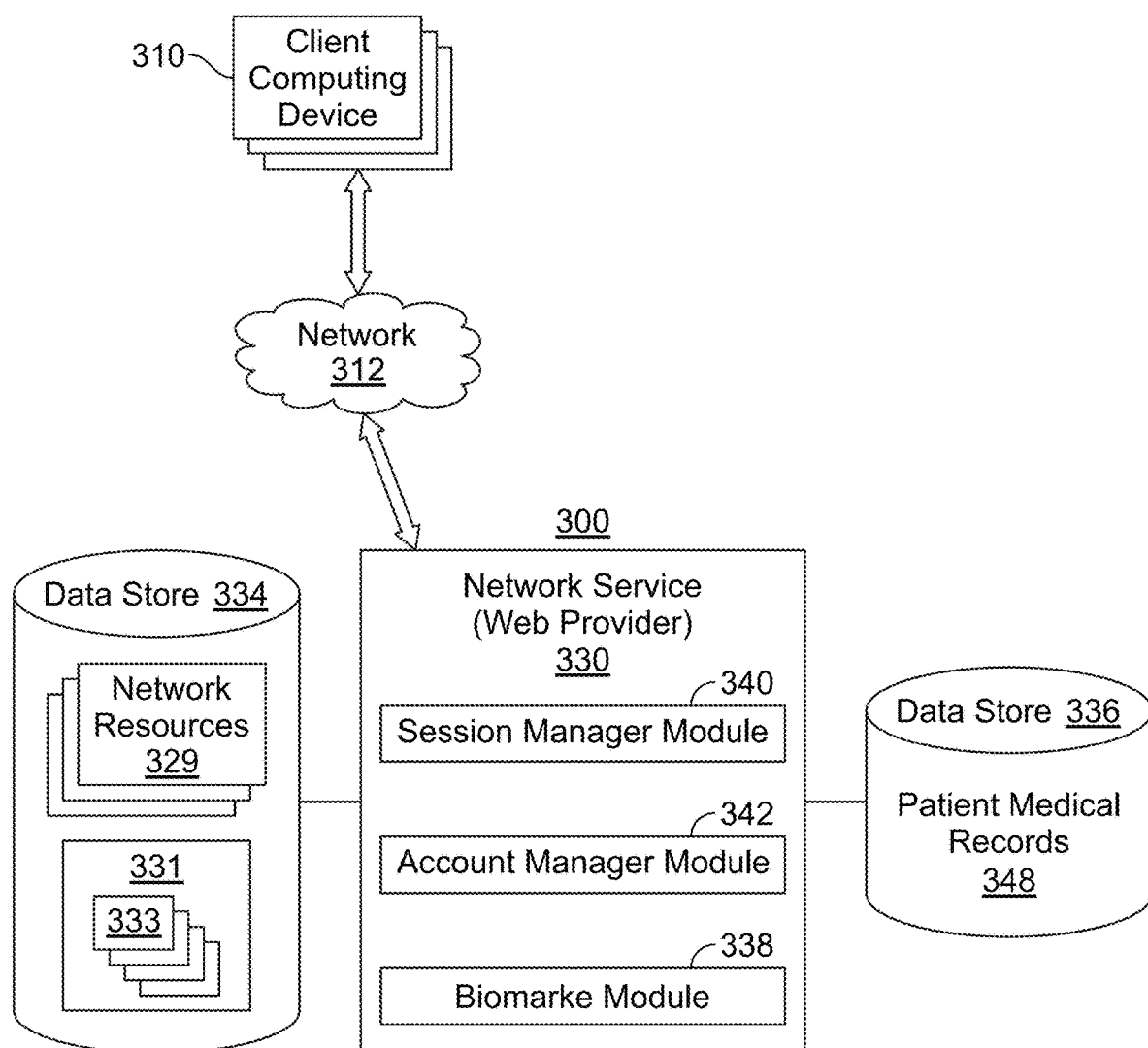
FIG. 3A is a block diagram illustrating a web-based US/OA image reading system 300 formed in accordance with embodiments herein.

One or more displays 112, 114, which may be touch screen displays, are provided for displaying images and all or portions of the device 100 user interface. One or more other user input devices (not shown) such as a keyboard, mouse and various other input devices (e.g., styluses, light pens, dials and switches) may be provided for receiving input from an operator. As an option, power and control path(s) 109 carry power to the probe 102 and control signals between the probe 102 and the computing subsystem 128. System and Method for Managing Imaging Reading FIG. 3A is a block diagram illustrating a web-based US/OA image reading system 300 formed in accordance with embodiments herein. The system 300 includes one or more client computing devices 310 that communicate over a network 312, such as the Internet, with a web-based network service (e.g., web hosting provider) 330. The network service 330 may communicate with the client computing devices 310 over a common network or different networks. The client computing devices 310 may be implemented as any number of other types of computing devices. These devices may include, for instance, PCs, laptop computers, mobile phones, set-top boxes, game consoles, electronic book readers, a personal computer and a personal digital assistant (PDA) and so forth. The network 312 represents any one or combination of multiple different types of networks, such as cable networks, the Internet, private intranets, local area networks, wide area networks, wireless networks, and the like.

The network service 330 represents a site (e.g., a website) that is capable of handling requests from many users and serving, in response, various pages (e.g., web pages) that are rendered at the client computing devices 310. For instance, the site can be any type of medical network related site that supports user interaction, such as a medical network within a healthcare system, a privately managed medical record network and the like. The exchange of request and renderings between the client computing devices 310 and network service 330 will vary depending upon the level of applications and functionality performed locally on the client computing devices 310 and the level of applications and functionality performed at the network service 330. For example, in a network-central architecture, the network service 330 maintains the data and applications to perform substantially all of the substantive processing, such as collection and storage of US/OA images, designation of interior and exterior outlines to be overlaid upon US/OA images, and the rendering of US/OA images with interior and exterior outlines thereon. The network service 330 may further render entry screens with entry fields associated with US/OA features of interest and convey the rendered US/OA images, entry fields and entry screens to the client computing devices 310. The client computing devices obtain feature scores for entry fields and return the feature scores to the network service 330. The network service 330 automatically enables and disables various entry fields to manage an order in which corresponding feature scores are entered such that the feature scores are obtained from at least one of the peripheral or boundary zones before feature scores are obtained from the internal zone of a corresponding one or more of the US/OA images.

Additionally or alternatively, the system of FIG. 3 may be implemented as a server—client distributed architecture, in which the network service 330 may provide applications for the client computing devices 310 to download, store, and run locally. For example, the applications may include a portion, or all of the operations implemented in connection with FIG. 13, as well as other processes described herein. In a distributed architecture, the network service 330 interacts with the client computing devices 310 to provide content as needed. For example, when a client computing device 310 does not already have US/OA images of interest, the client computing device 310 may request the US/OA images related to an examination or examinations for a particular patient. The client computing device 310 and/or the network service 330 may then designate the interior and exterior outlines to be overlaid upon US/OA images. For example, the interior and exterior outlines may be automatically generated based on image segmentation or otherwise. Additionally or alternatively, one or both of the client computing device 310 and network service 330 may support a GUI that allows a user to draw and/or modify the interior and external outlines. The client computing device 310 and/or network service 330 may further render entry screens with entry fields associated with US/OA features of interest. The client computing devices 310 obtain feature scores for entry fields. The client computing device 310 and/or network service 330 automatically enable and disable various entry fields to manage an order in which corresponding feature scores are entered such that the feature scores are obtained from at least one of the peripheral or boundary zones before feature scores are obtained from the internal zone of a corresponding one or more of the US/OA images.

The network service 330 may represents a medical facility/network website that hosts patient medical records 348 in a data store 336 and an image catalog 331 that stores images 333. The data store 336 stores patient medical records in connection with patient accounts. By way of example, the images 333 may represent image reference keys provided in connection with assisting readers and scoring features. Additionally or alternatively, the images 333 may represent US images, OA images, mammogram images, and/or images from other modalities for the current patient, such as during prior examinations. Additionally or alternatively, the images 333 may represent US images and/or OA images for other patients, that may be utilized by the reader to assist in assigning feature scores. The patient medical record may include one or more of the following types of information (among other things): (a) patient medical history, (b) a history of examinations, medication, test results, (c) measurements taken in connection with a lesion, (d) mass diameter, (e) depth to posterior margin of the mass and the like. Additionally or alternatively, the patient medical records may also include diagnostic imaging data collected from prior examinations, including but not limited to, ultrasound data sets, optoacoustic data sets, mammography data sets, Mill data sets, computed tomography sit data sets, positron emission tomography (PET) data sets, x-ray data sets, single photon emission computed tomography (SPECT) data sets, and the like. The data store 336 may include, within or linked to the patient medical record, US images, OA images, BI-RADS ratings assigned in connection with reading mammography images and the like.

The image catalog 331 may store diagnostic imaging data collected from patient examinations, including but not limited to, ultrasound data sets, optoacoustic data sets, mammography data sets, Mill data sets, computed tomography sit data sets, positron emission tomography (PET) data sets, x-ray data sets, single photon emission computed tomography (SPECT) data sets, and the like. The images 333 may be linked to the patient medical record. The images 331 may include one or more US images, OA images, mammogram images and the like. When a patient has obtained a mammogram, and the mammogram has been analyzed to assign a BI-RADS rating, the BI-RADS rating may be stored with the mammogram images 333 and/or separately within the patient medical record 348 (in data store 336). Additionally or alternatively, the network service 330 may maintain images 333 for image reference keys that may be utilized by a user when assigning a feature score. As nonlimiting examples, the images 333 may include an image reference key for one or more of the following, US peripheral zones, US boundary zone, US internal zone shapes, US internal zone echo textures, US internal zone sound transmission, OA peripheral radiating vessels, OA boundary zone vessels, OA internal zone vessels, OA internal zone total hemoglobin, OA internal zone deoxygenated blush and the like.

The images 333 and other information are returned to client computing devices 310 in response to individual client requests. It is recognized that the various content may be stored at locations distributed between various data storage areas, geographic locations, file structures, recommendation services, e-commerce catalogs and the like.

The network service 330 may also maintain authorization and licensing information in connection with client computing devices 310. For example, software applications, configured to implement portions or all of the functionality described herein, may be purchased or licensed by users, with the applications downloaded to the client computing device 310. The network service 330 would then maintain any subscription related information concerning purchase, rental, licensing, viewing authorizations and the like in connection with each corresponding subscription.

The network service 330 includes, among other things, a session manager module 340, an account manager module 342 and a biomarker machine learning classifier (MLC) module 338. The modules 338, 340 and 342 cooperate, as described herein. The modules 338, 340 and 342 may be operated to improve technical efficiency, such as by providing offline or asynchronous data analytics on a per-account basis to provide recommendations and other features. The modules 338, 340 and 342, as well as other modules and services described herein, are implemented by one or more processors performing program instructions (stored in data store 334 or 336) to perform the operations described herein. The network service 330 interacts with one or more memories or data stores 334 and 336 in various manners as explained herein. One or both of the memories or data stores 334 and 336 may store program instructions to direct one or more processors to carry out the instructions described herein.

Further, the data store 334 may store network resources 329, such as files containing HTML code or other codes to define individual resources. A network resource 329 may correspond to a functionality provided in connection with embodiments herein. For example, a network resource 329 or a collection of network resources 329 may afford functionality to view various US images and select a US image of interest, view various OA images and select an OA image of interest, draw and/or modify interior and exterior outlines on the US and/or OA image, present entry screens for feature score entry fields, present pop-up windows with image reference keys and the like. As another example, one or a collection of network resources 329 may represent one or more classification models that are used to determine a predictive result based on a set of feature scores.

Network resources 329 are provided to the client computing device 310 in response to requests, such as one or more client requests. As one example, a network resource 329 may be defined by an index.html file that is saved at a particular HTTP address in the data store 334. Upon request from the client computing device 310, the network service 330 retrieves and provides a corresponding index.html file to the client computing device 310. As a client computing device 310 (e.g., a web browser operating on the client computing device 310) seeks to open and render web content component (e.g., HTTP elements) within the index.html file, the client computing device 310 encounters various HTML code strings/elements, for which additional request may be made of the network server 330 before a complete rendered webpage or other network resource may be presented. Among other things, a client request may include a query string seeking a response.

During operation, the session manager module 340 maintains network sessions with various client computing devices 310. The session manager module 340 reviews incoming requests and determines whether the incoming requests seek access to authenticated or unauthenticated network resources. Requests for an authenticated network resource involve (e.g., require) privilege authentication before the session manager module 340 responds by granting access to the authenticated network resource. The account manager module 342 returns a candidate account page that includes a list of one or more account designators associated with the one or more user accounts. The account designators relate to the sign-in credentials of the one or more user accounts.

By way of example, the system of FIG. 3A may be implemented with various client computing devices 310 distributed about the world and with one or more network services 330 provided in support thereof. Client computing devices 310 may be provided smart phones, tablet devices, laptop computers, workstations, local networks and otherwise, that store local versions of a software/hardware computing package configured to perform all or portions of the operations described herein. For example, an individual computing device 310 may operate a native version of a software package stored thereon in connection with displaying US/OA images to a reader or other clinician, receiving feature scores from the reader/clinician and computing prognostic and/or predictive results based thereon. The individual computing device 310 may store one or more classification models that are used to calculate the prognostic and/or predictive results from feature scores entered by the clinician. The computing device 310 may manage the manner in which the reader or clinician enters feature scores, such as in connection with the outside—in scoring process described herein, in which the computing device 310 requires the reader/clinician to enter scores for a peripheral or boundary zone feature before entering a score for an internal zone feature. The computing device 310 may operate a version of software that is licensed to the user for a period of time. Periodically, in connection with the licensing terms, the computing device 310 may be updated, such as when the network service 330 pushes updates or newer versions of the software package to the computing device 310.

Additionally or alternatively, different versions of a software package may be operated on different client computing devices. For example, one client computing device may operate a software package with classification models, entry screens and other modules configured to present only US images, receive feature scores only related to US images and generate prognostic and/or predictive results based only on US image feature scores. A second client computing device may operate a software package with classification models, entry screens and other modules configured to present only OA images, receive feature scores only related to OA images and generate prognostic and/or predictive results based only on OA image feature scores. A third client computing device may operate a software package with classification models, entry screens and other modules configured to present both US/OA images, receive feature scores both related to US/OA images and generate prognostic and/or predictive results based both on US/OA image feature scores. Optionally, an individual client computing device 310 may store a software package with the full capabilities of all US/OA features, including but not limited to, automatically analyzing US/OA images, receiving reader feature scores, applying classification models to generate prognostic and/or predictive results, but only enable a subset of the features, such as based on a subscription paid by the user. For example, a user may only pay for the US functionality, in which case the OA functionality would be disabled or turned off or otherwise maintained unavailable to the user. Alternatively, a user may only pay for the OA functionality, in which case the US only functionality would be disabled or turned off or otherwise maintained unavailable to the user. In the event that a user changes the subscription to pay an additional fee for additional functionality, the network server 330 may convey an electronic "key" to the computing device 310 to unlock the corresponding additional functionality that was already resident, but inactive.

As a further example, a use-based subscription may be maintained in which the user pays monthly, annually or on another periodic basis based on an extent to which the user uses certain features. For example, during the course of the year a user may only use the full US/OA functionality a limited number of times, but use the US functionality more often, and thereby pay a lesser subscription.

As explained in accordance with various embodiments herein, the computing devices, such as computing devices 310, may store all or substantial portions of the software utilized to implement the functionality herein. Alternatively, the computing device 310 may include little or none of the software/hardware computing package configured to perform all or portions of the operations described herein. Instead, the computing device 310 may implement a web browser or other generic software package with limited processing capability, but instead convey a request to the network service 330 for all the meaningful information. The network service 330 may maintain the software and firmware necessary to implement all or portions of the functionality described herein. The network service 330 may receive a request from client computing devices 310 and return responses, such as rendered webpages and/or hyperlinks to web content, with a browser on the computing device 310 performing the final rendering to present the webpage.

In at least some cases, for patient security, a temporary instance or portal may be initiated through a web browser on a client computing device 310 which prevents storage on the client competing device 310 of any patient data or any other information related to an image reading and scoring session. Instead, all of the underlying data and information, as well as all user entries, scores and results are maintained securely on the network service 330 and are only temporarily visible through a web browser on the client computing device 310.

For example, the client computing device 310 may initiate a session by conveying credentials to the network service 330 and a request to open a reader session. The credentials may include unique reader identification and password, two factor authentication and other security credentials. The request includes session identifying information, such as the patient ID, examining physician, a unique identifier for a US image data set and/or OA image data set acquired during a prior examination and the like. In response thereto, the network service 330 may return one or more webpages (network resources 329) enabling the reader to implement a reading operation in connection with one or more examinations. For example, the network service 330 may return one or more US images that are presented on the client computing device 310 to the user. The user may select a US image (or more than one US image) to be utilized in connection with scoring. Additionally or alternatively, the network service 330 may return one or more OA images that are presented on the client computing device 310 and from which the user selects one or more OA images to be utilized in connection with scoring.

The network service 330 may present the feature score entry screens and manage an order in which scores are entered, such as described in connection with FIGS. 13 and 14 A-14 D, with the client computing device 310 merely displaying rendered pages on a web browser. In at least one of limitation, the interior and exterior ROI outlines may already have been designated and saved with the US images and/or OA images. Alternatively, the network service 330 may allow the user to designate and/or modify interior and exterior ROI outlines through the web browser. User entries regarding the interior and exterior ROI outlines may be passed back to the network service 330 to be matched to a corresponding set of US/OA images.

The network service 330 may then present the entry screens as described in connection with FIGS. 14 A-14 D, along with image reference keys, where the processing associated with and the underlying data utilized to derive the entry screens an image reference keys are maintained on the network service 330, and not on the client computing device.

The network service 330 stores one or more classification models that are used to calculate the prognostic and/or predictive results from feature scores entered by the clinician. The network service 330 manages the manner in which the reader or clinician enters feature scores, such as in connection with the outside—in scoring process described herein. The network service 330 operates a version of software that is licensed to the user of the client computing device.

Additionally or alternatively, different versions of a software package may be operated on the network service 330 in connection with different readers, different types of examinations in the like. For example, one client computing device and/or user may be authorized to present only US images, receive feature scores only related to US images and generate prognostic and/or predictive results based only on US image feature scores. A second client computing device and/or user may be authorized to present only OA images, receive feature scores only related to OA images and generate prognostic and/or predictive results based only on OA image feature scores. A third client computing device and/or user may be authorized to present both US/OA images, receive feature scores both related to US/OA images and generate prognostic and/or predictive results based both on US/OA image feature scores.

As a further example, a use-based subscription may be maintained in which the user pays monthly, annually or on another periodic basis based on an extent to which the user uses certain features. For example, during the course of the year a user may only use the full US/OA functionality a limited number of times, but use the US functionality more often, and thereby pay a lesser subscription.

Figure 3B:
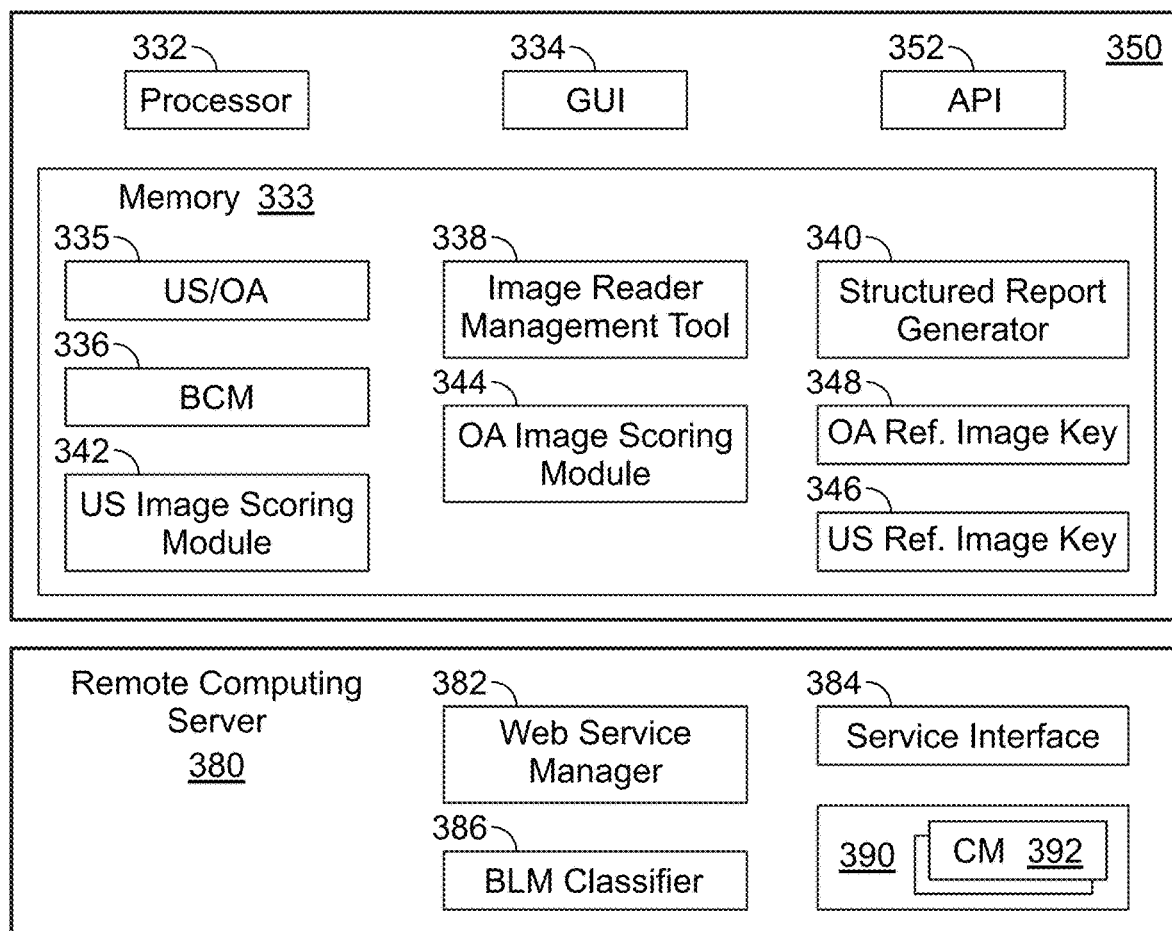
FIG. 3B is a block diagram illustrating a US/OA image reading system formed in accordance with embodiments herein.

FIG. 3B is a block diagram illustrating a US/OA image reading system formed in accordance with embodiments herein. The image reading system includes one or more client computing devices 350, like devices 310, that represent "reader computers" utilized by clinicians to analyze an individual patient's data set of US images, OA images or both and other medical information related to the individual patient. The computing device 350 may be implemented as various types of computers, such as a workstation, a laptop computer, a tablet device, a smart phone and the like. The computing device 350 includes one or more processors 332 executing program instructions stored in memory 333 to provide, among other things, a graphical user interface (GUI) 343. In addition to program instructions, the memory 333 stores US/OA data sets 335, and one or more native applications configured to implement operations herein, such as biomarker classification models (BCM) 336, image reader management tool 338, structured report generator 340, US image scoring module 342, OA image scoring module 344, and US and OA reference image keys 346, 348. Examples of the functionality and structure of the various native applications/modules are described herein.

The GUI 334 enables radiologists and other experts, among other things, to view US and/or OA images, view OA and/or US reference image keys, generate and view structured reports, enter features scores, and view predictive results that are determined based on the analysis of the features scores. Nonlimiting examples of predictive results that may be presented include prognostic indicators, qualitative diagnostic indicators, semi-quantitative diagnostic indicators and monitoring indicators that are derived from the feature scores. The GUI 334 may be developed in any suitable web language, such as HTML and JavaScript. The GUI 334 may be tailored for different situations, such as feasibility studies, pivotal studies, and commercial use. The GUI 334 may be implemented on any appropriate platform, including tablets and workstations.

The computing device 350 further includes an application programming interface (API) 352. The API 352 presents a protocol that defines the communication between the GUI 334 and the remote computing server 380 (e.g., between client computing device 310 and network service 330 in FIG. 3). The API 352 may also afford an interface to the US/OA data sets 335, BCM 336, image reader management tool 338, structured report generator 340, US image scoring module 342, OA image scoring module 344, and US and OA reference image keys 346, 348. The API 352 is a set of rules for communication between the various modules, applications, GUI 334 and server 380. The API 352 decouples the GUI 334 from the computation software implemented by the server 380 which simplifies the development and verification of the machine learning biomarker classification models, and encourages the building of GUIs 334 for various platforms such as tablets, smart phones and workstations.

The computing devices 350 communicate with a remote computing server 380. Nonlimiting examples of entities that may implement the remote computing server 380 include a medical network, a medical facility, a manufacturer of imaging equipment, a third-party data management service, third-party diagnostic image screening services, and the like. The computing server 380 includes one or more processors executing program instructions, to implement the operations described herein, as well as other operations associated with medical diagnostic imaging, diagnosis, therapy planning, therapy delivery and the like. The server 380 receives requests from the API 352, computes predictions, and returns the predictive results. The program instructions for the server 380 may be installed on computers in remote data centers, on a local network, one or more workstations, laptop computers, handheld electronic devices (e.g., tablet device, smart phone), the same physical device as the GUI 334 and the like.

The remote computing server 380 includes one or more processors implementing program instructions to provide a web service manager 382, a network service interface 384, and a biomarker machine learning (BML) classifier 386. The web service manager 382 receives request from computing devices 350 and returns corresponding replies. The network service interface 384 provides an interface between the web service manager 382 and the biomarker machine learning classifier 386. The remote computing server 380 includes a data storage 390 that comprises, among other things, biomarker classification models 392. As explained herein, the biomarker classification models 392 may be organized in various manners, such as one or more ensembles of biomarker classification models 392. In accordance with certain types of machine learning classifiers 386, each biomarker classification model 392 may be built to include one or more decision trees (e.g., 10, 50, 100 decision trees in one classification model). The server 380 may utilize various types of network and data security measures.

The biomarker classification models 392 are defined by a mathematical algorithm, independent variables representing features, and parameters determined by training based on one or more labeled data sets for a control group of individuals. The infrastructure of the classification system allows for multiple models 392 to be built to better support various feature sets and improvements over time. For example, an ensemble of biomarker classification models 392 may be utilized with US features only, or OA features only, while another ensemble of biomarker classification models 392 may be utilized with a combination of OA and US features, as well as non-OA and non-US information (e.g., patient age, maximum diameter, depth to the posterior margin). As a further example, one ensemble of classification models 392 may be utilized in connection with one patient demographic (e.g., young versus old, ethnic base), while another ensemble of classification models may be utilized in connection with a second patient demographic. As a further example, different ensembles of classification models 392 may be utilized in connection with different types of ultrasound imaging. For example, one ensemble of classification models may be utilized in connection with ultrasound images derived through B-mode imaging, while a second ensemble of classification models may be utilized in connection with ultrasound imaging derived through color Doppler or power Doppler imaging, while a third ensemble of classification models may be utilized in connection with ultrasound imaging derived utilizing strain or shear wave elastographic imaging, while a $4^{th}$ ensemble of classification models may be utilized in connection with injected intravenous contrast agents that are used with either ultrasound and/or OA. As another example, different ensembles of classification models may be utilized with different types of ultrasound probes, such as one-dimensional probes, two-dimensional probes, 3-dimensional probes and 3-D workstation software, and the like. As another example, different ensembles of classification models may be utilized in connection with different manufacturers of ultrasound machines, different models of ultrasound machines, different versions within a model of an ultrasound machine and the like. As another example, the OA module might be used as an external stand-alone unit that can be plugged into different manufacturers ultrasound machines, different models of ultrasound machines, different versions within a model of an ultrasound machine, and the like. As another example, different ensembles of classification models may be utilized in connection with different types of optical systems within an optoacoustic system. For example, one optoacoustic system may utilize a single optical source for multiple wavelengths of light, while another optoacoustic system may utilize separate optical sources for each wavelength of light, in which case different ensembles of classification models may be utilized in connection with each type of optoacoustic system. Different ensembles of classification models may be utilized in connection with different manufacturers of optoacoustic systems, different models of optoacoustic systems, different versions within a model and the like.

The classification models 392 may be developed and trained by a biomarker machine learning (BML) classifier 386 that utilizes various languages, such as the R language for statistical computing and graphics (available from https://www.r-project.org). For example, the server 380 implements the machine learning classifier 386 as a set of R scripts that compute classification probabilities from the classification models 392. The classification models 392 are not a single model; but rather a collection or ensemble of models that utilize different algorithms, features, and training data sets. The classification models 392 implement classification through machine learning in which the models are trained based on labeled data for OA images and non-OA images. For example, the classification models may be built with a master model that is built based on all or substantially all of the available labeled data set and may be built to include one or more bootstrapped models and hold out models. Bootstrapped models represent classification models that are formed from a select subset of the labeled data set. Hold out models represent classification models that are formed utilizing cross validation or another related model evaluation technique. In embodiments herein, the classification is a pattern recognition problem that uses a binary classifier as a special case in which there are only two outcomes. The classifier may have many classes. Each classification model 392 is defined by three elements: an algorithm, features, and parameters, which are described hereafter in general, along with an explanation for a model "learns" from a training data set. Classification approaches are of two basic types: parametric equations and machine learning algorithms. Parametric equations are more transparent in that the effect of each feature is easy to understand.

However, equations are limited in what they can model. Machine learning methods can be applied more broadly, but it is often difficult to understand how the model works and what it finds important.

Embodiments herein utilize machine learning algorithms within the biomarker machine learning classifier. Non-limiting examples of machine learning algorithms include classification and regression trees (CART), C4.5 decision trees, K nearest-neighbor, Support Vector Machines (SVM), and Naïve Bayes classifiers. Irrespective of the algorithm, a single model often suffers from either inaccuracy or overfitting. To overcome the potential for inaccuracy or overfitting, embodiments herein train and utilize multiple models to generate multiple predictions for an observation. The collection of the classification models is referred to as an "ensemble" of models. Embodiments herein utilize the random forest algorithm to form an ensemble of decision trees and/or the extreme gradient boosting (XGB) algorithm to form an ensemble that can be used with CART decision trees or with linear classifiers. The XGBOOST algorithm often outperforms other algorithms when properly tuned and can be used on massive data sets.

Managing Order of Image Reading

Figure 13:
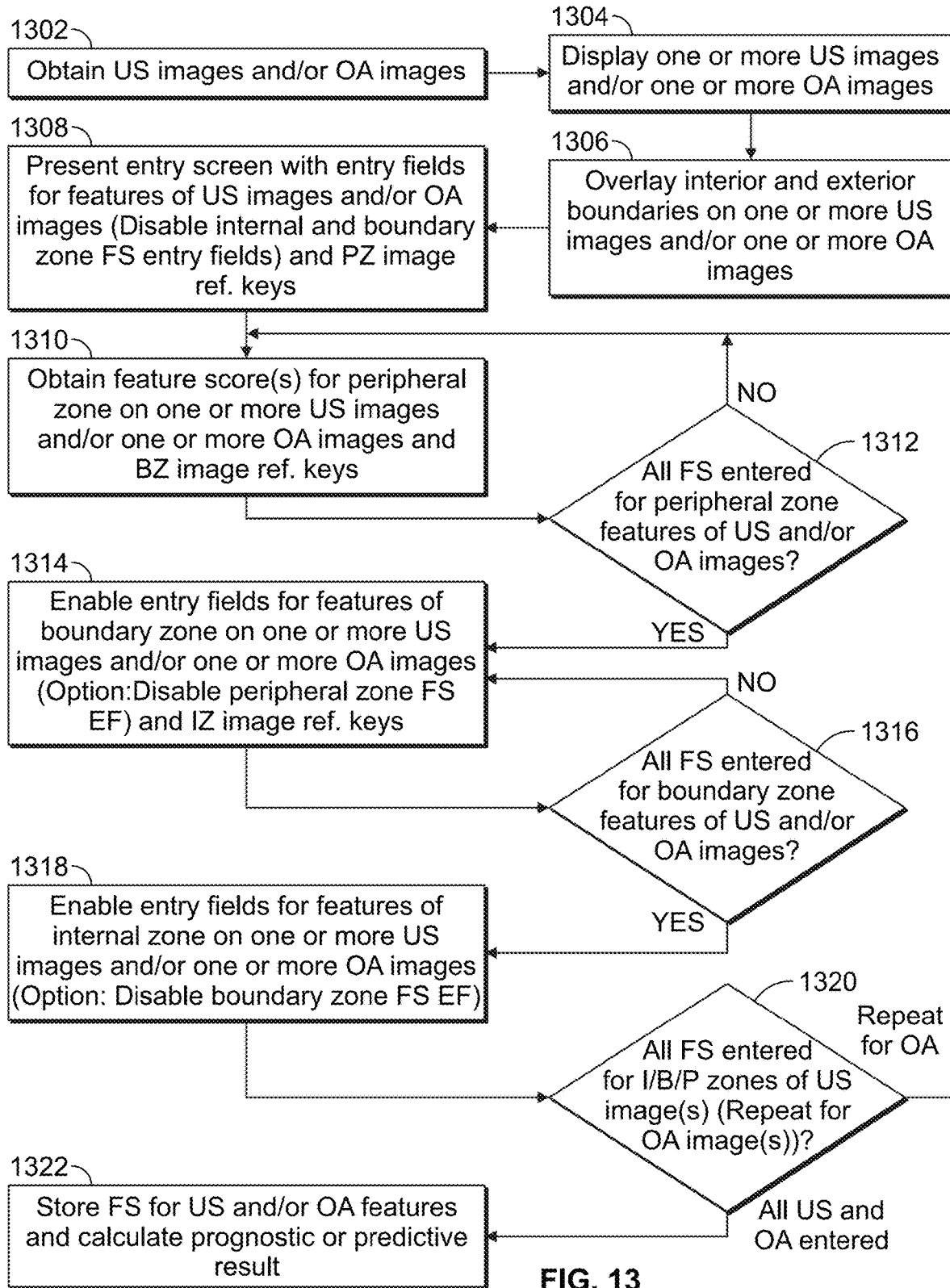
FIG. 13 illustrates a computer implemented method for managing image reading of at least one of ultrasound (US) images or optoacoustic (OA) images (collectively US/OA images).

FIG. 13 illustrates a computer implemented method for managing image reading of at least one of ultrasound (US) images or optoacoustic (OA) images (collectively US/OA images). The operations of FIG. 13 may be implemented by one or more processors, configured to execute programmable instructions, within a computing device (e.g., device 310 in FIG. 3A and 350 in FIG. 3B), one or more processors, configured to execute programmable instructions, at a server (e.g., service 330 or server 450), by other computing devices and/or by a combination thereof. While the operations described hereafter are generally in the context of a combination of ultrasound and optoacoustic, it is understood that the operations of FIG. 13 may be implemented solely with either, namely solely in connection with ultrasound images, and feature scoring of ultrasound images and ultrasound features. Alternatively, the operations of FIG. 13 may be implemented solely in connection with optoacoustic images, and features scoring of optoacoustic images and optoacoustic features.

At 1302, the one or more processors obtain US/OA images that include at least one of OA images or US images acquired in connection with an examination for a region of interest (ROI). For example, the obtaining operation may be performed in real-time during an examination of a patient, where the one or more processors of the optoacoustic system (e.g., system 100) obtain a set of OA images and a set of US images. Additionally or alternatively, the obtaining operation may represent accessing US/OA images stored in a memory, where the US/OA images were previously acquired.

At 1304, the one or more processors display at least a first image from the US/OA images. For example, the display may display one or more US images alone or in combination with one or more OA images. The one or more US images may be displayed alone, followed by a presentation of related OA images. Alternatively, when the process of FIG. 13 is implemented only in connection with US images (and not OA images), US images would only be displayed and analyzed as described herein to obtain feature scores and a predictive result that is based on the US images and not on OA images. In connection with the operation at 1304, the one or more processors may enable the user to step through various US images and/or OA images until the user identifies a US image and/or OA image of interest.

At 1306, the one or more processors overlay interior and exterior region of interest (ROI) outlines on at least the first US image as displayed. The interior ROI outline separates an internal zone from a boundary zone. The exterior ROI outline separates the boundary zone from a peripheral zone. The interior and exterior ROI outlines may be defined in various manners as described in the present application and elsewhere in the patents and publications incorporated herein. As a nonlimiting example, the interior and exterior ROI outlines may be automatically defined by the one or more processors based upon auto-segmentation and/or other image analysis techniques. As another nonlimiting example, the interior and exterior ROI outlines may be manually drawn, utilizing the GUI, by the medical personnel performing the reading and scoring process. Additionally or alternatively, the interior and exterior ROI outlines may be drawn on the one or more US images at the time that the examination is performed, which may be a point in time prior to the process of FIG. 13. Additionally or alternatively, the interior and exterior ROI outlines may be defined by a combination of user inputs from the medical personnel and automated adjustments performed by the one or more processors. For example, medical personnel may enter a set of points on the US image, utilizing the GUI, where the points denote boundary points between the internal zone and the boundary zone and/or the boundary zone and peripheral zone. Based on the user entered points, the one or more processors may then automatically draw a remainder of the interior and exterior ROI outlines. The medical personnel may then be afforded the opportunity to adjust the interior and exterior ROI outlines as drawn, such as by clicking on and dragging segments of the outlines, clicking on points outside of the outline, where the ROI outline is redrawn to include the selected points and the like. As another option, the one or more processors may automatically generate initial candidate interior and exterior ROI outlines and overlay the candidate ROI outlines on the US image. The medical personnel may then be afforded the opportunity to adjust the interior and exterior ROI outlines.

At 1308, the one or more processors present a feature score entry screen/window on the display. The entry screen may be co-displayed with the US/OA images or alternatively displayed on a separate monitor or displayed on a separate point in time from the US/OA images. The entry screen may be formatted in various manners. The entry screen includes at least a first entry field that is associated with at least one of the peripheral zone or boundary zone for a first US image and/or OA image.

Figure 14A:
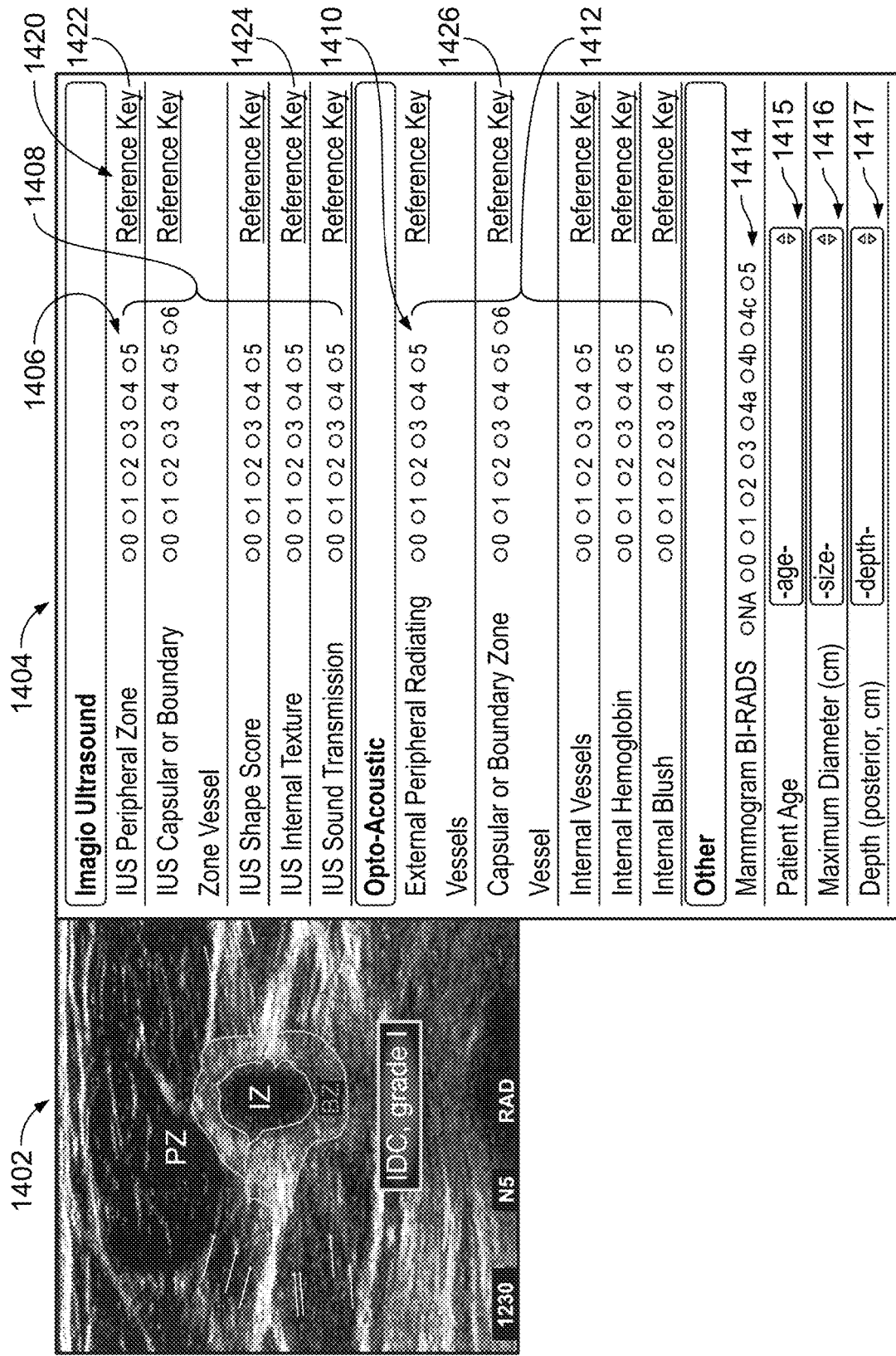
FIG. 14A illustrates an example of a screenshot for a display presented in connection with feature scoring in accordance with embodiments herein.

FIG. 14A illustrates an example of a screenshot for a display presented in connection with feature scoring in accordance with embodiments herein. The screenshot illustrates a US image 1402 that is co-displayed with an entry screen 1404. The US image 1402 includes an internal zone (IZ) and boundary zone (BZ) that are separated by an interior ROI outline (white colored), the US image 1402 also includes a peripheral zone (PC) is separated from the boundary zone BZ by an exterior ROI outline (aqua-colored). The entry screen 1404 includes entry fields 1406. The entry fields 1406 are grouped to include a first set of entry fields 1408 associated with US features. The entry screen 1404 further includes entry fields 1410 that are grouped to include a second set of entry fields 1412 associated with OA features. The entry screen 1404 further includes non-US/OA entry fields 1414-1417. The entry fields 1414 corresponds to a BI-RADS rating assigned in connection with a mammogram that the patient separately received. The entry field 1415 corresponds the patient age. The entry field 1416 represents the maximum diameter of a mass within the US or OA image. The entry field 1417 corresponds to a depth to a posterior margin of the mass in the US/OA image.

The entry field may be presented in various manners. For example, the entry field may present a list of available options/values, from which a user is allowed to provide a user input selecting from the list of available values. For example, as illustrated herein, an entry field may correspond to the "US peripheral zone", with a list of available score values between 0 and 5 displayed next to user selectable elements (e.g., as "O" or radio buttons) that may be chosen by the user to assign a feature score. Additionally or alternatively, the range of available scores may be greater or smaller. It is recognized that the list of available scores represents one form of indicia that may be presented to facilitate user entry of feature scores. Additionally or alternatively, numerous alternative types of indicia may be presented to facilitate user entry of a feature score. For example, a scale may be presented with an indicator that may be slid by the user along a scale to select a feature score. As another example, various types of alphanumeric information may be presented along with user selectable elements. Additionally or alternatively, the user may be allowed to directly enter an alphanumeric value, such as 0-5, A-G and the like. The user input may be entered through various entry mechanisms of a computing device, such as utilizing a mouse, keyboard, touch sensitive screen, verbal command with speech recognition, trackball, softkeys on a display, hard keys proximate a display and the like.

In the example of FIG. 14A, the entry screen 1404 includes entry fields associated with an entire set of the features of interest in the present embodiment. It is recognized that additional entry fields for further features of interest may be included. It is also recognized that fewer features may be of interest and thus fewer entry fields may be presented. Additionally or alternatively, a subset of the entry fields 1406, 1410 and 1414-1417 may be presented at one time on the entry screen. For example, only a single entry field (e.g., entry field 1406) may be presented at one point in time, and the next entry field not presented until a feature score is assigned to the single entry field that is presented. As feature scores are assigned to each entry field, a next entry field may be presented, with the prior entry fields (already assigned feature scores) removed from the screen or retained on the entry screen 1404. Additionally or alternatively, the entry screen 1404 may code display the entry field 1406 within the set 1408 associated with the US image at one point in time, without displaying the entry fields 1410 within the set 1412 associated with the OA image. Once the entry fields 1406 are assigned feature scores, the display may then present the entry field 1410 within the set 1412 for the OA image. When the entry fields 1410 for the OA image are presented, the prior entry fields 1406 (that of already received scores) for the US image may be removed from the display or retained on the display. Once the entry fields 1410 are assigned feature scores, one or more of the entry field 1414-1417 may be presented in a serial manner or co-displayed at the same time. As in the foregoing examples, the entry field 1414-1417 may be displayed individually or together, and the entry field 1414-1417 may be displayed with or without co-display of the set 1408 or set 1412.

The entry field 1404 also includes active elements 1420, each of which are associated with a different feature. The active elements 1420 each correspond to a corresponding "image reference key" associated with the corresponding feature. For example, the reference key 1422 corresponds to the US peripheral zone, the reference key 1424 corresponds to the US internal zone texture, the reference key 1426 corresponds to the boundary zone vessel of the OA image and the like. When a reference key is selected, the display presents a collection of reference key images as explained hereafter.

In accordance with new and unique aspects herein, embodiments display a first entry field and receive a feature score at the first entry field, and automatically disable the second entry field until the first entry field receives the feature score associated with the at least one of the peripheral zone or boundary zone. Further, embodiments co-display at least first and second entry fields, wherein the second entry field is disabled until the first entry field receives the corresponding feature score. For example, when the first entry field is associated with the peripheral zone of a US image, and the second entry field is associated with the boundary zone of the US image, the entry screen includes and co-displays the first and second entry fields with a third entry field. The third entry field is associated with at least one of an internal zone shape, internal zone texture or internal zone sound transmission of the US image.

The entry screen may include at least three out of five of the following features associated with US images: US peripheral zone, US boundary zone, US internal zone shape, US internal zone texture, and US internal zone sound transmission. The first entry field may be associated with the peripheral zone of an OA image, and the second entry field associated with the boundary zone of the OA image. In accordance with embodiments herein, the entry screen includes and co-displays the first and second entry fields with a third entry field, the third entry field associated with at least one of an internal zone shape, internal zone texture or internal zone sound transmission of the OA image. The automatically enabling and disabling further comprises automatically disabling the second and third entry fields until the first entry field receives the corresponding feature score and disabling the third entry field until the second entry field receives the corresponding feature score.

Returning to FIG. 13, when the entry screen is presented, one or more of the entry fields may be disabled or rendered in active. For example, at the beginning of a scoring process for the US image, the entry field for the US peripheral zone may be displayed alone or in combination with other entry fields, such as the entry fields associated with the boundary zone and internal zone. The boundary zone and internal zone entry fields may be disabled/rendered inactive in various manners. For example, the boundary zone may be "disabled" by not displaying the boundary zone entry field. Alternatively, when the boundary zone entry field is co-displayed with the peripheral zone entry field, the boundary zone entry field may be disabled by rendering the boundary zone entry field inactive, unavailable or otherwise nonresponsive to user inputs.

At 1310, the one or more processors obtain a feature score at a first entry field associated with at least one of the peripheral zone or boundary zone for the first image. For example, the one or more processors obtain one or more feature scores for the peripheral zone in connection with one or more US images and/or one or more OA images. For example, during a first iteration through the operations of FIG. 13, when a US image is displayed, at 1310, the one or more processors may receive a single feature score for the peripheral zone of the US image. Additionally or alternatively, an image reference key (IRK) window is co-displayed with the US image. The IRK window may be a pop up window or presented in another manner. The IRK window illustrates, among other things, examples of reference US images having masses that exhibit different characteristic with corresponding PZ feature scores. The IRK window may be presented in response to an IRK request entered by the user, such as by selecting a "reference key" request element on the GUI. Additionally or alternatively, the IRK request may be initiated automatically when the user selects a score for the PZ feature. Additionally or alternatively, the IRK request may be initiated automatically when the user merely hovers the "cursor" over a feature entry field (e.g., over the header "IUS Peripheral Zone"). Additionally or alternatively, the IRK window may be presented automatically without any input from the user.

During a second iterations through the operations of FIG. 13, one or more OA images are displayed and, at 1310, the one or more processors receive a feature score for the peripheral zone of the OA image. Additionally or alternatively, an IRK window is co-displayed with the OA image. The IRK window may be a pop up window or presented in another manner. The IRK window illustrates, among other things, examples of reference OA images having masses that exhibit different characteristic with corresponding PZ feature scores. The IRK window may be presented in response to an IRK request entered by the user, such as by selecting a "reference key" request element on the GUI. Additionally or alternatively, the IRK request may be initiated automatically when the user selects a score for the PZ feature. Additionally or alternatively, the IRK request may be initiated automatically when the user merely hovers the "cursor" over a feature entry field (e.g., over the header "External Peripheral Radiating Vessels"). Additionally or alternatively, the IRK window may be presented automatically without any input from the user.

Figure 14B:
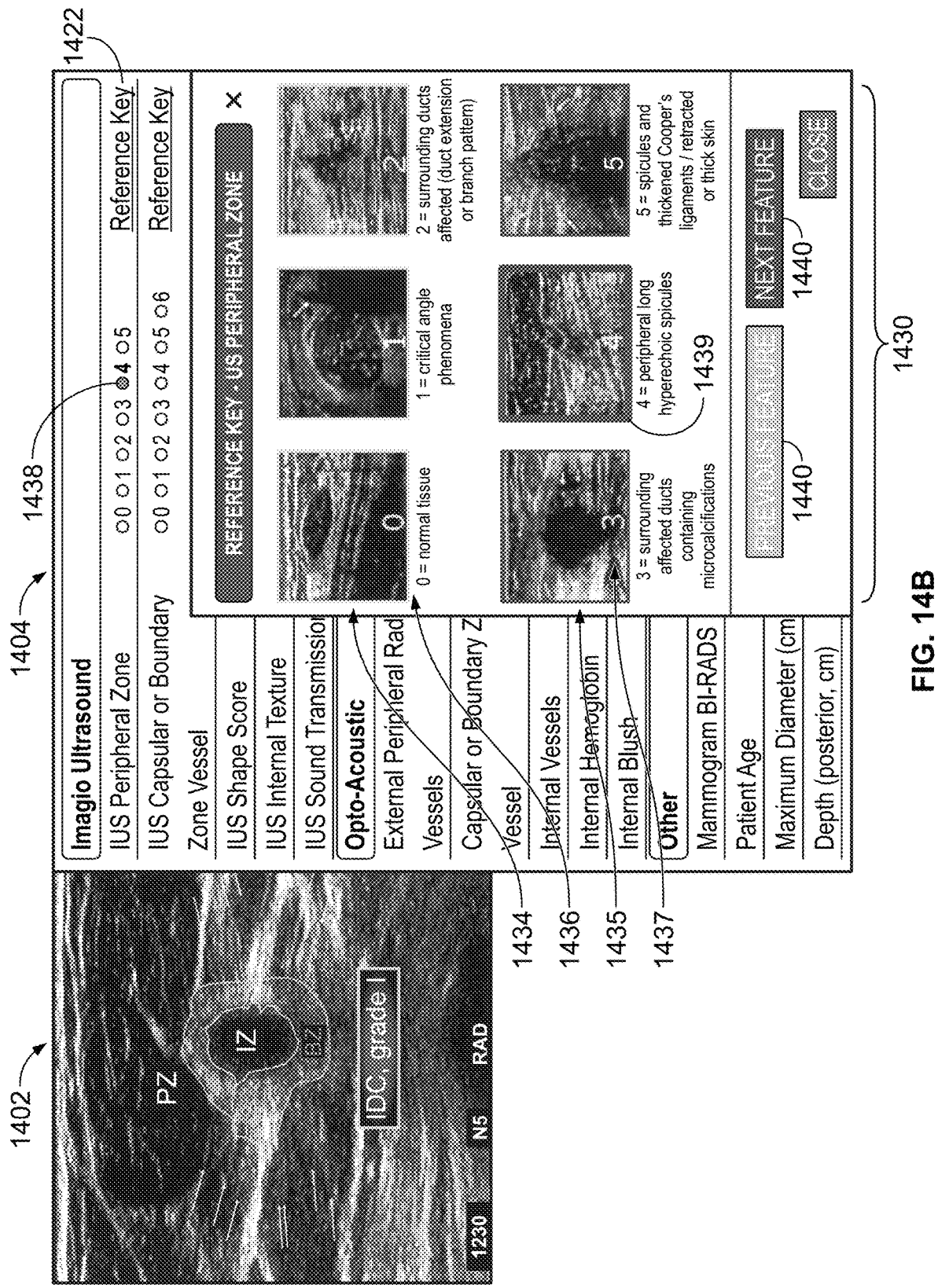
FIG. 14B illustrates the screenshot of FIG. 14A in combination with a reference key pop up window presented in accordance with embodiments herein.

FIG. 14B illustrates the screenshot of FIG. 14A in combination with an image reference key pop up window presented in accordance with embodiments herein. The image reference key 1422 is selected by the user in connection with determining what feature score to assigned to the US peripheral zone. In response to the selection of the reference key 1422, a reference key pop up window 1430 is displayed. The reference key pop up window 1430 includes a collection of US images 1434-1435 that illustrate examples of different key images for US boundary zone feature scores along with corresponding reference scores 1436-1437 and their associated text feature descriptors. For example, a first reference key US image illustrates normal tissue which should be afforded a score of "0", while the second-sixth reference key US images illustrate US images of regions having different peripheral zone characteristics (e.g., associated with masses that exhibit different levels/stages of malignancy/cancer) which should be afforded scores of "1" to "5". The user may select a desired score in various manners. In the example of FIG. 14B, the US peripheral zone is assigned a score of "4", such as by clicking on the active element at 1438 and/or selecting the reference key US image 1439. By way of example, when a score is selected either at 1438 or 1439, a border of the reference key US image may be enlarged or otherwise emphasized to indicate to the user which reference key US image corresponds to the selected score, thereby avoiding confusion by the user and ensuring that the user recognizes which reference key US image corresponds to the selected score.

Additionally or alternatively, the reference key pop up window 1430 may also include navigation icons 1440 that may be selected by the user to advance to the next feature to be scored or to step backwards to a prior feature that is already been scored. Additionally or alternatively, a subset or all of the entry fields may be populated through verbal commands and voice recognition software. For example, a user may state "Assign a feature score of three to the US peripheral zone", "Assign a feature score 5 to the US boundary zone vessel", and the like. While not illustrated, it is recognized that a user may step through the reference keys in connection with each of the US images to provide assistance for assigning a score to the corresponding feature.

At 1312, the one or more processors determine whether the peripheral zone feature scores have been entered for the US image and/or OA image. FIG. 13 illustrates an iterative process, in which, during a first iteration at 1312, the one or more processors determine whether the feature score been entered for the peripheral zone of the US image. When the US peripheral zone feature score is not entered, flow returns to 1310. Additionally or alternatively, more than one US peripheral zone feature may be of interest, in which case flow returns from 1312 to 1310 until all of the US peripheral zone features have been scored. When the US peripheral zone feature score is entered, flow continues to 1314. During a first iteration the operations at 1310 to 1322 are completed in connection with an US image. As explained herein, during a second iteration through the operations at 1310-1322, the one or more processors apply the determination at 1312 to an OA image, namely it is determined whether the feature score has been entered for the peripheral zone of an OA image. Additionally or alternatively, the order may be reversed such that OA feature scores are determined first, followed by US feature scores.

At 1314, the one or more processors enable one or more entry fields for features related to the boundary zone. During examination of a US image, the one or more processors enable one or more US boundary zone entry fields. During examination of an OA image, the one or more processors enable one or more OA boundary zone entry fields. Additionally or alternatively, at 1314, the one or more processors may disable one or more entry fields that have already received feature scores. For example, when a US peripheral zone feature score has already been entered, the corresponding entry field may be disabled. The disabling operation may include removing display of the US peripheral zone feature score entry field from the entry screen, graying out the US peripheral zone feature score entry field or otherwise rendering the US peripheral zone feature score entry field inactive or nonresponsive to further user input. As another option, the US peripheral zone feature score entry field may remain active to allow the user to change the corresponding feature score while entering a feature score for the boundary zone.

At 1316, the one or more processors determine whether boundary zone feature scores have been entered for the US image and/or OA image. FIG. 13 illustrates an iterative process, in which, during a first iteration at 1316, the one or more processors determine whether the feature score been entered for the boundary zone of the US image. When the US boundary zone feature score is not entered, flow returns to 1314. Additionally or alternatively, more than one US boundary zone feature may be of interest, in which case flow returns from 1316 to 1314 until all of the US boundary zone features have been scored. When the US boundary zone feature score is entered, flow continues to 1318. As explained herein, during a second iteration through the operations at 1314-1316, the one or more processors apply the determination at 1316 to an OA image, namely it is determined whether the feature score has been entered for the boundary zone of an OA image. Additionally or alternatively, the order may be reversed such that OA feature scores are determined first, followed by US feature scores.

The operations of FIG. 13 automatically enable and disable the entry fields to manage an order in which the corresponding feature scores are entered such that the feature score is obtained for the at least one of the peripheral zone or the boundary zone before the feature score is obtained for the internal zone. In accordance with new and unique aspects herein, the automatically enabling and disabling includes managing an order in which the feature scores are assigned to a predetermined outside—to—inside order. The outside-to-inside order requires first assignment of one or more feature scores to a US/OA peripheral zone, second assignment of one or more feature scores to a US/OA boundary zone and third assignment of one or more feature scores to a US/OA internal zone. In accordance with embodiments herein, the automatically enabling and disabling further comprises automatically disabling the second and third entry fields until the first entry field receives the corresponding feature score and disabling the third entry field until the second entry field receives the corresponding feature score.

At 1318, the one or more processors enable one or more entry fields for features related to the internal zone. For example, the processors obtain a feature score at a second entry field associated with the internal zone for the first image. During examination of a US image, the one or more processors enable one or more US internal zone entry fields. During examination of an OA image, the one or more processors enable one or more OA internal zone entry fields. Additionally or alternatively, at 1318, the one or more processors may disable one or more entry fields that have already received feature scores. For example, when US peripheral and/or boundary zone feature scores have already been entered, the corresponding entry fields may be disabled. The disabling operation may include removing display of the US peripheral and/or boundary zone feature score entry fields from the entry screen, graying out the US peripheral and/or boundary zone feature score entry fields or otherwise rendering the US peripheral and/or boundary zone feature score entry fields inactive or nonresponsive to further user input. As another option, the US peripheral and/or boundary zone feature score entry fields may remain active to allow the user to change the corresponding feature score while entering feature scores for the internal zone.

At 1320, the one or more processors determine whether feature scores have been entered for all of the features for one of the US image or OA image, or all features for both of the US image and OA image.

Figure 14C:
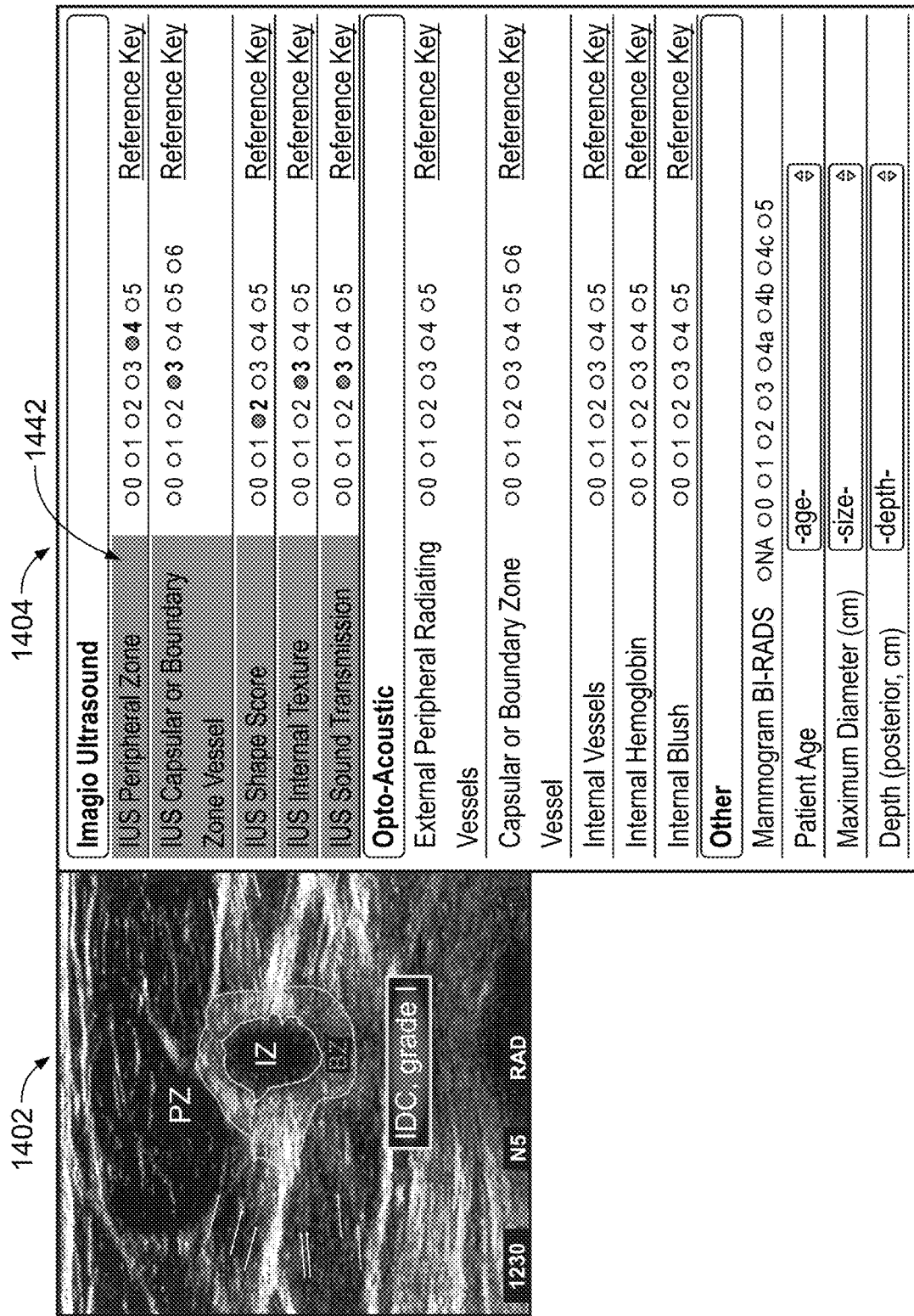
FIG. 14C illustrates a screenshot of a display in which the entry screen has been utilized to select scores for all of the US features.

FIG. 14C illustrates a screenshot of a display in which the entry screen 1404 has been utilized to select scores for all of the US features. In the example of FIG. 14C, the US peripheral zone, boundary zone, internal shape, internal texture and internal sound transmission are assigned scores of 4, 3, 2, 3, 3, respectively. Additionally or alternatively, when a score is assigned to a feature, the header for the feature may be modified, such as by reversing the background as noted at 1442, in order to indicate user that all of the corresponding features have been scored.

Returning to FIG. 13, when all of the US feature scores are entered, but not all of the OA feature scores, flow returns to 1310, where the operations at 1310-1320 are repeated in connection with OA images and OA feature scores. Additionally or alternatively, the process may be reversed such that all of the OA feature scores are obtained first, after which flow branches from 1320, back to 1310 where all of the US feature scores are then obtain second. Alternatively, when all of the US and OA feature scores are entered, flow continues to 1322.

Figure 14D:
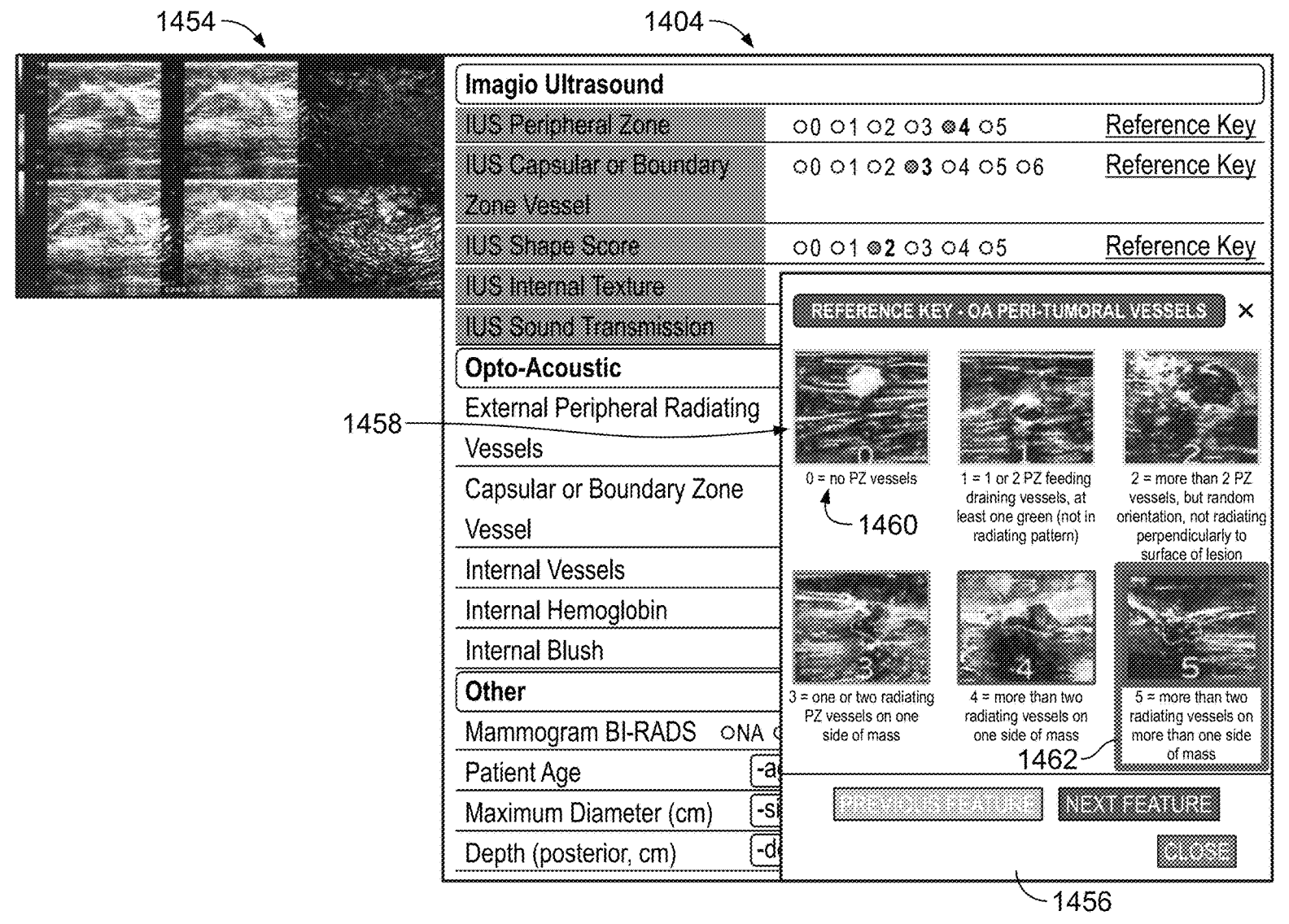

FIG. 14D illustrates an example of a screenshot for a display presented in connection with OA feature scoring in accordance with embodiments herein. The screenshot illustrates a six image panel 1452 that is co-displayed with the entry screen 1404. The six-image panel 1452 includes various types of US/OA images described herein and, in the patents, and publications incorporated by reference. By way of example, the six-image panel 1452 may include the same or a different US image as described above in connection with FIGS. 14A-14C. The six image panel 1452 also includes a long waveform image (e.g., an OA image derived in response to the long waveform OA light source), a short waveform image (e.g., an OA image derived in response to the short waveform OA light source), a total hemoglobin image/map, a relative OA image/map and a combined OA image/map.

The entry screen 1404 is again presented with a reference key pop-up window 1456 that is provided in response to selection of the corresponding reference key for the OA peripheral radiating vessels. The reference key pop up window 1456 includes a collection of OA images 1458 that illustrate examples of different types of OA peripheral radiating vessels along with corresponding image reference key scores 1460. For example, first-sixth reference key OA images illustrate OA images of regions having different peripheral zone characteristics which should be afforded scores of "0" to "5". The user may select a desired score in various manners. In the example of FIG. 14D, the OA peripheral zone radiating vessels is assigned a score of "5", such as by clicking on the active radio button element at and/or selecting the reference key OA image 1462. By way of example, when a score is selected by using the pop-up image reference key, a border of the reference key OA image may be enlarged or otherwise emphasized to indicate to the user which reference key OA image corresponds to the selected score, thereby avoiding confusion by the user and ensuring that the user recognizes which reference key OA image corresponds to the selected score.

Figure 14E:
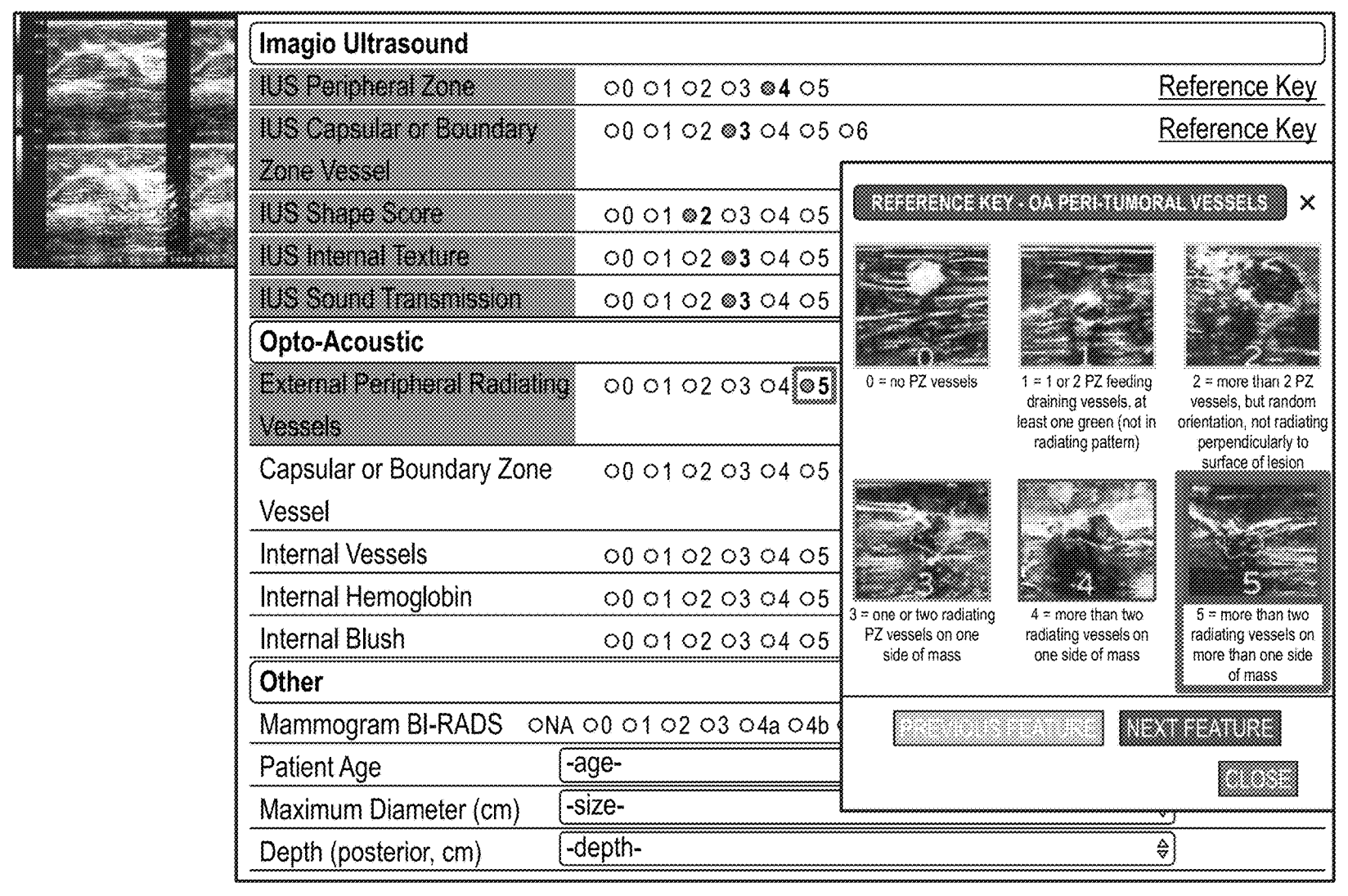

FIG. 14E illustrates an example of a screenshot for the display once the score is selected for the peripheral radiating vessel. The entry field may be highlighted or otherwise emphasized in a different manner to indicate the selection of a score.

Additionally or alternatively, the entry screen includes at least three out of five of the following features associated with OA images: OA peripheral radiating vessels, OA boundary zone vessels, OA internal zone vessels, OA internal zone hemoglobin, and OA internal zone blush. The display may go display a first US image and a first OA image. The method further comprises: displaying a set of US entry fields associated with features of the US image, the set of US entry fields including the first entry field; displaying a set of OA entry fields associated with features of the OA image, the set of OA entry fields including the second entry field; and display a set of non-US/OA entry fields associated with at least one of i) a mammogram Bi-RADS rating, ii) patient age, iii) mass diameter or iv) depth to posterior margin of a mass.

Additionally or alternatively, the display may further display an entry field for a depth of a posterior margin of a mass in the first image.

Returning to FIG. 13, once all of the OA features are scored, flow continues to the non-US and non-OA features. Values are entered for the mammogram BI-RADS rating assigned to the examination, the patient age, the maximum diameter of the mass and the depth to the posterior margin of the mass.

At 1322, the one or more processors store the feature scores for the US features and/or store the feature scores for the OA features. At 1322, the one or more processors then utilize the US/OA feature scores to calculate at least one of a prognostic or predictive result as explained herein.

The one or more processors may calculate different types of prognostic and/or predictive results in various manners. For example, the one or more processors may implement machine learning models, as part of the biomarker machine learning classifier (MLC). The prognostic and/or predictive result may be output as a predicted mean likelihood of malignancy (LOM) or probability of malignancy (POM), such as with a 90% LOM/POM confidence interval (CI). Additionally or alternatively the machine learning models, as a biomarker MLC, may output a mean false negative rate (FNR) with a select confidence interval, such as with a false negative rate 90% confidence interval. The predictive result (e.g., the LOM and FNR outputs) may be displayed in various manners, such as graphically, numerically and the like. For example, the LOM and FNR outputs may be displayed graphically on a bar than extends from 0% FNR to 100% LOM. Additionally or alternatively, the FNR and/or LOM bar will include a vertical line at a select FNR level, such as at the 2% FNR, with the segment of the bar to the left of the 2% line corresponding to predicted FNRs and the segment of the bar to the right of the 2% line corresponding to predicted LOM. The predicted LOM may be mapped to FNR on the part of the display to the left of the predicted 2% FNR. For example, a predicted LOM of 5% may correspond to an FNR of 2%. Additionally or alternatively, the graphic display may be color coded in a fashion in which a gradient of colors corresponds to higher or lower FNR or LOM, with the colors changing gradually from the left end of the bar to the right end of the bar.

Additionally or alternatively, the graphic display may show the mean predicted FNR or LOM with a circle, square, or other polygonal shape that is colored differently from the gradient color on the underlying FNR-LOM bar. Additionally or alternatively, the 90% FNR CI and/or 90% LOM bar may be represented with a horizontal line with vertical bars or whiskers on each end that correspond to the $5^{th}$ FNR or LOM percentile and the $95^{th}$ FNR or LOM percentile, respectively. The color of the line and whiskers that represent the 90% CI may be colored differently from the background FNR-LOM gradient color and may be the same as or different from the color of the circle, square, or other polygonal shape that represents the mean predicted FNR or LOM. Additionally or alternatively, there may be second BI-RADS conversion bar that is displayed parallel to and just above or just below the predicted FNR-LOM bar that is of the same length, and is subdivided into sections based upon ACR benchmark PPV-LOM ranges for each BI-RADS category, such as:

BI-RADS 3: >0% and ≤2% FNR
BI-RADS 4A: >2% and ≤10% PPV/LOM
BI-RADS 4B: >10% and ≤50% PPV/LOM
BI-RADS 4C: >50% and <95% PPV/LOM
BI-RADS 5: >95% PPV/LOM Additionally or alternatively, the BI-RADS conversion bar may be colored coded in a fashion that differs from the continuous color gradient of the predicted FNR/LOM bar. The BI-RADS conversion bar may be colored so that the range of the bar for each of the BI-RADS category is assigned a different color. The user may then manually select a probability of malignancy (POM) from a drop-down list or wheel, and then manually select a BI-RADS category that corresponds to the predicted FNR or LOM. Additionally or alternatively, the entry program may use error trapping to prevent the user from entering a BI-RADS category whose ACR benchmark FNR/PPV/LOM range for which the predicted FNR/LOM does not correspond.

Alternatively, the AI machine learning component may automatically assign mean FNR or LOM from the predicted FNR or LOM that it outputs, and then subsequently, automatically assigned an appropriate BI-RADS category for the predicted FNR or LOM. The user may be allowed to over-ride the output of the AI machine learning predicted mean FNR or LOM output, after confirmatory prompting.

The ACR benchmark FNR range for BI-RADS 3 extends from greater than 0% to less than or equal to 2%. The assignment of BI-RADS 2 category to a solid mass from the results of its baseline ultrasound examination is not recommended by the ACR. However, $5^{th}$ edition US BI-RADS functions only as a qualitative diagnostic biomarker that helps decide whether the FNR is greater than 2% or less than or equal to 2%. Ultrasound BI-RADS $5^{th}$ edition cannot function as a semi-quantitative diagnostic biomarker to objectively and precisely predict an FNR or LOM and its 90% CI. The system described herein was purpose-designed to function as both a qualitative diagnostic biomarker and as a semi-quantitative diagnostic biomarker. It can objectively and precisely predict an FNR/LOM and its 90% CI. Therefore, the user of this system may have the option of assigning a BI-RADS 2 category if the mean predicted FNR and its entire NR 90% CI is 0.5% or less that currently does not and cannot exist in BI-RADS 5th edition.

Next, a more detailed discussion of examples of OA and US features is provided, along with a more discussion of how the OA and US features may be scored and then used to identify molecular subtypes and/or histologic grades.

Feature Scores

Next, the discussion turns to certain feature scores that are assigned in connection with the three different zones, namely the internal zone, boundary zone and peripheral zone. Certain feature scores are assigned in connection with US features, while other feature scores are assigned in connection with OA features.

In accordance with new and unique aspects herein, a number of feature scores have been identified and are described hereafter. The feature scores include a group of US feature scores and a group of OA feature scores that may be used separately or in combination to identify a predictive result. The predictive result may represent one or more of monitoring biomarkers, qualitative and semi-quantitative diagnostic biomarkers, predictive biomarkers, prognostic biomarkers, a POM (Probability of Malignancy), LOM (Likelihood of Malignancy), PPV (Positive Predictive Value), FNR (False Negative Rate), for a mass, molecular subtypes for a malignant mass, and also histologic grades for the mass.

The qualitative diagnostic biomarker may represent a measurable and quantifiable indicator of whether to perform a biopsy or forgo a biopsy of a mass or other definable structure within a patient region of interest. As another example, a predictive biomarker may be used to identify individuals who are more likely to experience a favorable or unfavorable response to an intervention, medical product, or environmental exposure compared with individuals without the predictive biomarker. For example, the predictive biomarker may represent a possibility that mutations in BRCA genes are predictive of response to PARP inhibitors in patients with advanced breast and ovarian cancer. As another example, the predictive biomarker may represent the likelihood that ER- and PR-positive breast cancers respond to endocrine therapy. As another example, the predictive biomarker may represent a possibility that dense breast tissue is predictive of decreased sensitivity of mammography for detecting noncalcified breast cancer. As another example, a prognostic biomarker may represent a degree of angiogenesis and/or a likelihood of lymph node metastasis. A prognostic biomarker may indicate a percentage chance/probability of malignancy for a mass or other definable structure. As another example, a prognostic biomarker may reflect a likelihood of a clinical event, disease progression, or recurrence irrespective of an intervention (e.g TNM stage, tumor grade, tumor receptor status). The prognostic biomarker may be an indicator of a molecular subtype for a malignancy. As another example, a monitoring biomarker may be serially measured to assess a status of a disease or condition or to find evidence of exposure to, or effects of, a medical product or environmental agent. Monitoring biomarkers may focus on changes in a patient's condition (e.g., tumor size and volume by imaging; prostate-specific antigen for monitoring of prostate cancer). The monitoring biomarker may provide an indicator of an effect a response to an exposure or intervention, including a therapeutic intervention or other treatment with respect to a malignancy.

It is recognized that not all of the US feature scores and not all of the OA feature scores are necessarily utilized in each and every embodiment. Instead, a subset of the US feature scores may be utilized in combination with all or a subset of the OA feature scores. Similarly, a subset of the OA feature scores may be utilized in combination with all or a subset of the US feature scores. Different combinations of the US and OA feature scores may be utilized for different purposes, such as whether in connection with diagnostic biomarkers, prognostic biomarkers, predictive biomarkers, or monitoring biomarkers. As another example of a purpose, different combinations of the OA/US feature scores may be utilized when attempting to downgrade or upgrade a BI-RADS classification of a tumor. Further, different combinations of the OA/US feature scores may be utilized when attempting to identify particular molecular subtypes for a malignant mass. Based on the identified molecular subtype, different types of treatments may be identified that are better suited to particular molecular subtypes.

Shape US Feature Score

Conventional BI-RADS scoring of US images is based on examination of the internal zone, without regard for a boundary zone category. The boundary zone represents the transition between the outer surface(margin) of the inner zone and the surrounding tissues. However, in accordance with new and unique aspects herein, the old margin category is removed and a new boundary zone is defined in a manner that exhibits features, that have heretofore never been scored, but provide important information concerning an aggressiveness of a mass or other structure of interest. The boundary zone represents an extra layer that lies between the margin and the peripheral zone. Malignancies represent disorders, not only of genetics, but also of epigenetics. In a malignant mass that has both invasive and in situ components, genetics of the invasiveness and the in situ epithelial cells are substantially identical to each other. The items that distinguish the invasive from the in situ parts of the malignant mass represent the epigenetic microenvironment and intercell signaling. Intercell signaling occurs between malignant cells and tumor associated stromal cells (e.g., tumor associated fibroblast, tumor associated endothelial cells, tumor associated lipocytes). Intercell signaling also occurs between malignant epithelial cells and tumor associated immune cells (e.g., tumor associated lymphocytes, tumor associated macrophages). Also, intercell signaling occurs between tumor associated immune cells and tumor associated stromal cells. As such, the internal zone and its margins reflect the genetics of the tumor, the site of origin, and the resistance of tissues to tumor growth. The boundary zone, and the appearance of how the internal zone transitions into the peripheral zone is largely a reflection of the epigenetics of the tumor and a manifestation of its aggressiveness.

Embodiments herein recognize and take advantage of the differences between internal hypoechoic central nidus and the newly defined boundary zone. The internal center nidus (internal zone) defines a shape and an orientation of a mass, but does not define an aggressiveness for a malignancy. The shape reflects the genetics of the malignancy, site origin of the malignancy (TDLU versus duct versus stroma), and the resistance of surrounding tissues to growth of the malignancy. However, the appearance of the newly defined boundary zone is a manifestation of the aggressiveness of the malignancy. The boundary zone appearance reflects epigenetics of the malignancy, how the cancer interacts with surroundings stroma, and how effectively the malignancy usurps the host stromal and immune apparatus. The foregoing differences between the internal zone and boundary zone are not accounted for through conventional BI-RADS scoring systems that do recognize a boundary zone and not score features of the newly defined boundary zone.

Existing BI-RADS scoring features are utilized as a partial subset of a new scoring system that adds new features and feature scoring criteria, mixes and matches new and old features and feature scoring criteria. In addition, embodiments herein place the various features in a unique order, namely in an order of increasing PPV. Additionally or alternatively, the feature scoring may include one or more of the features described in connection with lesion classification in U.S. Pat. No. 9,398,893.

A unique and novel aspect herein is the combination of the shape and orientation features into a single shape ordinal feature score for the internal zone. Nonlimiting examples of the internal zone shape include oval, round or irregular, while examples of the orientation include parallel or nonparallel. Shape and orientation represent strong predictors of a risk of malignancy. For example, the shape feature score may be assigned an ordinal value between 0-5 based on whether the shape is oval, round, irregular, parallel or nonparallel.

A unique and novel aspect herein adds, to the shape feature score, an angular characteristic (e.g., irregular with angles) and a microlobulated characteristic (irregular without angles). Previously, angularity and microlobulation characteristics were not considered when scoring the internal zone shape, but instead, if considered at all, were only considered in connection with analyzing a margin category. A new and unique aspect of at least some embodiments herein represents the addition of the angular and microlobulation characteristics to the determination of what value to be assigned to the internal zone shape feature score. Previously, the value for the internal zone shape feature score was not based on the angular and microlobulation characteristics.

The improvement, of adding the angular and microlobulation characteristics to the IZ shape feature score, is due, in part, to recognition that an oval and microlobulated mass may be roughly oval in shape, but is not strictly oval in shape. US BI-RADS 5$^{th}$ edition allows a reassuring oval shape to be combined with margins that are microlobulated and/or angular. However, allowing microlobulated or angular margins to be combined with an oval shape violates the BI-RADS 5$^{th}$ edition shape rules. BI-RADS shape rules allow only 3 possible shapes. In BI-RADS, any shape that is neither oval nor round must be classified as irregular. Roughly oval shaped masses that have microlobulated or angular margins are not truly oval or round in shape. Thus, by BI-RADS rules, they cannot be classified as round or oval, and instead, and should only be classified as irregular. The only way to prevent this inherent BI-RADS discordance between shape and margin features is to move microlobulated and angular features out the margin category and into the shape category, where they now become mutually exclusive with oval shape. Thus, this shape scoring system incorporates microlobulations and angles as shape features, which improves its ability to predict LOM/PPV and avoids the shape-margin discordance that is present in BI-RADS. By way of example, the US internal zone shape feature score may be assigned an integer value between 0-5, each of which has a corresponding BI-RADS rating (denoted "BR"), LOM/PPV as noted, such as based on the following:

0=Oval-shaped, parallel orientation, (wider than tall), >=2/1 ratio max width to AP dimension="flat" oval-shaped (BR 4A, >2%-<=10% PPV)

1=Oval-shaped, parallel orientation, (wider than tall)<2/1 ratio width to AP="plump" oval-shaped (BR 4A, >2%-<=10% PPV)

2=Round (lower BR 4B, <=25% PPV)

3=Irregular without angles, parallel orientation (upper BR 4B, >25% PPV) (can include microlobulations)

4=Irregular without angles, non-parallel orientation (taller-than-wide) (lower BR 4C, <=75% PPV) (can include microlobulations)

5=Irregular with angles, parallel or non-parallel (any angle of ≤90°

(lower BR 4C, <=75% PPV)

The foregoing internal zone shape scores are assigned in connection with the hypoechoic central nidus and are not based on the shape or orientation of the boundary zone. FIG. 4C illustrates an example of an image key for images with different internal zone shapes that warrant corresponding different internal zone feature scores 0-5. The color coded key at the bottom of FIG. 4C illustrates corresponding LOM/PPV associated with the internal zone shape feature scores (assuming no other feature scoring information).

Figure 4A:
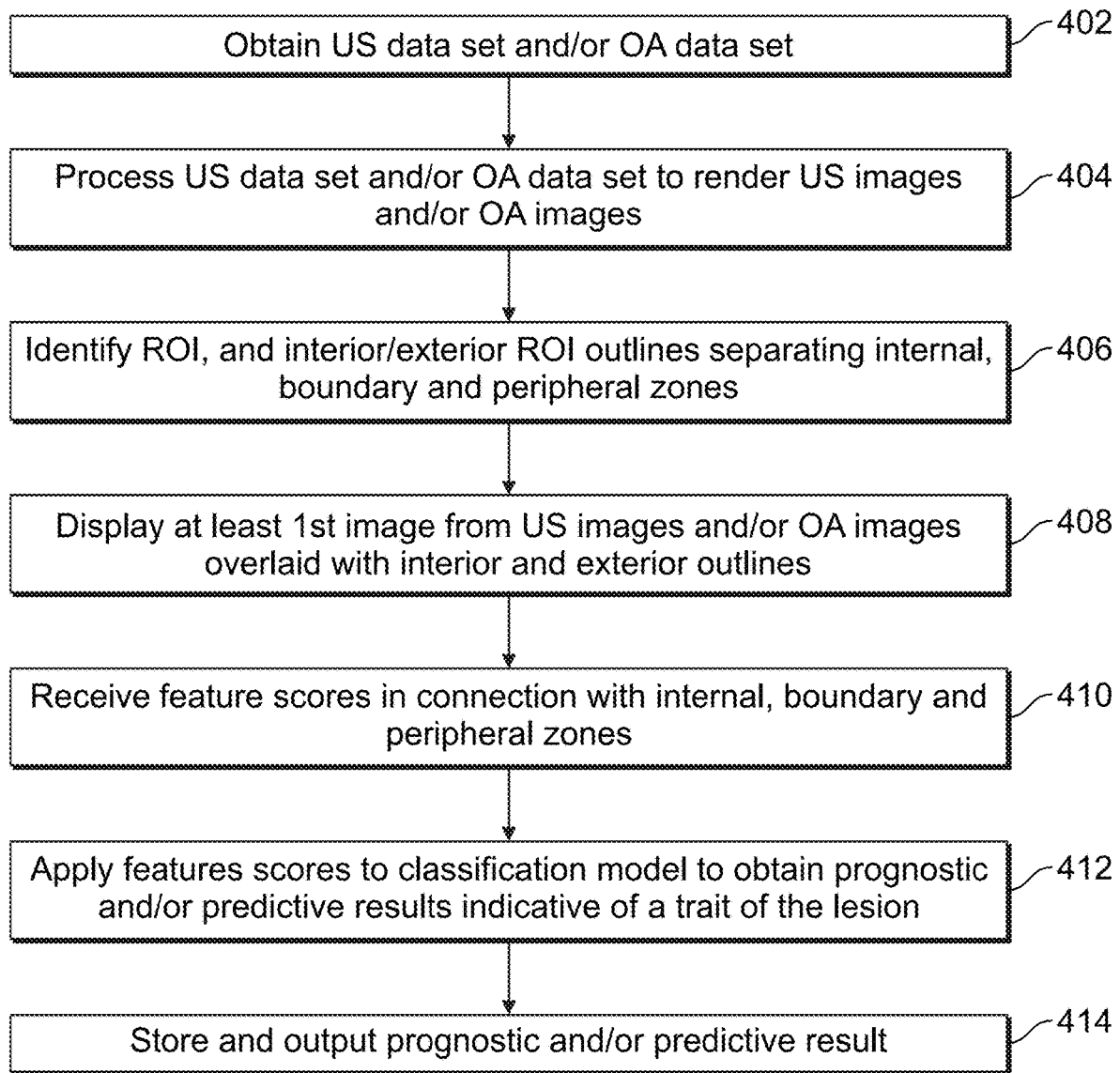
FIG. 4A illustrates a process for utilizing US and/or OA feature scores as biomarkers to obtain at least one of the prognostic result or predictive results in accordance with embodiments herein.
Figure 4B:
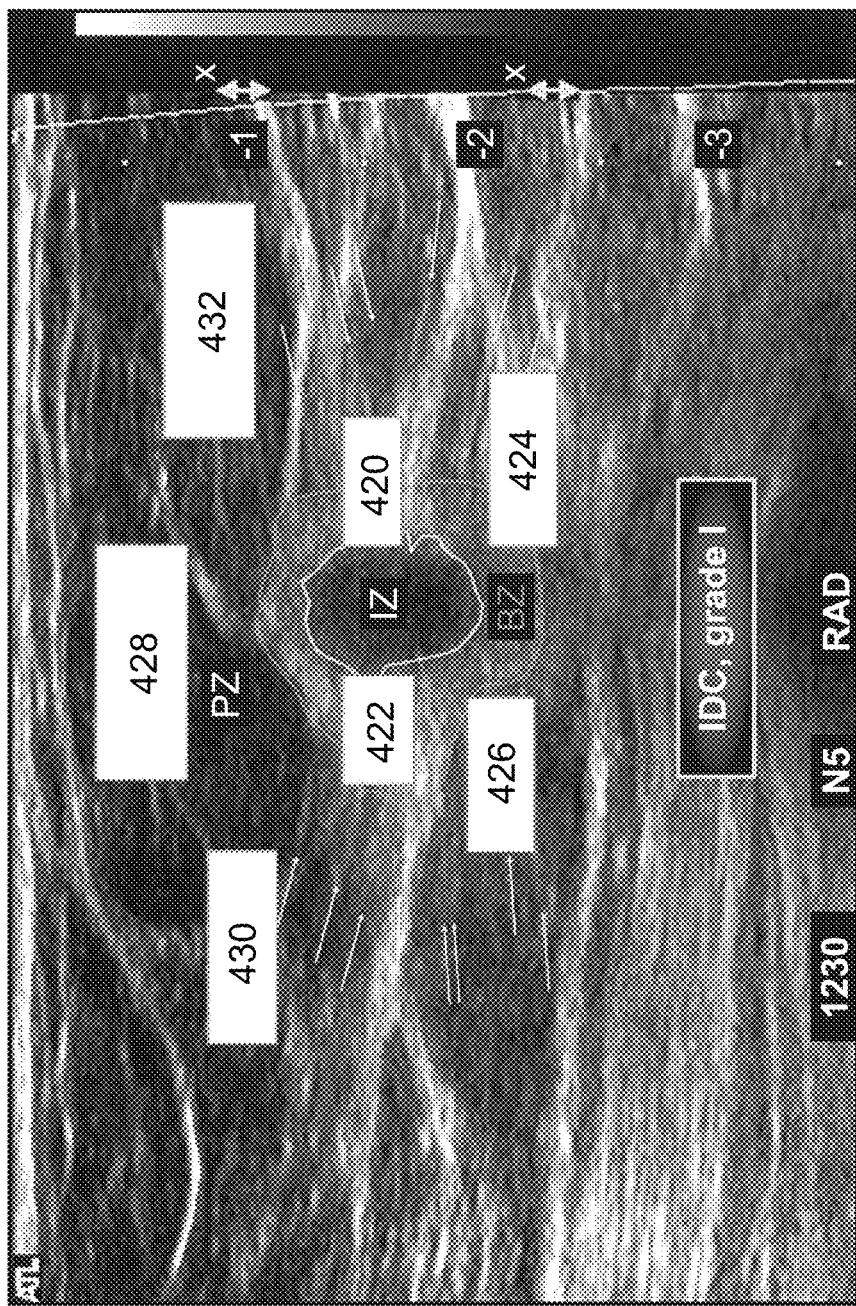
FIG. 4B illustrates an example of a US image displayed in accordance with an embodiment herein.
Figure 4C:
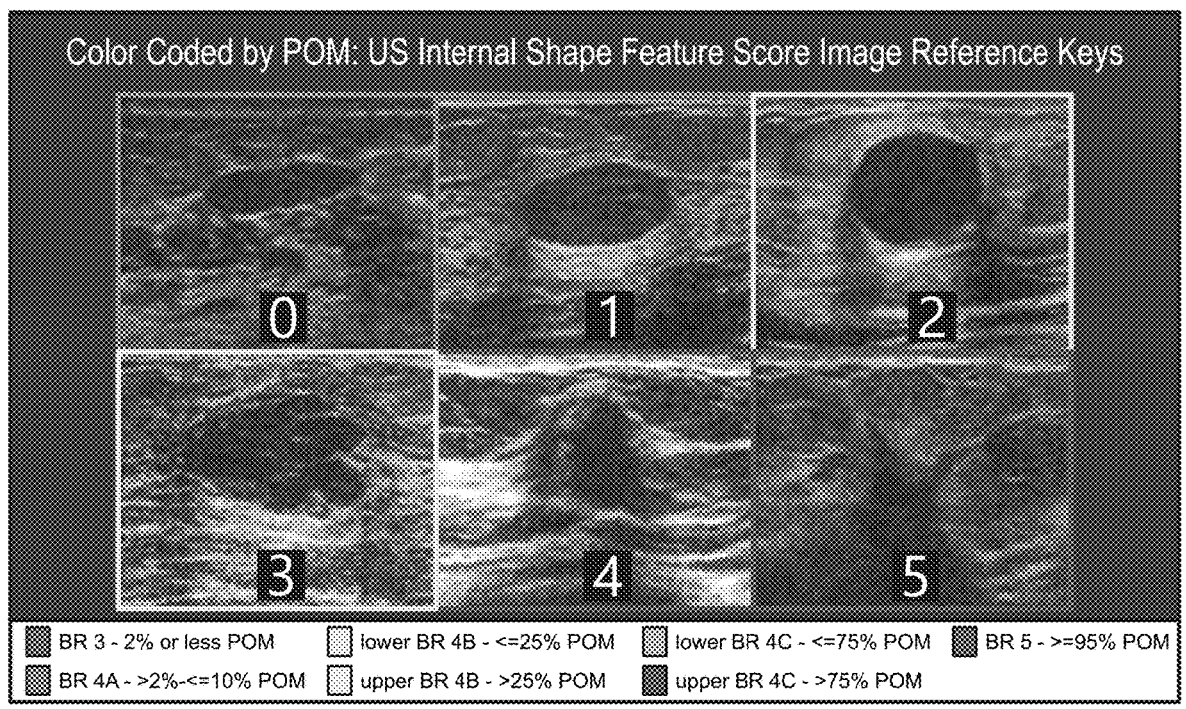
FIG. 4C illustrates an example of an image key for images with different internal zone shapes that warrant corresponding different internal zone feature scores 0-5.
Figure 4D:
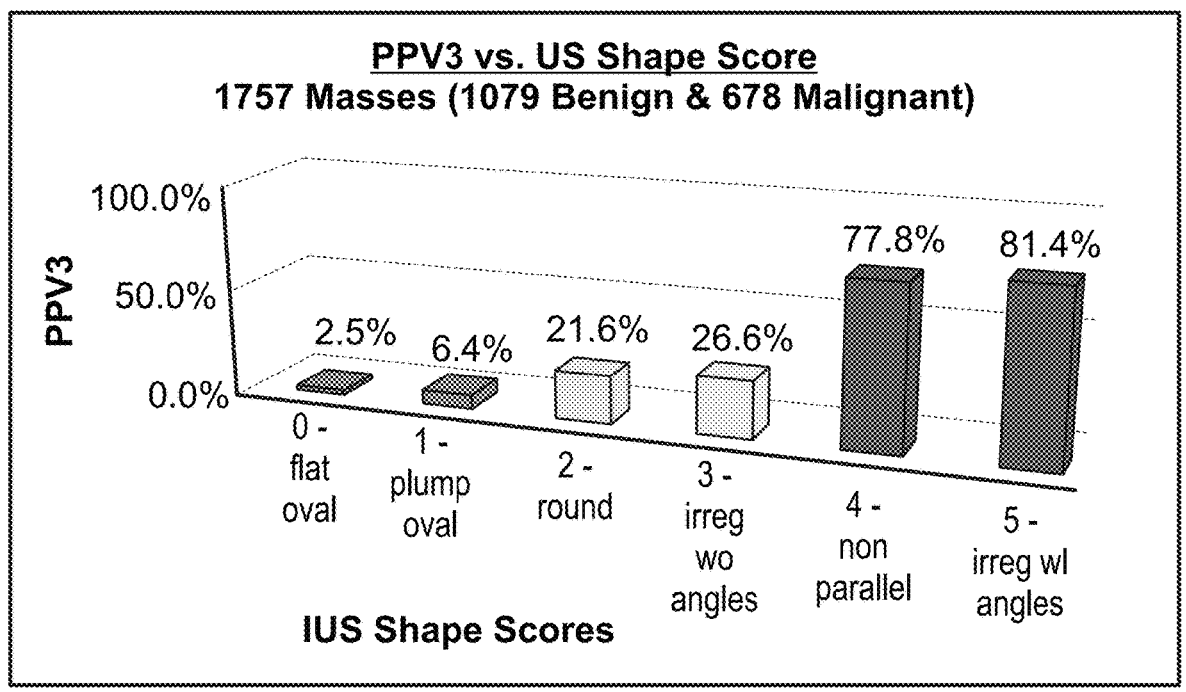
FIG. 4D illustrates an example of a relation between positive predictive values and feature scores for the internal zone shape.

FIG. 4D illustrates an example of a relation between positive predictive values and feature scores for the internal zone shape. The PPV rises continuously with increasing feature score. In accordance with new and unique aspects herein, it is recognized that a single feature score cannot provide both a good positive predictor and a good negative predictor. An interior zone that is severely hypoechoic and heterogeneous with microcalcifications provides a good positive predictor of CA (e.g., a high BI-RADS 4C score). However, the hyperechoic characteristic is not a good enough negative predictor to be used alone when it does not achieve a PPV of less than or equal to 2%.

In accordance with aspects herein, to assign a feature score associated with an oval shape, a mass should be truly oval in shape. When distinguishing between masses that have a flat oval or a plump oval shape, a predetermined cut off may be utilized. For example, a flat oval shape may be defined as shapes having a predetermined horizontal/vertical diameter ratio (e.g., ≥2/1 maximum diameter/AP diameter ratio), whereas plump oval shapes have a ratio of less than two. Embodiments herein measure each mass from multiple directions in OA/US images oriented along different axes to calculate the ratio of the horizontal and vertical diameters. Masses having an approximately oval shape, but should be classified as irregular, usually exhibit an irregular shape along the sides of the mass (relative to the vertical direction), within the coronal plane, where resistance to invasion is lower or lowest. The irregular components on the sides of approximately, but not truly oval shaped masses are usually microlobulated and/or angular. Masses having an approximately oval shape with microlobulations and or angles that are limited to the sides of the mass should not be classified as oval shaped. Instead, such masses should be classified as irregular, with angles or without angles when only microlobulated. Irregular shapes with angles have a much higher risk of malignancy then irregular shapes without angles. Angles occur where resistance to invasion is lowest and tend to occur where 1) a mass intersects the bases of Coopers ligaments, and/or 2) along sides of the mass between the coronally oriented tissue planes. Nonparallel orientations exhibit a higher risk than do irregular shapes without angles but exhibit a lower risk than irregular shapes with angles. An orientation of a mass may be heterogeneous, with part of the mass being oriented nonparallel, and with part of the mass being oriented parallel. Masses that are only partially nonparallel in orientation should be classified as nonparallel (e.g., taller than wide) in orientation. Flat oval masses usually have normal sound transmission, while plump oval masses often have enhanced sound transmission. Flat oval masses usually represent old, senescent and biologically inactive FAs, while plump oval shapes more typically represent cellular and/or actively growing FAs. Solid oval-shaped masses should never be assigned less than a BI-RADS 3 rating until stable for one-three years, and then can be assigned a BI-RADS 2 rating. Some grade III IDCs and TNBCs can simulate plump oval FAs, but they uncommonly simulate flat oval FAs. The presence of a complete thin hyperechoic capsule will help distinguish a benign fibroadenoma from a TNBC (triple negative breast cancer). The benign fibroadenoma will usually have a thin hyperechoic capsule that surrounds the entire mass, including its sides. A TNBC, on the other hand, will often have a thin capsule anteriorly and posteriorly, but will lack an identifiable thin capsule on its sides within the coronal plane.

In accordance with unique and novel aspects herein it has been recognized that the internal zone shape feature score should account for irregular shapes with angles. Invasive cancers tend to form angles where they invade surrounding tissue where resistance to invasion is lowest. For example, resistance to invasion is low in fat areas, where the anterior mammary fascia is absent, in the bases of Coopers ligaments, and between collagen fibers along the sides of masses, which are roughly oriented in a coronal or slanted coronal plane. The coronal plane may be best viewed in 3-D/4D OA/US reconstructions. Surrogates for 3-D reconstructions may include short axis video sweeps and close examination of the sides of masses, which lie within the coronal plane. Masses may have limited numbers of angles and thus the process may examine the whole mass into orthogonal planes, and/or overweight the presence of angles when most of the mass shape is not angular.

Internal Zone EchoTexture US Feature Score

Next, the discussion turns to an US IZ echotexture feature score assigned in connection with the internal zone. When combined with other US features, the US IZ echotexture feature score may be assigned a lesser weight because of its lower NPV (negative predictive value), as compared to the NPV of the internal zone shape feature score. The US IZ echotexture feature score is assigned a value based on various echo pattern characteristics exhibited by the internal zone of a mass, such as whether the echo pattern is anechoic, hyperechoic, complex cystic and solid, mildly or severely hypoechoic, isoechoic, or heterogeneous (with or without microcalcifications). Previously, there was no distinction in the level/degree of the hypoechoic characteristic, but instead the analysis merely determined whether a mass was hypoechoic or not hypoechoic.

A unique and novel aspect herein adds, to the US IZ echotexture feature score, a distinction between first and second classes of the hypoechoic characteristic, namely whether the echotexture is mildly hypoechoic or markedly hypoechoic. This clearly distinguishes this echotexture scoring system from the echo pattern scoring system of BI-RADS 5$^{th}$ edition, which incorrectly does not distinguish between various levels of hypoechogenicity. The distinction is important because the LOM/PPV differs greatly between masses whose echotextures are mildly hypoechoic and those whose echotextures are severely hypoechoic. Masses with an IZ that has the first/mildly hypoechoic characteristic is indicative of a lower risk of malignancy, similar to masses exhibiting and isoechoic characteristic. Masses with an IZ that has the second/severely hypoechoic characteristic exhibit a much higher risk of malignancy as compared to the first/mildly hypoechoic characteristic. The hyperechoic and hypoechoic characteristics are considered relative to fat echogenicity. It was shown that mild hypoechogenicity had has no predictive usefulness and carried the same relatively low risk of malignancy as did isoechogenicity. On the other hand, it was shown that marked hypoechogenicity compared to that of fat carried a very high risk of malignancy. In the internal echotexture scoring system, severe or marked hypoechogenicity is distinguished from mild hypoechogenicity or isoechogenicity. Marked hypoechogenicity carries a much higher risk of malignancy (69.6%) than did mild hypoechogenicity or isoechogenicity (25.5%). Furthermore, in BI-RADS editions 4 and 5, no distinction was made between different degrees of hypoechogenicity. This adversely affects the predictive value of hypoechogenicity.

In the BI-RADS 5$^{th}$ edition system, the hyperechoic feature could include a mixture of hypoechoic and hyperechoic characteristics which is highly undesirable. Mixing hypoechoic and hyperechoic characteristics formed a heterogeneous hyperechogenicity. Including heterogeneously hyperechogenicity substantially destroys the negative predictive value of the echotexture shape feature score. Instead, a unique and novel aspect herein recognizes that, in order to have good negative predictive value, the hyperechoic characteristic should be defined to be homogeneously as echogenic as normal inter-lobular stromal fibrous tissue and also should contain no isoechoic nor hypoechoic areas larger than normal ducts or lobules. Thus, embodiments herein enforce a rigid distinction between the mixed hyperechoic and hypoechoic or isoechoic features and purely hyperechoic features when assigning a value to the echotexture feature score. BI-RADS 5$^{th}$ edition less strict definition of hyperechogenicity adversely affects its NPV. The stricter definition of hyperechogenicity used in this echotexture scoring system gives it a much lower LOM/PPV and makes it a better negative predictor of cancer.

Masses that exhibit a purely severely hyperechoic characteristic carry close to a 100% negative predictive value. The severely hypoechoic characteristic is a strong predictor of malignancy in a tumor. The mildly hypoechoic and iso-echoic characteristics are not as strongly of positive predictors as the severely hyperechoic characteristic. A heterogeneous internal echotexture can be seen in benign masses, but more commonly in malignant masses due to polyclonal nature, areas of necrosis and hemorrhage, areas of fibrosis and unresolved microcalcifications. Microcalcifications in a mass increase the risk of the mass being malignant.

By way of example, the US internal zone echotexture feature score may be assigned an integer value between 0-5, each of which has a corresponding LOM/PPV as noted, such as based on the following:

0=Homogeneously hyperechoic (as hyperechoic as normal interlobular stromal fibrous tissue) (lower BR 4B, <25% PPV)
1=Complex mixed cystic and solid (lower BR 4B, <25% PPV)
2=Homogeneously isoechoic or mildly hypoechoic (upper BR 4B, >25% PPV)
3=Heterogeneous without internal microcalcifications (upper BR 4B, >25% PPV)
4=Heterogeneous with internal microcalcifications (lower BR 4C, <=75% PPV)
5=Severely or markedly hypoechoic (compared to fat) (lower BR 4C, <=75% PPV)

Figure 4E:
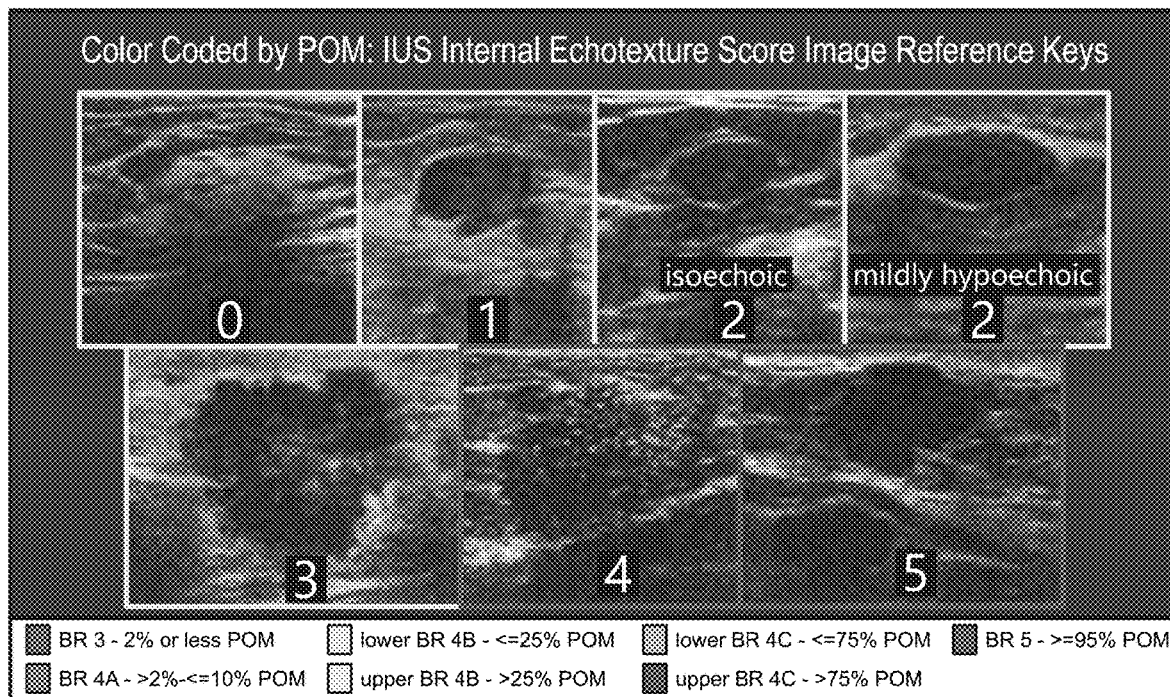
FIG. 4E illustrates an example of an image key for images with different internal zone echotexture patterns that warrant corresponding different internal zone feature scores 0-5.
Figure 4F:
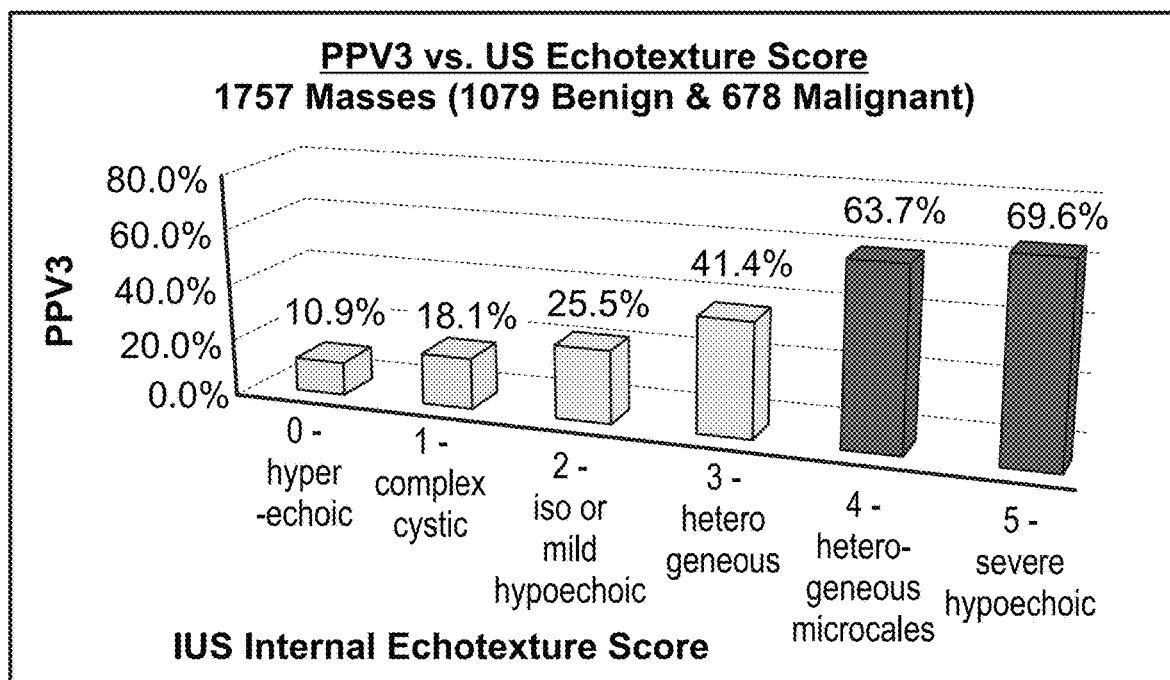
FIG. 4F illustrates an example of a relation between positive predictive values and feature scores for the internal zone echotexture.

FIG. 4E illustrates an example of an image key for images with different internal zone echotexture patterns that warrant corresponding different internal zone feature scores 0-5. The color coded key at the bottom of FIG. 4E illustrates corresponding LOMs/PPVs associated with the internal zone echotexture feature scores (assuming no other feature scoring information). FIG. 4F illustrates an example of a relation between positive predictive values and feature scores for the internal zone echotexture. The PPV rises continuously with increasing feature score. In accordance with new and unique aspects herein, it is recognized that a single feature score cannot provide both a good positive predictor and a good negative predictor. Masses that exhibit the severely hypoechoic or heterogeneous microcalcification characteristics represent good positive predictors of malignancy (e.g., BI-RADS 4C).

When utilizing the conventional BI-RADS scoring system, masses that exhibit the hyperechoic characteristic do not afford good negative predictive values because of sub optimal definitions in the BI-RADS scoring system. The BI-RADS scoring system more broadly defines hyperechoic as having increased echogenicity: 1) relative to fat "or" 2) equal to fibroglandular tissue. This system more strictly and narrowly defines hyperechogenicity as: 1) Relative to fat "and" 2) As homogeneously echogenic as normal interlobular stromal fibrous tissue "and" 3) Containing no isoechoic or hypoechoic areas larger than normal ducts or TDLUs.

In accordance with unique and novel aspects herein, it has been recognized that the foregoing definition of hyperechoic is too broad by covering the alternative factors 1) and 2), thereby resulting in the hyperechoic characteristic not affording good negative predictive values. The unduly broad definition in the conventional BI-RADS scoring system allows the hyperechoic characteristic to be defined as having heterogeneous echotexture which destroys the NPV value. Instead, in accordance with aspects herein, the hyperechoic characteristic should be (and is) defined as having increased echogenicity 1) relative to fat "and" 2) equal to fibroglandular tissue. Also, the conventional BI-RADS scoring system did not distinguish between markedly and mildly hypoechogenicity, whereas unique and novel aspects herein recognize and take advantage of the differences therebetween.

By redefining the definition to include both of the foregoing factors 1) and 2), and not simply either of the foregoing factors, new and unique aspects herein render the hyperechoic characteristic to have very low PPV, but very high in NPV. Heterogeneous internal zone echotexture is more common in malignant masses, as compared to benign masses because of 1) polyclonal nature of cancer, and/or 2) central fibrosis, and/or 3) central necrosis, and/or 4) central microcalcifications. However, heterogeneous internal zone echotexture may be found in some benign conditions, such as 1) internal fibrocystic changes, and/or 2) sub nodules of different ages and biologic activity, and/or 3) internal microcalcifications.

Sound Transmission US Feature Score

Next, the discussion turns to an US IZ sound transmission feature score assigned in connection with the internal zone (e.g., posterior acoustic features). The posterior acoustic features category, in the prior BI-RADS rating system, included the following characteristics: no posterior acoustic features, enhancement, shadowing, or a combined pattern. In the prior BI-RADS rating system, the combined pattern represented one/binary characteristic, such that a mass either included a combined pattern or did not include a combined pattern.

In accordance with new and unique aspects herein, the combined pattern characteristic is broken into three subcategories, namely 1) partial enhancement with partial normal sound transmission, 2) partial enhancement with partial shadowing, and 3) partial shadowing with partial normal sound transmission. A significant percentage of malignant masses do not cast acoustic shadows and have normal or enhanced sound transmission. Thus, while a finding such as shadowing can be a good positive predictor of malignancy, in accordance with aspects herein, it is not expected that any of the posterior acoustic features would exhibit good negative predictive values of an absence of malignancy.

When determining a distinction between an enhanced sound transmission characteristic versus a normal sound transmission characteristic, the following points should be considered. Many solid masses with enhanced sound transmission are misdiagnosed benign complicated cysts that contain fluid that is echogenic enough to simulate the echogenicity of solid masses, potentially accounting for the low percentage of malignancies with enhanced sound transmissions. Young, actively growing, plump oval-shaped FAs tend to have enhanced sound transmission as well. Mixed sound transmission in ACR BI-RADS can be any combination. Mixed sound transmission with partial shadowing is more concerning then mixed sound transmission with enhanced sound transmission. Thus, a new and unique aspect herein separates mixed sound transmission into different groups depending whether or not there is partial shadowing. Because malignant masses may be internally heterogeneous, only part of a malignant mass may exhibit shadowing.

By way of example, the US internal zone sound transmission feature score may be assigned an integer value between 0-5, each of which has a corresponding BI-RADS rating and LOM/PPV as noted, such as based on the following:

0=Enhanced (lower BR 4B, <=25% PPV)
1=Normal (upper BR 4B, >25% PPV)
2=Mixed normal and enhanced (upper BR 4B, >25% PPV)
3=Mixed enhanced and partial or weak shadowing (lower BR 4C, <=75% PPV)
4=Mixed normal and partial or weak shadowing (lower BR 4C, <=75% PPV)
5=Complete and strong shadowing (upper BR 4C, >75% PPV)

Figure 4G:
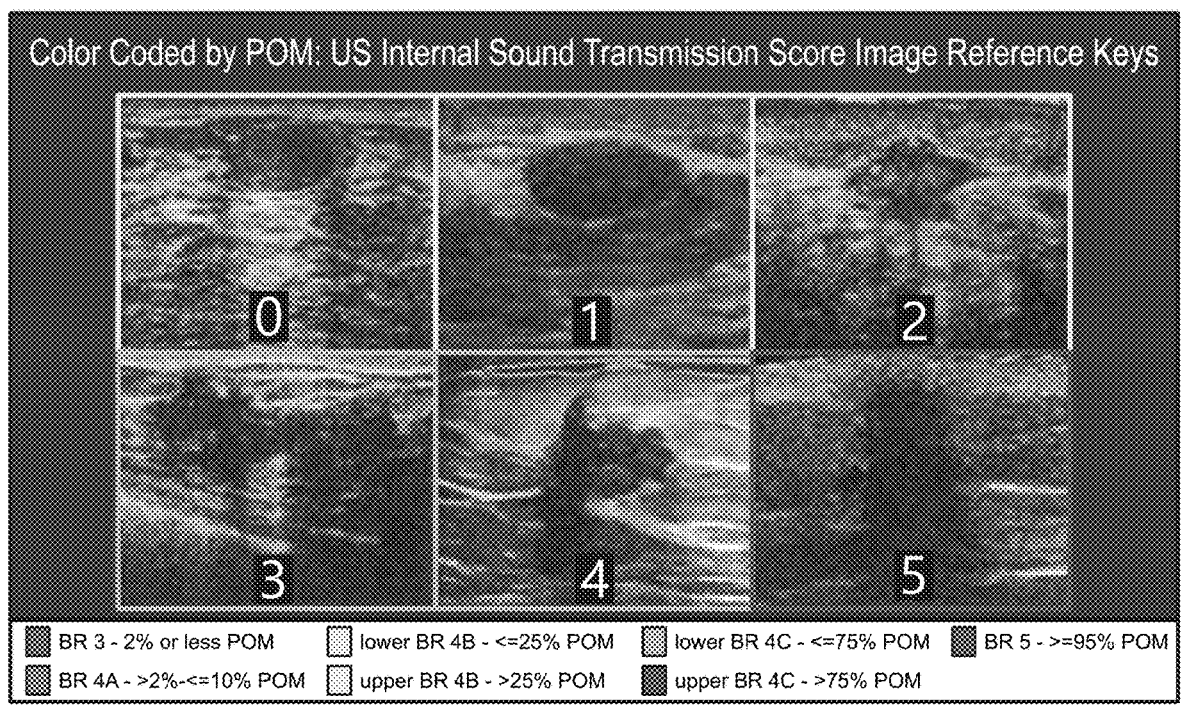
FIG. 4G illustrates an example of an image key for images with different internal zone sound transmissions that warrant corresponding different internal zone feature scores 0-5.

FIG. 4G illustrates an example of an image key for images with different internal zone sound transmissions that warrant corresponding different internal zone feature scores 0-5. The color coded key at the bottom of FIG. 4G illustrates corresponding LOMs/PPVs associated with the internal zone sound transmission feature scores (assuming no other feature scoring information). Partial and weak shadowing effect only part of a breadth of a mass. Complete and weak shadowing effects and entire breadth of the mass. Weak shadowing means that the posterior margin of the mass is not completely obscured by the shadowing. Partial and strong shadowing affect only part of the breadth of the mass, while complete and strong shadowing affect the entire breadth of the mass. Strong shadowing means that the posterior margin of the mass is completely obscured by the shadowing. Complete and strong shadowing obscures entire posterior margins of the mass. Strong shadowing completely obscures at least part of the posterior margin of the mass, while partial shadowing effects only part of a lesion and can be strong or weak. Weak shadowing does not completely obscure posterior margins in the area of shadowing.

Figure 4H:
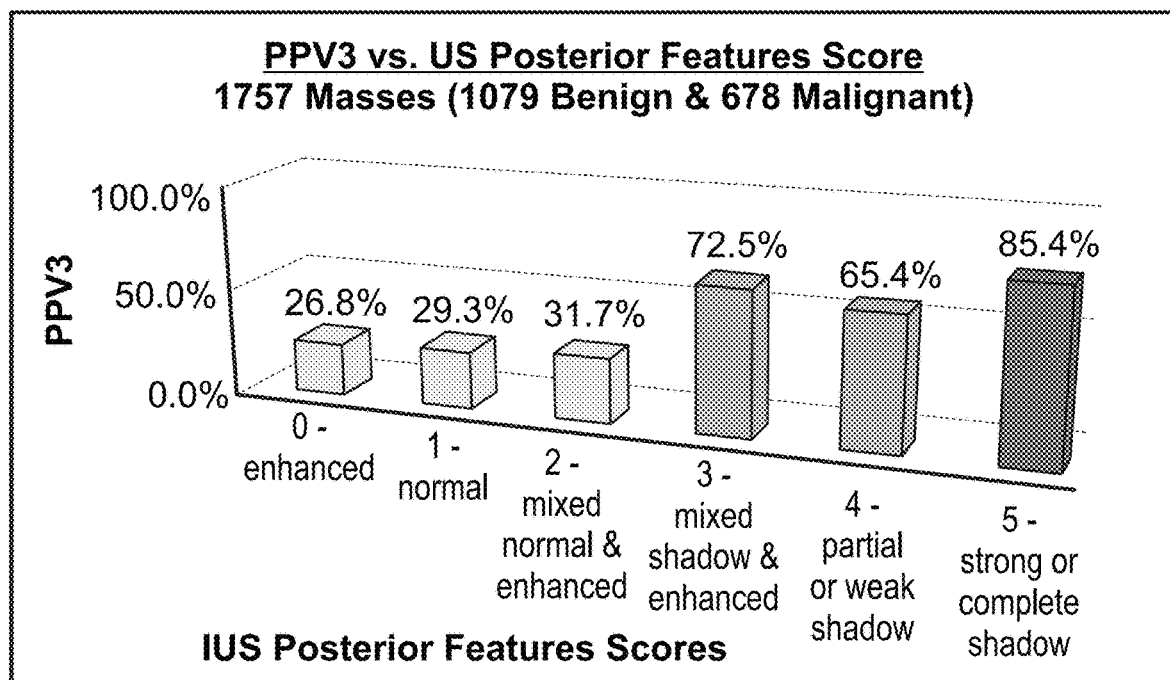
FIG. 4H illustrates an example of a relation between positive predictive values and sound transmission feature scores.

FIG. 4H illustrates an example of a relation between positive predictive values and sound transmission feature scores. The PPV rises continuously with increasing feature score. In accordance with new and unique aspects herein, it is recognized that a single feature score cannot provide both a good positive predictor and a good negative predictor. From FIG. 4H, it can be seen that complete or partial shadowing is a good positive predictor of cancer (e.g., BI-RADS 4C). Enhanced and normal sound transmission are poor negative predictors of an absence of cancer. Thus, while shadowing is suspicious, normal or enhanced sound transmission is not necessarily reassuring. Acoustic shadowing is a good positive predictor of malignancy. A relatively large percentage of cancers may have normal sound transmission or have enhanced sound transmission. Thus, in accordance with new and unique aspects herein, it can be predicted that sound transmission will be a relatively poor negative predictor and that a probability of malignancy will be higher at low scores than for other US characteristics and feature scores. However, embodiments herein can use the good positive predictions based on the sound transmission feature score without suffering from the weaker negative predictions. Because high US IZ sound transmission feature scores are good positive predictors of the presence of cancers, but low IZ sound transmission feature scores have lower NPVs than do low US IZ shape scores, US sound transmission scores will tend to be relatively underweighted when combining them with other US feature scores.

US Boundary Zone Feature Score

In the BI-RADS 5th edition rating system, a margin category was utilized, and ratings were assigned based on whether the margin area was circumscribed or not circumscribed. When the margin area was not circumscribed, the BI-RADS 5$^{th}$ edition rating system considered whether the margin area was indistinct, angular, microlobulated or spiculated. However, the BI-RADS 5$^{th}$ edition rating system, did not provide any subcategories or further breakdown when the margin area was circumscribed, simply the margin area either was or was not circumscribed. In the BI-RADS 5$^{th}$ edition rating system, the margin was defined generally as:
 the edge or border of the lesion; the descriptors of the margin, like the descriptors of the shape, are important predictors of whether a mass is benign or malignant; a circumscribed margin is one that is well-defined with an abrupt transition between the lesion and the surrounding tissue; for ultrasound, to describe the mass as circumscribed, its entire margin must be sharply defined; most circumscribed lesions have round or oval shapes.

In the BI-RADS 5$^{th}$ edition rating system, there is no mention, in connection with the margin, of the thin hyperechoic capsule. In accordance with new and unique aspects herein, a US boundary zone feature score has been identified that includes the circumscribed characteristic and that breaks the circumscribed characteristic into four subcategories, namely 0) circumscribed with a complete thin hyperechoic capsule, 1) circumscribed with a partial thin hyperechoic capsule, 2) circumscribed with a complete thick hyper or isoechoic capsule, and 3) circumscribed without visible discrete capsule. At the high end of the boundary zone scoring system are 5) the thick echogenic rim and 6) frank short boundary zone spiculations. The middle of the spectrum includes two scores in which a hyperechoic transition layer cannot be identified:
 3) circumscribed without an identifiable thin capsule and indistinct, but without a thick hyperechoic rim or spiculations being identifiable, and
 4) indistinct, without a thick echogenic rim or short spicules.

Thus, the boundary zone system includes identification of variable completeness and thickness of a capsule and the low end, various descriptions of a thick ill-defined rim at the upper end, and lack of a hyperechoic thin rim or thick halo in the middle of the spectrum of scores. In accordance with new and unique aspects herein, a separate feature score is no longer assigned based on the margin area, but instead one or more feature scores are assigned based on a larger boundary zone. The boundary zone described herein does not correspond to the margin area in the prior BI-RADS rating system. The boundary zone is substantially larger than the margin area considered in the prior BI-RADS rating system. The boundary zone is the zone of transition between the margin and the peripheral zone.

Among other things, as noted above, new and unique aspects herein remove the angular and microlobulated characteristics as subcategories from the margin area (and from the boundaries own), and instead use the angular and microlobulated characteristics to the determination of the value it assigned for the internal zone shape feature score. Also, the angular and microlobulated characteristics were redefined for use in the internal zone shape feature score. The angular characteristic refers to irregular shapes with angles, while the microlobulated characteristic refers to irregular shapes without angles, both of which are factors in assigning the internal zone shape feature score. In BI-RADS 5$^{th}$ edition, a mass could paradoxically be classified being as either oval-shaped with a microlobulated margin or oval-shaped with an angular margin. The problem with such a system is the presence of a microlobulated margin or and angular margin, by definition meant that the mass was not oval-shaped. By ACR BI-RADS 5$^{th}$ edition definition, there are only 3 shapes: oval, round, and irregular. In ACR BI-RADS 5$^{th}$ edition, everything that is not oval or round, is irregular. Since an oval-shaped mass with microlobulated or angular margins is no longer oval in shape, it cannot be classified as oval-shaped, The only solution to this unique paradox within the BI-RADS 5$^{th}$ edition was to move microlobulation and angular margins out of the margin category and into the shape category, where they would necessarily be mutually exclusive with the oval shape category. Thus, in the boundary zone scoring system, microlobulations are included in the "irregular shape without angles, parallel orientation category and angles were moved into the irregular shape with angles category. Note that the irregular shape with angles carries a much higher risk of malignancy (81.4%) than does the irregular shape without angles, parallel orientation category (26.6%), verifying the validity of this reclassification of microlobulation and angles into the shape category.

In accordance with new and unique aspects herein, the US boundary zone is assigned a distinct characteristic that is broken into two subcategories, namely 1) indistinct and 2) ill defined, thick echogenic rim (e.g., a halo). In accordance with new and unique aspects herein, the spiculated characteristic is considered as a characteristic for the boundary zone and for the peripheral zone. One or both of the boundary zone and peripheral zone may be spiculated. The spiculated characteristic may appear as short spiculated hypoechoic and/or hyperechoic regions in the boundary zone. Also, the spiculated characteristic may appear as long hyperechoic regions in the peripheral zone.

In accordance with new and unique aspects herein, it has been determined that showing a thin hyperechoic capsular around benign masses, in many instances, is very important to achieving a probability of malignancy of less than or equal to 2%. Further, consideration must be afforded for masses in which the thin hyperechoic capsule cannot be seen. In connection there with, new and unique aspects herein overcome the conventional ideas 1) that the hypoechoic central nidus of the mass represents the entire lesion, and 2) that only hypoechoic elements of a mass matter. The conventional approach substantially over emphasizes the hypoechoic elements.

In accordance with new and unique aspects herein, characteristics of the hyperechoic boundary zone and peripheral zone are analyzed to achieve the desired sensitivity of 98% or better with grayscale US or OA images. By looking at the boundary zone and peripheral zone, embodiments herein are able to accurately analyze masses that do not include a thin capsule. The boundary and peripheral zones, including but not limited to sides of the mass within the coronal plane, are analyzed for, among other things, indistinct margins, thick echogenic halo, hyperechoic spicules, and hyperechoic thickened and/or retracted Coopers ligaments.

By way of example, the US boundary zone feature score may be assigned an integer value between 0-6, each of which has a corresponding LOM/PPV as noted, such as based on the following:
 0=Well circumscribed with complete thin hyperechoic capsule (BR 4A, >2%-<=10% PPV)
 1=Well-circumscribed with partial thin hyperechoic capsule (BR 4A, >2%-<=10% PPV)
 2=Thick well-defined capsule (lower BR 4B, <=25% PPV)
 3=Circumscribed, but without thin hyperechoic capsule (lower BR 4B, <=25% PPV)
 4=Indistinct margin (upper BR 4B, >25% PPV)
 5=Thick ill-defined echogenic rim (halo) in boundary zone (lower BR 4C, <=75% PPV)
 6=Frank short hypoechoic and/or hyperechoic spiculations within boundary zone. (Upper BR 4C, >75% PPV)

Figure 4I:
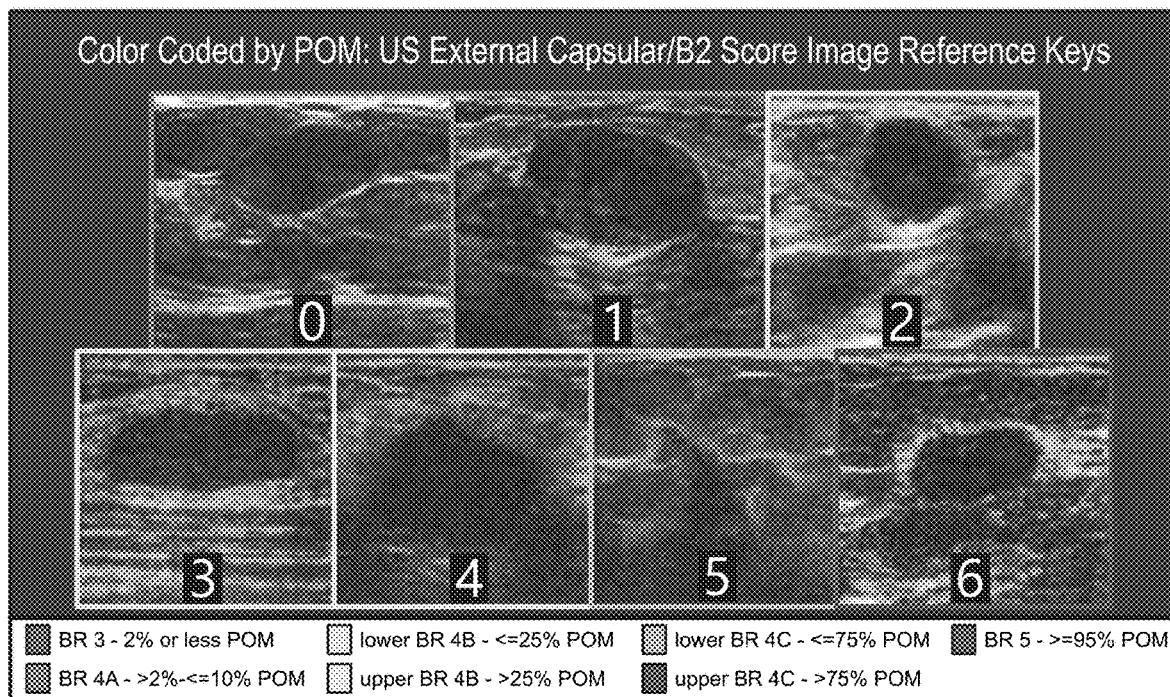
FIG. 4I illustrates an example of an image key for images with different US boundary zones that warrant corresponding different external capsular/boundary zone feature scores 0-6.

FIG. 4I illustrates an example of an image key for images with different boundary zones that warrant corresponding different external capsular/boundary zone feature scores 0-6. The color coded key at the bottom of FIG. 4I illustrates corresponding LOMs/PPVs associated with the different external capsular/boundary zone feature scores (assuming no other feature scoring information).

Figure 4J:
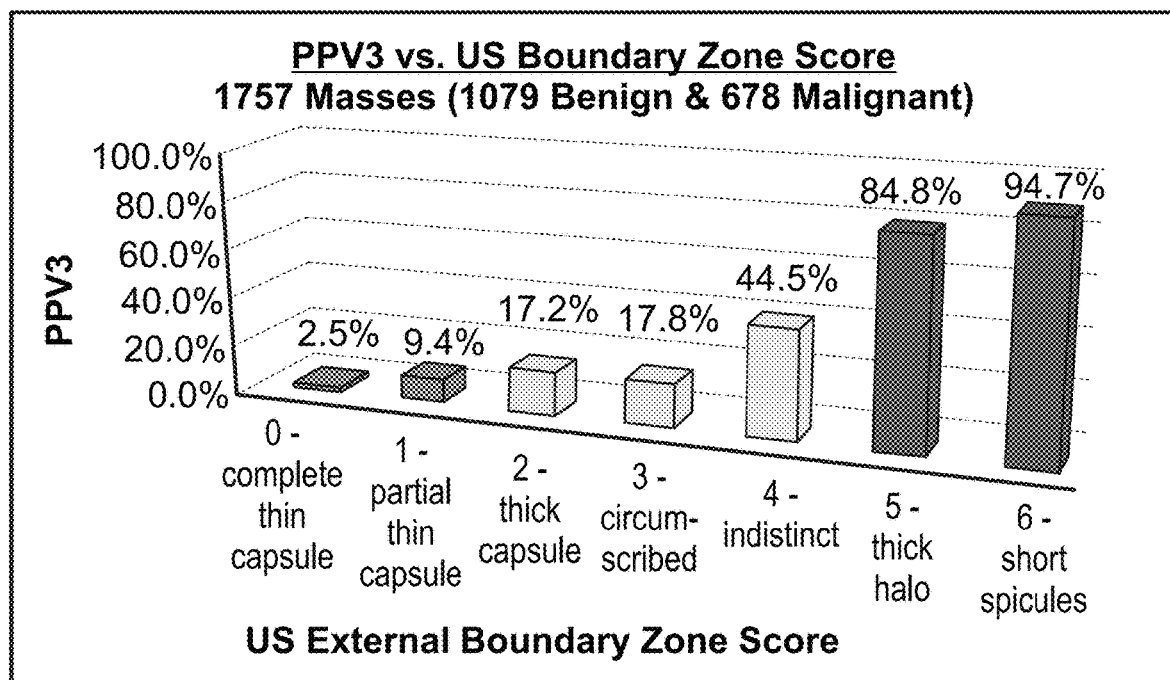
FIG. 4J illustrates an example of a relation between positive predictive values and US boundary zone feature scores.

FIG. 4J illustrates an example of a relation between positive predictive values and boundary feature scores. The PPV rises continuously with increasing feature score. In accordance with new and unique aspects herein, it is recognized that a single feature score cannot provide both a good positive predictor and a good negative predictor. However, the boundary zone feature score may come the closest to any feature that could stand alone as a positive predictor of malignancy. The boundary zone exhibits a PPV at the zero score of 2.5%, which is only slightly above the cut off between BI-RADS 3 and 4A. The PPV at a score of six is 94.7% which is very close to the 95.0% associated with a BI-RADS 5 rating.

The scores of 0-2 correspond to masses with boundary zones that exhibit well-defined capsules that are identified to various degrees and variable thicknesses. The scores 3-4 correspond to masses with boundary zones that do not exhibit to a well-defined capsule, nor a thick rim. The scores 5-6 correspond to masses with a boundary zone that exhibits an ill-defined echogenic rim or spicules.

In the BI-RADS $5^{th}$ edition rating system, the boundary zone was considered to be of no significance, and therefore, was discarded. Only the margin was considered and rated. In accordance with new and unique aspects herein, it is recognized that the boundary zone feature score represents the single most valuable feature score. The boundary zone feature score offers a very steep slope of the PPV versus score graph. As compared to other feature scores, the boundary zone feature score exhibits the steepest and most uniform PPV slope, offers the lowest PPV at the feature score 0, and exhibits almost the highest PPV at the feature score of 6. As compared to other feature scores, the boundary zone feature score affords very good, if not the best, visual separation of scoring distribution curves between benign and malignant masses. As compared to other feature scores, the boundary zone feature score offers a very wide, if not the widest, separation of means and 99% CIs. As compared to other feature scores, the boundary zone feature score offers a very wide, if not the widest, separation of medians and interquartile ranges, as well as the greatest AUC (area under the curve) under ROC (receiver operator characteristics) curve.

The boundary zone feature score accounts for a thin hyperechoic pseudo-capsule of compressed tissue around a benign mass. The hyperechoic capsule is difficult to demonstrate on the coronal ends of masses on single freeze-frame images because of poor angles of incidence with the ultrasound beam and the resulting critical angle phenomena. Furthermore, apart from angle of incidence issues, demonstration of the thin hyperechoic capsule on the sides of the mass must be done with the lesser lateral resolution of the ultrasound beam (about 300-500 microns). On the other hand, the thin hyperechoic capsule on the anterior and posterior surfaces of the mass are scanned at more optimal angles of incidence that do not suffer from critical angle phenomena and are visualized with the better axial resolution of the ultrasound beam (about 100 microns at 12-14 MHz).

Various techniques may be implemented to better demonstrate the thin hyperechoic capsule surrounding a benign mass. For example, video sweeps may be stored through the short axis of the mass in orthogonal planes. Heel-and-toe compression may be applied manually with a probe to improve angles of incidence on coronal ends of the mass. Spatial compounding may be utilized, to implement, in effect, an electronic form of heel and toe compression. A scan may also be implemented with lighter compression to allow surrounding hyperechoic fibrous tissue to separate away from the equally hyperechoic capsule.

Spiculations are another characteristic of the boundary zone feature score. A mass may exhibit alternating hypoechoic and hyperechoic spicules. Hypoechoic elements represent either fingers of invasive tumors or in situ malignant components. Hyperechoic elements represent the interface between the tumor and tissue or desmoplastic stromal elements. A variant of spiculation represents a thick echogenic halo which is thicker along sides of the mass and is less apparent anteriorly and posteriorly. The spiculation variant may arise due to spicules that extend in a direction parallel to a transmit/receive beam on anterior and posterior surfaces, thereby making poor specular reflections, while they are perpendicular to beams located along either sides of the mass and make strong specular reflections. The spiculation variant may also arise due to the fact that the coronal plane may represent the path of lowest resistance to invasion and spicules most commonly formed in the coronal plane on sides of the mass.

In short, the boundary zone is a very complex in etiology that is substantially caused by infiltration of surrounding tissues (e.g., mainly fat). The infiltration may arise from edema (e.g., leaking from abnormally leaky tumor neovessels), cancer cells infiltrating between fat cells, lymphocytes infiltrating between fat cells, desmoplasia between fat cells (e.g., a cursor to spicules), unresolved micro-spicules and tumor neovessels. The boundary zone is complex and includes one or more of active tumor cell growth, immune cell response, high cellularity, high neovessel density, desmoplasia, tumor associated macrophages, tumor associated fibroblasts, tumor associated lipocytes, edema, and proteinaceous debris.

US peripheral zone Feature Score

In accordance with new and unique aspects herein, an additional US feature score has been defined for the peripheral zone. The peripheral zone feature score accounts for calcifications, some associated features in BI-RADS, and spiculation outside of the boundary zone. The calcifications are located outside of a mass and may include intraductal calcifications outside of the mass. The associated features may include architectural distortion and/or duct changes outside of the boundary zone. The peripheral zone feature score is also assigned based on spiculations outside of the boundary zone. The peripheral zone feature score combines duct changes and calcifications outside of a mass into 2 characteristics, namely 1) enlarged ducts outside of a mass (without internal microcalcifications) and 2) enlarged ducts outside of a mass that contain microcalcifications. The architectural distortion and associated features were divided into two characteristics, namely 1) hyperechoic spiculations (or interrupted tissue planes) and 2) thickened Coopers ligaments and/or skin (moved from the associated features).

By way of example, the US peripheral zone feature score may be assigned an integer value between 0-5, each of which has a corresponding LOM/PPV as noted, such as based on the following:

0=Normal tissue (lower BR 4B, <=25% PPV)
1=Critical angle phenomena=(shadowing from adjacent structures) (upper BR 4B, >25% PPV)

2=Enlarged surrounding ducts not containing microcalcifications (duct extension or branch pattern) (upper BR 4B, >25% PPV)

3=Enlarged Surrounding ducts containing microcalcifications (upper BR 4C, >75% PPV)

4=Peripheral long, thin hyperechoic spicules (or interrupted tissue plane) (upper BR 4C, >75% PPV)

5=Thickened spicules and/or Coopers ligaments and/or retracted or thick skin (BR 5, >=95% PPV)

Figure 4K:
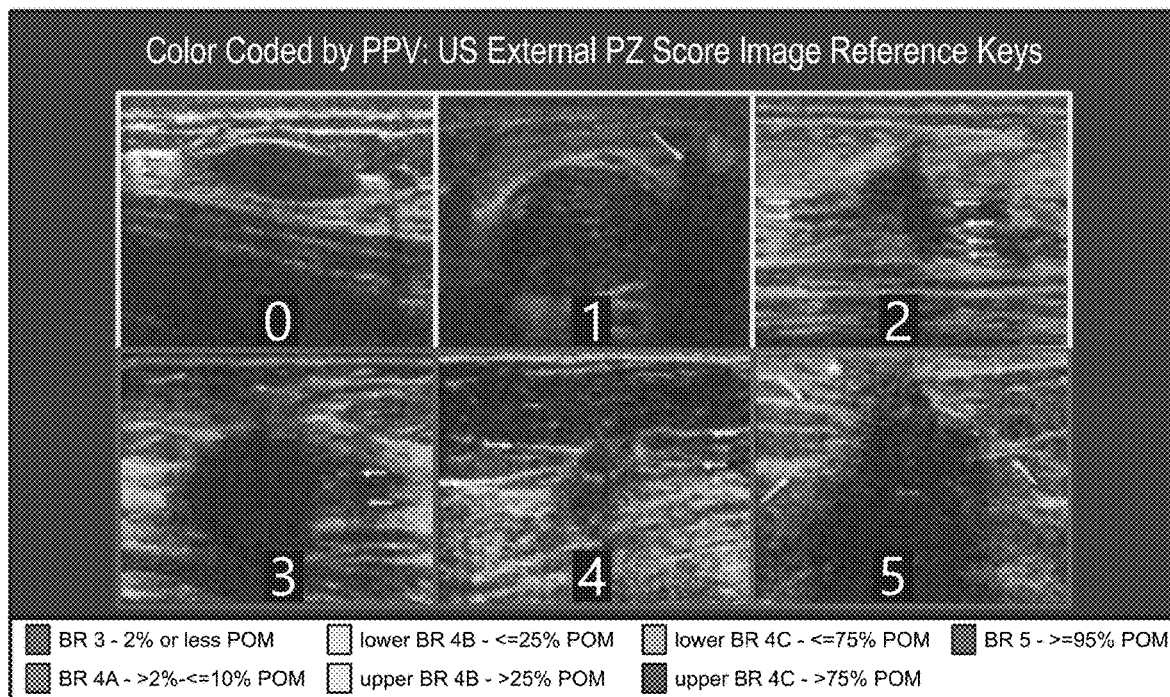
FIG. 4K illustrates an example of an image key for images with different US peripheral zones that warrant corresponding different peripheral zone feature scores 0-5.
Figure 4L:
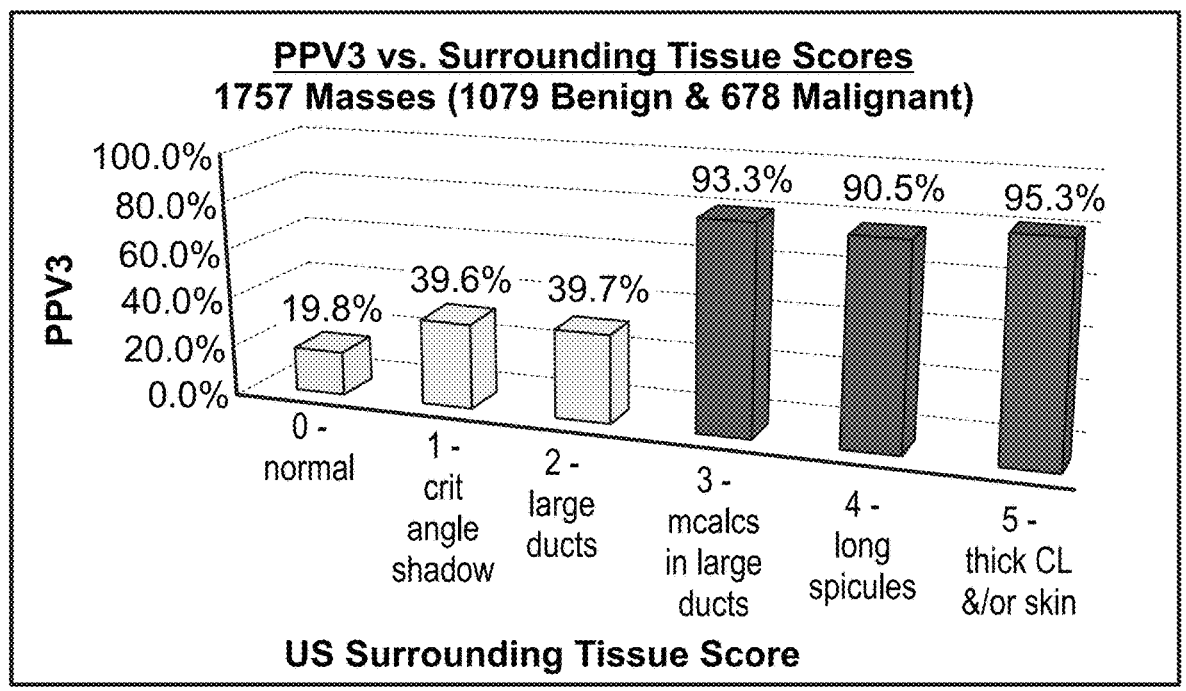
FIG. 4L illustrates an example of a relation between positive predictive values and US peripheral zone feature scores.

FIG. 4K illustrates an example of an image key for images with different peripheral zones that warrant corresponding different peripheral zone feature scores 0-5. The color coded key at the bottom of FIG. 4K illustrates corresponding PPVs associated with the different peripheral zone feature scores (assuming no other feature scoring information). FIG. 4L illustrates an example of a relation between positive predictive values and peripheral zone feature scores. The PPV rises continuously with increasing feature score. The peripheral feature score exhibits a great positive predictor of cancer with scores of 3, 4 and 5 having PPVs over 90%. However, the peripheral feature score exhibits a poor negative predictor in the absence of CA because some cancers are not spiculated. The peripheral zone may exhibit an interrupted tissue plane. The interrupted tissue plane may be considered in the same manner as thin peripheral zone spicules. For example, a peripheral zone that exhibits an interrupted tissue plane may be assigned a PZ score of 4.

In accordance with new and unique aspects herein, it has been recognized that peripheral zone spicules are always hyperechoic to fat but can be hypoechoic relative to hyperechoic interlobular stromal fibrous tissue. Interrupted tissue planes should be scored in the same manner as hyperechoic spicules, by assigning a score of 4. Peripheral zone spicules can extend greater than or equal to 2 cm into surrounding tissues on each side of a mass. Peripheral zone spicules and interrupted tissue planes may occur only on one side of a mass. Peripheral zone spicules can be oriented parallel to each other, but often diverge in a butterfly or bowtie fashion. Diverging hyperechoic spicule lines have a higher probability of malignancy than do parallel spicule lines. Peripheral zone spicules are most common on sides of a mass in the coronal plane. Peripheral zone spicules often appear on a SAX (short axis) sweep across a mass and appear to retract in toward the mass in a bowtie or butterfly pattern.

A single frame of a video sweep or a still image can show either no spicules or only a single spicule in one side of the mass. The video sweep across the short axis of the mass, on the other hand usually shows more numerous spicules that are more widely distributed around the mass. To facilitate recognition of hyperechoic spicules, the following points should be considered. The analysis should analyze images in the coronal plane along the sides of the mass, as the path of lowest resistance for invasion and for formation of spicules is within the coronal plane. While 3-D images with coronal plane imaging facilitate demonstration of spicules, short axis video sweeps may represent a more widely available type of 3-D imaging. In connection with 2-D imaging, spicules in the coronal plane are readily seen in the video SAX sweep where spicules can be seen "pulling in" and "pushing out" in a bowtie or butterfly fashion from the central nidus as the 2-D probe is swept back and forth through the lesion. Hyperechoic lines diverging in a bowtie or butterfly fashion are an indicator of a very high LOM/PPV and exhibit fewer false positives. Parallel hyperechoic lines, on the other hand, sometimes merely represent compressed tissue planes or septi within the breast and will have lower LOM/PPV and exhibit more false positives.

In accordance with new and unique aspects herein, it has been recognized that enlarged surrounding ducts within the peripheral zone are a good characteristic of interest when assigning a peripheral zone feature score. Certain items can be derived from the fact that the greatest ductal or acinar enlargement requires four components. The OA/US imaging can see 3 CIS because it grossly enlarges ducts and the viewer can readily distinguish them from normal docs (e.g., 4-20 times larger than a normal docs size, up to 2-3 mm). Also, the OA/US imaging can see some grade 2 CIS because some grade 2 CIS enlarge ducts enough to enable distinction of the ducts from normal docs (e.g., 2-4 times a normal duct size). The OA/US imaging may not notably illustrate grade 1 CIS because it does not enlarge the ducts enough to distinguish effected ducts from normal docs. Grade 1 CIS are generally only visible on OA/US images when the region is intra-cystic, grossly enlarges a single TDLU, or develops into a pre-existing papilloma or radial scar.

High peripheral zone feature scores exhibit one of the highest (or the highest) PPV as compared to any other internal or boundary zone feature score, whether based on US only, OA only, or a combination thereof. Recognizing the presence of characteristics of interest within the peripheral zone will always create a BI-RADS 4C or greater classification. Not recognizing the existence of a characteristic of interest in the peripheral zone could lead to under classification of masses to the downgrade of a BI-RADS 4A category. Trying to downgrade BI-RADS 4C or 5 masses that are under classified as BI-RADS 4A will contribute to false negatives and could cause a significant loss of US or OA sensitivity.

OA Feature Scores

OA feature scores are based upon a mixture of morphologic and functional changes that tend to occur within and around malignant breast masses. The ability of OA to help to better distinguish between benign and malignant breast masses is based upon its ability to demonstrate the presence of tumor neovessels and also the relatively greater metabolic activity of malignant masses that manifests as relatively greater degrees of deoxygenation caused by malignancies. OA can show these changes both within a malignant mass and within the tissues that surround the malignant mass. The morphologic features that OA demonstrates include:

1) the gray scale ultrasound appearance of the mass and its effect upon surrounding tissues, 2) the presence or absence of malignant neovessels, 3) the number and distribution of neovessels, and 4) anatomy and orientation of the neovessels versus normal vessels. The functional feature that OA demonstrates.

The functional feature that OA demonstrates is the relative degree of deoxygenation within and around the malignant mass.

The novel ordinal scoring system described below is based upon the extent of the combination of morphologic and functional changes that OA demonstrates with a malignant breast mass and within the tissues that surround a malignant breast mass. The ordinal scores for each OA feature are arranged so that the more morphologically and functionally abnormal the features are, the higher the ordinal feature score that will be assigned.

Next, the discussion turns to OA feature scores and the use of OA feature scoring as a biomarker in general, as well as for molecular subtyping of tumors. The OA feature scoring may be utilized in various manners. For example, OA feature scoring may be utilized as a qualitative diagnostic biomarker, such as to assist in making a binary decision (e.g., biopsy versus no biopsy). Additionally or alternatively, the qualitative diagnostic biomarker may be utilized to identify a BI-RADS 3 or less versus BI-RADS 4A or higher. The OA feature scores may also be utilized as semi-quantitative predictive biomarkers, such as to help objectively assign a LOM/PPV and BI-RADS category when a risk of malignancy is above 2%. The OA feature scores may also be utilized as a prognostic biomarker, such as when correlating particular OA feature scores with primary biomarkers and molecular subtypes. For example, the primary biomarkers may represent histologic grade, size and positive LN rates. The secondary biomarkers represent ER, PR, HDR to status, and KI-67 proliferative index. The secondary biomarkers may be utilized as a surrogate for genetic assays to identify molecular subtypes. As further examples, the OA feature scores may be utilized to determine one or more of i) percentage chance/probability of malignancy of a mass, ii) a likelihood of a clinical event, disease progression or reoccurrence, iii) molecular subtype, iv) histologic grade, v) degree of angiogenesis, vi) likelihood of lymph node metastasis, vii) assess the status of a disease or condition to find evidence of exposure to, or effects of, a medical product or environmental agent, viii) change in a patient condition (e.g., tumor size and volume), ix) indicator of an effect of a response to an exposure intervention, x) detect or confirm a disease or condition, xi) identify specific disease subtype, xii) possibility that mutations in genes are predictive of response to certain inhibitors, xiv) likelihood that ER and PR possible breast cancers respond to endocrine therapy, xv) possibility that dense breast tissue is predictive of decreased sensitivity of mammography for detecting noncalcified breast cancer.

Figure 5A:
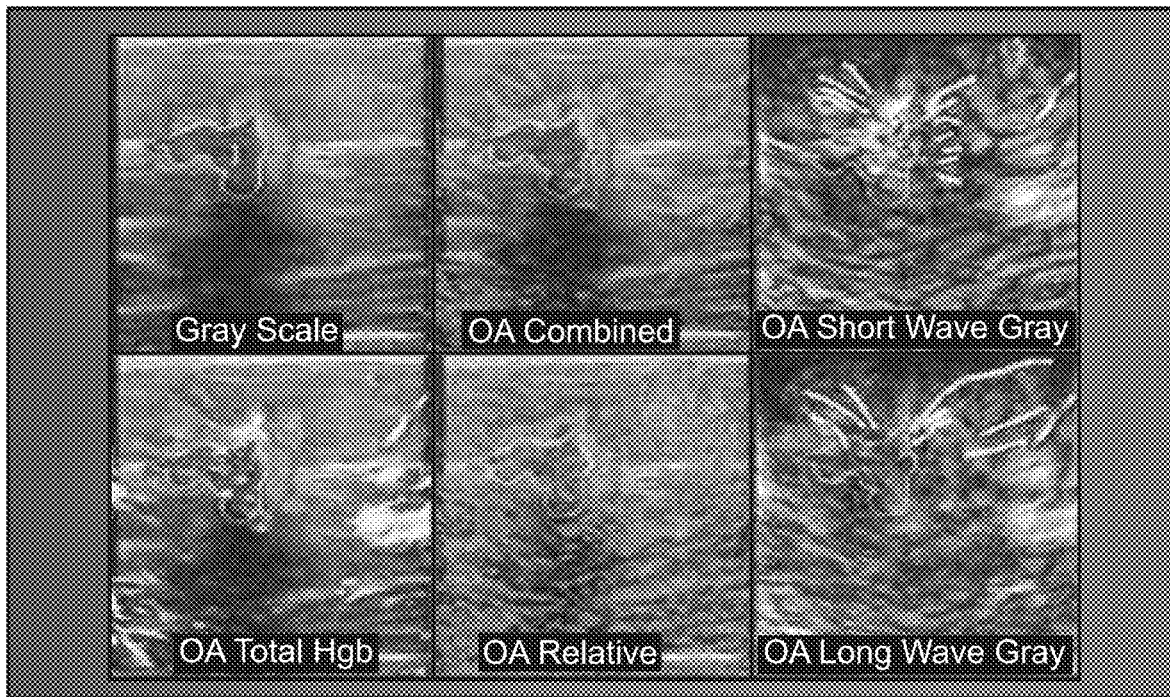
FIG. 5A illustrates an example of a set of images that may be co-displayed while medical personnel are assigning the various US feature scores and/or OA feature scores.

FIG. 5A illustrates an example of a set of images that may be co-displayed while medical personnel are assigning the various US feature scores and/or OA feature scores. The six co-registered two-dimensional images comprise:

1) a grayscale ultrasound image in the left upper corner,
2) an OA gray scale short wavelength image in the right upper corner,
3) an OA gray scale long wavelength image in the right lower corner,
4) a yellow-colored total hemoglobin image in the left lower corner,
5) a red-green colored relative OA map in the bottom center panel, and
6) a red-green colored combined OA image in the upper central panel.

The 5 OA images are co-registered the gray scale ultrasound image and include interior and exterior region of interest (ROI) outlines separating the internal zone, boundary zone and peripheral zone from each other. Three internal zone feature scores and to external zone feature scores, as well as various combinations thereof, are assigned in connection with one or more masses in the region of interest. The three internal OA feature scores represent:

1) an internal vessel feature score (usually assigned from the OA combined map),
2) an internal deoxygenated blush score (always assigned from the OA relative map),
3) a total hemoglobin score (always assigned from in the OA total hemoglobin map).

The two external feature scores include:

1) the external OA boundary zone vessel score and
2) the external OA peripheral zone vessel score.

The boundary zone vessels may be scored based on capsular vessels (usually the OA combined map, sometimes the OA relative map or OA total map), and boundary zone deoxygenated blood (the OA relative map). The peripheral zone vessels are scored based on peripheral zone radiating vessels (the OA total hemoglobin map, and any other map except the OA relative map).

By way of example, the scores may range between 0-5 or 0-6 with an OA feature scores of zero representing a benign condition and with scores of 5 or 6 representing an OA feature score that is highly suspicious for malignancy. In accordance with embodiments herein, the medical personnel may be directed to assign the corresponding feature scores in a particular order, such as to score the peripheral zone first, followed by the boundary zone, followed by the three feature scores for the internal zone. Additionally or alternatively, when a subset of the feature scores are utilized, the order in which features are scored may vary.

Various combinations of the images in FIG. 5A may be utilized in connection with scoring different features. For example, the OA combining image/map may be utilized to score internal zone features, such as the internal vessels and their relative degrees of oxygenation. The OA combined image/map may also be used, occasionally, for scoring the boundary zone and/or the peripheral zone. The OA grayscale short wavelength image/map may be utilized as a confirmation for internal deoxygenated blush, and as a confirmation of peripheral radiating vessels. The OA total image/map may be utilized for scoring internal vessels and must be used for scoring the internal total hemoglobin. The OA total image/map may also be utilized in connection with scoring the boundary zone and identifying radiating vessels in the peripheral zone. The OA relative image/map must be utilized to score the internal the oxygenation blush and boundary zone blush. The OA relative image/map may also be utilized to identify high to confirm pretest probabilities of cancer or to compensate for relative under colorization, to determine when the background is too noisy for peripheral vessel evaluation, to determine whether a high pretest probability exists and to determine when there is a relative under colorization. The OA grayscale long wavelength image/map may be utilized as a confirmation of radiating vessel patterns in the peripheral region and is a confirmation for interference lines.

In accordance with new and unique aspects herein, it has been recognized that scores, aside from the OA images/maps may be relatively overweighted in different manners in connection with scoring. For example, the OA total image/map and the OA combined image/map (which represent the quietest maps) may be overweighted when 1) a mass has already been assigned a LOM/PPV of 10% or less through analysis with another modality, such as US only, MRI, CT, etc. and prior to OA imaging, 2) there is no relative under colorization and 3) downgrading is a primary goal of the analysis. As another example, the OA relative image/map may be overweighted (which represents the most sensitive map) when 1) a pre-OA LOM/PPV is 20% or more, 2) there is relative under colorization and 3) upgrading or confirming high index of suspicion is a main goal. As another example, the OA short wavelength image/map may be utilized as a supplement to confirm radiating red vessels in the boundary zone or peripheral zone and to confirm red gel standoff or nipple artifacts. As another example, the OA long wavelength image/map may be utilized as a supplement to confirm green radiating vessels in the boundary zone or peripheral zone and to confirm green interference lines.

While certain aspects herein utilize all five OA maps, it is recognized that certain maps have different relative strengths. The OA total and OA combined maps represent the quietest maps and may be utilized as the primary maps in connection with downgrading pre-OA BI-RADS classifications. The OA relative map may be overweighted as the main map in connection with upgrading pre-OA BI-RADS classifications and as the main map to confirm high pre-OA suspicion of malignancy. The OA relative map may be overweighted when there is relative under colorization. The OA short wavelength map may be utilized to confirm certain colors, particularly in the peripheral zone. The OA long wavelength map may be utilized to confirm certain colors, particularly in interference artifacts.

OA Internal Vessel Score

By way of example, the OA internal vessel feature score may be assigned an integer value between 0-5, each of which has a corresponding LOM/PPV range as noted, such as based on the following:

0=No internal vessels (lower BR 4B, <=25% PPV)
1=Normal internal vessel(s) without branches, green or red (lower BR 4B, <=25% PPV)
2=Normal internal vessel(s) with branches, green or red (upper BR 4B, >25% PPV)
3=Internal speckle–green≥red in amount and red<background red (upper BR 4B, >25% PPV)
4=Internal speckle–red>green and IZ red>red in background (lower BR 4C, <=75% PPV)
5=Multiple internal red (deoxygenated) polymorphic vessels (lower BR 4C, <=75% PPV)

Figure 6A:
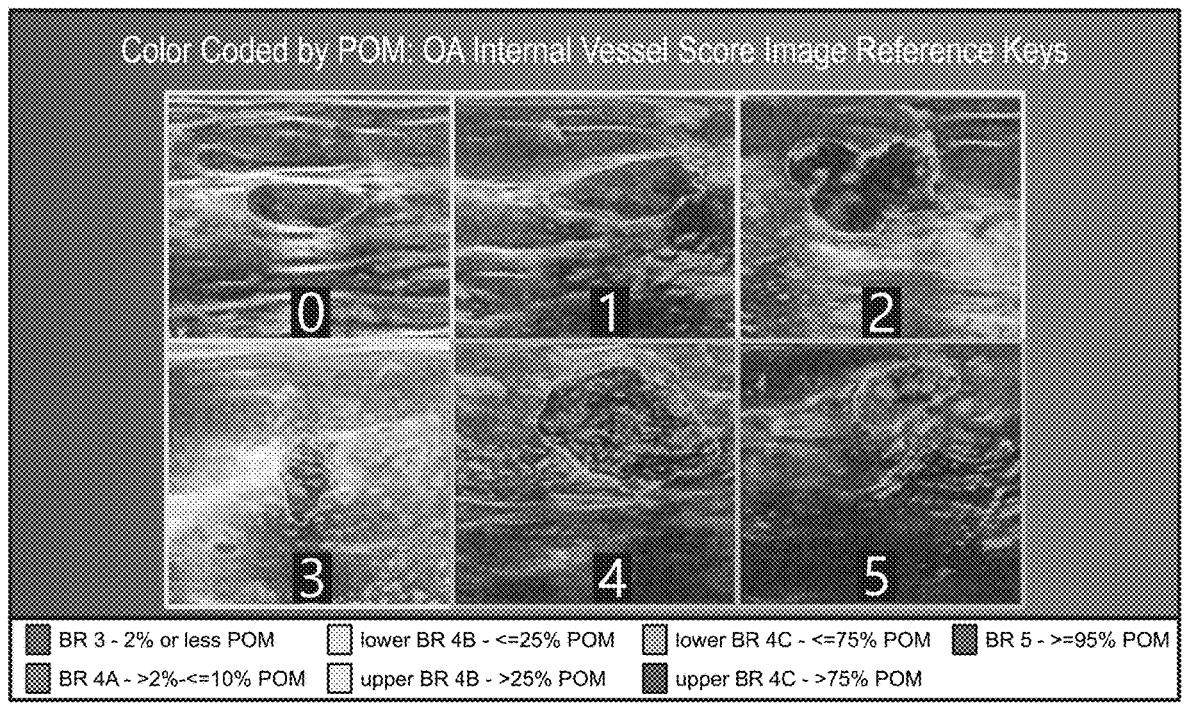
FIG. 6A illustrates an example of an image reference key for images with different OA internal zones that warrant corresponding different OA internal vessel feature scores 0-5.

FIG. 6A illustrates an example of an image reference key for images with different OA internal zones that warrant corresponding different OA internal vessel feature scores 0-5. The color coded PPV key at the bottom of FIG. 6A illustrates corresponding color coded PPVs associated with the different OA internal vessel feature scores (assuming no other feature scoring information).

Figure 6B:
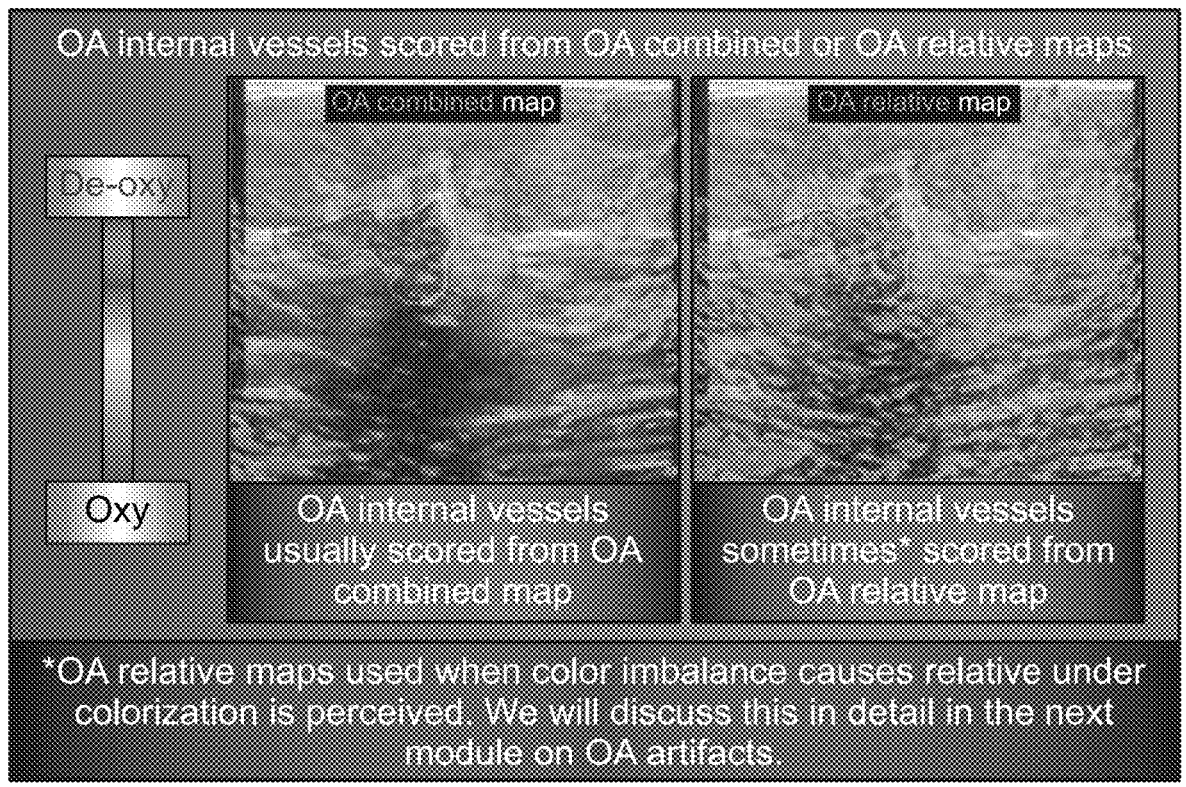
FIG. 6B illustrates an example of an OA combined map and OA relative map with interior and exterior ROI lines drawn to separate the internal, boundary and peripheral zones.
Figure 6C:
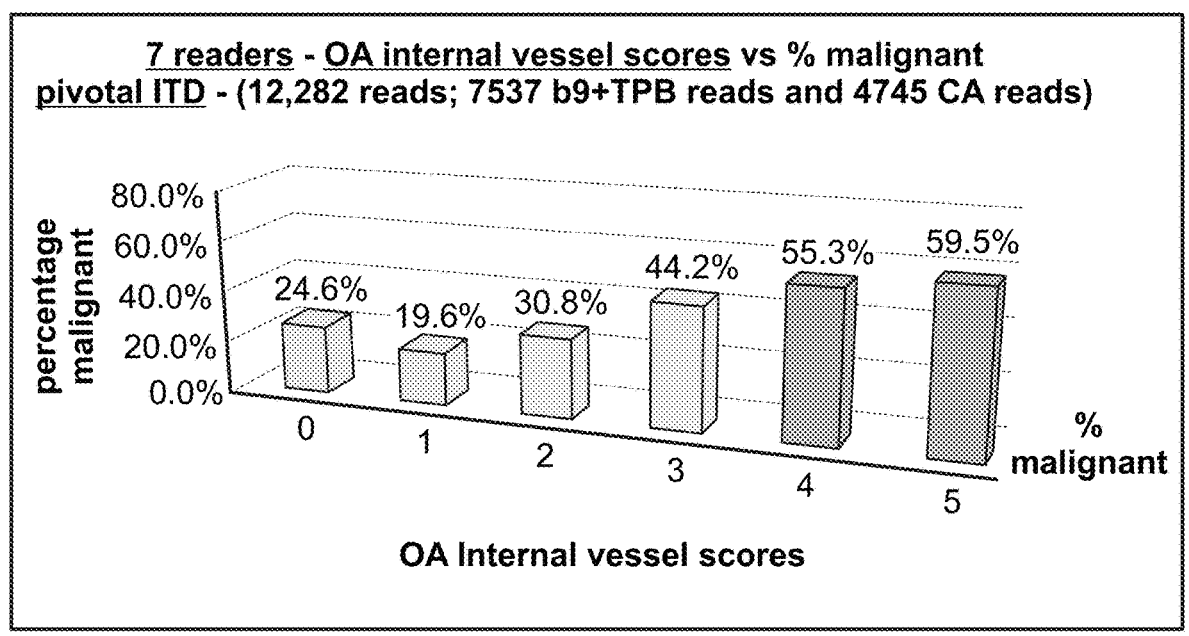
FIG. 6C illustrates an example of a relation between positive predictive values (PPVs) and OA internal vessel feature scores.

FIG. 6B illustrates an example of and OA combined map and OA relative map with interior and exterior ROI lines drawn to separate the internal, boundary and peripheral zones. The OA relative map may be utilized in connection with scoring the OA internal vessels, such as when a color imbalance causes relative under colorization. FIG. 6C illustrates an example of a relation between positive predictive values (PPVs) and OA internal vessel feature scores. The PPV rises continuously with increasing feature score. The graph of FIG. 6C illustrates that the OA internal vessel score is a good positive predictor of malignancy but, taken alone, is not necessarily a good negative predictor of the absence of malignancy. Instead, the OA internal vessel score should be combined with one or more other feature scores that have lower PPVs at scores of zero and one in order to exclude cancers.

A false negative low OA internal vessel score may be caused by:
1) acoustic shadowing which tends to contribute to significant OA shadowing, thereby diminishing the internal OA signals.
2) Also, the OA internal vessel score, when taken alone, may indicate false negatives in connection with central fibrous in grade I and II and lumen A invasive breast cancers.
3) As another example, the OA internal vessel score, when taken alone, may indicate false negatives in connection with central necrosis in grade III and triple negative invasive breast cancers.

OA Internal Total Hemoglobin Score

By way of example, the OA internal total hemoglobin feature score may be assigned an integer value between 0-5, each of which has a corresponding LOM/PPV as noted, such as based on the following:

0=No internal hemoglobin (lower BR 4B, <=25% PPV)
1=Minimal internal hemoglobin<background (lower BR 4B, <=25% PPV)
2=Minimal # internal discrete vessels<=background (upper BR 4B, >25% PPV)
3=Moderate # internal discrete vessels=background (lower BR 4C, <=75% PPV)
4=Many large polymorphic internal vessels>background (lower BR 4C, <=75% PPV)
5=Many large polymorphic vessels almost fill lesion (lower BR 4C, <=75% PPV)

Figure 6D:
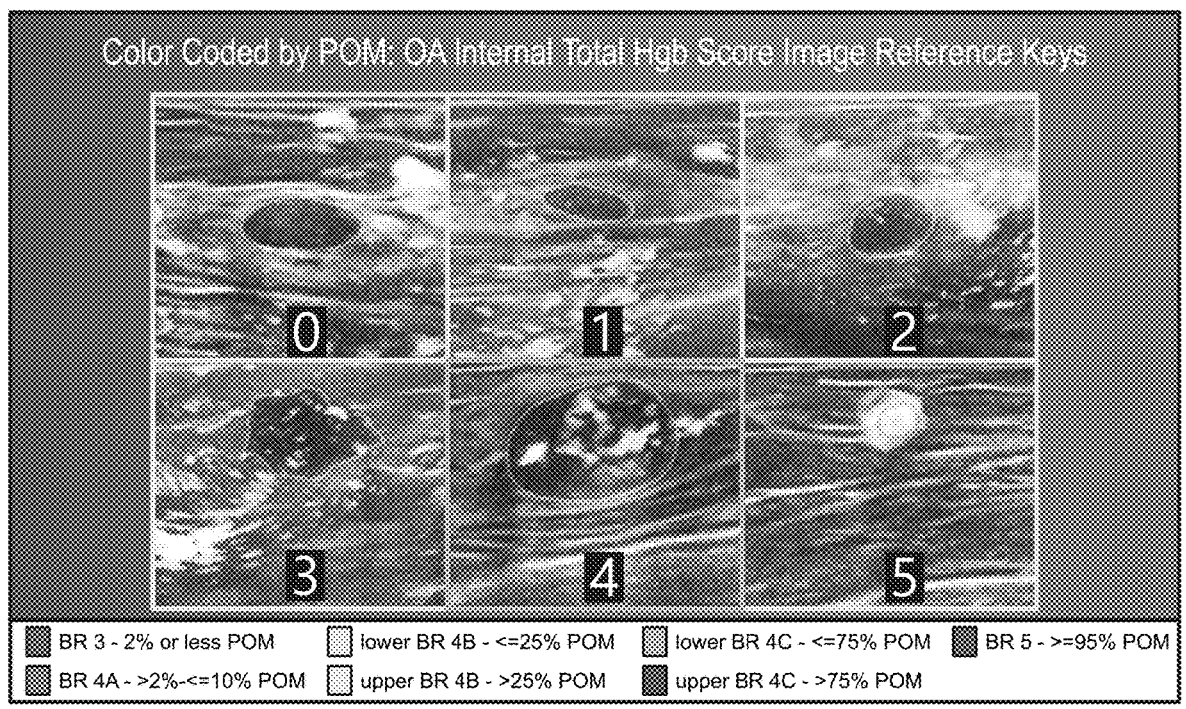
FIG. 6D illustrates an example of an image reference key for images with different OA internal zones that warrant corresponding different OA internal total hemoglobin feature scores 0-5.
Figure 6E:
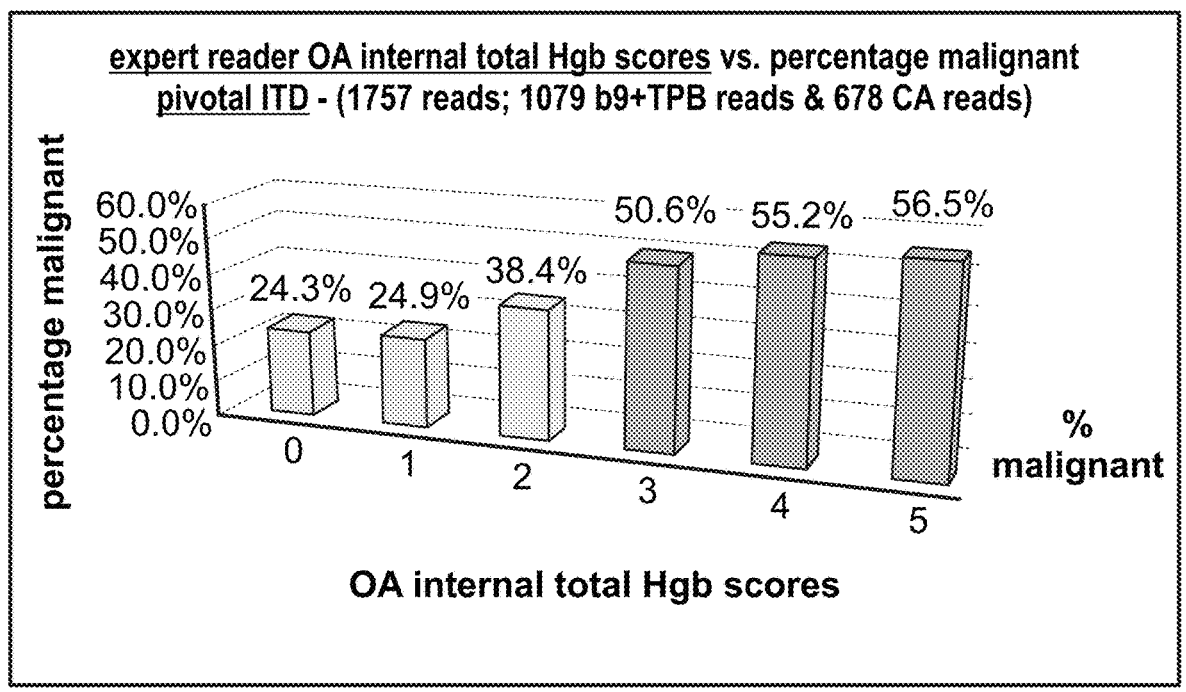
FIG. 6E illustrates an example of a relation between positive predictive values and OA internal total hemoglobin feature scores.

FIG. 6D illustrates an example of an image reference key for images with different OA internal zones that warrant corresponding different OA internal total hemoglobin feature scores 0-5. The color-coded PPV key at the bottom of FIG. 6D illustrates corresponding color-coded PPVs associated with the different OA internal total hemoglobin feature scores (assuming no other feature scoring information). FIG. 6E illustrates an example of a relation between positive predictive values and OA internal total hemoglobin feature scores. As shown in FIG. 6D, the OA internal total hemoglobin score is a good positive predictor of malignancy, but when taken alone, is not a good negative predictor of the absence of malignancy. The OA internal total hemoglobin score should be considered in combination with one or more other feature scores that have lower PPVs at scores of zero and one in order to exclude malignancies.

OA Internal Deoxygenated Blush Score

By way of example, the OA internal deoxygenated blush feature score may be assigned an integer value between 0-5, each of which has a corresponding LOM/PPV as noted, such as based on the following:

0=No internal vessels (lower BR 4B, <=25% PPV)
1=Minimal internal speckle, all or mostly green (lower BR 4B, <=25% PPV)
2=Mild internal speckle; red<green and red<background red (upper BR 4B, >25% PPV)
3=Mild internal speckle; red≥green, but red<bkgd red (lower BR 4C, <=75% PPV)
4=Moderate internal speckle–red>green and red also>background red (lower BR 4C, <=75% PPV)
5=Internal red blush almost fills lesion (lower BR 4C, <=75% PPV)

Figure 6F:
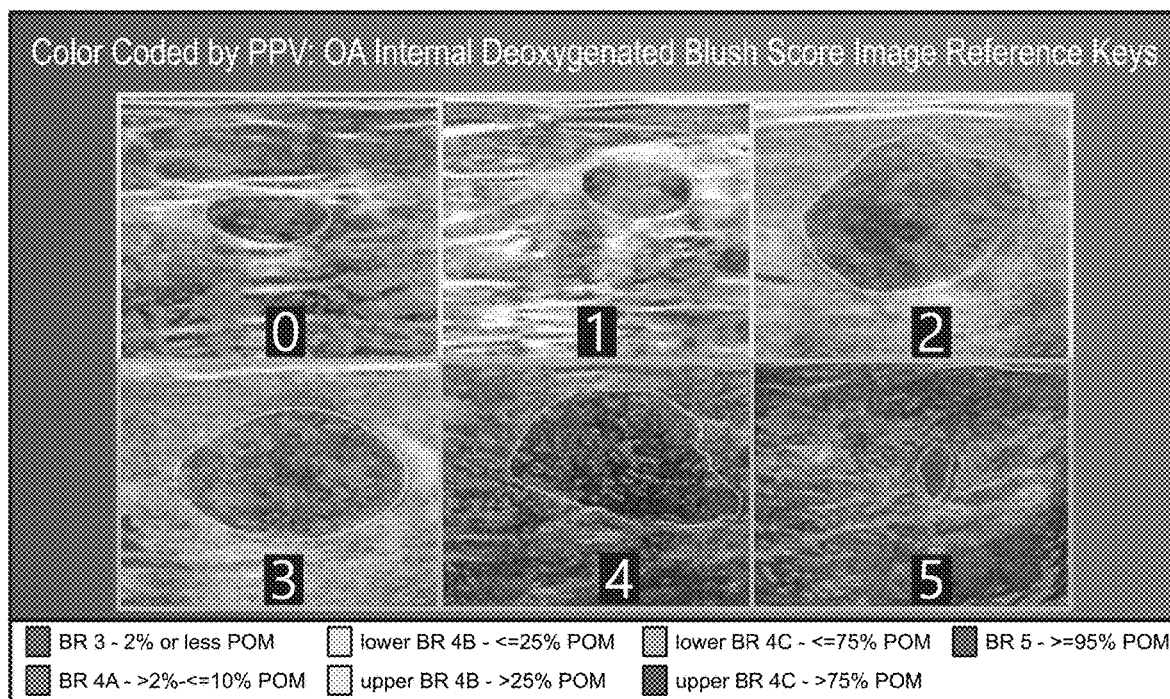
FIG. 6F illustrates an example of an image reference key for images with different OA internal zones that warrant corresponding different OA internal deoxygenated blush feature scores 0-5.
Figure 6G:
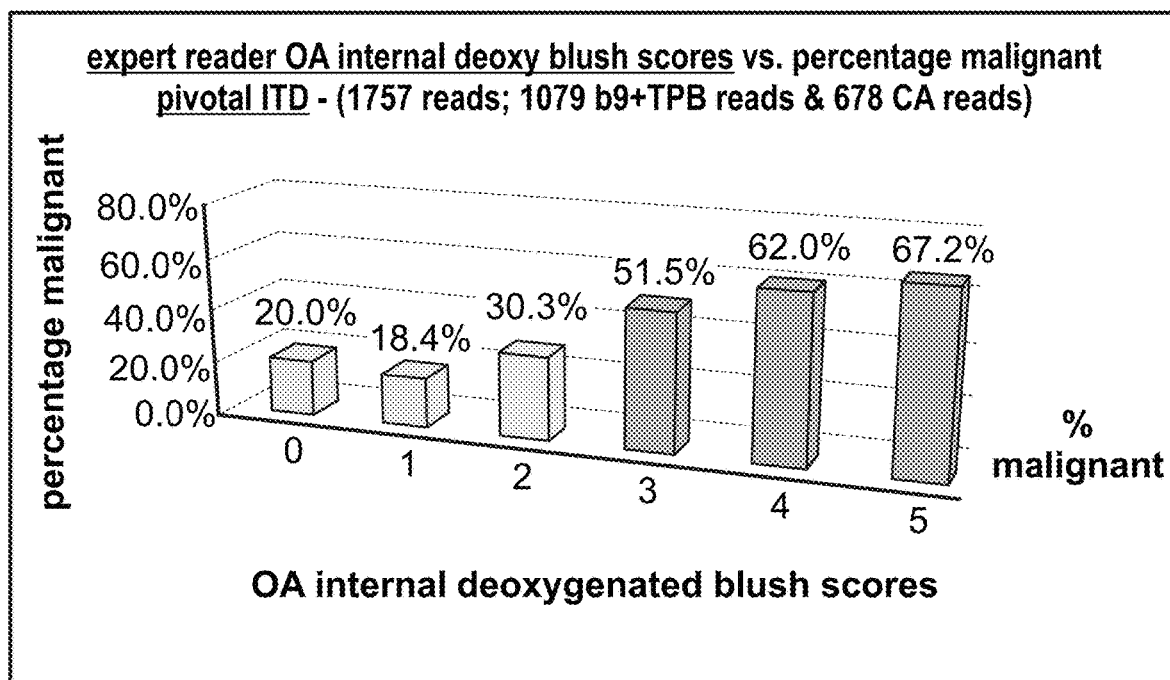
FIG. 6G illustrates an example of a relation between positive predictive values and OA internal deoxygenated blush feature scores.

FIG. 6F illustrates an example of an image reference key for images with different OA internal zones that warrant corresponding different OA internal deoxygenated blush feature scores 0-5. The color-coded PPV key at the bottom of FIG. 6F illustrates corresponding PPVs associated with the different OA internal deoxygenated blush feature scores (assuming no other feature scoring information). FIG. 6G illustrates an example of a relation between positive predictive values and OA internal deoxygenated blush feature scores. As shown in FIG. 6G, the OA internal deoxygenated blush score is a good positive predictor of malignancy, but when taken alone, is not a good negative predictor of the absence of malignancy. The OA internal deoxygenated blush score should be considered in combination with one or more other feature scores that have lower PPVs at scores of zero and one in order to exclude malignancies.

In accordance with new and unique aspects herein it has been recognized that the OA internal feature scores provide certain key information. All living tissues, including benign and malignant masses, have blood flow and use oxygen. All masses, benign and malignant will have some red and some green vessels (associated with responsiveness to Long wavelength and short wavelength OA transmissions). Distinguishing benign versus malignant vessels is not simply based on distinguishing between vessel responsiveness to long and short wavelength OA energy. The morphology of the vessels is important in distinguishing between benign and malignant vessels. Malignant internal vessels are polymorphic, which is evident from immediately adjacent vessels at similar depths that vary in size, shape and orientation. Benign internal vessels are monomorphic, which is evident from adjacent vessels at similar depths within a mass having similar size, shape and orientation. Usually vessel color and vessel morphology are concordant, namely both are similarly suspicious, or both are reassuring. However, vessel color and morphology may be discordant, namely:

1) vessels are relatively deoxygenated and red, but vessel morphology is reassuring, or
2) vessels are relatively oxygenated and green, but vessel morphology is suspiciously polymorphic.

The morphologic findings are more important, the morphologic features should be over weighted, and the mass should be scored from the more robust morphologic vessel features rather than from the less robust functional feature of relative deoxygenation.

OA Capsular/Boundary Zone Vessel Score

In accordance with new and unique aspects herein, and OA capsular/boundary zone vessel feature score is defined that provides a mechanism to robustly distinguish between benign and malignant masses. A surprising and unexpected result resulted from the recognition that the OA BZ vessel feature score is unaffected by shadowing, unaffected by central fibrosis, unaffected by central new grosses, is present in all three histologic grades of invasive breast cancer and is present in all molecular subtypes of invasive breast cancer. A surprising and unexpected result is the recognition that the OA BZ vessel feature score is indicative of the most actively growing portion of a tumor and corresponds to the region in which the immune system most actively attacks/helps the tumor.

Figure 7A:
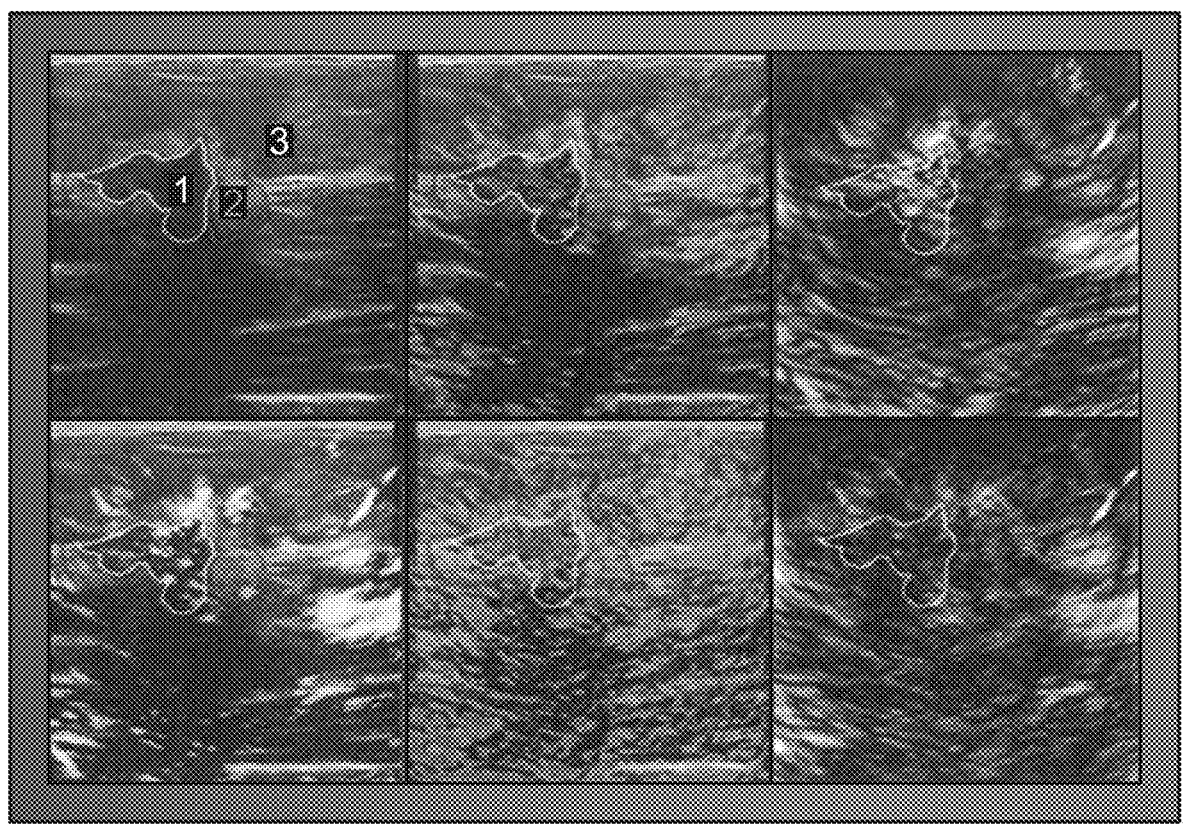
FIG. 7A illustrates an example of a set of six co-registered UL/OA images illustrating the internal zone "1", the boundary zone "2", and the peripheral zone "3".

FIG. 7A illustrates an example of a set of six co-registered UL/OA images illustrating the internal zone "1", the boundary zone "2", and the peripheral zone "3". The boundary zone includes the thick echogenic halo in invasive masses and then hyperechoic thin capsule in benign masses. The peripheral zone lies outside the exterior outline (aqua colored line) and is outside of the thick echogenic halo.

By way of example, the OA capsular/boundary zone vessel feature score may be assigned an integer value between 0-6, each of which has a corresponding LOM/PPV as noted, such as based on the following:

0=No capsular vessels (BR 4A, >2%-<=10% PPV)
1=Normal capsular vessels without branches, parallel to capsule, not perpendicular, long, gently curved, and gradually tapered (green &/or red) (BR 4A, >2%<=10% PPV)
2=Normal capsular vessels with normal tapering acutely angled branches, (green &/or red) (BR 4A, >2%-<=10% PPV)
3=Boundary zone speckle–green≥red in amount and red<background red (upper BR 4B,>25% PPV)
4=Boundary zone speckle–red>green and red>background red (upper BR 4B,>25% PPV)
5=Multiple boundary zone neovessels–short red and/or green perpendicular "whiskers" or red enlarged tortuous vessels in "dot-dash" pattern) (lower BR 4C, <=75% PPV)
6=Boundary zone deoxygenated blush (partial or complete) (lower BR 4C, <=75% PPV).

The OA capsular/BZ vessel score can be obtained from one or more of the OA combined map, OA total map and OA relative map.

Figure 7B:
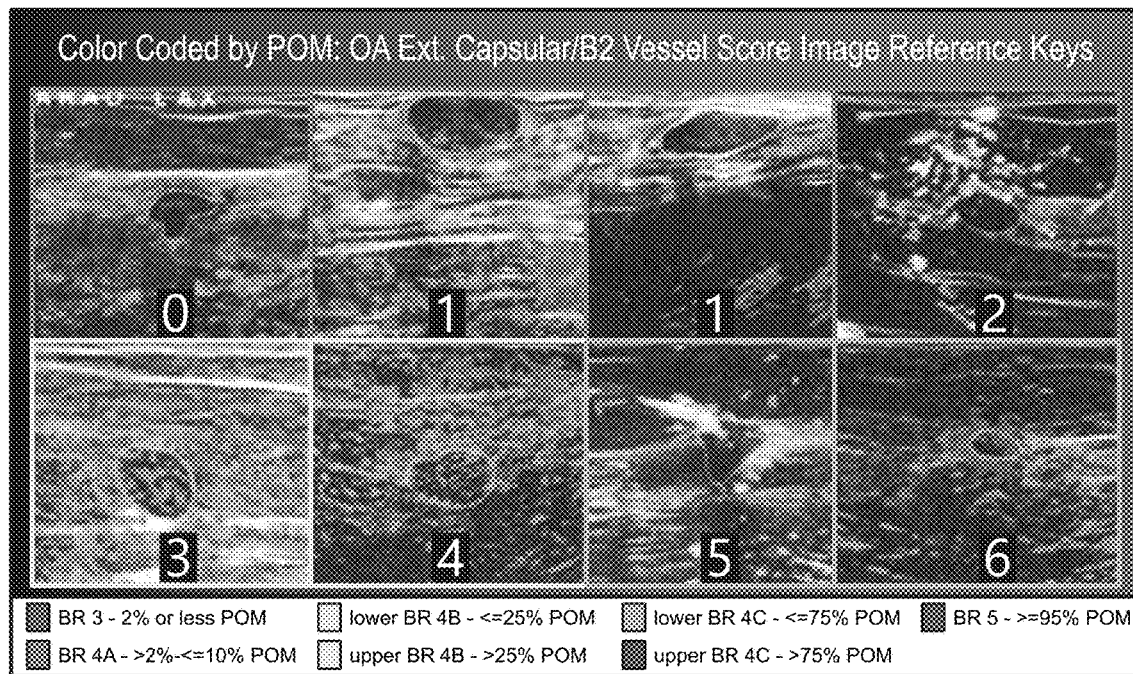
FIG. 7B illustrates an example of an image reference key for images with different OA boundary zones that warrant corresponding different OA capsular/BZ vessel feature scores 0-6.
Figure 7C:
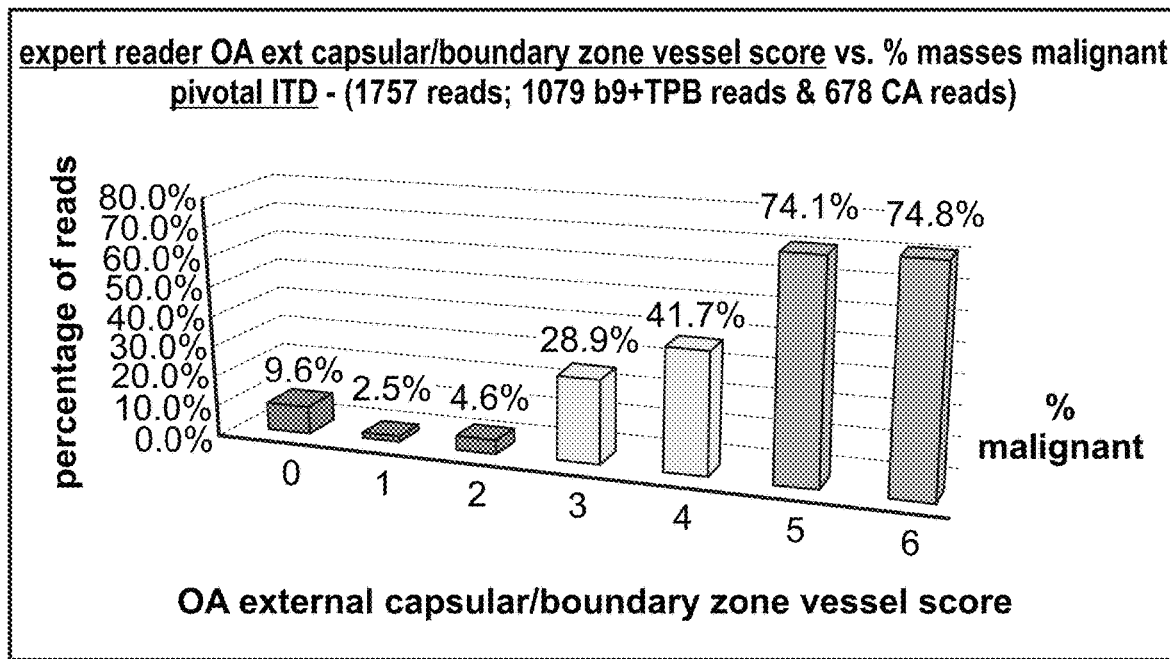
FIG. 7C illustrates an example of a relation between positive predictive values and OA capsular/BZ vessel feature scores.

FIG. 7B illustrates an example of an image reference key for images with different OA boundary zones that warrant corresponding different OA capsular/BZ vessel feature scores 0-6. The color-coded PPV key at the bottom of FIG. 7B illustrates corresponding PPVs associated with the different OA capsular/BZ vessel feature scores. FIG. 7C illustrates an example of a relation between positive predictive values and OA capsular/BZ vessel feature scores. As shown in FIG. 7C, the OA capsular/BZ vessel scores are a good positive predictor of malignancy. In addition, in accordance with new and unique aspects herein, it was found that the OA capsular/BZ vessel score, when taken by itself, also affords a good negative predictor of the absence of malignancy. The OA capsular/BZ vessel score should still be combined with other feature scores that have low PPVs at scores of 0 and 1 in order to exclude cancer.

In accordance with new and unique aspects herein, it was found that a capsular/BZ vessel feature score of 5 should be assigned when a dotted or dashed pattern of tortuous morphologic vessels is present in the boundary zone. It was also found that vessels exhibiting a whisker pattern in the boundary zone are typically present in histologic grade I and II invasive breast cancers and in luminal A molecular subtype invasive breast cancers. It was also found that vessels exhibiting the dotted or dashed pattern in the boundary zone or more typical in histologic grade III invasive breast cancers and triple-negative molecular subtype invasive breast cancers.

Further, in accordance with new and unique aspects herein, it was found that the OA capsular/BZ vessel feature score represents a very robust (if not the most robust) score of the OA feature scores described herein for distinguishing benign from malignant masses and assessing the LOM of the mass. Between benign and malignant masses, the capsular/BZ vessel feature score exhibits a very good (e.g., if not the best) visual separation of scoring distributions, a very wide (if not the widest) separation of means, 99% CIs, medians and interquartile ranges, and a very steep (if not the steepest) PPV slope with the second highest PPV for high scores and the lowest PPV for low scores (relative to the other OA features described herein).

In the event that changes are mistakenly assigned to the internal zone, where such changes should have been assigned to the boundary zone, the mis-assignment may lead to an underestimation of the LOM. Accordingly, an accurate distinction between the internal and boundary zones should be drawn with the interior outline of the ROI. Histologic correlation from various exams show that the interior outline separating the internal and boundary zone should typically be drawn 0.5-1.0 mm inside of the border between the hyperechoic central nidus and the boundary zone (thick echogenic rim—Halo).

In accordance with new and unique aspects herein, it has been found that most boundary zone vessels and malignant masses are neovessels, but some are parasitized native vessels. Boundary zone neovessels are usually, but not always, relatively deoxygenated, although a very strong red signal (indicating deoxygenated blood) elsewhere in the image could cause the vessels to be mis-color to green (incorrectly indicating oxygenated blood). Boundary zone parasitized native vessels can be either arteries or veins, and thus, can be relatively oxygenated (appearing in green color) or relatively deoxygenated (appearing in red color). Thus, the boundary zone vessels having a whisker pattern can be relatively deoxygenated (red) in most cases, relatively oxygenated (green) in some cases, or mixed red and green in some cases.

In accordance with new and unique aspects herein, it has been determined what extent of the boundary zone vessels should exhibit the whisker pattern to be classified as exhibiting a vessel whisker characteristic. The more vessels that exhibit the whisker pattern, the more confident the characterization. The number of vessels exhibiting a whisker pattern necessary to classify a vessel whisker characteristic may be proportional to the background tissue OA signal. In images with a high background OA tissue signal present, it is preferable to have a larger number of vessels exhibiting the whisker pattern. In images with a low the background signal and good colorization, it may be acceptable to have a smaller number of vessels exhibit the whisker pattern.

The whisker pattern in the boundary zone vessels should be distinguished from interference lines. More perpendicular BZ signals have better PPV than fewer perpendicular OA easy signals. More red (deoxygenated) perpendicular BZ signals have better PPV than green (oxygenated) perpendicular OA BZ signals. If three or fewer perpendicular OA BZ signals are present, radiating perpendicular signals have better PPV as compared to parallel concave anterior OA BZ signals (which are more likely interference lines). While a mixture of OA functional information (relative oxygenation/deoxygenation) and also morphology are used for all OA feature scores, vessel morphology is generally more important than oxygenation/deoxygenation in the external capsular/boundary zone.

OA Capsular/Boundary Zone Vessel Score

In accordance with new and unique aspects herein, an OA peripheral zone vessel feature score is defined that provides a mechanism to robustly distinguish between benign and malignant masses. By way of example, the OA peripheral zone vessel feature score may be assigned an integer value between 0-5, each of which has a corresponding LOM/PPV as noted, such as based on the following:

0=No PZ vessels (lower BR 4B, <=25% PPV)
  1=Normal non-branching or branching non-radiating vessels in surrounding tissues (lower BR 4B, <=25% PPV)
  2=Cluster of enlarged, tortuous non-radiating vessels in PZ on one side of mass. (Upper BR 4B, >25% PPV)
  3=One or two radiating PZ vessels on one side of mass (lower BR 4C, <=75% PPV)
  4=More than two radiating vessels on one side of mass (upper BR 4C, >75% PPV)
  5=3 or more radiating vessels on more than one side of mass (i.e., 2 on 1 side, and 1 on another side) (upper BR 4C, >75% PPV)

Figure 8A:
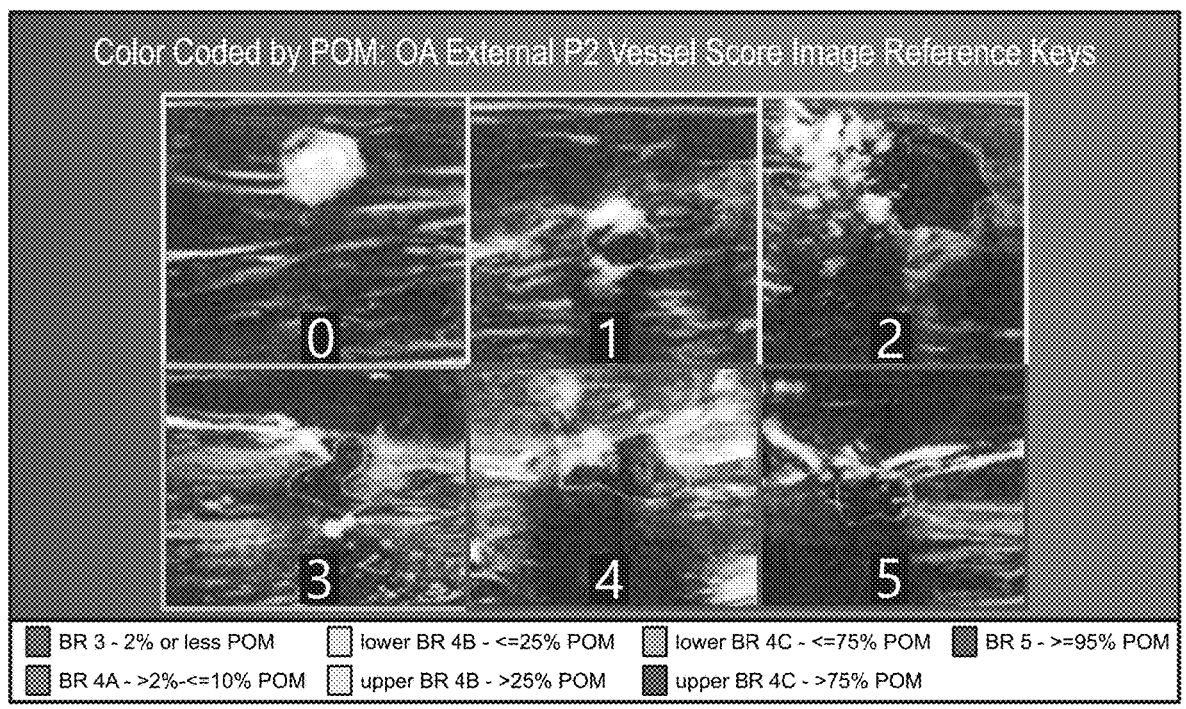
FIG. 8A illustrates an example of an image key for images with different OA peripheral zones that warrant corresponding different OA peripheral zone vessel feature scores 0-5.
Figure 8B:
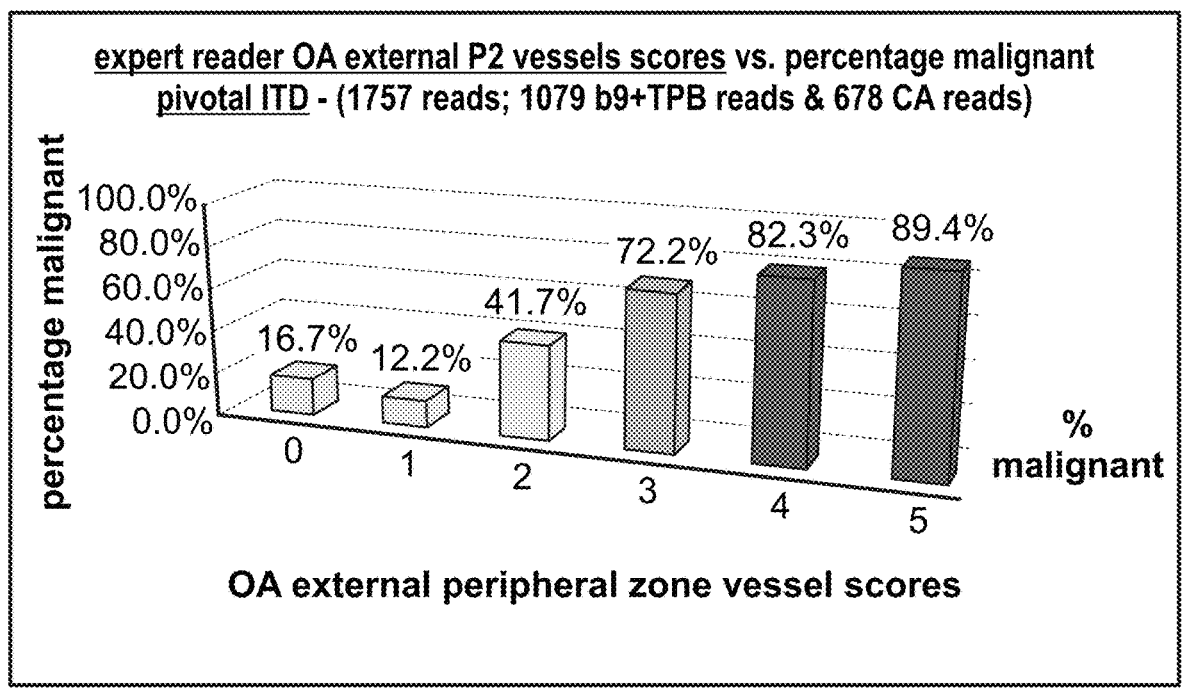
FIG. 8B illustrates an example of a relation between positive predictive values and OA peripheral zone vessel feature scores.

The peripheral zone vessel feature score may be best determined from the OA total map, but optionally may be determined from one or more other maps. In determining the peripheral zone vessel score, care should be taken to distinguish between PC radiating vessels as compared to interference lines. FIG. 8A illustrates an example of an image key for images with different OA peripheral zones that warrant corresponding different OA peripheral zone vessel feature scores 0-5. The color-coded PPV key at the bottom of FIG. 8A illustrates corresponding PPVs associated with the different OA peripheral zone vessel feature scores. FIG. 8B illustrates an example of a relation between positive predictive values and OA peripheral zone vessel feature scores. As shown in FIG. 8B, the OA peripheral zone vessel scores are a good positive predictor of malignancy, and potentially the best PPV as compared to other OA features described herein. However, the peripheral zone feature score may not be a good negative predictor of an absence of malignancy when taken alone, but instead should be combined with one or more other OA feature scores that have lower PPVs at scores of 0 and 1 in order to exclude cancers.

In accordance with new and unique aspects herein, it has been recognized that an OA PZ vessel feature score may be applied in a manner similar to the BZ feature scoring and relies more heavily upon vessel morphology then on relative degrees of oxygenation/deoxygenation. In malignant masses, most vessels within the internal zone and within the boundary zone are relatively deoxygenated neovessels. In the peripheral zone, most vessels or a mixture of oxygenated parasitized native arteries and parasitized deoxygenated native veins. Therefore, in the peripheral zone there will more often be a mixture of red (deoxygenated) and green (oxygenated) vessels that are seen within the internal and boundary zones of most malignant masses. A more important morphologic characteristic of the vessels in the peripheral zone is whether the vessels are radiating or not.

It has been recognized that the OA peripheral zone vessel features are generally most visible on the OA total hemoglobin map. Visibility on the OA total hemoglobin map is due in part to the peripheral zone radiating vessels around invasive malignant masses having mixed oxygenated and deoxygenated vessels which appear as red and green vessels. Is more difficult to appreciate the number of radiating vessels when the vessels are different in color as they are in the OA relative map and/or the OA combined map. In contrast, it is easier to appreciate the number of radiating vessels when they are a single color, such as when the vessels appear in yellow in the OA total hemoglobin map or all appear white as in the OA short wavelength map or OA long wavelength map. The OA total map is subjected to a threshold and us has less interfering background OA noise that surrounds the PZ radiating vessels as compared to the background OA signals in the OA relative map. Parallel adjacent parasitized radiating arteries and veins that appear in the same image voxel can cancel out one another on the OA relative and OA combined maps, making the paried red and green vessels invisible on red and green maps. However, parallel adjacent parasitized radiating arteries and veins, that appear in the same voxel, can add to each other in the total hemoglobin map, appearing wider and more readily visible on the yellow OA total hemoglobin map.

In accordance with new and unique aspects herein, it has been recognized that the OA long wavelength and OA short wavelength maps can be very useful in confirming the presence of peripheral zone radiating vessels. The peripheral zone reading vessels on the grade OA long wavelength and short wavelength maps are the OA counterpart of architectural distortion and mammography. Radiologists are used to looking for architectural distortion on a grayscale background mammography image. The OA short wavelength and long wavelength maps often show longer segments of the peripheral zone radiating vessels then do any of the three colored OA maps (OA total hemoglobin map, OA relative map and OA combined map).

The number of peripheral radiating vessels in various sides of the mass can be determined from the summation of frames in a complete short axis sweep across a mass. The number of peripheral zone radiating vessels should not be determined from the still OA images or from a single frame of a complete video sweep. In a certain percentage (e.g., 15-20%) of invasive malignant masses, all or most tumor vessels are located in a cluster anteriorly between the mass and the skin. When the foregoing condition is present, the mass should be scored to in the OA PZ vessel features score as "a cluster of enlarged and tortious PZ vessels on the side of the mass". A pattern of a cluster of tumor vessels within the anterior boundary zone and peripheral zone of the tumor is relatively common in the subgroup of DCIS that represents a mammographic soft tissue density or palpable mass. The cluster pattern may also be seen in some invasive cancers. While the PPV of a tumor vessel cluster pattern is less than the PPV of peripheral zone radiating vessels, it does have a mild BI-RADS 4B PPV of about 40%.

OA Interfering Artifact Feature Score

In accordance with new and unique aspects herein, an OA interfering artifact feature score is defined that does not provide a mechanism to robustly distinguish between benign and malignant masses. There is no correlation between PPV and OA artifact scores. Rather, the OA artifact score offers an indication about the reliability of the 5 previously discussed feature scores. By way of example, the OA interfering artifact feature score may be assigned an integer value between 0-5, such as based on the following:

0=No significant artifact
1=Minimal artifact, does not interfere with interpretation
2=Moderate artifact, does not interfere with interpretation
3=Moderate artifact, interferes with interpretation
4=Severe artifact, interferes with interpretation
5=Severe artifact, makes OA images uninterpretable.

Figure 9:
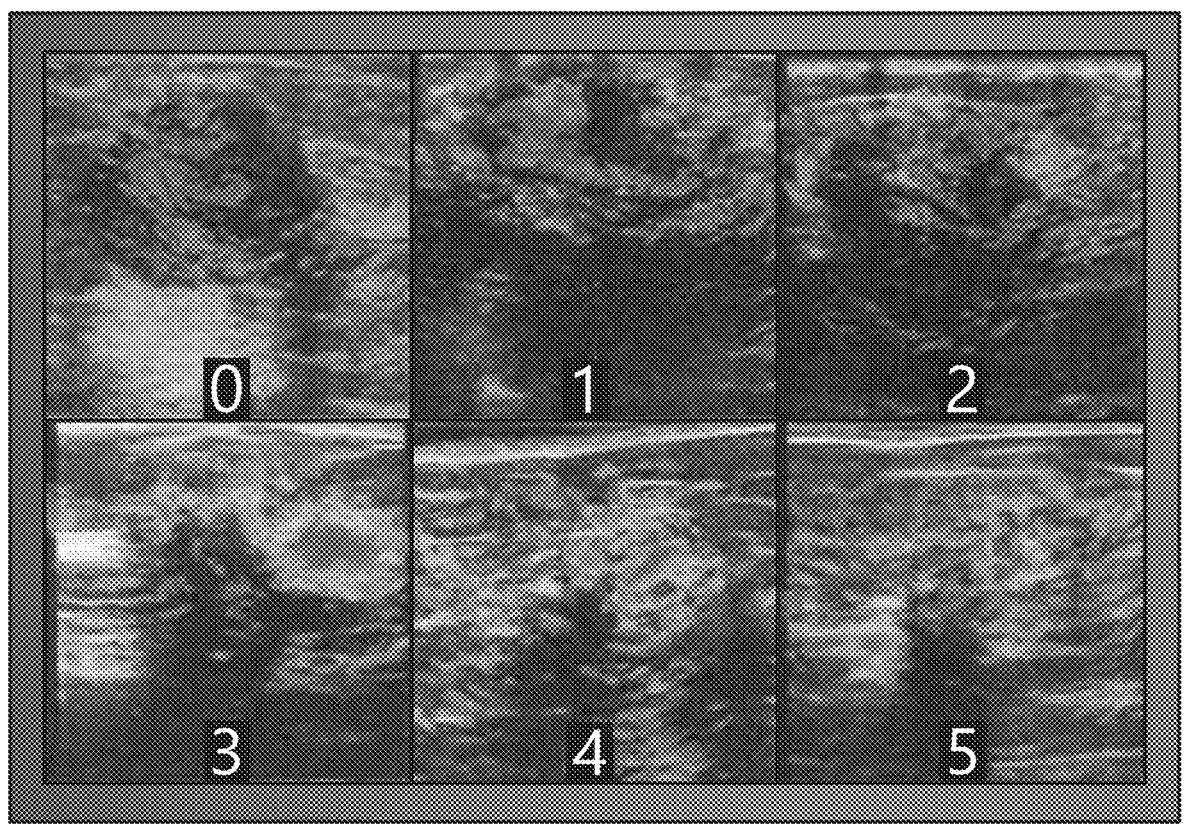
FIG. 9 illustrates an example of an image reference key for images that warrant corresponding different OA interference artifact feature scores 0-5.

The OA interfering artifact feature score may be derived from any of the OA maps, usually the worst of the maps or views. FIG. 9 illustrates an example of an image reference key for images that warrant corresponding different OA interference artifact feature scores 0-5. The OA interfering artifact scores are not necessarily used when estimating a LOM. Instead, the OA artifact score suggests reliability of the OA data, such as whether or not to upgrade or downgrade a rating and how aggressive to be when upgrading or downgrading. For example, artifact scores of 0-3 generally imply reliable OA feature scoring and facilitate aggressive upgrading or downgrading (e.g., including to BI-RADS 2). As another example, an OA artifact scores of 4 imply somewhat less reliable data, allowing a very careful upgrade or downgrade of 1 BI-Rad category in some cases, but never a downgrade to BI-RADS 2 or of 2 steps. And artifact score of 5 indicates that the OA data too unreliable to allow accurate feature scoring, and suggest that the MG, CDU, and/or US LOM/PPV and BI-RADS category should be left unchanged.

Figure 10A:
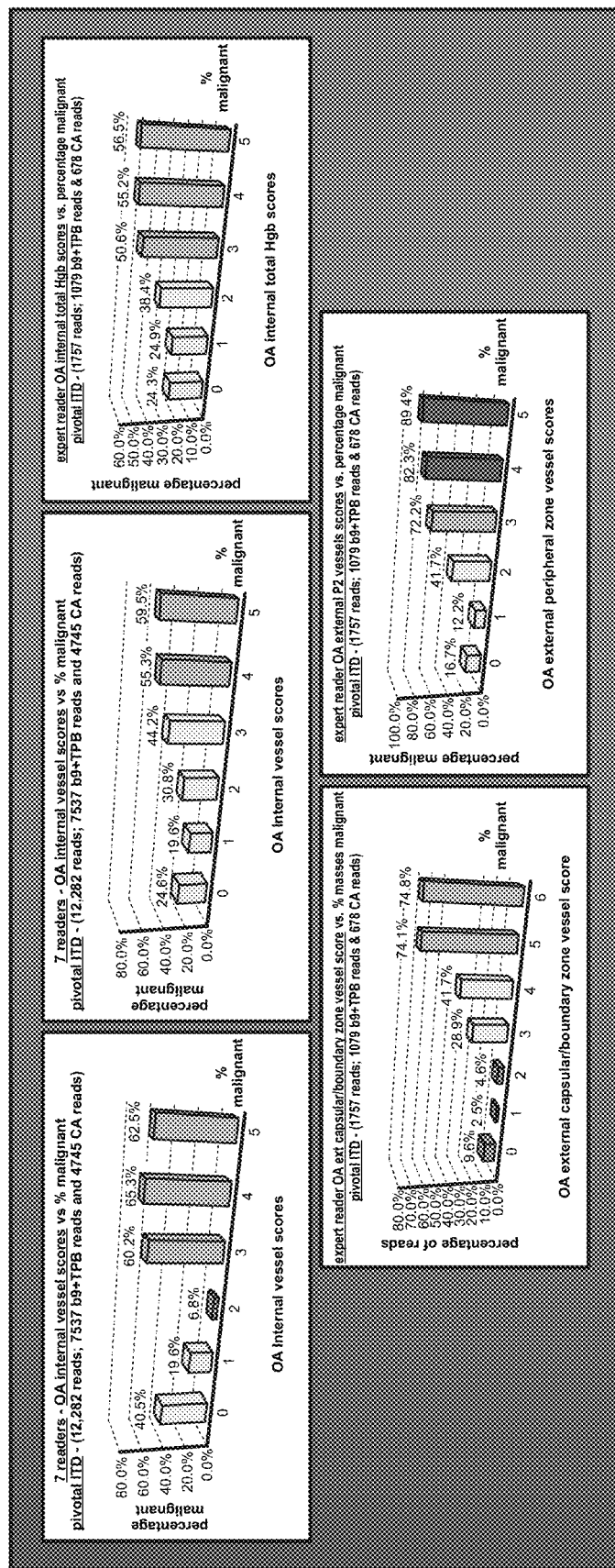
FIG. 10A illustrates an example of individual feature scores derived in connection with an analysis of a number of subjects.
Figure 10B:
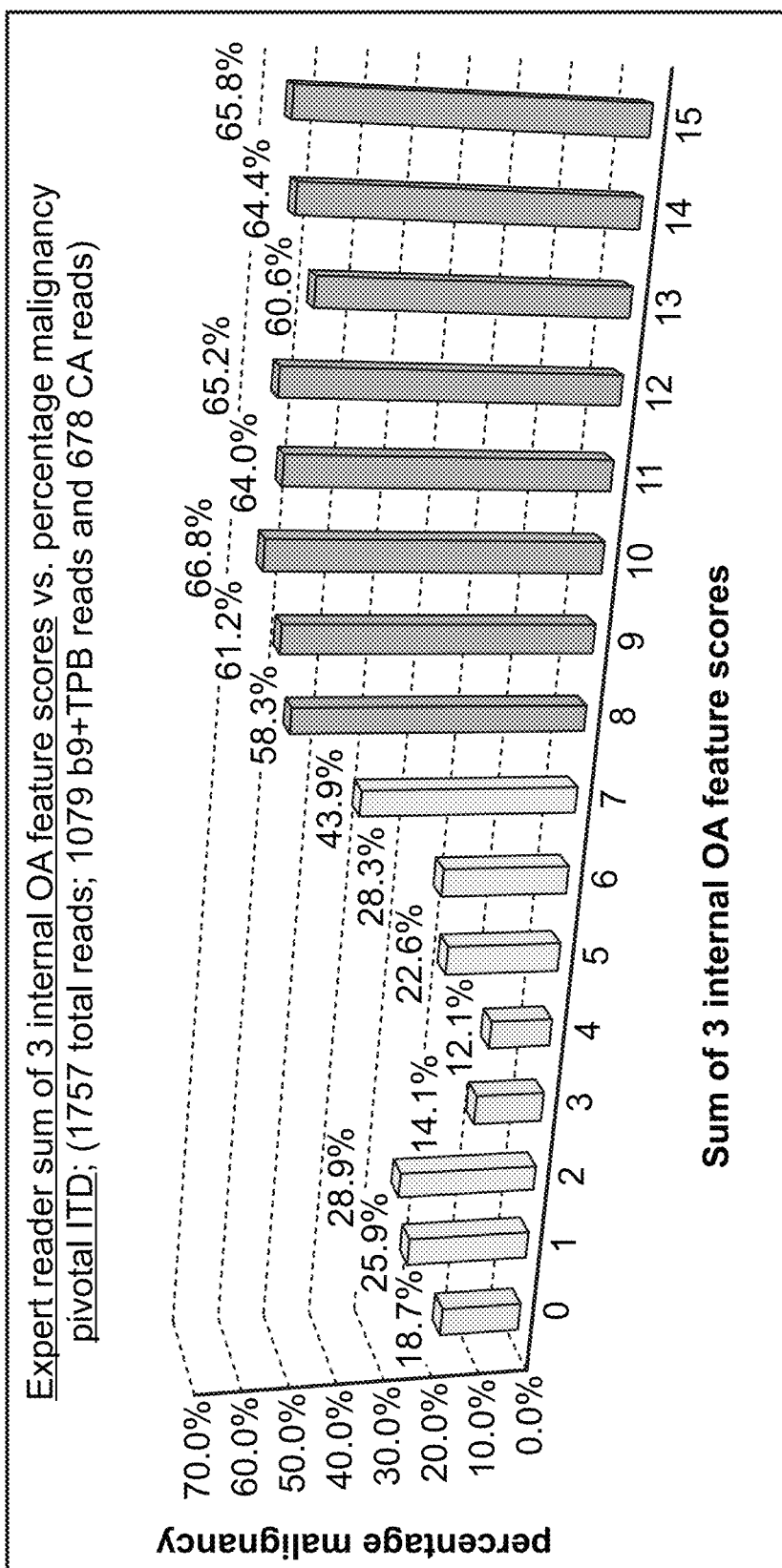
FIG. 10B illustrates an example of a sum of the OA internal feature scores as compared to the PPV.
Figure 10C:
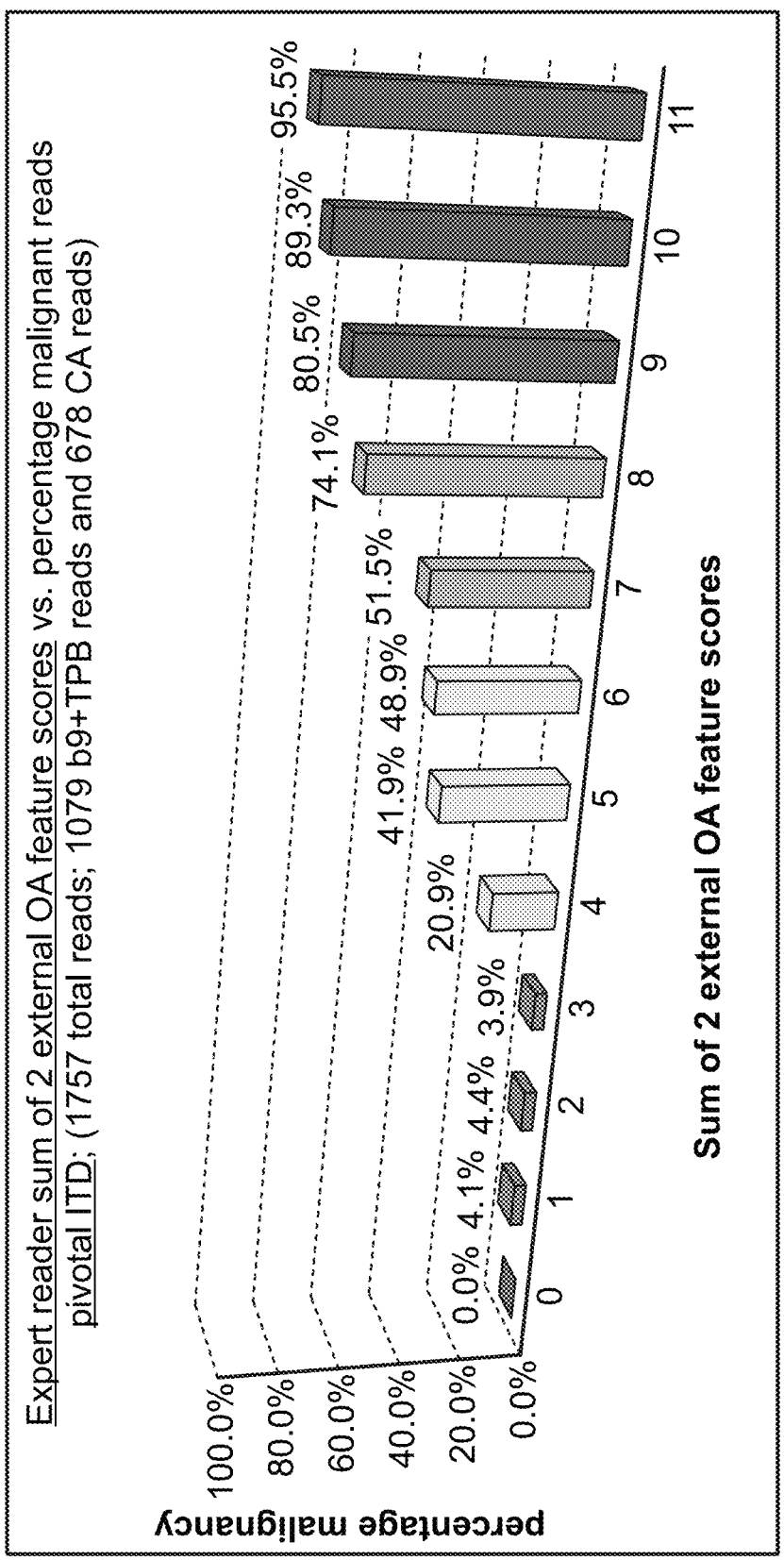
FIG. 10C illustrates an example of a sum of the two OA external feature scores as compared to the PPV.
Figure 10D:
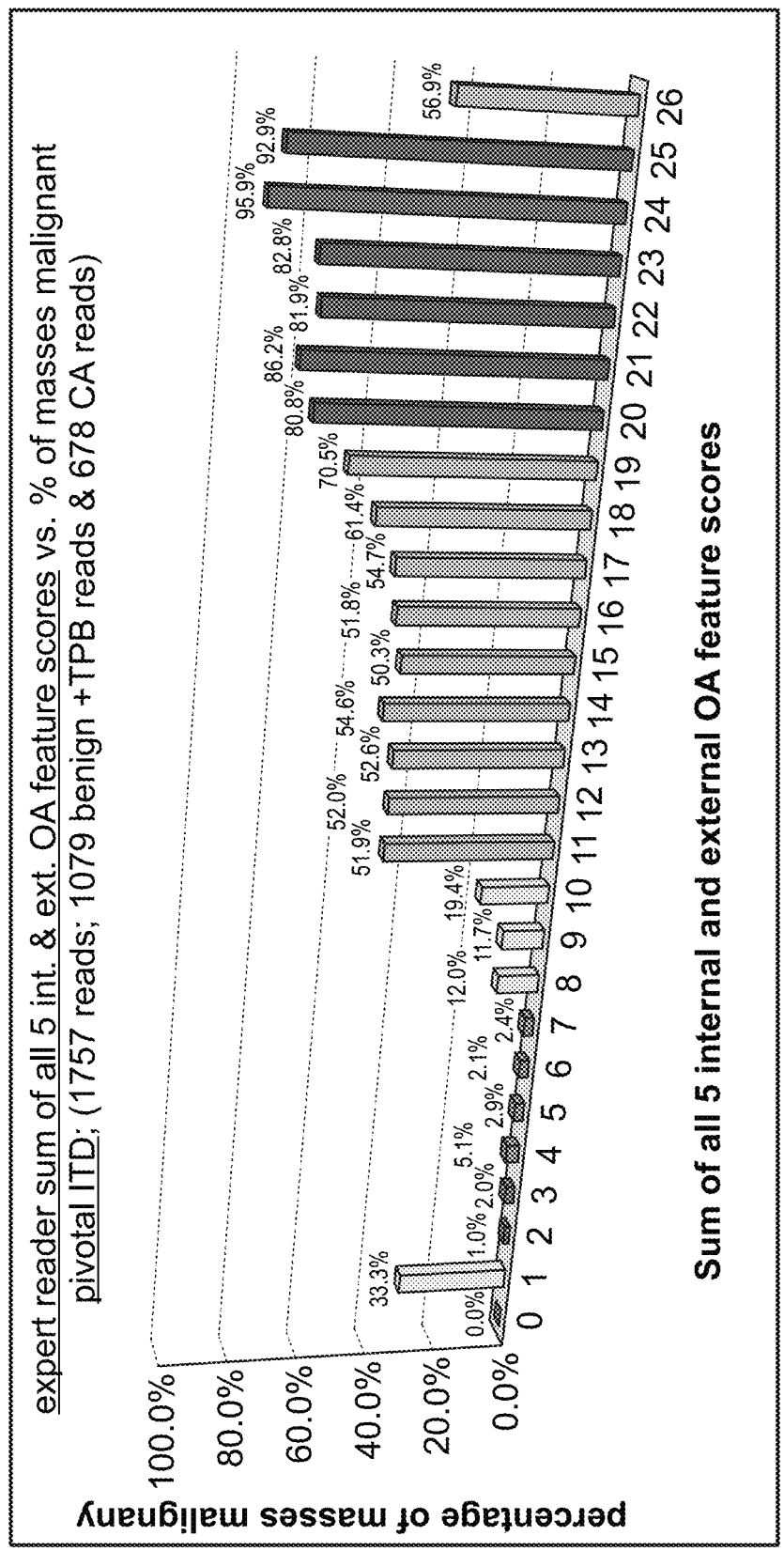
FIG. 10D illustrates an example of a sum of all five OA feature scores as compared to the PPV.

As explained herein, the one or more processors analyze the US feature scores and/or the OA feature scores to obtain one or more probabilities that a region of interest in the US image(s) and/or OA images(s) corresponds to one or more particular molecular subtypes. As part of the analysis, the one or more processors may calculate an unweighted sum of the three OA internal feature scores, namely an unweighted sum of the OA internal vessel score, OA internal deoxygenated blush score and OA internal total hemoglobin score. FIG. 10A illustrates an example of individual feature scores derived in connection with an analysis of a number of subjects. Each individual feature score includes a plot for each score value (e.g., 0-6 or 0-5), along with a PPV. FIG. 10B illustrates an example of a sum of the OA internal feature scores as compared to the PPV. The graph of the PPV versus the sum of the three OA internal stores shows that it is a good positive predictor of cancer, but by itself is not a good negative predictor of the apps of cancer. It shows that the sum of the three internal OA scores should be considered in connection with one or more boundary and/or peripheral scores that have lower PPVs at lower score values in order to exclude cancers. As part of the analysis, one or more processors also calculate an unweighted sum of the two OA external feature scores. The unweighted sum of two external feature scores includes the OA external capsular/boundary zone vessel score and OA external peripheral zone radiating vessel score. FIG. 10C illustrates an example of a sum of the two OA external feature scores as compared to the PPV. The graph of the PPV versus the sum of the OA external scores shows that it is a very, very good positive predictor of cancer and by itself is also a very good negative predictor of the absence of malignancy. In accordance with new and unique aspects herein, it has been surprisingly recognized that the sum of the two external OA scores could function as both a positive and a negative predictor for cancer alone without any other feature scores. FIG. 10D illustrates an example of a sum of all five OA feature scores as compared to the PPV. The graph of FIG. 10D illustrates that the unweighted sum of the five OA feature scores exhibits a superior positive predictor of cancer and a superior negative predictor of the absence of malignancy. In accordance with new and unique aspects herein, it has been recognized that the sum of all five OA feature scores provides a preferred PPV and NPV, as compared to using only the sum of the three internal feature scores or the sum of the two external feature scores alone. In accordance with at least some embodiments, the one or more processors automatically utilize one or more feature score(s)-to-classification models as a basis to generate probabilities that a particular mass corresponds to i) percentage chance/probability of malignancy of a mass (LOM/PPV), ii) a likelihood of a clinical event, disease progression or reoccurrence, iii) molecular subtype, iv) histologic grade, v) degree of angiogenesis, vi) likelihood of lymph node metastasis, vii) assess the status of a disease or condition to find evidence of exposure to, or effects of, a medical product or environmental agent, viii) change in a patient condition (e.g., tumor size and volume), ix) indicator of an effect of a response to an exposure intervention, x) detect or confirm a disease or condition, xi) identify specific disease subtype, xii) possibility that mutations in genes are predictive of response to certain inhibitors, xiv) likelihood that ER and PR possible breast cancers respond to endocrine therapy, xv) possibility that dense breast tissue is predictive of decreased sensitivity of mammography for detecting noncalcified breast cancer.

Feature Scores as Qualitative Diagnostic Biomarkers, Quantitative Predictive Biomarkers, Prognostic Biomarkers or Monitoring Biomarkers to Obtain Predictive Results In accordance with new and unique aspects herein, it is been recognized that feature scores for features of interest within the boundary and peripheral zones can be combined with feature scores for internal zone feature scores in various manners to obtain predictive results of one or more traits of the lesion. The feature scores can be utilized, as image findings, to derive different types of predictive results, namely qualitative diagnostic results, semi-quantitative predictive results and prognostic results. A probability or likelihood of malignancy is one non-limiting example of a manner in which a prognostic biomarker may be ultimately characterized, stored and presented. In accordance with new and unique aspects herein, it is been recognized that feature scores based solely on ultrasound images (not accompanied by an OA image) can be utilized to obtain predictive results of one or more traits of the lesion. The predictive results are determined based on qualitative diagnostic biomarkers, semi-quantitative predictive biomarkers and prognostic biomarkers (including but not limited to the LOM/PPV).

Historically, ultrasound BI-RADS 5$^{th}$ edition features have been utilized to provide only qualitative information regarding features in US images that facilitate the decisions about:

Whether or not to recommend biopsy

Whether a mass is classified as ≤BI-RADS 3 or ≥BI-RADS 4A

Whether the false negative rate (FNR) is ≤2% or >2%.

ACR Ultrasound BI-RADS 5$^{th}$ edition offers no guidance about how to objectively or precisely estimate the LOM when the risk of FNR is >2%. Thus, heretofore, no methods or systems had been proposed to interpret features within US images with sufficient sensitivity and/or specificity to develop quantitative information from the ultrasound images. Thus, BI-RADS features cannot be objectively used as semi-quantitative diagnostic biomarkers to predict a LOM when FNR is >2%. On the other hand, the ultrasound and OA feature scores described herein were purpose-designed to function as both qualitative diagnostic biomarkers and as semi-quantitative diagnostic biomarkers that can help to both:

1) Better decide whether or not to recommend biopsy (qualitative diagnostic)
2) More objectively and precisely assign LOM (semi-quantitative diagnostic)

In accordance with new and unique aspects herein, feature scoring systems and methods are described that provide sufficient sensitivity and specificity to convert US features to qualitative diagnostic biomarkers, semi-quantitative predictive biomarkers and prognostic biomarkers. In general, a biomarker may be defined in an ordinal manner. As one example, in order to qualify as a semi-quantitative biomarker, it is desirable for a percentage chance of malignancy to increase continuously with each score. For example, the positive predictive value (PPV) of a feature score should increase continuously from the lowest to the highest value assigned to the feature score. In a study of 1757 masses, it was found that the PPV for the US sound transmission score assigned for an internal zone increases (as a general trend) as the score value progresses from 0 to 5 (e.g., score 0=26.8%; score 1=29.3%; score 2=31.7%; score 3=72.5%; score 4=65.4%; score 5=85.4%). While the score of 3 exhibited a slightly lower PPV (72.5%) as compared to the score of 4 (PPV of 65.4%), this slight drop in PPV does not negate the overall increasing trend in US internal zone sound transmission score relative to PPV.

FIGS. 4D, 4F, 4H, 4J, and 4L illustrate further examples of the continually increasing relation between PPV and feature scores for US internal zone shape, US internal zone texture, US internal zone sound transmission, US boundary zone, and US peripheral zone, respectively.

By developing criteria for assigning feature scores, ultrasound feature scoring can be utilized to provide ordinal data, namely semi-quantitative statistical data in which variables have natural, ordered categories where the data exists on an ordinal scale. Further, it is been recognized that select mathematical combinations (e.g., sums, ratios, waited combinations) of certain combinations of the US feature scores provide a longer ordinal series that more closely approach a numeric value. As one example, the ratio of the sum of three internal US feature scores divided by the sum of the two external feature scores substantially approximates a numeric value that correlates to particular traits of a lesion. For example, the ratio may correlate well with a LOM/PPV, histologic grade, molecular subtype and the like. Additionally or alternatively, individual external peripheral zone radiating vessel US scores and some OA external feature scores correlate better with a total degree of angiogenesis and a likelihood of lymph node metastasis, than the ratio of the above noted sums.

Additionally or alternatively, an unweighted sum of the 5 US feature scores may be utilized as semi-quantitative diagnostic biomarkers. Additionally or alternatively, classification models (e.g., regression equations or machine learning models) may be defined that apply a select over-weight to one or more of the boundary and peripheral zone US feature scores. As explained herein, machine learning may be utilized to define classification models that apply an appropriate over weighting of the boundary and/or peripheral zone feature scores. Additionally or alternatively, the classification model(s) may utilize non-US data in addition to the US feature scores. For example, the non-US data may be OA feature scores, numerical data (e.g., mass size, depth of anterior or posterior boundary of mass, ratio of height to width of mass relative to skin surface, percentage that mass orientation is aligned with or tilted from perpendicular relative to skin surface). As another example, the non-US data may be ordinal data such as OA feature scores, and/or feature scores derived from imaging modalities other than US or OA (e.g., feature scores assigned to CT images, NM images, MM images, PET images, SPECT images, X-ray images). As another example, the non-US data may be categorical data such as a BI-RADS category assigned based on mammographic images, conventional US image reading techniques or images from another modality.

In accordance with new and unique aspects herein, has been recognized that BI-RADS categorizations that are assigned based on mammographic images, conventional US image reading techniques and other imaging modalities, may inhibit a human reader from downgrading a BI-RADS rating of a later image. Stated another way, sometimes a BI-RADS rating based on a mammogram may be afforded undo importance to a human reader. In some instances, a false negative rate may be too high for a diagnostic imaging human reader to downgrade (e.g., downgrading a BI-RADS 4C or BI-RADS 5 mammogram to a BI-RADS 3. A human reader may be unwilling to "second-guess" such a high prior BI-RADS rating. Accordingly, methods and systems herein integrate the prior BI-RADS rating into the features that are considered when obtaining a predictive result. The classification model uses the US features and/or OA features, along with the ancillary diagnostic breast imaging rating together to develop the models and utilized models to obtain the predictive results.

Additionally or alternatively, patient age may be utilized as another non-US and non-OA score. Age affects a level of suspicion or LOM. Patients with malignant masses, on average, are 10 years or more older than a mean age of patients with benign masses. The classification models herein utilize patient age in combination with US features and/or OA features when obtaining the predictive result. The age of the patient may be weighted differently, based on the nature of the predictive result, as well is based on other factors.

Additionally or alternatively, a maximum diameter of the mass may be utilized as another non-US and non-OA score. Maximum mass diameter affects a level of suspicion. Malignant masses have a mean diameter slightly larger than a diameter of benign masses, by a few millimeters. The classification models herein may utilize mass diameter when obtaining the predictive result.

Additionally or alternatively, a depth to a posterior margin of the mass may be utilized as another non-US and non-OA score. The depth to the posterior margin of the mass may be useful in part due to the fact that the laser light reduces an energy with depth below a surface. Consequently, the sensitivity will vary with depth. For example, feature scoring of a mass located closer to the surface of a breast may result in better sensitivity as compared to feature scoring of a substantially similar mass but located at a greater depth from the skin surface. While the sensitivity may vary with depth, the relation between sensitivity and depth is not continuous from the surface to all depths. In accordance with new and unique aspects herein, it is been recognized that sensitivity may decrease for masses in the near field due to depth, whereas mass is located at deeper depths from the surface do not necessarily exhibit a decrease in sensitivity due to further depth. For example, the depth zone over which sensitivity decreases is in the near field (e.g., 02 1.0 cm in depth, not in the far field (greater than 2 cm in depth). Furthermore, there are other reasons that depth of the posterior margin of a malignant mass may differ from that of a benign mass. Many malignant masses are oriented in a plane that is non-parallel to the skin. For this reason, malignant masses that have non-parallel orientations will have deeper posterior margins than benign masses of the same maximum diameter. Finally, depth to posterior margin of a mass is not entirely independent of its maximum diameter. Masses with larger diameters will tend to have deeper posterior margins. Since malignant masses tend to be slightly larger than benign masses, the larger size of malignant masses will also contribute to their posterior margins lying more deeply.

In accordance with new and unique aspects herein, unique combinations of US feature scores and/or OA feature scores have been identified that can be correlated to BI-RADS descriptors and enable BI-RADS descriptors to no longer be limited to qualitative diagnostics. Instead, the unique combinations of US feature scores and/or OA feature scores are correlated to BI-RADS descriptors in a manner that allows the BI-RADS descriptors to be utilized as quantitative predictive and prognostic biomarkers.

In accordance with new and unique aspects herein, mass sound transmission in a US image is able to be utilized as a prognostic biomarker for assigning a histologic grade of an invasive tumor. In accordance with new and unique aspects herein, it is been found that the "taller than wide orientation" of an ROI can be used as a prognostic biomarker to predict an acinar adenocarcinoma of the breast (the AAB represents a positive characteristic" versus the ductal adenocarcinoma of the breast (the DAB represents a negative characteristic". It has also been found that taller than wide orientation (non-parallel) can be used as a prognostic biomarker for histologic grade I and luminal A molecular subtype malignant masses. In accordance with new and unique aspects herein, it is been found that masses that are oriented in a nonparallel manner to the skin surface are more likely to have a lower histologic grade. In accordance with new and unique aspects herein, has been found that the size of enlarged ducts represents a good prognostic biomarker concerning a nuclear grade of a carcinoma in situ (CIS), namely enlarged ducts around a mass have been shown to correlate with luminal B, HER2 and grade 3 invasive breast carcinoma. In accordance with new and unique aspects herein it has been found that the relative thickness of the halo and the length of the spicules represent a good prognostic biomarker concerning nuclear grade of a CIS, namely boundary zone spicules and thickened Coopers ligaments have been shown to correlate with low histologic grade and luminal molecular subtypes.

In accordance with new and unique aspects herein, it has been found that a differential diagnosis may be rendered in connection with altered sound transmission. Certain histologic groups of breast malignancies are more likely to cause acoustic shadowing or to be associated with enhanced sound transmission. In fact, there are differential diagnoses for acoustic shadowing and enhanced sound transmission. The differential diagnosis for acoustic shadowing in order of likelihood is: 1) low to intermediate grade invasive duct carcinoma, 2) invasive lobular carcinoma, and 3) tubular carcinomas, particularly those greater than 1.5 cm in diameter. The differential diagnosis for enhanced sound transmission in order of likelihood is: 1) high grade invasive duct carcinoma, 2) larger colloid carcinomas (>1.5 cm), 3) high nuclear grade DCIS, 4) medullary carcinoma, and 5) encapsulated and invasive papillary carcinoma. Accordingly, a degree of acoustic shadowing in a US image has been found to differentiate between IDC, grades I or II, versus ILC, grades I or II, versus tubular carcinoma (greater than 1.5 cm). An extent to which sound transmission is enhanced has been found to differentiate between i) IDC, grade III (especially TNBC), ii) colloid carcinoma>1.0 cm, iii) CIS, grade III, iv) medullary carcinoma (basal-like TNBC), and v) invasive papillary carcinoma.

FIG. 4A illustrates a process for utilizing US and/or OA feature scores as biomarkers to obtain at least one of prognostic and/or predictive results in accordance with embodiments herein. The operations of FIG. 4A may be implemented by one or more processors of a US imaging system, an OA imaging system, a picture archive computing system (PACS), a network server (e.g., within a medical network), a workstation provided at a doctor's office or other medical facility, as well as other types of computing devices utilized by medical personnel (e.g., desktop computer, laptop computer, tablet device, smart phone). The operations of FIG. 4A may be divided between different physical systems, such that a portion of the operations are implemented by a first one of the example devices or systems described herein, while another portion of the operations are implemented by a second one of the example devices or systems described herein.

At 402, one or more processors of the system obtain a US data set and/or an OA data set. The US data set and/or OA data set may represent one or more corresponding individual imaging frames/slices, and/or corresponding volumetric data sets. The US data set and/or OA data set may be obtained from a single or multiple diagnostic imaging sessions prior to or in real time during the remainder of the operations of FIG. 4A. The US data set and/or OA data set may be attained from a single common imaging system and/or from multiple separate imaging systems. For example, during one clinical visit, a US data set may be obtained for the patient utilizing an ultrasound only imaging system. During a separate second clinical visit, an OA data set may be obtained for the patient utilizing an OA imaging system. Additionally or alternatively, the US data set and OA data set may be obtained by a single imaging system having the capability to perform a US imaging session and to separately perform an OA imaging session.

At 404, the one or more processors analyze the US data set and/or OA data set to render one or more US images and/or OA images. One or more of the US images and/or OA images are displayed on a display of the system to one or more medical personnel.

At 406, one or more ROIs are identified from the US images and/or OA images. Additionally, an interior ROI outline is identified that separates the internal zone from the boundary zone and an exterior ROI outline is identified that separates the boundary zone from the peripheral zone. At 408, the one or more processors direct the display to display at least a first image from at least one of the US images and/or first image from at least one of the OA images overlaid with the interior and exterior outlines.

FIG. 4B illustrates an example of a US image displayed in accordance with an embodiment herein. The US image includes an ROI that includes an internal zone 420 that is surrounded by an interior outline 422. The interior outline 422 separates the internal zone 420 from a boundary zone 424. An exterior outline 426 separates the boundary zone 424 from the peripheral zone 428. The internal zone 420 represents a hypoechoic central nidus, while the boundary zone 424 may represent a thin hyperechoic capsule or thick echogenic rim (e.g., halo). The peripheral zone 428 is outside of the boundary zone 424. The peripheral zone 428 may include, among other things, hyperechoic spicules, hyperechoic thickened collateral ligaments (CLs), and the like (as generally indicated by the arrows in the regions 430, 432. The identification of 406 may be implemented in various manners, such as described in U.S. Pat. No. 9,398,893, titled "System and Method for Diagnostic Vector Classification Support", issue date Jul. 26, 2016. The identification at 406 may be performed by medical personnel while viewing the images. For example, the medical personnel may utilize various tools within a user interface to designate the interior and exterior outlines (e.g., a mouse, trackball, stylus and touch screen, and the like). Additionally or alternatively, the identification at 406 may be performed entirely automatically by the one or more processors of the system, such as based on image recognition algorithms, deep learning algorithms and the like. As a further option, at 406 and 408, the user may input an initial determination for the position and shapes of the interior and exterior boundaries, in response to which the one or more processors may automatically generate recommendations for adjustments in the interior and exterior boundaries. As a further option, at 406 and 408, the one or more processors may automatically generate the initial recommendation for the position and shapes of the interior and exterior boundaries. The user may be then afforded the opportunity to adjust the position and/or shape of the interior and exterior boundaries. For example, the user interface may be configured to allow the user to click on points along a boundary of interest and dragging the boundary to a new position. As another example, the user interface may be configured to allow the user to draw new segments within the interior and exterior boundaries that are then tied to the original automated recommendation.

In accordance with new and unique aspects herein, the operations of FIG. 4A may be performed only in connection with US data, US images, and US feature scores, to determine predictive result indications (e.g., molecular subtypes and/or histologic grades) for a trait of a lesion (e.g., pathology) based only on ultrasound. In accordance with new and unique aspects herein, the operations of FIG. 4A may be performed only in connection with OA data, OA images, and OA feature scores, to determine predictive result indications (e.g., molecular subtypes and/or histologic grades) for a trait of a lesion (e.g., pathology) based only on optoacoustics. When inner and outer ROIs are deployed to aid in scoring OA features, the ROIs are drawn on the gray scale US image in the 6-on-1 display, and the 5 copies of each of the two ROIs are propagated into co-registered locations in the 5 OA maps.

Figure 5B:
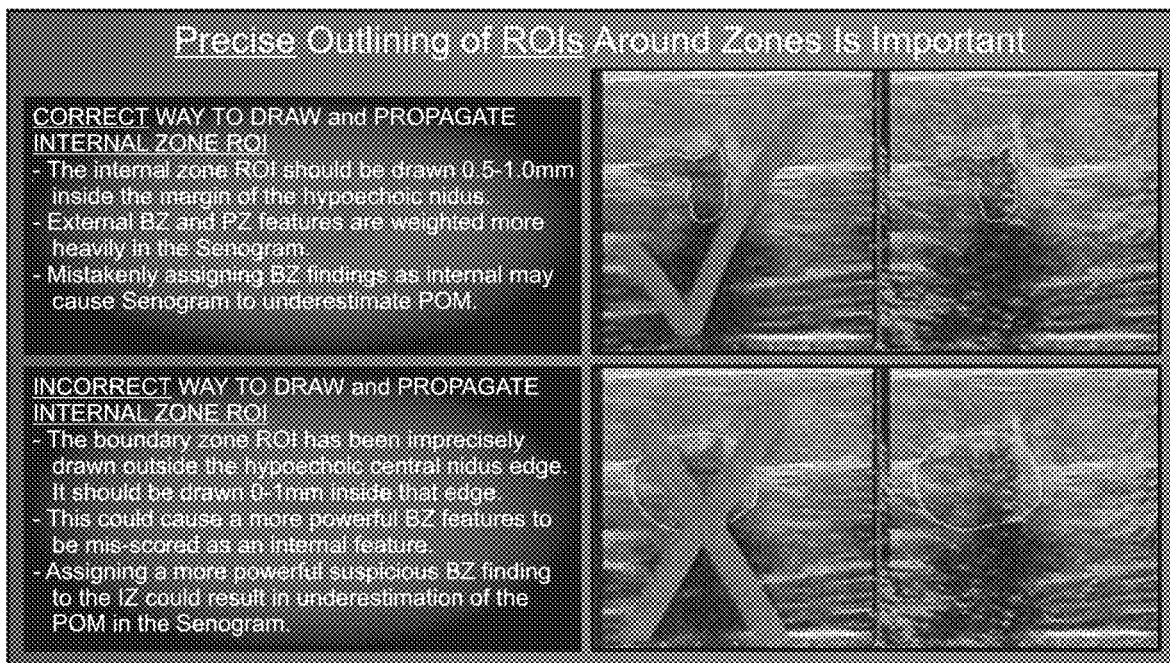
FIG. 5B illustrates (in the upper left and upper right panels) the interior outline drawn in a manner to avoid mistakenly assigning boundary zone regions to the internal zone which will otherwise lead to underestimation of the predictive result.
Figure 5C:
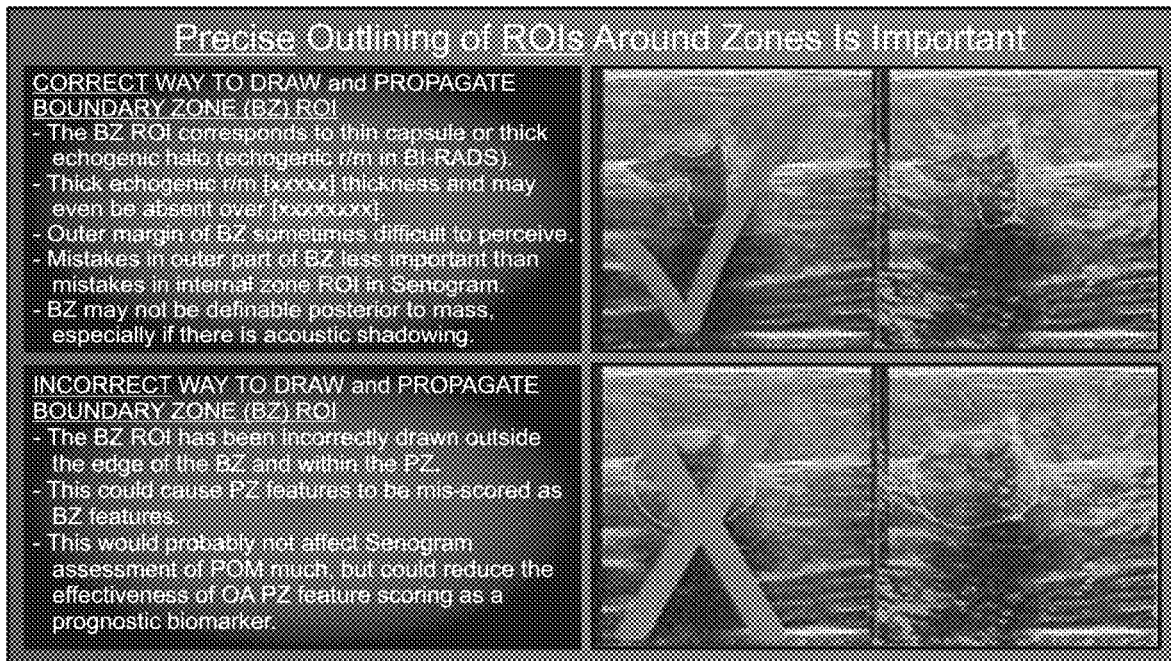
FIG. 5C illustrates additional examples of correctly and incorrectly drawn exterior outlines to separate the boundary zone from the peripheral zone.
Figure 5D:
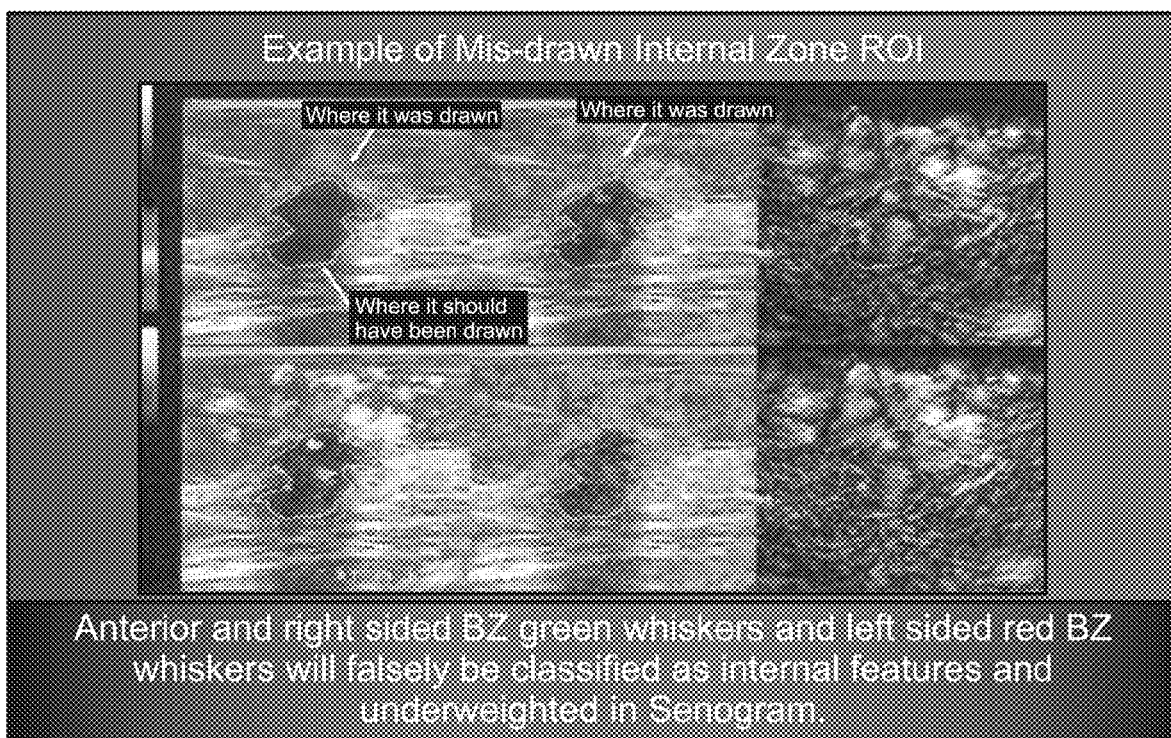
FIG. 5D illustrates another example of a mis-drawn interior outline around the internal zone.
Figure 5E:
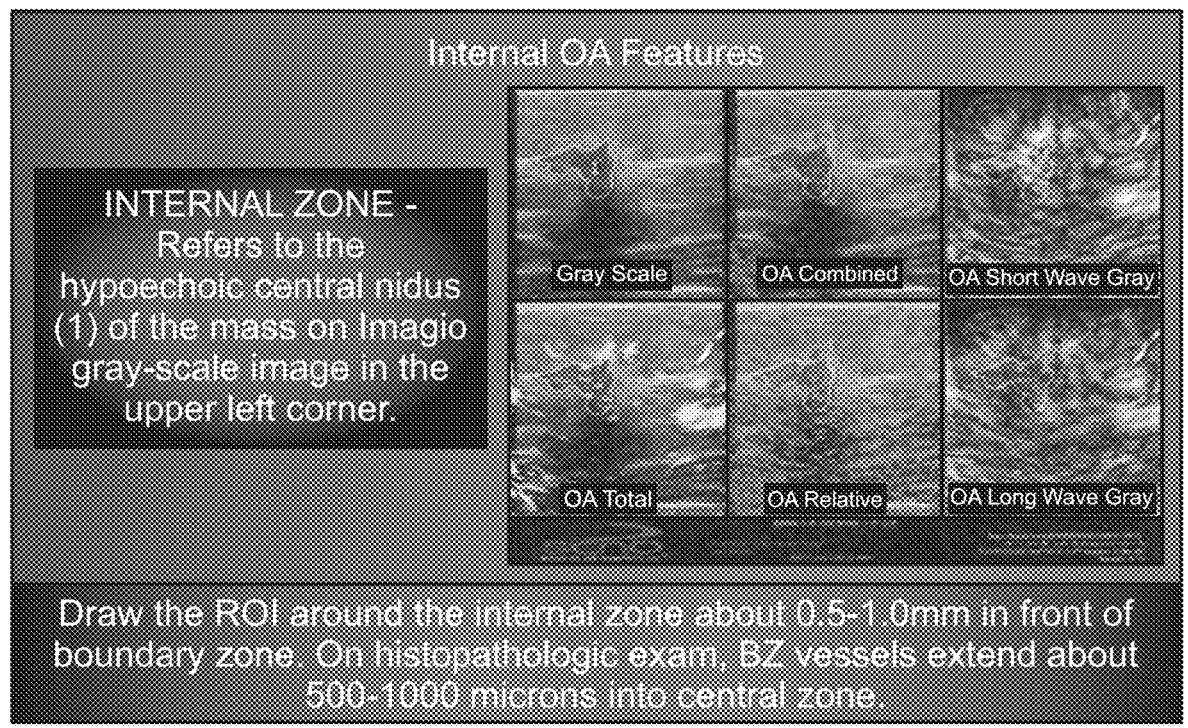
FIG. 5E illustrates an example of a 6-on-1 display presenting gray scale ultrasound in the left upper corner and 5 co-registered images/maps in the other 5 frames, yielding a total of six types of information used when scoring OA features.

In accordance with new and unique aspects herein, techniques have been identified to precisely outline the internal zone with the interior outline. FIGS. 5B-5D illustrate examples in connection with correctly identifying the interior outline of the internal zone for the ROI. For example, the interior outline is drawn between 0.5 and 1.0 mm inside of the margin of the hypoechoic nidus.

FIG. 5B illustrates (in the upper left and upper right panels) the interior outline drawn in a manner to avoid mistakenly assigning boundary zone regions to the internal zone which will otherwise lead to underestimation of the predictive result (e.g., LOM/PPV). The upper left panel illustrates an ultrasound image, while the upper right panel illustrates either and OA combined image or an OA relative image. The internal zone ROI should be drawn 0.5-1.0 mm inside the margin of the hypoechoic nidus. By way of example, the boundary zone and peripheral zone feature scores may be weighted more heavily, as compared to the internal zone feature scores. It is desirable to avoid drawing the interior outline at or beyond the margin of the hypoechoic nidus, as doing so presents the potential risk of mistakenly scoring the boundary zone features as if the portion of the image were in the internal zone, thereby raising the potential that a classification model may underestimate a predictive result, such as underestimating a probability of malignancy.

FIG. 5B also illustrates (in the lower left and lower right panels) an improperly drawn interior outline that includes a portion of the boundary zone within the internal zone. The lower panels of FIG. 5B incorrectly include areas outside of the hypoechoic central nidus edge, whereas the interior outline should have been drawn 0-1 mm inside of the hypoechoic central nidus edge. Incorrectly drawing the interior outline introduces the potential that a powerful boundary feature characteristic could be mis-scored as an internal feature characteristic, and/or assigning a more powerful suspicious boundary zone finding to the internal zone which could result in underestimation of the predictive result (e.g., LOM/PPV).

FIG. 5C illustrates additional examples of correctly and incorrectly drawn exterior outlines to separate the boundary zone from the peripheral zone. The exterior outline for the boundary zone should be drawn to correspond to the thin capsule or thick echogenic halo. The thick echogenic halo varies in thickness and at times may be absent over parts of the mass. The border for the boundary zone may not be definable in the area posterior to the mass, such as when there is acoustic shadowing. The upper left and right panels in FIG. 5C illustrate a correctly drawn exterior outline to separate the boundary and peripheral zones. The lower left and right panels illustrate and incorrectly drawn exterior outline. In the lower panels, the exterior outline has been drawn outside of the edge of the boundary zone which will cause peripheral zone features to be mis-scored as boundary zone features, which could affect an assessment of the LOM/PPV and reduce and effectiveness of NOA peripheral zone feature score is a prognostic biomarker.

FIG. 5D illustrates another example of a mis-drawn interior outline around the internal zone. In the example of FIG. 5D, by drawing the interior outline to include part of the boundary zone, anterior and right-sided boundary zone "whiskers" and left-sided boundary zone "whiskers" will be falsely classified as internal features and under weighted in the calculation of the LOM/PPV. FIG. 5B illustrates an example of a 6-on-1 display presenting gray scale ultrasound in the left upper corner and 5 co-registered images/maps in the other 5 frames, yielding a total of six types of information used when scoring OA features. An interior outline is drawn around the internal zone in the left upper gray scale ultrasound image, and then propagated to a co-registered location in the 5 different OA images/maps. The interior outline is drawn approximately 0.5-1.0 mm in from the boundary zone because boundary zone vessels may extend 500-1000 μm into the internal zone.

Returning to FIG. 4A, at 410, the one or more processors, receive feature scores in connection with the internal, boundary and peripheral zones of one or more US images and/or one or more OA images. The feature scores may be generated automatically by the one or more processors or with input through a user interface by one or more medical personnel. Examples are described herein in connection with identifying internal US feature scores, external US feature scores, sums of internal and external feature scores and ratios there between. Additionally or alternatively, the one or more processors, automatically or with input through a user interface by one or more medical personnel, obtain an identification of one or more OA feature scores for corresponding OA features within the OA images. Examples are described below in connection with identifying internal OA feature scores, external OA feature scores, sums of internal and external feature scores and ratios there between. Various US feature scores and/or OA feature scores may be assigned in connection with the three zones, namely the internal zone, boundary zone and peripheral zone.

In accordance with new and unique aspects herein, the machine learning classifiers or other models described herein analyze US/OA images based on the image feature characteristics of interest to automatically determine feature scores for two or more of the features described herein. The automatic determination of the feature scores may be performed in real time during an examination of the patient, such as when implementing the machine learning classifier or other model in the software operating on the diagnostic imaging system. Additionally or alternatively, a separate computing device may be connected through a wired or wireless connection to a diagnostic imaging system. The diagnostic imaging system may provide US/OA raw data and/or rendered US/OA images to the separate computing system in real time while examining a patient and while the US/OA data is collected. During the patient examination, in real time, the separate computing device may apply one or more of the machine learning classifiers or other models described herein to analyze the US/OA images based on the characteristics of the feature scores described herein to automatically determine feature scores for two or more of the features described herein.

In accordance with new and unique aspects herein, when scoring features is performed manually by medical personnel, the one or more processors may manage scoring of the OA/US feature scores to be assigned to the respective zones in a predetermined order, namely an "outside—to—inside" order. One or more processors of a computing device (e.g., diagnostic imaging system, PACS workstation, medical workstation, desktop computer, laptop computer, tablet device, smart phone or remote server) manage scoring of the OA/US feature scores in a predetermined outside-to-inside order, that includes first requiring a user to assign one or more OA/US peripheral zone feature scores, second requiring a user to assign one or more OA/US boundary zone feature scores, third requiring a user to assign one or more OA/US internal zone feature scores. For example, the system may limit the user's ability to assign feature scores in a manner that the OA/US feature scores must first be assigned to the peripheral zone before the user is afforded an input window to assign feature scores for another zone. The system may limit the users score entry options by first only presenting one or more score entry windows and/or OA/US images associated with OA/US peripheral zone feature scores. Next, the system may limit the users score entry options by next only presenting one or more score entry windows and/or OA/US images associated with OA/US boundary zone feature scores. Next, the system may limit the users score entry options by only presenting one or more score entry windows and/or OA/US images associated with OA/US internal zone feature scores. While limiting entry of new data to the next zone in the series of zones working from the outside to inside, the user may be allowed to review prior data entries and prior OA/US images, but may be prevented from changing a previously entered feature score. For example, while scoring the OA/US internal zone feature scores, the user may be allowed to review the images associated with the peripheral zone and boundary zone but may be blocked from changing scores for peripheral and boundary zone features. Once the OA/US feature scores are completed for the peripheral zone, the system may then present a window that allows the user to enter OA/US feature scores for the boundary zone. The system may limit the user's ability to assign feature scores such that the feature scores for the boundary zone must be completed second before the user is afforded an input window to assign feature scores for the peripheral zone. Once the OA/US feature scores are completed for the boundary zone, the system then presents a window that allows user to enter the OA/US feature scores for the peripheral zone. By way of example, it may be desirable to require a particular order for feature scoring from outside to inside, because medical personnel are not accustomed to looking at external features. Many key features of OA/US images are hyperechoic features (appearing in the boundary zone), but traditionally medical personnel may be accustomed to looking only for hypoechoic features (appearing in the internal zone). Also, external boundary zone features are more robust and distinguishing benign from malignant masses and more robust at assessing LOM/PPV and BI-RADS categories. Further, requiring scoring to follow an outside to inside order may further prevent the risk of placing excessive importance on the hypoechoic features of the internal zone, which may otherwise lead to false scoring of boundary zone features and/or peripheral zone features. Before scoring features, it may be desirable to find the images best useful for scoring, such as by looking at still images and/or surveying multiple video suites. Once the preferred still images and/or individual frame from a video sweep is identified, the interior outline surrounding internal zone ROI is drawn. Next, the exterior outline surrounding the boundary zone is drawn. After the interior and exterior outlines are drawn, a series of scoring windows are presented to the medical personnel. In accordance with at least certain embodiments, the order in which scoring is performed begins by scoring features of the peripheral zone, followed by features of the boundary zone, followed by features of the interior zone.

At 412, the one or more processors apply the feature scores to a classification model to obtain at least one of the prognostic result or predictive result indicative of a trait of the lesion. By way of example, the one or more processors may analyze the US feature scores and/or the OA feature scores to obtain one or more probabilities that a region of interest in the US image(s) and/or OA images(s) corresponds to one or more prognostic and/or predictive results. As part of the analysis, the one or more processors may calculate an unweighted sum of the three OA internal feature scores, namely an unweighted sum of the OA internal vessel score, OA internal deoxygenated blood score and OA internal total hemoglobin score. At 412, the one or more processors also calculate an unweighted sum of the two OA external feature scores. The unweighted sum is for the OA external capsular/boundary zone vessel score and OA external peripheral zone radiating vessel score. In accordance with new and unique aspects herein, it has been surprisingly recognized that the sum of the two external OA scores could function as both a positive and a negative predictor for cancer alone without any other feature scores. In accordance with new and unique aspects herein, it has been recognized that the sum of all five OA feature scores provides a preferred PPV and NPV, as compared to using only the sum of the three internal feature scores or the sum of the two external feature scores alone. In accordance with at least some embodiments, the one or more processors at 412 may automatically utilize one or more classification models as a basis to generate probabilities that a particular mass corresponds to certain prognostic and/or predictive result. The models defines a correlation between one or more of the OA/US feature scores and one or more of the following prognostic or predictive results: i) percentage chance/probability of malignancy of a mass, ii) a likelihood of a clinical event, disease progression or reoccurrence, iii) molecular subtype, iv) histologic grade, v) degree of angiogenesis, vi) likelihood of lymph node metastasis, vii) assess the status of a disease or condition to find evidence of exposure to, or effects of, a medical product or environmental agent, viii) change in a patient condition (e.g., tumor size and volume), ix) indicator of an effect of a response to an exposure intervention, x) detect or confirm a disease or condition, xi) identify specific disease subtype, xii) possibility that mutations in genes are predictive of response to certain inhibitors, xiv) likelihood that ER and PR possible breast cancers respond to endocrine therapy, xv) possibility that dense breast tissue is predictive of decreased sensitivity of mammography for detecting noncalcified breast cancer, xvi) one of one or more molecular subtypes or xvii) histologic grades.

For example, the classification model may be configured to overweight the US internal zone sound transmission feature score with respect to at least one other US feature score to obtain, as the predictive result, an indication of lymph node metastasis. As a further example, the classification model may be configured to recognize that shadowing in the US internal zone is indicative of an increased risk of lymph node metastasis, while enhanced sound transmission is indicative of a lowered risk of lymph node metastasis. The feature scores may include a US internal zone sound transmission feature score, and wherein the classification model is configured to overweight the US internal zone sound transmission feature score with respect to at least one other feature scores to obtain, as the prognostic result, a distinction between TNBC molecular subtype, luminal a molecular subtype and HER2 molecular subtype. Additionally or alternatively, the feature scores include an indication of an extent to which ducts and/or lobules are disproportionately enlarged relative to a reference, the classification model accounting for the extent of the enlargement of the ducts and/or lobules when outputting the prognostic result. Additionally or alternatively, the one or more processors are further configured to obtain an initial BI-RADS rating based on non-OA images, wherein the semi-quantitative diagnostic result includes a determination of whether to at least one of i) downgrade the initial BI-RADS rating or ii) modify the initial BI-RADS rating to add a sub-categorization. Additionally or alternatively, the initial BI-RADS rating is a BI-RADS 4 rating, without sub categorization, wherein the semi-quantitative diagnostic result includes modifying the BI-RADS 4 rating to at least one of i) downgrading the BI-RADS 4 rating to a BI-RADS 3 rating or lower or ii) revising the BI-RADS 4 rating to add sub categorization for one of BI-RADS 4A or 4B. As another example, a prognostic biomarker may reflect a likelihood of a clinical event, disease progression, or recurrence irrespective of an intervention (e.g. TNM stage, tumor grade, tumor receptor status). The prognostic biomarker may be an indicator of a molecular subtype for a malignancy.

At 414, the one or more processors store and output at least one of the prognostic or predictive results. For example, the prognostic result or predictive result may include at least one of: i) percentage chance/probability of malignancy of a mass, ii) a likelihood of a clinical event, disease progression or reoccurrence, iii) molecular subtype, iv) histologic grade, v) degree of angiogenesis, vi) likelihood of lymph node metastasis, vii) assess the status of a disease or condition to find evidence of exposure to, or effects of, a medical product or environmental agent, viii) change in a patient condition (e.g., tumor size and volume), ix) indicator of an effect of a response to an exposure intervention, x) detect or confirm a disease or condition, xi) identify specific disease subtype, xii) possibility that mutations in genes are predictive of response to certain inhibitors, xiv) likelihood that ER and PR possible breast cancers respond to endocrine therapy, xv) possibility that dense breast tissue is predictive of decreased sensitivity of mammography for detecting noncalcified breast cancer, xvi) one of one or more molecular subtypes or xvii) histologic grades.

By way of example, the prognostic and/or predictive results may be displayed in various manners. The prognostic and/or predictive results may be displayed on a display in connection with a graphical user interface of a workstation being utilized by an image reader or other clinician when analyzing US/OA images. Additionally or alternatively, the prognostic and/or predictive results may be conveyed over a network from a remote server to a client computing device, from one client computing device to another client computing device and the like.

Figure 10E:
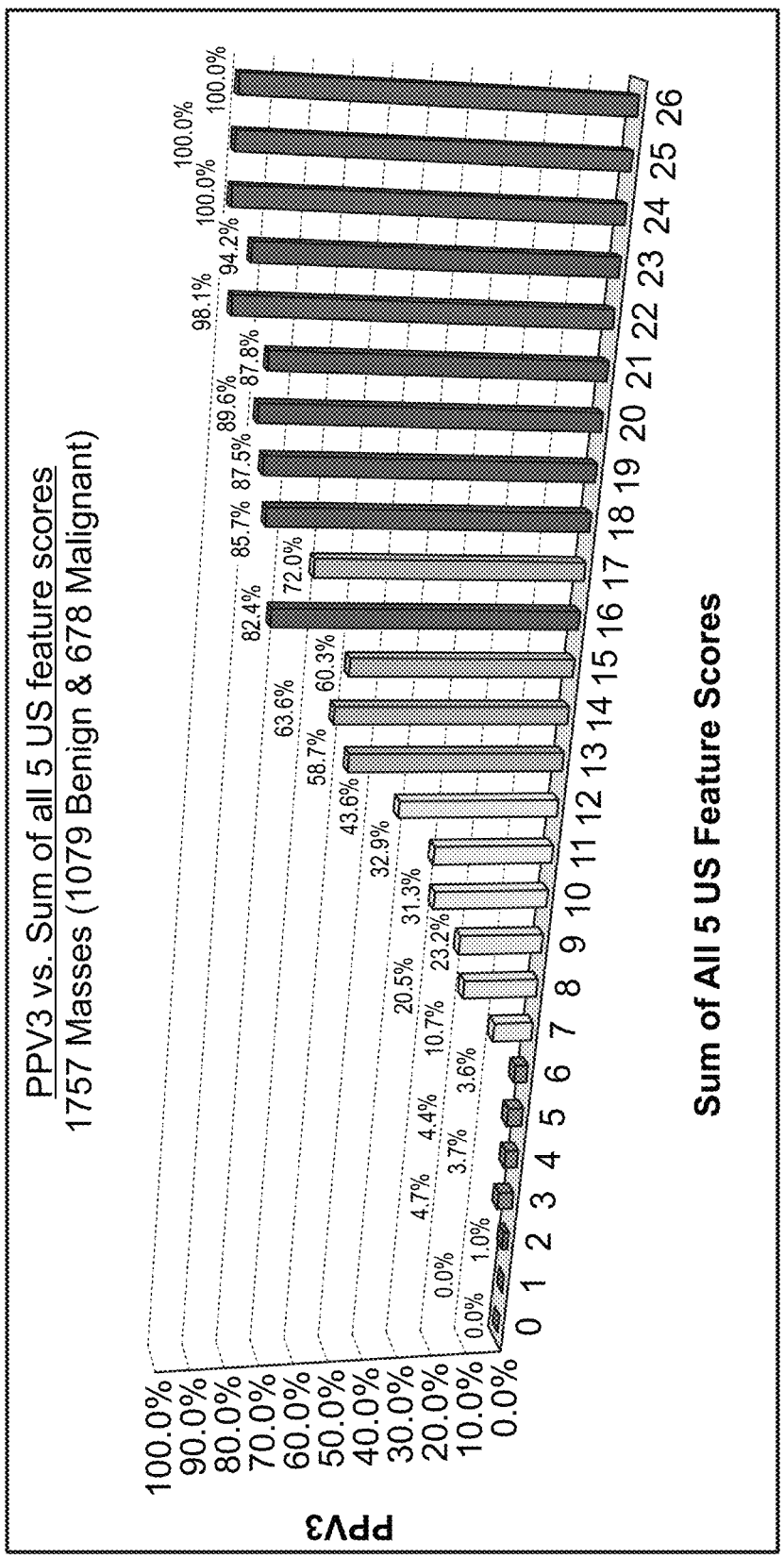
FIG. 10E illustrates an example of an unweighted sum of five US feature scores as related to PPV.

FIGS. 10A to 10E illustrates examples of PPV vs. feature scores of individual feature scores derived and combined in connection with an analysis of a number of subjects. Additionally or alternatively, the one or more processors may analyze the US feature scores alone, without utilizing any OA feature scores. FIG. 10E illustrates an example of an unweighted sum of five US feature scores as related to PPV. The sums illustrated in FIG. 10 E were derived from readings of 1757 masses, from which one thousand and 79 were benign and 678 were malignant. As shown in FIG. 10E, a feature score sum of 0 to 6 correlated to a PPV of 0.0%, 0.0%, 1.0%, 4.7%, 3.7%, 4.4% and 3.6%, respectively. A feature score sum of 7 to 12 correlated to a PPV of 10.7%, 20.5%, 23.2%, 31.3%, 32.9% and 43.6%, respectively. A feature score sum of 13 to 26 corresponded to a PPV of 58.7%, 63.6%, 60.3%, 82.4%, 72.0%, 85.7%, 87.5%, 89.6%, 87.8%, 98.1%, 94.2%, 100%, 100% and 100%, respectively. The relation between the feature score sum and the PPV illustrates a generally continuously increasing slope.

For example, the classification model may apply a regression equation that over-weights one or more of the boundary zone and/or peripheral zone feature scores for a US image relative to the internal zone feature scores, such as when the external feature scores are deemed to be more robust indicators of a particular predictive result. For example, the regression equation may use US feature scores to obtain a probability of malignancy, as the predictive result. A nonlimiting example of US only feature scores may be that the US internal zone US shape=5, US internal texture feature=3, US internal sound transmission=2, US boundaries zone=4, and US peripheral zone=6. The foregoing combination of US only feature scores may yield a predictive result that a mass has a probability of malignancy=94.35 percent. Additionally or alternatively, the classification model may further utilize non-US data that has a lesser weighting, such as the BI-RADS rating, maximum mass diameter and depth to posterior boundary of the mass.

The classification model may provide, as the predictive result, a probability of malignancy. Additionally or alternatively, the classification model may provide, as the predictive result, the probability of malignancy correlated to a BI-RADS rating.

Figure 12:
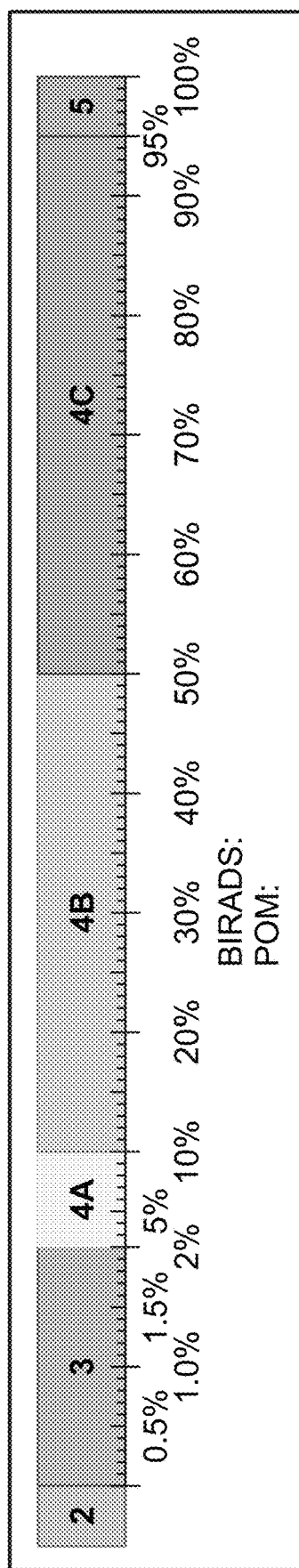
FIG. 12 illustrates an example of a relation between BI-RADs ratings and LOM/POM/PPV scores.

FIG. 12 illustrates a relation that may be defined between probabilities of malignancy and BI-RADS ratings. For example, BI-RADS ratings of 0, 1 and 2, may be defined to correspond to a LOM/PPV of 0%. A BI-RADS 3 rating may be defined to correspond to a LOM/PPV of 0% to 2%, while BI-RADS 4A, 4B, 4C and 5 ratings are defined to correspond to LOM/PPV ranges of >2% and ≤10%, >10% and ≤50%, >50% and <95% and ≥95%-100%, respectively. The predictive results calculated herein afford substantially more objective and precise estimated LOM/PPV information than a mere binary indication/decision between whether to perform a biopsy or not perform a biopsy. When the mean and the entire 5th-95$^{th}$ percentage range of the false negative rate (FNR) lies far to the left of the 2% FNR line, the mass can be classified as BI-RADS 3, and there is an option perform short interval follow-up imaging rather than performing biopsy. When the mean and the entire 5th-95$^{th}$ percentile range the FNR lie well left of the 0.5% FNR, there is an option to classify the mass as BI-RADS 2 rather than as BI-RADS 3, and to omit the 6 month follow-up imaging examination.

Additionally or alternatively, the classification model may apply US feature scores to generate a prognostic result that corresponds to one or more prognostic biomarkers. For example, feature scores may be correlated with surrogate receptor biomarkers, such as in connection with the estrogen receptor, progesterone receptor, HER2 receptor status, KI-67. For example, the predictive result may utilize the ER/PR status to upgrade or downgrade a staging. As a further example, classification model may utilize US internal zone sound transmission is a strong prognostic biomarker for ER, PR, HER2 and KI 67. In accordance with new and unique aspects herein, it has been found that the US internal zone sound transmission correlates well with ER status and PR status ($p=9.8713\times10^{-16}$) and ($p=3.6206\times10^{-15}$), distinguishes ER+/PR+ from ER+/PR− ($p=0.003$), correlates well with HER2 status ($p=0.008$), correlates with continuous Ki-67 (($p=5.1302\times10^{-13}$) and helps distinguish negative axillary LNs from positive axillary LNs ($p=0.013$).

There are three primary clinical and pathologic prognostic indicators of breast cancer, namely size, histologic grade and lymph node status. In accordance with new and unique aspects herein, it has been found that sound transmission has a different relation with lymph node metastasis than sound transmission has with other biomarkers. Additionally or alternatively, the classification model may US feature scores, OA feature scores and/or non-US/OA data to obtain a predictive result indicative of lymph node status. For example, the classification model may overweight the internal zone sound transmission feature to obtain an indication of lymph node metastasis. Shadowing appears to indicate an increased risk of lymph node metastasis, while enhanced sound transmission appears to indicate a lowered risk of lymph node metastasis. It is been found that sound transmission is a powerful prognostic indicator of biomarker for histologic grade. Sound transmission is able to distinguish grade III from the other grades ($p=9.8609\times10^{-17}$), to distinguish histologic grade II from the other grades ($p=0.000011$), to distinguish histologic grade I from the other grades ($p=0.000196$).

It is been found that sound transmission is a powerful prognostic indicator of biomarker for molecular subtypes. Sound transmission is able to distinguish TNBC from the other molecular subtypes ($p=1.164\times10^{-13}$), to distinguish Luminal A from the other molecular subtypes ($p=4.2103\times10^{-14}$), to distinguish HER2 from the other molecular subtypes ($p=0.003$).

Mass Orientation as Prognostic Indicator

Additionally or alternatively, the classification model may apply US feature scores to generate a predictive result that corresponds to one or more prognostic biomarkers. In accordance with new and unique aspects herein, it has been found that a nonparallel orientation of a mass (with respect to an axis extending perpendicular to the skin surface) affords a good prognostic indicator. The nonparallel orientation correlates well with acinar adenocarcinomas of the breast (AABs) that are small enough in size that they affect only a single terminal duct lobular unit (TDLU), such as less than 20 mm, and more preferably less than 15 mm, and more preferably less than 10 mm. TDLUs are most numerous anteriorly within the memory zone and at the periphery of the memory zone. The memory zone has a hilar-like structure. AABs arise from TDLUs at the periphery of the memory zone, a fact that early and are mammogram detectable when small. DABs arise from ducts in the center of the memory zone and rejected later when calcification occurs and often involve an entire "sick lobe" at the time of discovery. DABs are more likely to be stem cell carcinomas. Cancers that arise from prostate acini (acinar adenocarcinoma of the prostate or AAP) have a much better prognosis than cancers that arise from prostate ducts ductal adenocarcinoma of the prostate or DAP). Cancers that arise from breast acini have a much better prognosis than cancers that arise from memory ducts. For example, it is been found that the cumulative survival of women with a cancerous mass having a size of 1-14 mm that is AAB is 92.5% at approximately 20 years after diagnosis versus a 62% cumulative survival rate for DABs after the same period of time.

Further, masses having a nonparallel orientation with respect to an axis extending perpendicular to the skin indicate a higher likelihood that the mass is grade 1 or grade 2 or luminal A. Grade III IBCs have a lower percentage of nonparallel orientation as compared to grade I and II, but the difference is not statistically significant. TNBCs have a lower percentage of nonparallel orientation than do luminal A subtype masses ($p=0.002$). Masses exhibiting a shape characteristic having a nonparallel orientation are 1.7 times more likely to correspond to a grade I, as compared to a grade III. The right panel compares the molecular subtypes to the shape feature of irregularity without angles and nonparallel. Masses, that exhibit a shape characteristic of irregular without angles and nonparallel, exhibits a 1.6 times greater likelihood to be a luminal A subtype, as compared to a TNBC subtype. Masses, that exhibit the irregular without angles and nonparallel shape characteristic, exhibit a 0.33 times greater likelihood to be a HER-2 subtype as compared to a luminal A subtype. The HER-2 cancer subtype often exhibits large DAB components with ducts that are oriented parallel.

Additionally or alternatively, the classification model may apply US feature scores to generate a predictive result based on an extent to which ducts and lobules are disproportionately enlarged relative to a reference. The extent of disproportionate enlargement of the ducts and lobules is accounted for within one or more of the feature scores described herein. When ducts and lobules are disproportionately enlarged, the condition will result in a corresponding feature score being increased appropriately. In accordance with new and unique aspects herein, it has been found that a relation exists between grade and acinar or ductal size. Nuclear grade 3 corresponds to ducts and lobules that are disproportionately enlarged enough to more easily recognize them as being abnormal (e.g., four, six, eight, 10 times larger than a normal size) in most cases. Nuclear grade 2 corresponds to ducts and lobules that are sometimes disproportionately enlarged enough to recognize an abnormality (e.g., two or four times larger than normal). A nuclear grade 1 frequently does not enlarge the ducts and/or lobules enough to be recognized as abnormal.

Masses, that exhibit enlarged ducts in the peripheral zone, exhibits a two-point times greater likelihood to be a HER-2 subtype, as compared to a TNBC subtype. Masses, that exhibit enlarged ducts in the peripheral zone, exhibit a 2.3 times greater likelihood to be a HER-2 subtype as compared to a luminal A subtype. The HER-2 cancer subtype has a large percentage of associated DCIS (DAB), while luminal A and TNBC do not.

Additionally or alternatively, the classification model may apply US feature scores to generate a predictive result based on a relative thickness of a marginal echogenic rim and a length of the hyperechoic spicules. In accordance with new and unique aspects herein, it is been recognized that a relation exists between the histologic grade and the relative thickness of the marginal echogenic rim and length of the hyperechoic spicules. Each microlobulation represents an enlarged acinus or an enlarged duct or neoduct. The variable halo thickness and spicule length correlates with histologic grade. Thicker echogenic rims and longer spicules relative to the hypoechoic central nidus are indicative of AAB, histologic grade I or II. Thinner echogenic rims and shorter or absent spicules, relative to hypoechoic central nidus, are indicative of AAB, histologic grade III and/or triple negative invasive breast cancer.

US and/or OA Feature Scores as Semi-Quantitative Predictive Biomarkers

In accordance with new and unique aspects herein, methods and systems are described that utilize US and/or OA ordinally arranged feature scores as semi-quantitative diagnostic biomarkers to calculate a predicted likelihood of malignancy. One non-limiting example of a semi-quantitative result is an estimate of a risk of cancer. The semi-quantitative diagnostic result is not simply a binary output as to whether a biopsy should or should not be obtained. The semi-quantitative diagnostic result is a value along a continuous or discrete range. Among other things, the semi-quantitative diagnostic result may indicate a likelihood of malignancy (LOM) or PPV that is greater than the biopsy threshold 2% FNR. The semi-quantitative diagnostic result provides information beyond simply whether a mass satisfies a biopsy threshold FNR. Heretofore, a biopsy threshold FNR was provided at 2%, such that when the LOM/PPV is greater than 2%, a biopsy is obtained and when the FNR is at or below 2%, no biopsy is obtained. Methods and systems herein calculate the semi-quantitative diagnostic mean predicted LOM/PPV a confidence interval of 90% (from the $5^{th}$ percentile to the $95^{th}$ percentile). By determining a predicted LOM to have a value along a continuous or discrete range, embodiments herein offer objective and precise methods and systems to assign specific BI-RADS categories higher than BI-RADS 3 and to assign BI-RADS 4 subcategories by determining where within the ACR BI-RADS benchmark PPV ranges for each of the BI-RADS categories a predicted LOM/PPV lies.

In accordance with new and unique aspects herein, it is been recognized that, by calculating a LOM/PPV over a range extending beyond the conventional biopsy threshold 2% FNR, a semi-quantitative diagnostic result may be further utilized to downgrade prior BI-RADS ratings that are obtained from a separate non-OA and non-US imaging modality, such as from a mammogram. Heretofore, no reliable process was known for downgrading general BI-RADS ratings, such as a BI-RADS 4 rating without sub categorization.

In order to maximize true negative downgrades while minimizing false-negative downgrade, it is desirable to start with a reasonable pretest probability of cancer. For example, the pre-test PPV range may be set to be narrow (e.g., greater than 2% and up to and equaling 10%, the ACR PPV benchmark range for BI-RADS category 4a). Also, the mean for the pre-test PPV should be set to a low enough level (e.g., greater than 2% and less than or equal to 10%). In accordance with embodiments herein, the quantitative predictive result provides an LOM/PPV value along a range, such as between zero and 100%, from which a BI-RADS classification may be derived, including ACR BI-RADS PPV benchmark ranges for sub categorizations within the BI-RADS 4 rating. Additionally or alternatively, the BI-RADS classification including sub categorization can then be used to downgrade a BI-RADS rating derived from another modality, such as from a mammogram.

In accordance with new and unique aspects herein, it has been recognized that a general classification, such as BI-RADS 4, without sub categorization, is not helpful to maximize true negative downgrades while minimizing false negative downgrades. The pre-test PPV range for BI-RADS 4 without sub categorization is far too wide (e.g., greater than 2% to less than 95%). Also, the mean pre-test PPV is too high (20% to 45%) for NLR of any currently existing diagnostic imaging test. The ACR ultrasound BI-RADS committee has not proposed guidelines for sub categorize and, instead, subcategories remain optional. A recent national mammography database paper shows that approximately 33% of national mammography database breast imagers use BI-RADS four subcategories with mammography.

In accordance with new and unique aspects herein, methods and systems are proposed to utilize classification models to more objectively and more precisely define BI-RADS 4 subcategories for particular masses in a manner that reduces false positive and negative biopsies than can be done with the ACR Ultrasound BI-RADS $5^{th}$ edition features alone. Conventional ultrasound features that use BI-RADS have been developed and are used to define the border between the BI-RADS three and BI-RADS 4 or 4A categories. None of the ACR conventional ultrasound BI-RADS $5^{th}$ edition features have been used in an objective way to assess a probability of malignancy greater than 2% or to objectively subdivide the BI-RADS 4 category. In accordance with new and unique aspects herein, methods and systems order multiple categories of feature scores by PPV to thereby create an objective and more precise basis for assignment of probabilities of malignancy above a LOM/PPV biopsy threshold (e.g., at 2%) and assignment of BI-RADS 4 subcategories. For example, the classification models described herein may define a probability of malignancy between 5% and 90%, and more particularly between 10% and 70%, and even more particularly between 25% and 60%.

In order to provide semi-quantitative diagnostic results, certain US features and/or OA features are identified as good semi-quantitative diagnostic biomarkers. To represent a semi-quantitative diagnostic US/OA biomarker, the US features and/or OA features should be distinguishable from one another and between cancer and benign masses. Each US feature is scored in a manner that the risk of cancer (PPV) increases with an increasing score. Alternatively, the scoring system may be defined such that the risk of cancer increases with a continuously decreasing score, provided that the scoring system for all of the US features and/or OA features is similar, namely the risk of cancer increases relative to each feature as the feature score decreases.

Figure 11A:
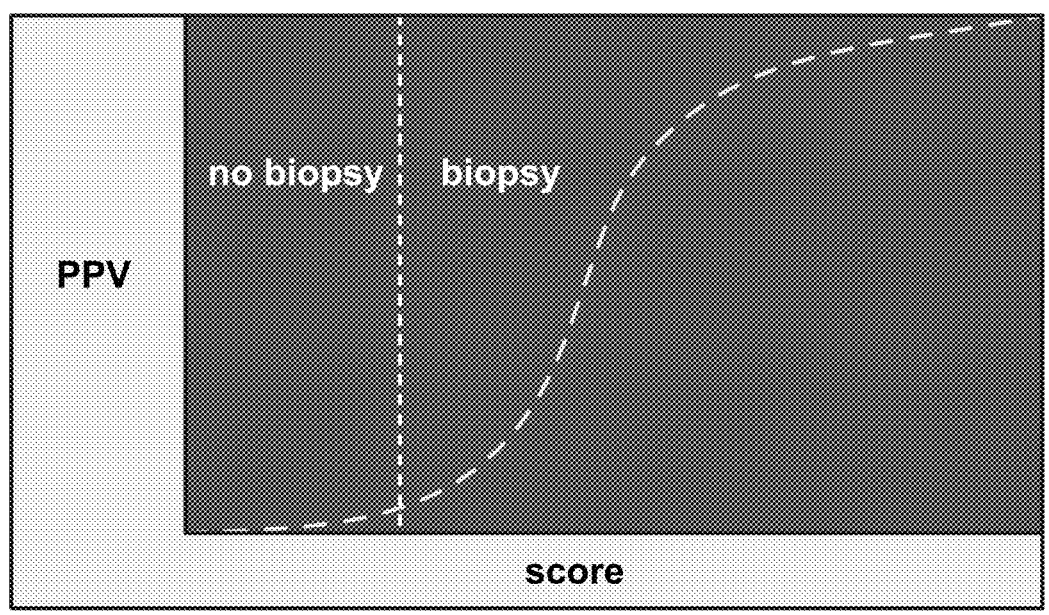
FIG. 11A illustrates an example of a nonlinear sigmoid shaped relation between PPV and sum of all individual features scores.

In accordance with new and unique aspects herein, feature scoring system for US features and/or OA features has been defined such that the slope of the PPV vs summer score graph exhibits a nonlinear sigmoid shaped. FIG. 11A illustrates an example of a nonlinear sigmoid shaped relation between PPV and sum of all individual features scores. The sigmoid shape of the PPV slope vs. summed scores is ideal because it enables the summed scores to function a both qualitative diagnostic biomarkers and as semi-quantitative diagnostic biomarkers. In the example of FIG. 11A, the ideal sigmoid-shaped PPV vs. summed score slope has 3 parts:

1) The low, left, and flat part of the slope where summed scores are lowest, and where PPVs are very low and increase very little with increasing summed scores
2) A middle section of mid summed scores that is steeply sloped, and where PPV increases rapidly within increasing summed scores.
3) The final right, high, and flat portion of the curve where summed scores are the highest, and where PPV increases more slowly with increasing summed scores.

To minimize false positives while not increasing false negatives, the 3 parts of the sigmoid shaped PPV vs. summed score slope should have the following characteristics:

1) The left initial part of the curve should be as low, as flat, and as long as is possible, since this is the segment of the curve where masses that can be classified as BI-RADS 3 are located and where biopsies can be avoided.
2) The final right part of the curve should be as high, as long, and as flat as possible, since this is the part of the curve where masses that are classified as BI-RADS 4C and 5 are located, where biopsy is always necessary, and where adjunctive diagnostic technologies are least useful.
3) The middle part of the curve should be a short and steeply sloped as possible, as this the part of the curve where BI-RADS 4A and 4B masses lie, where most false positives arise, and that gives rise to most of the biopsies that reveal benign histology.

Figure 11B:
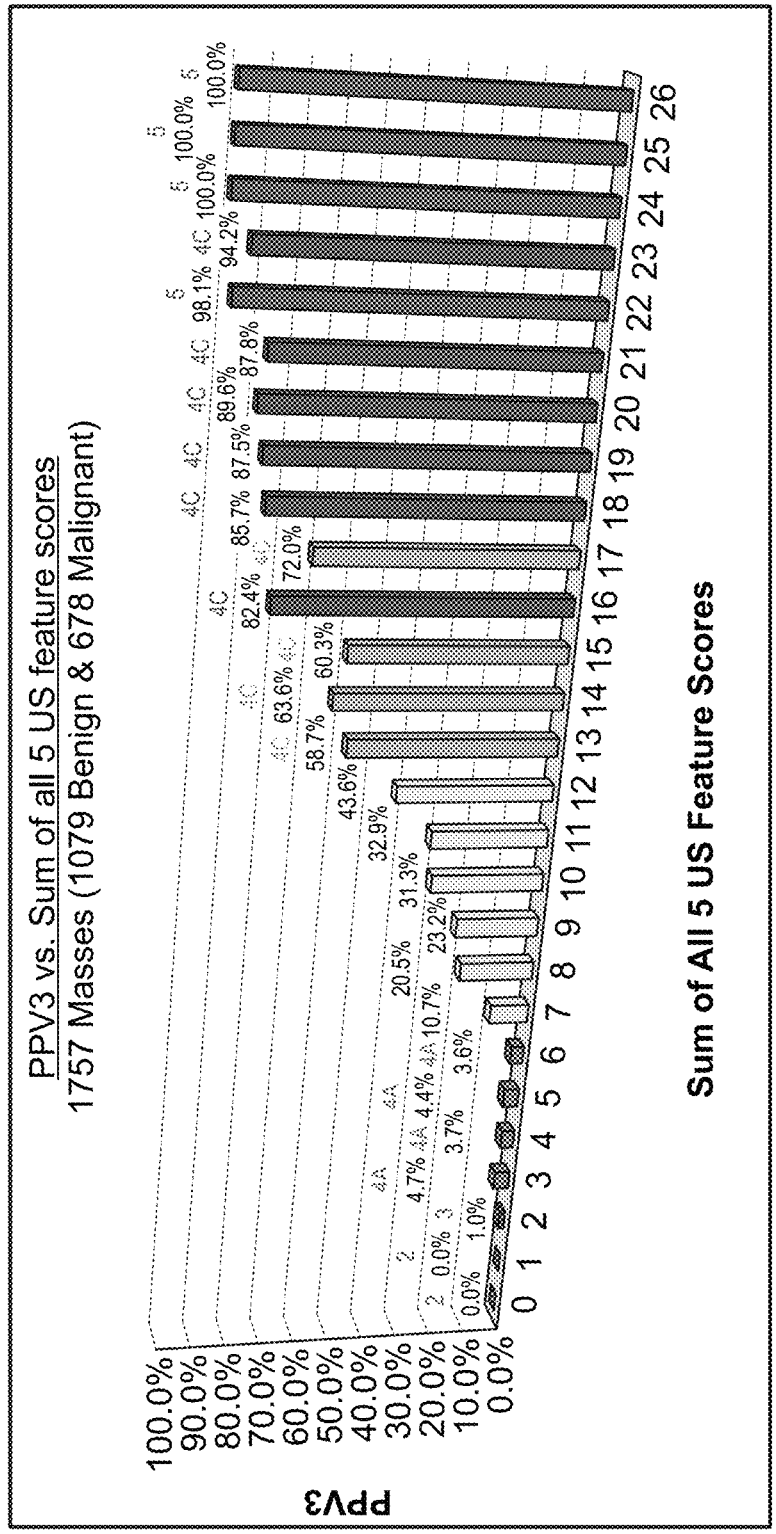
FIG. 11B illustrates a relation between PPV and a sum of all five US feature scores, along with corresponding BI-RADS ratings, there were derived from a number of patient studies.

FIG. 11B illustrates a relation between PPV and a sum of all five US feature scores, along with corresponding BI-RADS ratings, there were derived from a number of patient studies (1757 masses were analyzed, from which 1079 were benign and six and 78 were malignant). The summed feature scores of 0-6 have PPVs of 0%, 0%, 1%, 4.7%, 3.7%, 4.4%, 3.6%, respectively, from the 1757 masses that were analyzed. Feature score sums of 0 and 1 may be afforded a BI-RADS rating of 2 or 3, while feature score sum of 2 may be classified as Bi-RADS 3, and summed scores of 3-6 are afforded a BI-RADS rating of 4A. The feature score sums of 7-12 have PPVs of 10.7%, 20.5%, 23.2%, 31.3%, 32.9% and 43.6%, respectively. The feature score sums of 13-21 are afforded BI-RADS ratings of 4C and have PPVs of 58.7%, 63.6%, 60.3%, 82.4%, 72%, 85.7%, 87.5%, 89.6% and 87.8%, respectively. The feature score sums of 22 and 24-26 are afforded a BI-RADS rating of 5 and have PPVs of 98.1% and 100%.

The relation between PPV and the US feature score sums generally follows a nonlinear relation similar to the relation illustrated in FIG. 11A. For example, the nonlinear relation represents a sigmoidal curve, for which an initial portion (corresponding to low cumulative scores) exhibits a relatively flat gradually increasing slope, while an intermediate portion (corresponding to intermediate cumulative scores) exhibits a relatively steep sharply increasing slope, followed by a final portion (corresponding to high cumulative scores) exhibiting a relatively flat gradually decreasing slope.

Figure 11C:
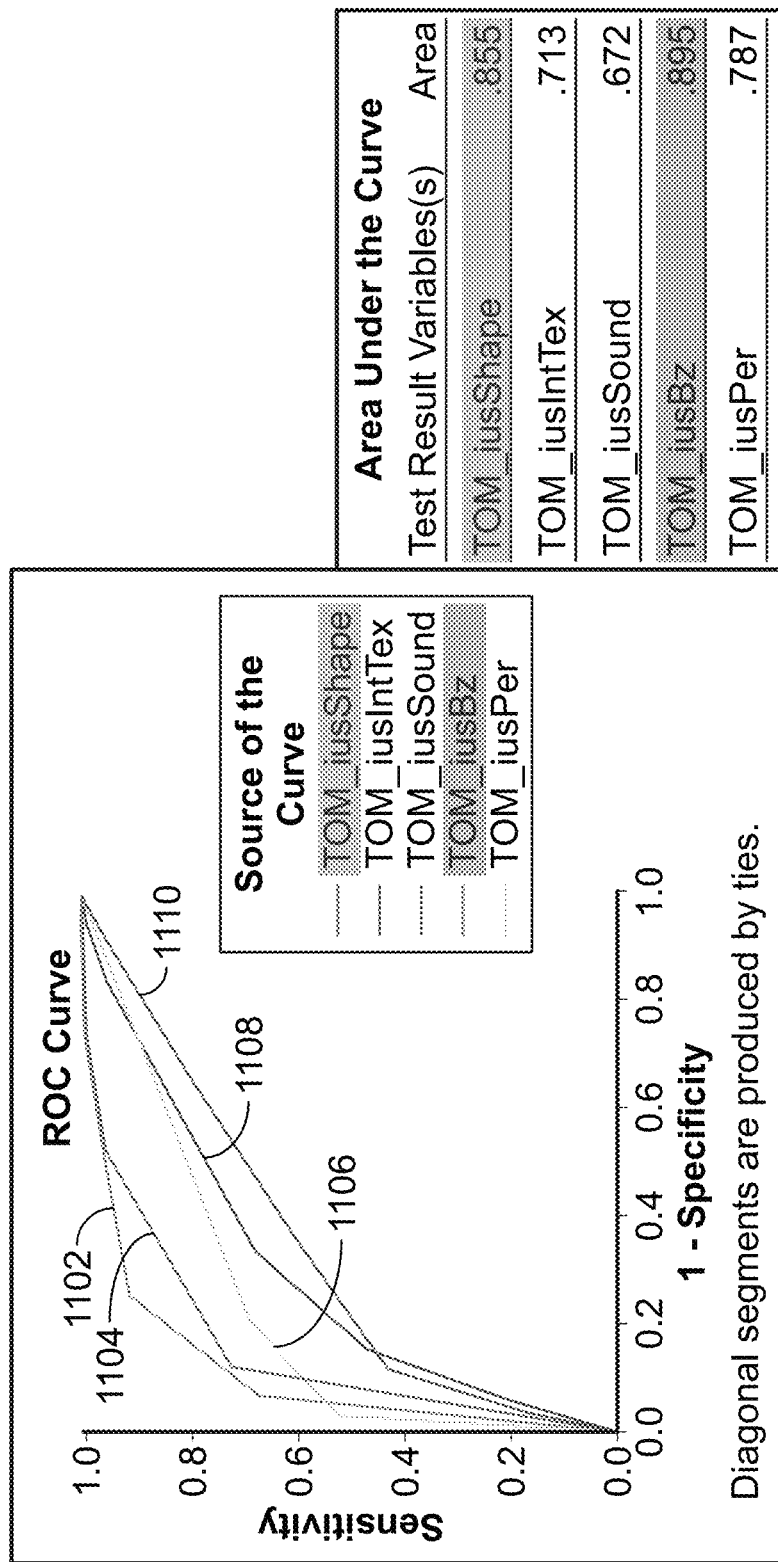
FIG. 11C illustrates an example comparing the areas under the curves (AUCs) of the receiver operating characteristic (ROC) curves of the individual US features.

FIG. 11C illustrates an example comparing the areas under the curves (AUCs) of the receiver operating characteristic (ROC) curves of the individual US features. The graphs 1102-1110 illustrate the relation between AUCs for the US boundary zone, US internal shape, US peripheral zone, US internal echotexture, and US internal sound transmission, respectively. The data in FIG. 11C was based on the collection of masses studied, as described in connection with FIG. 11B. The lower right panel titled "area under the curve" illustrates an area under each of the ROC (receiver operating characteristics) curves 1102-1110 for the corresponding US feature. As shown in FIG. 11 C, the boundary zone score exhibits highest AUC with (exhibiting an area under the curve of 0.895), with the internal zone shape being second best (exhibiting an area under the curve of 0.855).

Figure 11D:
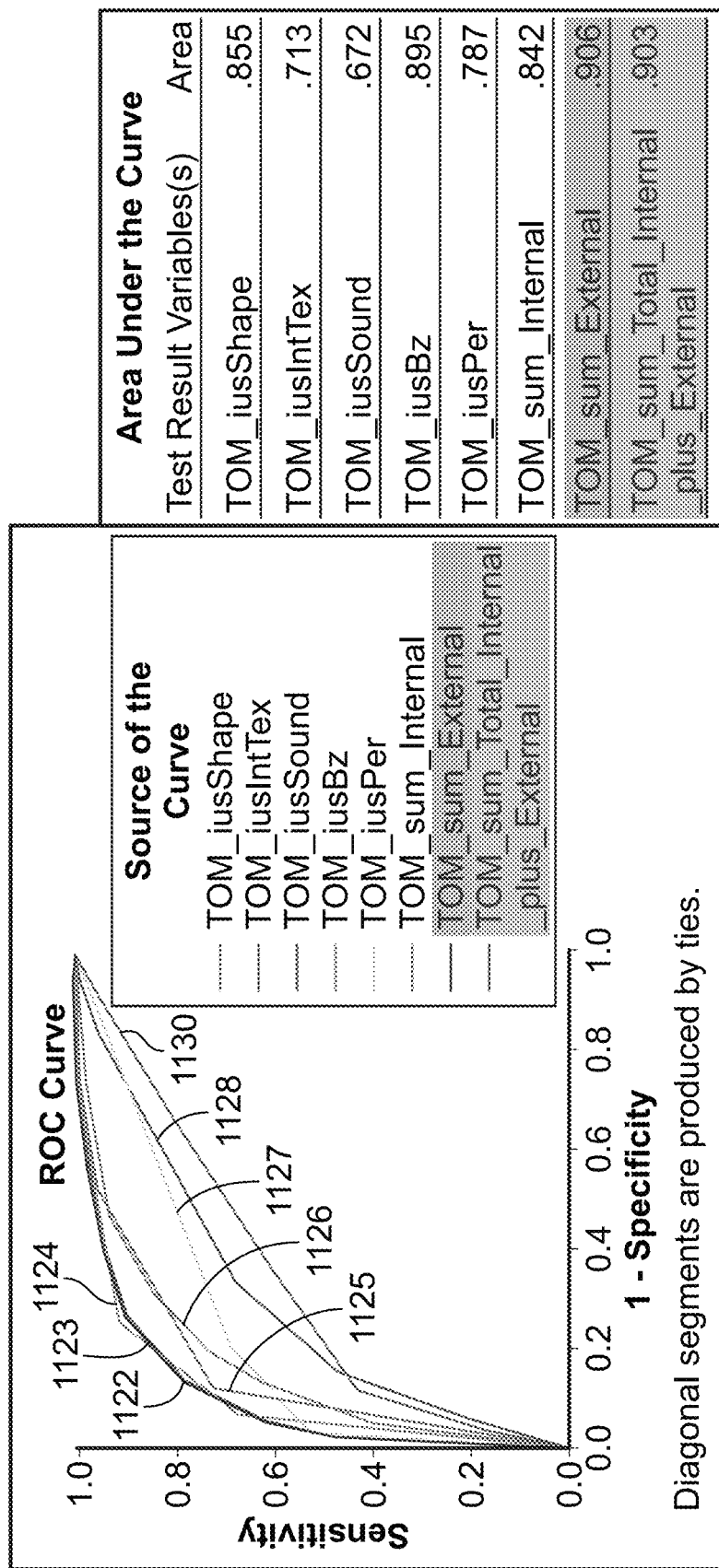
FIG. 11D illustrates an example comparing AUCs for the sums of the external features and the sum of all five features.

FIG. 11D illustrates an example comparing AUCs for the sums of the external features and the sum of all five features. The graph 1122 shows the relation between the AUCs for the sum of all five US feature scores, while graphs 1123 shows the relation for the sum of the external US feature scores (namely the boundary zone and peripheral zone). The sum of the external US feature scores has an area under the curve of approximately 0.906, while the sum of the five external US feature scores as an area under the curve of proximally 0.903. The graph 1124 shows the AU for the sum of the internal feature scores (e.g., shape, texture and sound transmission) (having an area of 0.842). The graph 1125 shows the AUC for the internal zone shape (having an area of 0.855). The graphs 1126 to 1130 show the AUCs for the remaining individual feature scores, namely internal zone texture, internal zone sound transmission, boundary zone and peripheral zone. As shown in FIG. 11D, the sum of the two external scores exhibits the highest and best AUC, followed next by the sum of all five feature scores.

The graphs 1122-1130 illustrate the relation between AUCs for the US boundary zone, US internal shape, US peripheral zone, US internal echotexture, and US internal sound transmission, respectively. The data in FIG. 11 C was based on the collection of masses studied, as described in connection with FIG. 11B. The lower right panel titled "area under the curve" illustrates an area under each of the curves 1102-1110 for the corresponding US feature. As shown in FIG. 11C, the boundary zone score exhibits the greatest and best AUC (exhibiting an area under the curve of 0.895), with the internal zone shape being second best (exhibiting an area under the curve of 0.855).

Using a combination of US feature scores offers several benefits. The scores complement one another and overcome weakness of individual scores. Combining the scores improves their positive predictors and improves low scores as negative predictors. Combining the scores forms low left and high right shelves in the relation of the PPV to the summed feature scores at the lowest some scores and at the highest some scores with a very steep rising slope in between. Using the scores together in a classification model, such as regression equation or other machine learning algorithm improves the performance over a simple unweighted sum.

In accordance with new and unique aspects herein, methods and systems have been developed that utilize a regression equation that over weights the more robust feature scores, such as the boundary zone score and the internal zone shape score. The over weighted combination of the feature scores may be used together with elastography to decrease false positives and potentially decrease biopsies of benign masses.

As example #1, assume that a US image of a mass exhibits normal surrounding tissue, a complete thin, hypoechoic capsule, enhanced sound transmission, uniform isoechoic internal echotexture, but with an irregular shape without angles in the internal zone. The foregoing shape may result in a combination of feature scores included US shape 3, US texture 1, US sound 0, boundary zone 0 and peripheral zone 0, leading to a LOM/PPV of 4.14%. Given that the ACR benchmark range of PPV for BI-RADS 4A is greater than 2% and less than or equal to 10%, and since the predicted LOM/PPV falls within the 4A benchmarked range, classification models herein may well identify a predictive result that classifies the mass as a BI-RADS 4A rating.

As example #2, assume that a US image of a mass exhibits the same characteristics as example #1, but with an irregular shape with angles in the internal zone. The foregoing shape may result in a combination of feature scores included US shape 5, US texture 1, US sound 0, boundary zone 0 and peripheral zone 0, leading to a LOM/PPV of 9.73%. Given that the ACR benchmark range of PPV for BI-RADS 4A is greater than 2% and less than or equal to 10%, and since the predicted LOM/PPV falls within the upper limit of the 4A benchmarked range, classification models herein may well identify a predictive result that classifies the mass as a BI-RAD S 4A rating.

As example #3, assume that a US image of a mass exhibits the same characteristics as example #1, but with a partial thin hyperechoic capsule (not a complete thin) and with an irregular shape with angles (not without angles). The foregoing shape may result in a combination of feature scores included US shape 5, US texture 1, US sound 0, boundary zone 1 and peripheral zone 0, leading to a LOM/PPV of 16.58%. Given that the ACR benchmark range of PPV for BI-RADS 4B is greater than 10% and less than or equal to 50%, and since the predicted LOM/PPV falls within the lower limit of the 4B benchmarked range, classification models would objectively classify the mass as a BI-RADS 4B rating.

As example #4, assume that a US image of a mass exhibits the same characteristics as example #3, but with a thin echogenic halo (not a partial thin hyperechoic capsule) and with a "plump" oval shape (max/AP diameter ratio less than two). The foregoing shape may result in a combination of feature scores included US shape 1, US texture 1, US sound 0, boundary zone 5 and peripheral zone 0, leading to a LOM/PPV of 27.01%. Given that the ACR benchmark range of PPV for BI-RADS 4B is greater than 10% and less than or equal to 50%, and since the predicted LOM/PPV falls within the middle of the 4B benchmarked range, classification models would objectively classify the mass as a BI-RADS 4B rating.

Methods and Systems to Build Biomarker Machine Learning Classification Models

Next, an example is described for methods and systems to build an ensemble of biomarker machine learning classification models in accordance with embodiments herein. The process may be implemented by processors at a system located at one location, or server or distributed between multiple remote locations or servers. For example, one or more of the systems described in connection with FIGS. 1-3B may build and/or utilize biomarker MLC models. One or more processors obtain a labeled data set for multiple patients, along with a collection of US/OA features and parameters. The operations step through the labeled data set in various manners, based on the type of biomarker machine learning classifier algorithm being utilized to build the ensemble of classification models. It is recognized that the particular branches, decision points and order of operations will vary within embodiments contemplated herein, but still result in an ensemble of biomarker classification models as described herein. The one or more processors begin analyzing the labeled data set for a current decision point in a current decision tree. The processors compute outcome scores for one or more features of interest. The outcome scores are indicative of how well a particular feature of interest separates the labeled patient data into a class of interest. The one or more processors review the outcome scores and select the desired feature, as well as a threshold to be applied to the feature. The feature and threshold selected may represent the "best" feature and threshold that separate the labeled data set into one or more classes based on the present point in the decision tree.

Although learning methods vary depending upon the algorithm, the core of the mathematics is an iterative search over the feature space. Iterative searching is computationally intensive, especially when there are a large number of features and/or a large amount of data. Reducing the search space speeds up the process but tends to find a less optimal solution. As before, consider decision trees as an example. Decision trees learn by finding the optimal criteria to split the tree into branches. Each path through the tree ends up at a leaf and the goal is to find the splits, or decision points, such that each leaf contains mostly one class. The feature chosen for a split is found by considering all possible features and their values and selecting the feature that provides a desired result (e.g., the best one). As one example, the selection may be whether to use a boundary score or an internal vessel score as the feature to analyze at the decision point. In addition to selecting the feature to use at each branch, the biomarker machine learning classifier also determines what threshold level to apply to the feature at the decision point. For example, when boundary score is selected as the feature of interest at a particular branch point, then the biomarker machine learning classifier also assigns a boundary threshold, such that when the boundary score is above the boundary threshold, the decision branches in a first direction and when the boundary score is below the boundary threshold, the decision branches in a second direction.

As one example, the operations may be performed by computing a score called a "Gini impurity index" which is used to choose a split with the lowest score. Each split considers many features, a tree contains multiple splits, and an ensemble contains many trees. Beyond the feature level parameters, embodiments may utilize machine learning algorithms that have hyper-parameters that are tuned. For example, embodiments that use XGBOOSTtrees have a large set of hyper-parameters, including the number of trees, the maximum tree layer depth, and the learning rate. Hyper-parameters add dimensions to the search space and hence increase the computation effort for training. The one or more processors save the decision point within a current decision tree. The one or more processors determine whether the analysis should continue for more decision points in the current decision tree and/or whether the analysis should continue for a next the decision tree. If so, the one or more processors step to the next decision point in the current decision tree. For example, branching continues until reaching the maximum tree depth, identifying a lesion trait or meeting other criteria. The number of branches, the features used at each branch, and values used for separation at each branch are all parameters of the model. The parameters embody the training data. When a decision tree is finalized, the processors also assign lesion traits (e.g., benign class, malignant class, cancer subtype) to the last layer. The lesion traits may be stored with a classification probability based on the individual corresponding decision tree.

Alternatively, when a decision tree is completed and a new decision tree is to be started, the operation steps to the next decision tree. The operations are continuously operated until all of the decision points in a desired number of decision trees are built. The one or more processors save, as a current model, the collection of decision trees, each of which is comprised of a set of decision points built from the feature scores, feature selections and threshold selections described above.

The one or more processors determine whether another model is to be built from the labeled data set. If so, the one or more processors populate starting points within the next model. Otherwise, the process ends. In accordance with the operations above, and/or alternative sequences of operations, embodiments herein fit the model parameters to the labeled data set through a training or learning process. The training/learning process is also referred to as "building" the model.

Logistic Regression Models

One example of a predictive machine learning algorithm that may be implemented herein is logistic regression. Logistic regression is a supervised machine learning algorithm because it uses true labels for training. A supervised learning algorithm has input variables (x) and a target variable (Y) when the model is train, as in logistic regression algorithms. Embodiments herein form an ensemble of logistic regression models (e.g., 100), each trained on a subset of the control data set. The prediction is returned as the mean confidence interval (probability/likelihood of malignancy or LOM) and a confidence interval range (e.g., 90%) of the predictions from the ensemble. The prediction is returned as the Positive Predictive Value (PPV) that corresponds to the classifier probability.

The logistic regression models utilize a training data set that comprises a collection of observations or reads (e.g., 100, 1000, 10000). Each of the observations contains a set of OA images, US images, combinations of OA/US images, OA feature scores, and US feature scores. The OA and US feature scores may be assigned automatically by a computing system that segments and analyzes the OA, US and/or combined images. Additionally or alternatively, the OA and US feature scores may be assigned by one or more human independent reader. The OA and US scores relate to one or more characteristics of one or more lesions in the OA and US image set for an individual patient. The training data set includes a collection of images for a number of positive cases (malignant) and a number of negative cases (benign). In connection with building models for use as prognostic indicators, the training data sets may include collections of images for patients exhibiting a particular BI-RADS level, such as X images of patients with BI-RADS to, Y images of patients with BI-RADS 3, Z images of patients with BI-RADS 4A, etc.

The logistic regression model utilizes a feature set that includes reader-assigned scores for OA and US features, the patient age and the mammogram (MMG) BI-RADS category assigned by the site radiologist. The MMG BI-RADS is not defined for all observations. By way of example, the logistic regression model includes 15 or more OA feature scores, 5 or more US feature scores, age, mass size and depth to posterior margin and MMG BI-RADS applied in a heuristic rule. For example, the MMG BI-RADS heuristic rule may be defined as {2, 3, 4a, 4b, 4c, 5}. Initially, MMG BI-RADS may not be utilized as a feature in the logistic regression algorithm because too many lesions in the data set may be missing MMG data. However, once a data set collects a sufficient amount of MMG data the logistic regression algorithm can be trained on the subset of data with MMG data. Additionally or alternatively, even while the MMG BI-RADS may not be utilizes as a feature, the MMG BI-RADS may be applied as a heuristic rule that prohibits a downgrade if the MMG BI-RADS is at a certain level (e.g., 4 c or 5). For cases with a MMG BI-RADS rating at or above the set level, the sinogram returns the maximum of the classifier prediction and the benchmark PPV for the category, computed as the midpoint of the range (e.g., 70% for 4c, and 95% for 5). The MMG BI-RADS heuristic rule is not applied if the MIG BI-RADS rating is missing or inconclusive.

Extreme Gradient Boost Trees (XGBTree)

Additionally or alternatively the machine learning algorithm (biomarker machine learning classifier) may be implemented utilizing an Extreme Gradient Boosting Trees (XGBTree) machine learning algorithm. In order to understand the XGBTree, the decision tree should first be understood. Decision trees are a method of splitting the data based on features to either classify or predict some value. Each branch in a decision tree divides the data into one of two (or several, if the tree is not binary) groups. Each leaf node is allocated with a single label (class or predicted value). When predicting using the decision tree, the data is allocated to the appropriate leaf node, and the prediction is the label of that leaf node. Decision trees are flexible and interpretable. However, a single decision tree is prone to overfitting and is unlikely to generalize well. There are various ways of restricting the flexibility of a decision tree, such as by limiting its depth, but those methods then cause the decision tree to underfit. This is why decision trees are generally not used alone: instead, multiple decision trees are used together. Gradient boosting decision trees are one method (among many) of combining the predictions of multiple decision trees to make predictions that generalize well. Despite their strength, the idea behind XGBTree algorithms is very basic: combine the predictions of multiple decision trees by adding the predictions together. XGBTrees are trained iteratively—i.e. one tree at a time. For instance, the XGBTree algorithm first train a simple, weak decision tree based on the data. The decision tree is trained to minimize an objective function—using a lost term—such as the mean squared error-by recursively splitting the data in a way that maximizes some criterion until some limit-such as the depth of the tree—is met. The criterion is chosen so that the loss function is (approximately) minimized by each split. One commonly used criterion is the classification accuracy which is the fraction of observations that are correctly partitioned by the split.

The training of a decision tree is a recursive processing. The next tree is then trained to minimize the loss function when its outputs are added to the first tree. This is (approximately) achieved by recursively splitting the data according to a new criterion. For example, the criterion can be simply calculated for any split of data based on the gradient statistics (the value of the gradient for each data point). It should be noted that computing the best split requires the model to go through various splits and compute the criterion for each split. There is no analytical solution for determining the best split at each stage.

The XGBTree machine learning algorithm forms an ensemble of XGBTree models, each trained on all or a subset of a data set. As with the logistics regression machine learning algorithm, the prediction is returned as the mean and 90% confidence intervals of the ensemble, with the classification probability mapped to the observed PPV in the training data. The XGBTree machine learning algorithm may utilize the same or different training data as the logistic regression MLA. Additionally, the XGBTree MLA may also utilize individual human expert data. The XGBTree MLA utilizes the same features as for logistic regression MLA, with the possible addition of artifact scores, lesion size and/or lesion orientation. The MMG BI-RADS category may be included as a feature of the XGBTree MLA rather than applied in a heuristic rule, depending upon the amount of missing MMG data.

When growing the XGBTree, both XGBoost and lightGBM use the leaf-wise growth strategy. When training each individual decision tree and splitting the data, there are two strategies that can be employed: level-wise and leaf-wise. The level-wise strategy maintains a balanced tree, whereas the leaf-wise strategy splits the leaf that reduces the loss the most. Level-wise training can be seen as a form of regularized training since leaf-wise training can construct any tree that level-wise training can, whereas the opposite does not hold. Therefore, leaf-wise training is more prone to overfitting but is more flexible. This makes it a better choice for large datasets. Compared to the case of level-wise growth, a tree grown with leaf-wise growth will be deeper when the number of leaves is the same. This means that the same max_depth parameter can result in trees with vastly different levels of complexity depending on the growth strategy.

An important challenge in training the XGBTree is the process of finding the best split for each leaf. When naively done, this step requires the algorithm to go through every feature of every data point. The computational complexity is thus $O(n\_\{data\}\ n\_\{features\})$. Modern datasets tend to be both large in the number of samples and the number of features. For instance, a tf-idf matrix of a million documents with a vocabulary size of 1 million would have a trillion entries. Thus, a naive GBDT would take forever to train on such datasets. There is no method that can find the best split while avoiding going through all features of all data points. Therefore, the various methods that XGBoost and lightGBM present are methods of finding the approximate best split.

Additionally or alternatively, histogram-based methods (XGBoost and lightGBM) may be utilized. The amount of time it takes to build a tree is proportional to the number of splits that have to be evaluated. Often, small changes in the split don't make much of a difference in the performance of the tree. Histogram-based methods take advantage of this fact by grouping features into a set of bins and perform splitting on the bins instead of the features. This is equivalent to sub sampling the number of splits that the model evaluates. Since the features can be binned before building each tree, this method can greatly speed up training, reducing the computational complexity to $O(n\_\{data\}\ n\_\{bins\})$. Though conceptually simple, histogram-based methods present several choices that the user has to make. Firstly the number of bins creates a trade-off between speed and accuracy: the more bins there are, the more accurate the algorithm is, but the slower it is as well. Secondly, how to divide the features into discrete bins is a non-trivial problem: dividing the bins into equal intervals (the most simple method) can often result in an unbalanced allocation of data. XGBoost offers the option tree_method=approx, which computes a new set of bins at each split using the gradient statistics. LightGBM and XGBoost with the tree_method set to histogram will both compute the bins at the beginning of training and reuse the same bins throughout the entire training process.

The operations discussed above, or another model building process may be implemented multiple times utilizing different combinations of the available labeled data set of the control patient population. For example, all or a majority of the label data set for all or majority of the patient population may be utilized to build a master model. In accordance with embodiments herein, the master classification model is then utilized to calculate predictive results and the like. In addition, the labeled data set may be subdivided into folds or subsets, wherein different subsets of the observations in the labeled data set are defined as "hold out" observations. Hold out models are built during cross validation utilizing the portions of the label data set that was not held out. As explained herein, the held out portions of the labeled data set may then be applied to the hold out models in connection with calculating classification probabilities, from which mapping functions are built for positive predictive values, false-negative rates and the like.

Additionally or alternatively, subsets of the observations from the labeled data set may be utilized to build bootstrapped models. For example, the labeled data set may include 100 observations, from which a random sampling of the observations are selected and utilized to build a first bootstrapped model. Multiple bootstrapped models are built based on different combinations of samples of the observations from the labeled data set for the control patient population. Once the classification models are built, when new observations for new patients are obtained, the bootstrapped models are then utilized in connection with calculating predictive results, namely for calculating a prediction interval for the new US/OA, US, OA and non-OA feature scores.

Figure 15:
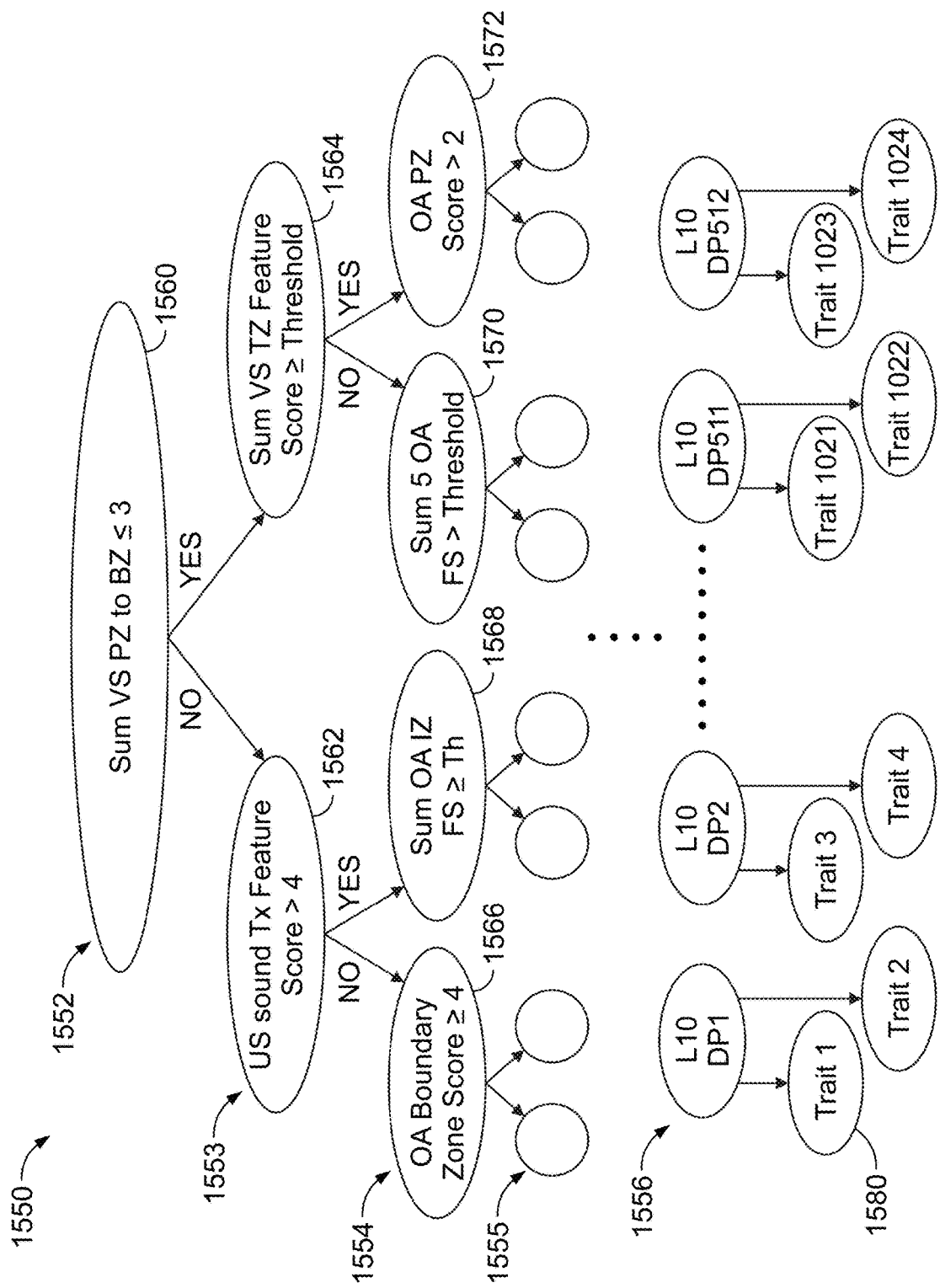
FIG. 15 illustrates an example of a decision tree implemented by a classification model built in accordance with an embodiment herein.

FIG. 15 illustrates an example of a decision tree from a classification model built in accordance with an embodiment herein. For example, the decision tree 1550 may be built by the XGBtree algorithm during one or more iterations through the operations of FIG. 15A. Alternatively, the decision tree 1550 may be built from an XGBtree or other algorithm following operations that differ from FIG. 15. The decision tree comprises decision points, branches between decision points and lesion traits. Lesion traits are obtained from multiple decision trees and mathematically combined to form a classification probability that a lesion exhibits a particular trait for a corresponding observation (e.g., based on the OA and non-OA feature scores assigned to the OA and non-OA images of the examination). The decision tree 1550 includes multiple layers 1552-565, including first through tenth layers. The tenth layer 1556 is also denoted by the labels "L10". Each layer 1552-1556 includes a set of decision points (DP). Each decision point tests a feature of interest relative to a threshold. For example, the decision points may test the OA and US features described herein, where each OA and/or US feature score is compared to a threshold.

In the example of FIG. 15, non-limiting examples of decision points are shown. A first decision point 1560 in the first layer 1552 may test whether the sum of the US peripheral zone and US boundary zone feature scores is less than or equal to 3. The US features are scored manually by a human expert and/or automatically by a machine learning classifier classification. The decision tree branches from DP 1560 to decision points 1562 and 1564 in the second layer 1553. As an example, the decision point 1562 tests whether the US IZ sound transmission feature score is greater than or equal to 4. The decision point 1564 may test whether the sum of the three US internal zone feature scores are greater than or equal to a threshold (e.g., 5). The classification model branches at 1562 or 1564 based on the corresponding decision. The decisions at 1560-1564 are based on US feature scores. As noted herein, in accordance with some embodiments, the classification model may be utilized to render final classifications based solely on US feature scores, without utilizing OA feature scores.

As other examples, the decision points 1566, 1568, 1570, 1572 test various corresponding OA/US feature scores. For example, at 1566, the model determines whether the OA boundary zone score is greater than or equal to 4. At 1568, the model determines whether the sum of the OA internal zone feature scores is greater than or equal to a threshold. At 1570, the model determines whether the sum of all five OA feature scores (internal and external) are greater than a threshold. At 1570, the model determines whether the sum of the 5 OA peripheral zone feature scores is greater than a threshold (e.g., greater than or equal to 2).

The decision tree 1550 continues for multiple layers until reaching a depth limit (e.g., 10 layers) as noted at L10_DP1 to L10_DP512. Each decision point in the 10th layer branches to two or more traits 1580 based on the feature scores tested and the score thresholds at layer 10. In the example of FIG. 15, 1024 traits (trait 1 to trait 1024) are available in a decision tree having 10 layers where each decision point splits into two branches. Additionally or alternatively, more or fewer resulting traits may be available at the layer of the final branch of the decision tree.

While the foregoing example illustrates a combination of US and OA feature scores, it is recognized that the model of FIG. 15 may be implemented based solely on US feature scores. When classification model is based solely on US feature scores, the numerous layers, similar to layers 1552-1553 are repeated to analyze various combinations of US feature scores relative to associated thresholds (and optionally other non-OA feature scores, such as age, depth to posterior margin, mass size, etc.), to arrive at a final decision point designating a final classification alone or in combination with an associated NPV and PPV.

Alternatively, the model of FIG. 15 may be implemented based solely on US features or based solely on OA feature scores. In the above example, the first few layers of the model may analyze only US feature scores, while the later layers of the model analyze only OA feature scores. Additionally or alternatively, the first few layers of the model may analyze US and OA feature scores for the peripheral and boundary zones, while the later layers of the model analyze US and OA feature scores for the internal boundary zones. Additional and alternative combinations of US and OA feature scores, as well as the corresponding internal, boundary and peripheral zones, may be analyzed in different combinations and orders, and with different thresholds within the layers of the model.

Additionally or alternatively, the decision trees may not simply be built to predict a likelihood of malignancy. It is recognized that the same decision tree and/or a different decision tree may be utilized to determine traits. The traits may correspond to different information, depending upon the nature of the decision tree. For example, the trait may simply represent a BI-RADS category/level. For example, traits 1-20 and 200-220 may designate the trait to correspond to BI-RADS 1, while traits 21-40 and 230-250 correspond to BI-RADS 2, traits 41-60 correspond to BI-RADS 3, trait 61-80 and 350-500 correspond to BI-RADS 4A, traits 81-120, 190-199, 255-275 and 1000-1024 correspond to BI-RADS 4B and the like. Additionally or alternatively, each trait may include a false negative value (FNV) and positive predictive value (PPV) associated therewith. For example, an output of a decision tree may designate a trait to be BI-RADS 3, the false negative value to be 0.7% and the PPV to be 99.2%.

The decision tree may be built to designate whether cancers will metastasize, in which the traits may be representative of more than two binary choices, instead designating a lesion trait to be one of various BI-RADS levels, with or without a likelihood to metastasize. Additionally or alternatively, a decision tree may output a classification probability that a type corresponds to a BI-RADS level. The classification probability provides a level of confidence that the observation (e.g., set of OA and non-OA feature scores for a current patient) is in a particular class, namely BI-RADS 3, BI-RADS 4A, BI-RADS 4B, etc.

The example of FIG. 15 illustrates a binary type decision tree. Additionally or alternatively, the decision trees may include more than 2 branches from each node, when a test at each decision point includes more than 2 outcomes. The examples of FIG. 15 at decision points show OA feature score tests. It is recognized that many of the decision points will include tests for US feature scores with respect to US feature score thresholds. The biomarker machine learning classifier algorithm builds a master model that comprises multiple decision trees similar to decision tree 1550 based on at least partially different labeled data sets, at least partially different features and/or at least partially different parameters. The feature set and parameters are adjusted as part of a trade-off of a false negative rate vs. probability of malignancy. Although the false negative rate is related to the probability of malignancy, it is a fundamentally different quantity. The difference is important because there is a dichotomy in the use of FNR, or sensitivity, for reporting clinical study results, and the use of PPV, or probability of malignancy, in the BI-RADS lexicon familiar to radiologists. While PPV and probability of malignancy are sometimes used interchangeably, this is not strictly correct, as probability of malignancy refers to the entire population; whereas PPV is an estimate of likelihood based on a sample of the population. The distinction is analogous to the difference between the population mean and the sample mean.

FNR, sensitivity and specificity are at least two of the preferred metrics for diagnostic tests because they are intrinsic to the test and do not rely on prevalence of the disease or condition in the study population. Conversely, PPV does depend upon prevalence; a higher prevalence increases the PPV. When PPV is reported for a study, the prevalence should also be reported.

Figure 16:
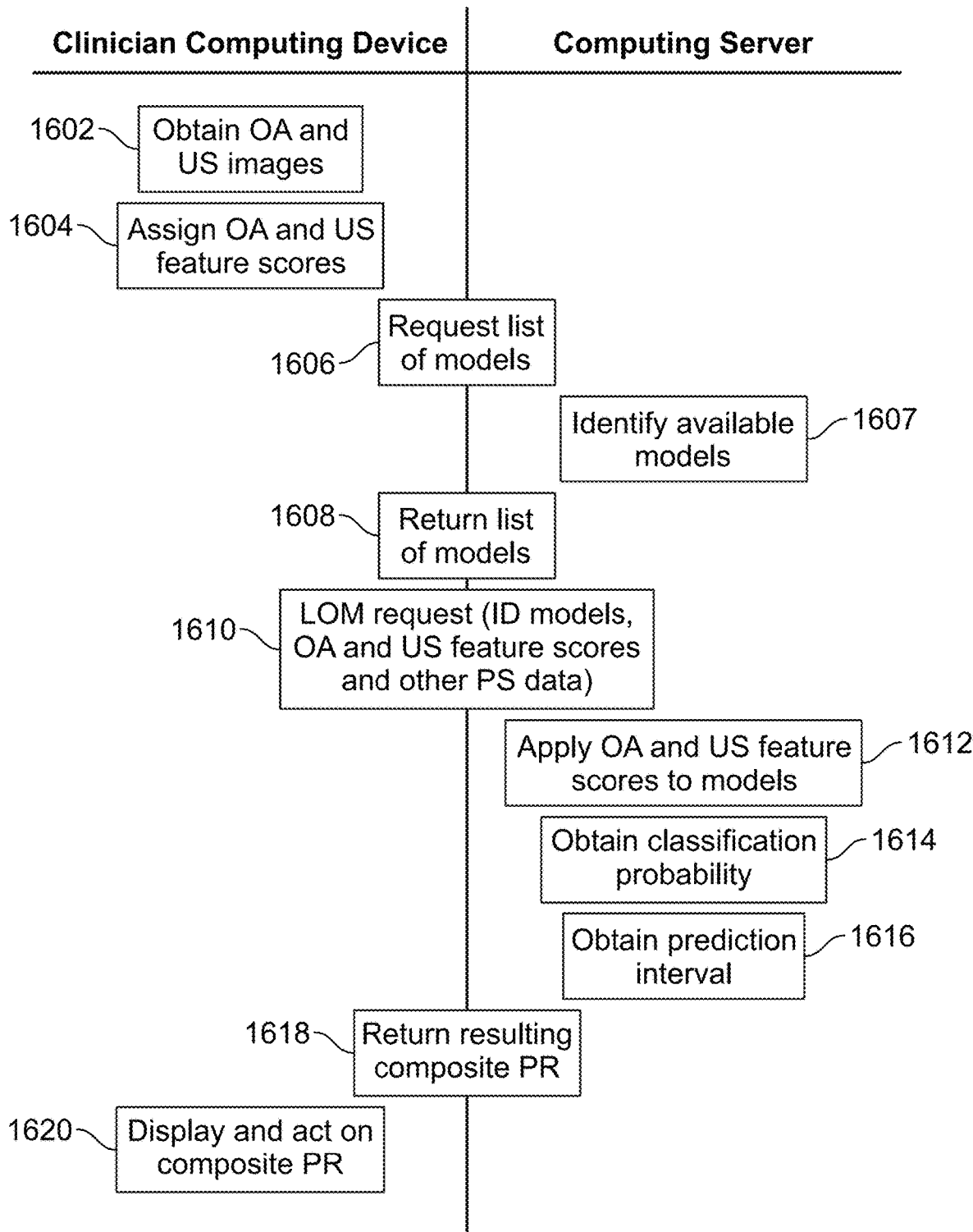
FIG. 16 illustrates a distributed operation diagram to further describe operations performed by a clinician computing device and a computing server in accordance with embodiments herein.

FIG. 16 illustrates a distributed operation diagram to further describe operations performed by a clinician computing device and a computing server in accordance with embodiments herein. The left side of the diagram represents operations performed by the clinician computing device, such as device 1620 in FIG. 16, while the operations on the right side of the diagram are performed by the server, such as server 1606. Beginning at 1602, one or more processors of the computing device 1620 obtain OA and US images. For example, the OA and US images may simply be read from a local or remote memory. Additionally or alternatively, the OA and US images may be obtained in real time, such as when the computing device 1620 is connected to or is formed interval with an optoacoustic imaging system. At 1604, the one or more processors of the computing device 1620 assign OA and US features scores. For example, the OA and US features scores may be assigned by a human expert while viewing the OA and US images. Additionally or alternatively, the OA and US features scores may be automatically assigned by the processors based on automated segmentation and analysis of the OA and US images. The automated assignment of OA in US features may be performed entirely separate from, or in conjunction with, the viewing by the human expert. For example, the OA feature score may relate to one or more of the following OA features: 1) internal vascularity and de-oxygenation, 2) peri-tumoral boundary zone vascularity and deoxygenation, 3) internal deoxygenated blush, 4) internal total blood, 5) external peri-tumoral radiating vessels, and 6) interfering artifact. For example, the non-OA feature score may relate to one or more of the following ultrasound features: 1) US Shape Score, 2) US Internal Texture, 3) US Sound Transmission, 4) US Capsular or Boundary Zone, 5) US Peripheral Zone, 6) Patient Age, 7) Mammogram-BIRADS, 8) Lesion Size, and/or 9) Lesion Posterior Depth.

Next, optional operations at 1606-1608 are described. At 1606, the computing device 1620 generates a request for a list of available models that may be utilized. The request to be generated automatically, without user input, by the computing device 1620. Additionally or alternatively, the request may be generated in response to an instruction from the clinician through the GUI. The processors of the server 106 receive the request for the list of models and based thereon, identify the available models at 1607. At 1608, the processors of the server 1606 return the list of available models to the computing device 1620. The available models may be determined in various manners. For example, multiple ensembles of models may be stored in connection with one type of biomarker machine learning classifier. For example, the XGBTree biomarker machine learning classifier may generate multiple ensembles of models, where each ensemble of models is based on a different control labeled data set. Additionally or alternatively, each ensemble of models may be generated utilizing a different type of biomarker machine learning classifier. For example, the XGB tree biomarker machine learning classifier may generate a first ensemble of models utilizing a control labeled data set, while a logistic regression biomarker machine learning classifier may generate a second ensemble of models utilizing the same control labeled data set. Ensembles of models may be formed utilizing other types of biomarker machine learning classifiers.

Once the list of models is returned at 1608, the computing device 1620 selects one ensemble of models in connection with the present individual patient. The selection of the ensemble of models may be performed manually by a clinician through the GUI. Additionally or alternatively, the processors of the computing device 1620 may automatically select the ensemble of models based on various criteria. For example, the computing device 120 may automatically selecting ensemble of models based upon the amount of information available for the present individual patient, based upon a nature of the OA and US images and the like. The operations at 1506-508 are utilized when multiple ensembles of models are available. Additionally or alternatively, when only a single ensemble of models is available, the operations at 1606-1608 may be omitted entirely.

At 1610, the computing device 1620 generates and sends a LOM/PPV request (more generally a predictive result request) to the server 1606. The LOM/PPV request (predictive result request) may include, among other things, an identification of the ensemble of models to be utilized, as well as OA and US features scores and other patient specific data (e.g., age, Bi-RAD scores). The server 106 receives the OA and non-OA features scores in connection with OA images and non-OA images collected from a patient examination for a volume of interest, where the volume of interest includes a suspect lesion. At 1612, the processors of the server 1606 apply the OA and non-OA features scores of the present observation to a designated master classification model and bootstrap classification models to obtain a predictive result indicative of a lesion trait (e.g., a likelihood that a lesion is in a malignant class or benign class). At 1614, the processors of the server 1606 obtain the classification probability based on the OA and non-OA features scores of the present observation as applied to the master classification model. Additionally or alternatively, the processors of the server 1606 may obtain a positive predictive value, based on the PPV mapping function and the current classification probability for the present observation. At 1616, the processors of the server 1606 obtain the prediction interval based on the OA and non-OA features scores of the present observation as applied to the bootstrap classification models.

At 1618, the processors of the server return, as a composite predictive result (PR) response the combination of the classification probability and/or PPV, and the reduction interval. As noted herein, the classification probability or the PPV may be utilized as the probability of malignancy. At 1620, the processors of the computing device output the composite PR (e.g., LOM/PPV and prediction interval for one or more classes or traits), such as displaying the composite PR through the GUI. The output of the composite PR may also include storing the composite PR in connection with a patient's records. Additionally or alternatively, the computing device may perform other actions based on the composite PR. For example, the computing device may send a notification to other medical personnel, initiate a report, initiate scheduling of a follow-up procedure and the like. As a further example, when the LOM/PPV and confidence interval indicate the class or trait, the computing device may send a notice or report automatically to the patient (e.g., via text message, email or other electronic notification means).

Figure 17A:
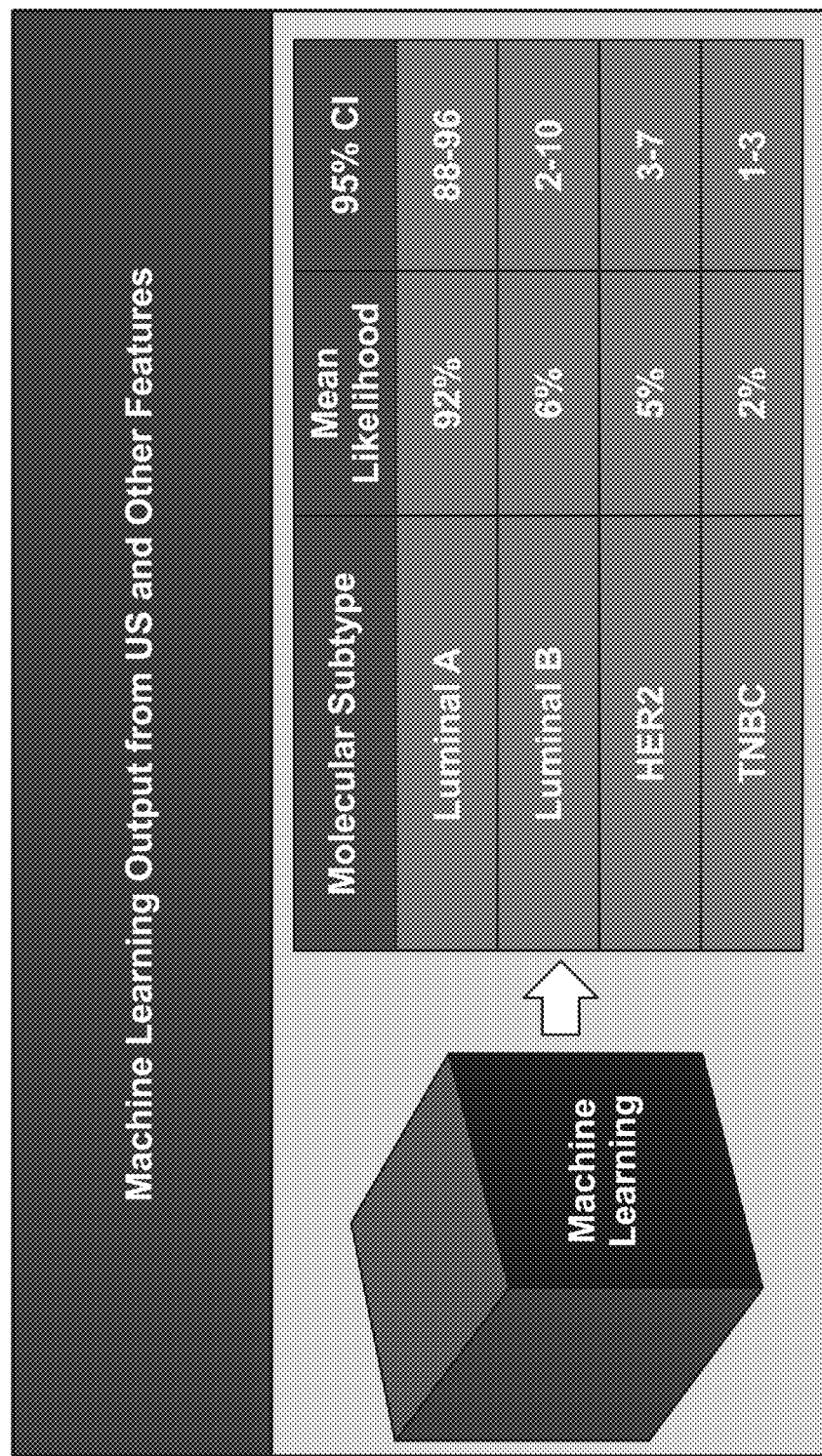
FIG. 17A illustrates an example of the output that may be generated by the machine learning model in accordance with embodiments herein.

FIG. 17A illustrates an example of the output that may be generated by the machine learning model in accordance with embodiments herein. The system may display prognostic and/or predictive results indicative of a trait of the lesion in various manners. For example, the display may present, in connection with each molecular subtype, graphical and/or alphanumeric text indicia indicative of a mean likelihood, as well as upper and lower confidence indicator boundaries. Additionally or alternatively, the display may present indicia indicative of at least one of qualitative diagnostic biomarkers, semi-quantitative diagnostic bio markers, prognostic biomarkers or monitoring biomarkers. When the display presents a prognostic result corresponding to a semi-quantitative diagnostic result, the indicia may present graphical and/or alphanumeric text indicative of one or more of the following: i) percentage likelihood of malignancy of a mass, ii) a likelihood of a clinical event, disease progression or reoccurrence, iii) molecular subtype, iv) histologic grade, v) degree of angiogenesis, vi) likelihood of lymph node metastasis, vii) assess the status of a disease or condition to find evidence of exposure to, or effects of, a medical product or environmental agent, viii) change in a patient condition (e.g., tumor size and volume), ix) indicator of an effect of a response to an exposure intervention, x) detect or confirm a disease or condition, xi) identify specific disease subtype, xii) possibility that mutations in genes are predictive of response to certain inhibitors, xiv) likelihood that ER and PR possible breast cancers respond to endocrine therapy, xv) possibility that dense breast tissue is predictive of decreased sensitivity of mammography for detecting noncalcified breast cancer, xvi) one of one or more molecular subtypes or xvii) histologic grades.

The displayed indicia may present graphical or alphanumeric indicia indicative of a predicted mean likelihood of malignancy (LOM) or probability of malignancy (POM), such as with a 90% LOM/POM confidence interval (CI). Additionally or alternatively, the displayed indicia may present graphical or alphanumeric indicia indicative of a mean false negative rate (FNR) with a select confidence interval, such as with a false negative rate 90% confidence interval. The predictive result (e.g., the LOM and FNR outputs) may be displayed in various manners, such as graphically, numerically and the like. For example, the LOM and FNR outputs may be displayed graphically on a bar than extends from 0% FNR to 100% LOM. Additionally or alternatively, the FNR and/or LOM bar will include a vertical line at a select FNR level, such as at the 2% FNR, with the segment of the bar to the left of the 2% line corresponding to predicted FNRs and the segment of the bar to the right of the 2% line corresponding to predicted LOM. The predicted LOM may be mapped to FNR on the part of the display to the left of the predicted 2% FNR. For example, a predicted LOM of 5% may correspond to an FNR of 2%. Additionally or alternatively, the graphic display may be color coded in a fashion in which a gradient of colors corresponds to higher or lower FNR or LOM, with the colors changing gradually from the left end of the bar to the right end of the bar.

Additionally or alternatively, the graphic display may show the mean predicted FNR or LOM with a circle, square, or other polygonal shape that is colored differently from the gradient color on the underlying FNR-LOM bar. Additionally or alternatively, the 90% FNR CI and/or 90% LOM bar may be represented with a horizontal line with vertical bars or whiskers on each end that correspond to the $5^{th}$ FNR or LOM percentile and the $95^{th}$ FNR or LOM percentile, respectively. The color of the line and whiskers that represent the 90% CI may be colored differently from the background FNR-LOM gradient color and may be the same as or different from the color of the circle, square, or other polygonal shape that represents the mean predicted FNR or LOM. Additionally or alternatively, there may be second BI-RADS conversion bar that is displayed parallel to and just above or just below the predicted FNR-LOM bar that is of the same length, and is subdivided into sections based upon ACR benchmark PPV-LOM ranges for each BI-RADS category, such as:

BI-RADS 3: >0% and ≤2% FNR
BI-RADS 4A: >2% and ≤10% PPV/LOM
BI-RADS 4B: >10% and ≤50% PPV/LOM
BI-RADS 4C: >50% and <95% PPV/LOM
BI-RADS 5: >95% PPV/LOM Additionally or alternatively, the BI-RADS conversion bar may be colored coded in a fashion that differs from the continuous color gradient of the predicted FNR/LOM bar. The BI-RADS conversion bar may be colored so that the range of the bar for each of the BI-RADS category is assigned a different color. The user may then manually select a probability of malignancy (POM) from a drop-down list or wheel, and then manually select a BI-RADS category that corresponds to the predicted FNR or LOM. Additionally or alternatively, the entry program may use error trapping to prevent the user from entering a BI-RADS category whose ACR benchmark FNR/PPV/LOM range for which the predicted FNR/LOM does not correspond.

Alternatively, the AI machine learning component may automatically assign mean FNR or LOM from the predicted FNR or LOM that it outputs, and then subsequently, automatically assign an appropriate BI-RADS category for the predicted FNR or LOM. The user may be allowed to over-ride the output of the AI machine learning predicted mean FNR or LOM output, after confirmatory prompting.

The ACR benchmark FNR range for BI-RADS 3 extends from greater than 0% to less than or equal to 2%. The assignment of BI-RADS 2 category to a solid mass from the results of its baseline ultrasound examination is not recommended by the ACR. However, $5^{th}$ edition US BI-RADS functions only as a qualitative diagnostic biomarker that helps decide whether the FNR is greater than 2% or less than or equal to 2%. Ultrasound BI-RADS $5^{th}$ edition cannot function as a semi-quantitative diagnostic biomarker to objectively and precisely predict an FNR or LOM and its 90% CI. The system described herein was purpose-designed to function as both a qualitative diagnostic biomarker and as a semi-quantitative diagnostic biomarker. It can objectively and precisely predict an FNR/LOM and its 90% CI. Therefore, the user of this system may have the option of assigning a BI-RADS 2 category if the mean predicted FNR and its entire NR 90% CI is 0.5% or less that currently does not and cannot exist in BI-RADS $5^{th}$ edition.

Figure 17B:
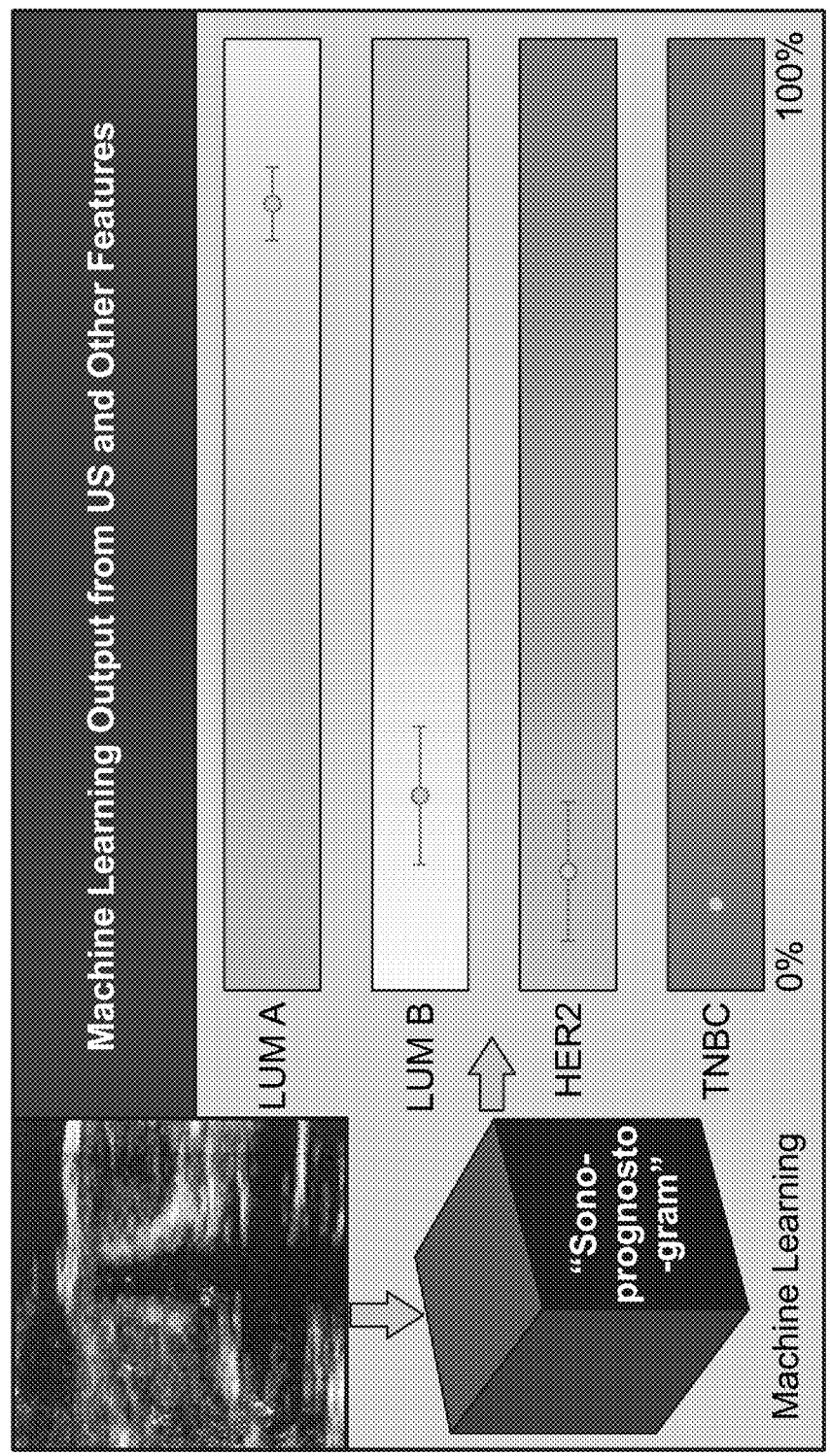
FIG. 17B illustrates another example of a format for the output indicia of the machine learning model.

FIG. 17B illustrates another example of a format for the output indicia of the machine learning model. The indicia are displayed in a manner and format representative of a collection of probabilities associated with a collection of the molecular subtypes. For example, the output may illustrate a LOM indicia in connection with each molecular subtype or a collection of the molecular subtypes. The LOM indicia may represent a bar graph associated with each molecular subtype, with an indicator on the graph denoting a central point/mean, and confidence intervals for the corresponding POM. In accordance with embodiments herein, the LOM indicia may represent a bar graph that denotes a central point/mean and confidence intervals for the semi-quantitative diagnostic result for one or more of the following: i) percentage likelihood of malignancy of a mass, ii) a likelihood of a clinical event, disease progression or reoccurrence, iii) molecular subtype, iv) histologic grade, v) degree of angiogenesis, vi) likelihood of lymph node metastasis, vii) assess the status of a disease or condition to find evidence of exposure to, or effects of, a medical product or environmental agent, viii) change in a patient condition (e.g., tumor size and volume), ix) indicator of an effect of a response to an exposure intervention, x) detect or confirm a disease or condition, xi) identify specific disease subtype, xii) possibility that mutations in genes are predictive of response to certain inhibitors, xiv) likelihood that ER and PR possible breast cancers respond to endocrine therapy, xv) possibility that dense breast tissue is predictive of decreased sensitivity of mammography for detecting noncalcified breast cancer, xvi) one of one or more molecular subtypes or xvii) histologic grades.

In the example of FIG. 17B, a high POM exists that the tumor has the luminal A subtype, while low LOMs exist that the tumor is a luminal B, HER-2 or TNBC subtype. Additionally or alternatively, the LOM indicia may represent a graph, alphanumeric characters, a color-coded scale, and the like. The LOM indicia in FIG. 17B represent examples of resultant predictive results may be displayed in accordance with embodiments herein. Embodiments for calculating resultant predictive results are described herein, such as in connection with machine learning classifiers. Each resultant predictive result corresponds to a different molecular subtype and/or histologic grade. An individual predictive result may be presented along a color-coded scale, representing a probability of malignancy scale for the molecular subtype and/or histologic grade, where the scale extends from a 0% (e.g., 0% probability of malignancy) at a start to 100% (e.g., 100% probability of malignancy) at an end. The color-coded scale may include color shades that transition, such as between a green zone at, the yellow zone, and orange zone and a red zone, where the colors merge between the zones. The predictive result includes a LOM for each denoted molecular subtype and/or histologic grade, which may correspond to the classification probability determined by the master composite model and/or the positive predictive value determined by the PPV mapping function. The predictive result may also include a prediction interval extending on either side of the LOM.

Figure 17C:
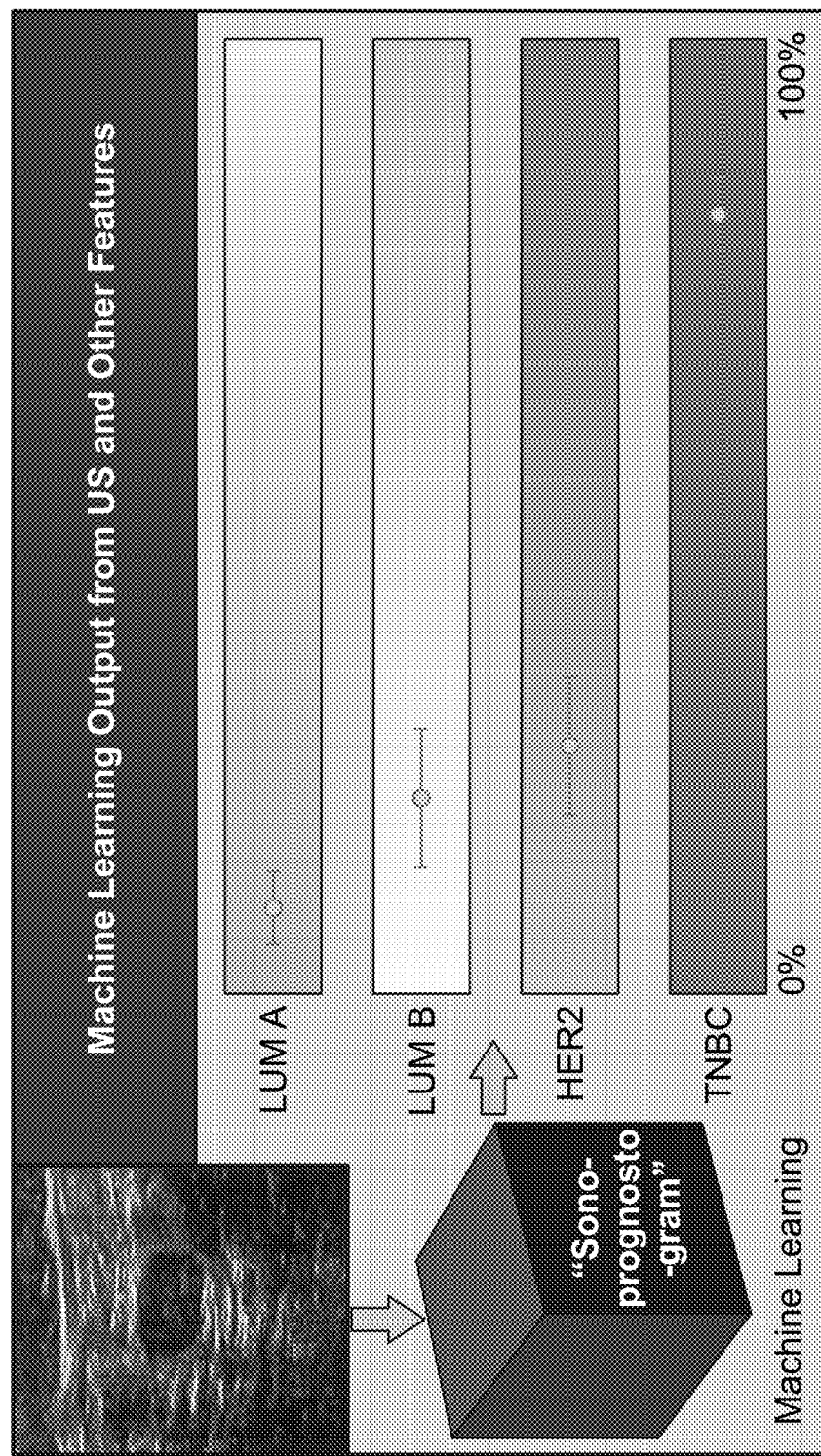
FIG. 17C illustrates another example of an output of the machine learning model.

FIG. 17C illustrates another example of an output of the machine learning model. For example, the output may illustrate POM indicia in connection with each molecular subtype. In the example of FIG. 17C, a high probability exists that the tumor has the TNBC subtype, while low probabilities exist that the tumor is Luminal A, luminal B, or HER-2.

Figure 17D:
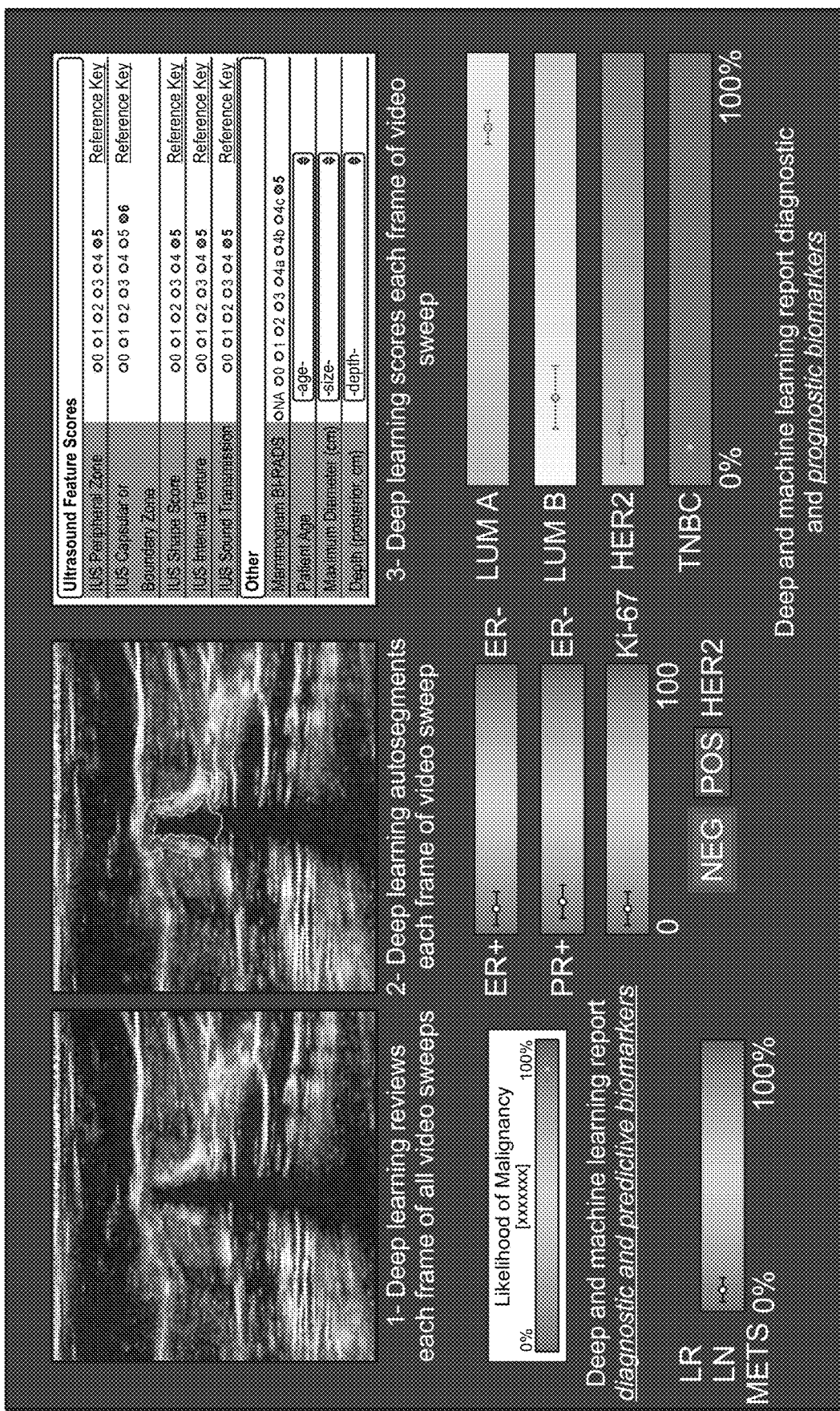
FIG. 17D illustrates of an output of the machine learning model where scoring 5 US and 5 OA features could lead to many different outputs simultaneously from machine learning.

FIG. 17D illustrates of an output of the machine learning model where scoring 5 US and 5 OA features could lead to many different outputs simultaneously from machine learning: 1) POM with 90% confidence intervals; 2) Mean likelihood with confidence intervals of ER positivity or negativity, 3) mean likelihood with confidence intervals of PR positivity or negativity, 4) mean likelihood of HER2 positivity 5) predicted Ki67 with confidence interval; 6) mean likelihood with confidence intervals of histologic grade; 7) mean likelihood with confidence intervals of each molecular subtype; and mean likelihood of lymph node metastases.

CLOSING STATEMENTS

It should be clearly understood that the various arrangements and processes broadly described and illustrated with respect to the Figures, and/or one or more individual components or elements of such arrangements and/or one or more process operations associated of such processes, can be employed independently from or together with one or more other components, elements and/or process operations described and illustrated herein. Accordingly, while various arrangements and processes are broadly contemplated, described and illustrated herein, it should be understood that they are provided merely in illustrative and non-restrictive fashion, and furthermore can be regarded as but mere examples of possible working environments in which one or more arrangements or processes may function or operate.

As will be appreciated by one skilled in the art, various aspects may be embodied as a system, method or computer (device) program product. Accordingly, aspects may take the form of an entirely hardware embodiment or an embodiment including hardware and software that may all generally be referred to herein as a "circuit," "module" or "system." Furthermore, aspects may take the form of a computer (device) program product embodied in one or more computer (device) readable storage medium(s) having computer (device) readable program code embodied thereon.

Any combination of one or more non-signal computer (device) readable medium(s) may be utilized. The non-signal medium may be a storage medium. A storage medium may be, for example, an electronic, magnetic, optical, electromagnetic, infrared, or semiconductor system, apparatus, or device, or any suitable combination of the foregoing. More specific examples of a storage medium would include the following: a portable computer diskette, a hard disk, a random access memory (RAM), a dynamic random access memory (DRAM), a read-only memory (ROM), an erasable programmable read-only memory (EPROM or Flash memory), a portable compact disc read-only memory (CD-ROM), an optical storage device, a magnetic storage device, or any suitable combination of the foregoing.

Program code for carrying out operations may be written in any combination of one or more programming languages. The program code may execute entirely on a single device, partly on a single device, as a stand-alone software package, partly on single device and partly on another device, or entirely on the other device. In some cases, the devices may be connected through any type of network, including a local area network (LAN) or a wide area network (WAN), or the connection may be made through other devices (for example, through the Internet using an Internet Service Provider) or through a hard wire connection, such as over a USB connection. For example, a server having a first processor, a network interface, and a storage device for storing code may store the program code for carrying out the operations and provide this code through its network interface via a network to a second device having a second processor for execution of the code on the second device.

Aspects are described herein with reference to the Figures, which illustrate example methods, devices and program products according to various example embodiments. These program instructions may be provided to a processor of a general purpose computer, special purpose computer, or other programmable data processing device or information handling device to produce a machine, such that the instructions, which execute via a processor of the device implement the functions/acts specified. The program instructions may also be stored in a device readable medium that can direct a device to function in a particular manner, such that the instructions stored in the device readable medium produce an article of manufacture including instructions which implement the function/act specified. The program instructions may also be loaded onto a device to cause a series of operational steps to be performed on the device to produce a device implemented process such that the instructions which execute on the device provide processes for implementing the functions/acts specified.

The units/modules/applications herein may include any processor-based or microprocessor-based system including systems using microcontrollers, reduced instruction set computers (RISC), application specific integrated circuits (ASICs), field-programmable gate arrays (FPGAs), logic circuits, and any other circuit or processor capable of executing the functions described herein. Additionally or alternatively, the modules/controllers herein may represent circuit modules that may be implemented as hardware with associated instructions (for example, software stored on a tangible and non-transitory computer readable storage medium, such as a computer hard drive, ROM, RAM, or the like) that perform the operations described herein. The above examples are exemplary only and are thus not intended to limit in any way the definition and/or meaning of the term "controller." The units/modules/applications herein may execute a set of instructions that are stored in one or more storage elements, in order to process data. The storage elements may also store data or other information as desired or needed. The storage element may be in the form of an information source or a physical memory element within the modules/controllers herein. The set of instructions may include various commands that instruct the modules/applications herein to perform specific operations such as the methods and processes of the various embodiments of the subject matter described herein. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to user commands, or in response to results of previous processing, or in response to a request made by another processing machine.

It is to be understood that the subject matter described herein is not limited in its application to the details of construction and the arrangement of components set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

It is to be understood that the above description is intended to be illustrative, and not restrictive. For example, the above-described embodiments (and/or aspects thereof) may be used in combination with each other. In addition, many modifications may be made to adapt a particular situation or material to the teachings herein without departing from its scope. While the dimensions, types of materials and coatings described herein are intended to define various parameters, they are by no means limiting and are illustrative in nature. Many other embodiments will be apparent to those of skill in the art upon reviewing the above description. The scope of the embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects or order of execution on their acts.

What is claimed is:

1. A system for analyzing at least one of ultrasound (US) images or optoacoustic (OA) images (US/OA images), comprising:
   a display configured to display at least a first image from at least one of OA images or US images acquired in connection with an examination for a region of interest (ROI), the first image including a lesion, the first image overlaid with an interior ROI outline separating an internal zone from a boundary zone of the ROI, the first image overlaid with an exterior ROI outline separating the boundary zone from a peripheral zone;
   a graphical user interface (GUI);
   memory configured to store program instructions; and
   one or more processors configured to execute the programmable instructions to:
      obtain feature scores in connection with at least the boundary zone and peripheral zone of the first image;
      apply the feature scores to a classification model to obtain at least one of a prognostic result or predictive result indicative of a trait of the lesion; and
   output the at least one of the prognostic result or predictive result,
   wherein the memory is configured to store the classification model, the classification model defining a relation between a combination of the feature scores and a positive predictive value of the at least one of the prognostic result or predictive result, the relation representing a sigmoidal curve having initial, intermediate and final portions, the initial portion corresponding to low positive predictive values (PPVs) for a select combination of the feature scores and exhibiting a first slope increasing at a first rate over the initial portion, the intermediate portion corresponding to intermediate PPVs for the select combination of the feature scores and exhibiting a second slope increasing at a second rate over the intermediate portion, the final portion corresponding to high PPVs for the select combination of the feature scores and exhibiting a third slope decreasing at a third rate over the final portion, the second slope and second rate being greater than the first slope and first rate, respectively.

2. The system of claim 1, wherein the feature scores represent at least one of qualitative diagnostic biomarkers, semi-quantitative diagnostic biomarkers, prognostic biomarkers or monitoring biomarkers.

3. The system of claim 2, wherein the one or more processors are further configured to apply the feature scores to the classification model to obtain, as the semi-quantitative diagnostic result, one or more of the following: i) percentage likelihood of malignancy of a mass, ii) a likelihood of a clinical event, disease progression or reoccurrence, iii) molecular subtype, iv) histologic grade, v) degree of angiogenesis, vi) likelihood of lymph node metastasis, vii) assess the status of a disease or condition to find evidence of exposure to, or effects of, a medical product or environmental agent, viii) change in a patient condition (e.g. tumor size and volume), ix) indicator of an effect of a response to an exposure intervention, x) detect or confirm a disease or condition, xi) identify specific disease subtype, xii) possibility that mutations in genes are predictive of response to certain inhibitors, xiv) likelihood that ER and PR possible breast cancers respond to endocrine therapy, xv) possibility that dense breast tissue is predictive of decreased sensitivity of mammography for detecting noncalcified breast cancer, xvi) one of one or more molecular subtypes or xvii) histologic grades.

4. A system for analyzing at least one of ultrasound (US) images or optoacoustic (OA) images (US/OA images), comprising:
a display configured to display at least a first image from at least one of OA images or US images acquired in connection with an examination for a region of interest (ROI), the first image including a lesion, the first image overlaid with an interior ROI outline separating an internal zone from a boundary zone of the ROI, the first image overlaid with an exterior ROI outline separating the boundary zone from a peripheral zone;
a graphical user interface (GUI);
memory configured to store program instructions; and
one or more processors configured to execute the programmable instructions to:
obtain feature scores in connection with at least the boundary zone and peripheral zone of the first image;
obtain a depth to a posterior margin of the mass;
apply the feature scores and the depth to a posterior margin of the mass, to a classification model, to obtain at least one of a prognostic result or predictive result indicative of a trait of the lesion, wherein the depth to the posterior margin of the mass to the classification model accounts for reduced energy reaching the posterior margin of the mass; and
output the at least one of the prognostic result or predictive result.

5. The system of claim 4, wherein the memory is configured to store the classification model, the classification model defining a nonlinear relation between a combination of the feature scores and a positive predictive value of the at least one of the prognostic result or predictive result.

6. The system of claim 5, wherein the nonlinear relation represents a sigmoidal curve.

7. The system of claim 6, wherein the sigmoidal curve has initial, intermediate and final portions, the initial portion corresponding to low positive predictive values (PPVs) for a select combination of the feature scores and exhibiting a first slope increasing at a first rate over the initial portion, the intermediate portion corresponding to intermediate values for the select combination of the feature scores and exhibiting a second slope increasing at a second rate over the intermediate portion, the final portion corresponding to high values for the select combination of the feature scores and exhibiting a third slope decreasing at a third rate over the final portion, the second slope and second rate being greater than the first slope and first rate, respectively.

8. The system of claim 1, wherein the one or more processors are further configured to obtain at least one of a maximum diameter of a mass or a depth to a posterior margin of the mass, and apply the at least one of the maximum diameter or depth to the posterior margin of the mass, to the classification model, to obtain the at least one of the prognostic result or predictive result.

9. The system of claim 1, wherein the feature scores include a US boundary zone feature score and a US peripheral zone feature score, both of which are utilized by the classification model to obtain the at least one of the prognostic result or predictive result, wherein the feature scores are obtained from at least one of 1) the GUI as user inputs, 2) an automatic segmentation and image analysis performed by the one or more processors or 3) from a remote computing device or server.

10. The system of claim 1, wherein the predictive result defines a likelihood of malignancy (LOM) having a value between 2% and 100%.

11. The system of claim 2, wherein the semi-quantitative diagnostic result is not a binary indication regarding whether to perform a biopsy or not perform a biopsy.

12. A system for analyzing at least one of ultrasound (US) images or optoacoustic (OA) images (US/OA images), comprising:
a display configured to display at least a first image from at least one of OA images or US images acquired in connection with an examination for a region of interest (ROI), the first image including a lesion, the first image overlaid with an interior ROI outline separating an internal zone from a boundary zone of the ROI, the first image overlaid with an exterior ROI outline separating the boundary zone from a peripheral zone;
a graphical user interface (GUI);
memory configured to store program instructions; and
one or more processors configured to execute the programmable instructions to:
obtain feature scores in connection with at least the boundary zone and peripheral zone of the first image;
apply the feature scores to a classification model to obtain at least one of a prognostic result or predictive result indicative of a trait of the lesion; and
output the at least one of the prognostic result or predictive result,
wherein the feature scores include a US internal zone sound transmission feature score, the memory configured to store the classification model, the classification model configured to overweight the US internal zone sound transmission feature score with respect to at least one other US feature score to obtain, as a prognostic result, an indication of lymph node metastasis, the classification model configured to recognize that shadowing in the US internal zone is indicative of an increased risk of lymph node metastasis, while enhanced sound transmission is indicative of a lowered risk of lymph node metastasis.

13. The system of claim 1, wherein the feature score includes a US internal zone sound transmission feature score, and wherein the classification model is configured to overweight the US internal zone sound transmission feature score with respect to at least one other feature scores to obtain, as the prognostic result, the prognostic result indicating a distinction between TNBC molecular subtype, luminal a molecular subtype and HER2 molecular subtype.

14. The system of claim 1, wherein the feature scores include an indication of an extent to which ducts and/or lobules are disproportionately enlarged relative to a reference, the classification model accounting for the extent of the enlargement of the ducts and/or lobules when outputting the prognostic result.

15. The system of claim 1, wherein the predictive result represents a semi-quantitative diagnostic result that includes a value for a likelihood of malignancy (LOM) along a range extending beyond 2% and 100%.

16. The system of claim 15, wherein the one or more processors are further configured to obtain an initial BI-RADS rating based on non-OA images, wherein the semi-quantitative diagnostic result includes a determination of whether to at least one of i) downgrade the initial BI-RADS rating or ii) modify the initial BI-RADS rating to add a sub-categorization.

17. The system of claim 16, wherein the initial BI-RADS rating is a BI-RADS 4 rating, without sub categorization, wherein the semi-quantitative diagnostic result includes modifying the BI-RADS 4 rating to at least one of i)

downgrading the BI-RADS 4 rating to a BI-RADS 3 rating or lower or ii) revising the BI-RADS 4 rating to add sub categorization for one of BI-RADS 4A or 4B.

18. The system of claim 1, wherein the one or more processors are further configured to calculate and the display is further configured to display, as the at least one of the prognostic result or predictive result, at least one of false negative ratio, likelihood of malignancy, confidence interval, BI-RADS conversion bars, assignment of a BI-RADS category or assignment of a BI-RADS subcategories.

19. A computer implemented method for analyzing at least one of ultrasound (US) images or optoacoustic (OA) images (US/OA images), comprising:
utilizing one or more processors configured to execute programmable instructions for,
displaying at least a first image from at least one of OA images or US images acquired in connection with an examination for a region of interest (ROI), the first image overlaid with an interior outline separating an internal zone from a boundary zone of the ROI, the first image overlaid with an exterior outline separating the boundary zone from a peripheral zone of the ROI;
receiving feature scores in connection with the internal zone, boundary zone and peripheral zone of the first image;
applying the feature scores to a classification model to obtain at least one of a prognostic result or predictive result indicative of a trait of the lesion; and
outputting the at least one of the prognostic result or predictive result,
wherein the classification model defines a relation between a combination of the feature scores and a positive predictive value of the at least one of the prognostic result or predictive result, the relation representing a sigmoidal curve having initial, intermediate and final portions, the initial portion corresponding to low positive predictive values (PPVs) for a select combination of the feature scores and exhibiting a first slope increasing at a first rate over the initial portion, the intermediate portion corresponding to intermediate PPVs for the select combination of the feature scores and exhibiting a second slope increasing at a second rate over the intermediate portion, the final portion corresponding to high PPVs for the select combination of the feature scores and exhibiting a third slope decreasing at a third rate over the final portion, the second slope and second rate being greater than the first slope and first rate, respectively.

20. The method of claim 19, wherein the feature scores represent at least one of qualitative diagnostic biomarkers, semi-quantitative diagnostic bio markers, prognostic biomarkers or monitoring biomarkers.

21. The method of claim 19, wherein the applying further comprises applying the feature scores to the classification model to obtain, as the semi-quantitative diagnostic result, one or more of the following: i) percentage likelihood of malignancy of a mass, ii) a likelihood of a clinical event, disease progression or reoccurrence, iii) molecular subtype, iv) histologic grade, v) degree of angiogenesis, vi) likelihood of lymph node metastasis, vii) assess the status of a disease or condition to find evidence of exposure to, or effects of, a medical product or environmental agent, viii) change in a patient condition (e.g. tumor size and volume), ix) indicator of an effect of a response to an exposure intervention, x) detect or confirm a disease or condition, xi) identify specific disease subtype, xii) possibility that mutations in genes are predictive of response to certain inhibitors, xiv) likelihood that ER and PR possible breast cancers respond to endocrine therapy, xv) possibility that dense breast tissue is predictive of decreased sensitivity of mammography for detecting noncalcified breast cancer, xvi) one of one or more molecular subtypes or xvii) histologic grades.

22. A computer implemented method for analyzing at least one of ultrasound (US) images or optoacoustic (OA) images (US/OA images), comprising:
utilizing one or more processors configured to execute programmable instructions for,
displaying at least a first image from at least one of OA images or US images acquired in connection with an examination for a region of interest (ROI), the first image overlaid with an interior outline separating an internal zone from a boundary zone of the ROI, the first image overlaid with an exterior outline separating the boundary zone from a peripheral zone of the ROI;
receiving feature scores in connection with the internal zone, boundary zone and peripheral zone of the first image;
obtaining a depth to a posterior margin of the mass;
applying the feature scores and the depth to the posterior margin of the mass, to a classification model, to obtain at least one of a prognostic result or predictive result indicative of a trait of the lesion, wherein the depth to the posterior margin of the mass accounts for reduced energy reaching the posterior margin of the mass; and
outputting the at least one of the prognostic result or predictive result.

23. The method of claim 22, wherein the classification model defines a nonlinear relation between a combination of the feature scores and a positive predictive value of the at least one of the prognostic result or predictive result.

24. The method of claim 23, wherein the nonlinear relation represents a sigmoidal curve.

25. The method of claim 24, wherein the sigmoidal curve has initial, intermediate and final portions, the initial portion corresponding to low PPVs for the combination of the feature scores and exhibiting a first slope increasing at a first rate over the initial portion, the intermediate portion corresponding to intermediate values for the combination of the feature scores and exhibiting a second slope increasing at a second rate over the intermediate portion, the final portion corresponding to high values for the combination of the feature scores and exhibiting a third slope decreasing at a third rate over the final portion, the second slope and second rate being greater than the first slope and first rate, respectively.

26. The method of claim 19, further comprising obtaining at least one of a maximum diameter of a mass or a depth to a posterior margin of the mass, and applying the at least one of the maximum diameter or depth to the posterior margin of the mass, to the classification model, to obtain the at least one of the prognostic result or predictive result.

27. The method of claim 19, wherein the feature scores include a US boundary zone feature score and a US peripheral zone feature score, both of which are utilized by the classification model to obtain the at least one of the prognostic result or predictive result.

28. The method of claim 19, wherein the predictive result defines a likelihood of malignancy (LOM) having a value between 2% and 100%.

29. The method of claim 19, wherein the semi-quantitative diagnostic result is not a binary indication regarding whether to perform a biopsy or not perform a biopsy.

30. A computer implemented method for analyzing at least one of ultrasound (US) images or optoacoustic (OA) images (US/OA images), comprising:
utilizing one or more processors configured to execute programmable instructions for,
displaying at least a first image from at least one of OA images or US images acquired in connection with an examination for a region of interest (ROI), the first image overlaid with an interior outline separating an internal zone from a boundary zone of the ROI, the first image overlaid with an exterior outline separating the boundary zone from a peripheral zone of the ROI;
receiving feature scores in connection with the internal zone, boundary zone and peripheral zone of the first image;
applying the feature scores to a classification model to obtain at least one of a prognostic result or predictive result indicative of a trait of the lesion; and
outputting the at least one of the prognostic result or predictive result,
wherein the feature scores include a US internal zone sound transmission feature score, the memory configured to store the classification model, the classification model configured to overweight the US internal zone sound transmission feature score with respect to at least one other US feature score to obtain, as a prognostic result, an indication of lymph node metastasis, the classification model configured to recognize that shadowing in the US internal zone is indicative of an increased risk of lymph node metastasis, while enhanced sound transmission is indicative of a lowered risk of lymph node metastasis.

31. The method of claim 19, wherein the feature score includes a US internal zone sound transmission feature score, and wherein the classification model is configured to overweight the US internal zone sound transmission feature score with respect to at least one other feature scores to obtain, as the prognostic result, a prognostic result indicating a distinction between TNBC molecular subtype, luminal a molecular subtype and HER2 molecular subtype.

32. The method of claim 19, wherein the feature scores include an indication of an extent to which ducts and/or lobules are disproportionately enlarged relative to a reference, the classification model accounting for the extent of the enlargement of the ducts and/or lobules when outputting the predictive result.

33. The method of claim 19, wherein the at least one of the prognostic result or predictive result represents a semi-quantitative diagnostic result that includes a value for a likelihood of malignancy (LOM) along a range extending beyond 2% and 100%.

34. The method of claim 33, further comprising: obtaining an initial BI-RADS rating based on non-OA images, wherein the semi-quantitative diagnostic result includes a determination of whether to at least one of i) downgrade the initial BI-RADS rating or ii) modify the initial BI-RADS rating to add a sub categorization.

35. The method of claim 34, wherein the initial BI-RADS rating is a BI-RADS 4 rating, without sub categorization, wherein the semi-quantitative diagnostic result includes modifying the BI-RADS 4 rating to at least one of i) downgrading the BI-RADS 4 rating to a BI-RADS 3 rating or lower or ii) revising the BI-RADS 4 rating to add sub categorization for one of BI-RADS 4A or 4B.

36. The system of claim 19, wherein the one or more processors are further configured to calculate and the display is further configured to display, as the at least one of the prognostic result or predictive result, at least one of false negative ratio, likelihood of malignancy, confidence interval, BI-RADS conversion bars, assignment of a BI-RADS category or assignment of a BI-RADS subcategories.

37. A system, comprising:
a graphical user interface (GUI) configured to receive user inputs;
memory configured to store program instructions and to store at least a first image from at least one of OA images or US images acquired in connection with an examination for a region of interest (ROI);
one or more processors configured to execute the programmable instructions to obtain at least one of a prognostic result or predictive result indicative of a trait of the lesion based on feature scores related to at least one of an internal zone, a boundary zone or a peripheral zone of the ROI in the first image; and
a display configured to display indicia indicative of the at least one of the prognostic result or predictive result, wherein the indicia displayed includes a graphical indicia than extends from 0% false negative ratio (FNR) to 100% likelihood of malignancy (LOM), the graphical indicia separated at a select FNR level into a first segment corresponding to predicted FNR and a second segment corresponding to predicted LOM.

38. The system of claim 37, wherein the display is further configured to present indicia indicative of a prognostic result corresponding to a semi-quantitative diagnostic result, the indicia presenting at least one of graphical or alphanumeric text indicative of one or more of: i) percentage likelihood of malignancy of a mass, ii) a likelihood of a clinical event, disease progression or reoccurrence, iii) molecular subtype, iv) histologic grade, v) degree of angiogenesis, vi) likelihood of lymph node metastasis, vii) assess the status of a disease or condition to find evidence of exposure to, or effects of, a medical product or environmental agent, viii) change in a patient condition (e.g. tumor size and volume), ix) indicator of an effect of a response to an exposure intervention, x) detect or confirm a disease or condition, xi) identify specific disease subtype, xii) possibility that mutations in genes are predictive of response to certain inhibitors, xiv) likelihood that ER and PR possible breast cancers respond to endocrine therapy, xv) possibility that dense breast tissue is predictive of decreased sensitivity of mammography for detecting noncalcified breast cancer, xvi) one of one or more molecular subtypes or xvii) histologic grades.

39. The system of claim 37, wherein the display is further configured to display at least a first image from at least one of OA images or US images acquired in connection with an examination for a region of interest (ROI).

40. The system of claim 37, wherein the display is further configured to present, in connection with molecular subtypes, at least one of graphical or alphanumeric text indicia indicative of at least one of a mean likelihood or upper and lower confidence indicator boundaries.

41. The system of claim 37, wherein the displays further configured to present at least one of graphical or alphanumeric indicia indicative of at least one of: 1) a predicted mean likelihood of malignancy (LOM) and a confidence interval, or 2) a mean false negative rate (FNR) with a select confidence interval.

42. The system of claim 37, wherein the graphical indicia including a vertical line at the select FNR level with the first segment of the graphical indicia to a left of the vertical line corresponding to the predicted FNR and the second segment of the graphical indicia to a right of the vertical line corresponding to the predicted LOM.

43. The system of claim 37, wherein the graphical indicia include color coding in which a gradient of colors corresponds to higher or lower FNR or LOM, with colors changing gradually from one end to another end of the graphical indicia.

44. The system of claim 37, wherein the graphical indicia shows a mean predicted FNR or LOM with a circle, square, or other polygonal shape that is colored differently from the gradient of colors on an underlying FNR-LOM bar.

45. The system of claim 37, wherein the indicia displayed further includes a BI-RADS conversion bar that is co-displayed with a predicted FNR-LOM bar, the BI-RADS conversion bar subdivided into sections based upon positive predictive value (PPV) LOM ranges for each category of BI-RADS.

46. A method, comprising:
under control of one or more processors configured with program instructions for,
providing a graphical user interface (GUI) configured to receive user inputs related to at least a first image from at least one of OA images or US images acquired in connection with an examination for a region of interest (ROI);
obtaining at least one of a prognostic result or predictive result indicative of a trait of the lesion based on feature scores related to at least one of an internal zone, a boundary zone or a peripheral zone of the ROI in the first image; and
displaying indicia indicative of the at least one of the prognostic result or predictive result, wherein the indicia displayed includes a graphical indicia than extends from 0% false negative ratio (FNR) to 100% likelihood of malignancy (LOM), the graphical indicia separated at a select FNR level into a first segment corresponding to predicted FNR and a second segment corresponding to predicted LOM.

47. The method of claim 46, wherein the indicia are indicative of a prognostic result corresponding to a semi-quantitative diagnostic result, the indicia presenting at least one of graphical or alphanumeric text indicative of one or more of: i) percentage likelihood of malignancy of a mass, ii) a likelihood of a clinical event, disease progression or reoccurrence, iii) molecular subtype, iv) histologic grade, v) degree of angiogenesis, vi) likelihood of lymph node metastasis, vii) assess the status of a disease or condition to find evidence of exposure to, or effects of, a medical product or environmental agent, viii) change in a patient condition (e.g. tumor size and volume), ix) indicator of an effect of a response to an exposure intervention, x) detect or confirm a disease or condition, xi) identify specific disease subtype, xii) possibility that mutations in genes are predictive of response to certain inhibitors, xiv) likelihood that ER and PR possible breast cancers respond to endocrine therapy, xv) possibility that dense breast tissue is predictive of decreased sensitivity of mammography for detecting noncalcified breast cancer, xvi) one of one or more molecular subtypes or xvii) histologic grades.

48. The method of claim 46, further comprising displaying at least the first image from at least one of OA images or US images acquired in connection with an examination for a region of interest (ROI).

49. The method of claim 46, wherein the indicia include, in connection with molecular subtypes, at least one of graphical or alphanumeric text indicia indicative of at least one of a mean likelihood or upper and lower confidence indicator boundaries.

50. The method of claim 46, wherein the indicia presents at least one of graphical or alphanumeric indicia indicative of at least one of: 1) a predicted mean likelihood of malignancy (LOM) and a confidence interval, or 2) a mean false negative rate (FNR) with a select confidence interval.

51. The method of claim 46, wherein the graphical indicia including a vertical line at the select FNR level with the first segment of the graphical indicia to a left of the vertical line corresponding to the predicted FNR and the second segment of the graphical indicia to a right of the vertical line corresponding to the predicted LOM.

52. The method of claim 46, wherein the graphical indicia include color coding in which a gradient of colors corresponds to higher or lower FNR or LOM, with colors changing gradually from one end to another end of the graphical indicia.

53. The method of claim 51, wherein the graphical indicia illustrate a mean predicted FNR or LOM with a circle, square, or other polygonal shape that is colored differently from the gradient of colors on an underlying FNR-LOM bar.

54. The method of claim 51, further comprising displaying a BI-RADS conversion bar that is co-displayed with a predicted FNR-LOM bar, the BI-RADS conversion bar subdivided into sections based upon positive predictive value (PPV) LOM ranges for each category of BI-RADS.

55. The system of claim 1, wherein the first image is an OA image and at least a portion of the feature scores are in connection with at least the boundary zone and peripheral zone of the OA image.

56. The method of claim 19, wherein the first image is an OA image and at least a portion of the feature scores are in connection with at least the boundary zone and peripheral zone of the OA image.

* * * * *

UNITED STATES PATENT AND TRADEMARK OFFICE
CERTIFICATE OF CORRECTION

PATENT NO. : 11,375,984 B2  
APPLICATION NO. : 16/905396  
DATED : July 5, 2022  
INVENTOR(S) : Anthony Thomas Stavros et al.

Page 1 of 1

It is certified that error appears in the above-identified patent and that said Letters Patent is hereby corrected as shown below:

In the Specification

Column 97, Lines 24 and 25, Delete "to the classification model"

Signed and Sealed this  
Twenty-fourth Day of June, 2025

Coke Morgan Stewart  
*Acting Director of the United States Patent and Trademark Office*